US012807941B2

(12) United States Patent
Roth et al.

(10) Patent No.: US 12,807,941 B2
(45) Date of Patent: Nov. 24, 2026

(54) POOLED KNOCK-IN SCREENING AND HETEROLOGOUS POLYPEPTIDES CO-EXPRESSED UNDER THE CONTROL OF ENDOGENOUS LOCI

(71) Applicant: The Regents of the University of California, Oakland, CA (US)

(72) Inventors: Theodore Lee Roth, San Francisco, CA (US); Po-Yi Jonathan Li, San Francisco, CA (US); Alexander Marson, San Francisco, CA (US); Jasper Nies, San Francisco, CA (US); Cody Mowery, San Francisco, CA (US); Eric Shifrut, San Francisco, CA (US); Franziska Blaeschke, San Francisco, CA (US); Ryan Apathy, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1434 days.

(21) Appl. No.: 17/439,328

(22) PCT Filed: Mar. 13, 2020

(86) PCT No.: PCT/US2020/022766

§ 371 (c)(1),
(2) Date: Sep. 14, 2021

(87) PCT Pub. No.: WO2020/186219

PCT Pub. Date: Sep. 17, 2020

(65) Prior Publication Data

US 2023/0066806 A1 Mar. 2, 2023

Related U.S. Application Data

(60) Provisional application No. 62/871,309, filed on Jul. 8, 2019, provisional application No. 62/871,467, filed on Jul. 8, 2019, provisional application No. 62/818,578, filed on Mar. 14, 2019, provisional application No. 62/818,535, filed on Mar. 14, 2019.

(51) Int. Cl.

| | |
|---|---|
| ***C12N 15/10*** | (2006.01) |
| ***A61K 40/11*** | (2025.01) |
| ***A61K 40/32*** | (2025.01) |
| ***A61K 40/42*** | (2025.01) |
| ***A61P 17/00*** | (2006.01) |
| ***A61P 35/00*** | (2006.01) |
| ***C12N 15/90*** | (2006.01) |

(52) U.S. Cl.

CPC .......... *C12N 15/1082* (2013.01); *A61K 40/11* (2025.01); *A61K 40/32* (2025.01); *A61K 40/4202* (2025.01); *A61K 40/4203* (2025.01); *A61K 40/4242* (2025.01); *A61K 40/4269* (2025.01); *A61P 17/00* (2018.01); *A61P 35/00* (2018.01); *C12N 15/1065* (2013.01); *C12N 15/907* (2013.01); *A61K 2239/31* (2023.05); *A61K 2239/38* (2023.05); *A61K 2239/57* (2023.05)

(58) Field of Classification Search

CPC .................................................. C12N 15/1082
USPC ........................................................ 435/455
See application file for complete search history.

(56) References Cited

U.S. PATENT DOCUMENTS

| | | | | |
|---|---|---|---|---|
| 10,017,760 | B2 * | 7/2018 | Gill | C12N 15/102 |
| 2008/0184380 | A1 | 7/2008 | Buelow et al. | |
| 2014/0242049 | A1 * | 8/2014 | Choi | C07K 14/70521 |
| 2015/0376650 | A1 | 12/2015 | Auerbach et al. | |
| 2017/0136458 | A1 | 5/2017 | Dunne et al. | |
| 2018/0371498 | A1 * | 12/2018 | Gill | C07K 14/195 |

FOREIGN PATENT DOCUMENTS

| | | | |
|---|---|---|---|
| WO | 2014172584 | A1 | 10/2014 |
| WO | 2018049226 | A1 | 3/2018 |
| WO | 2018152325 | A1 | 8/2018 |

OTHER PUBLICATIONS

Deyle, D. et al., The effects of polymorphisms on human gene targeting, Nucleic Acids Research, 2014, vol. 42, 3119-3124 (Year: 2014).*

Deyle et al., "The Effects of Polymorphisms on Human Gene Targeting," Nucleic Acids Research, vol. 42, No. 5, Mar. 2014, pp. 3119-3124.

EP20769842.4, Partial Supplementary European Search Report, Nov. 7, 2022, 15 pages.

Foster et al., "Antitumor Activity of EBV-Specific T Lymphocytes Transduced with a Dominant Negative TGF-β Receptor," Journal of Immunotherapy, vol. 31, No. 5, Jun. 2008, pp. 500-505.

Kloss et al., "Dominant-Negative TGF-β Receptor Enhances PSMA-Targeted Human CAR T Cell Proliferation and Augments Prostate Cancer Eradication", Molecular Therapy, vol. 26, No. 7, May 8, 2018, pp. 1855-1866.

Application No. PCT/US2020/022766, International Preliminary Report on Patentability, Mailed On Sep. 23, 2021, 12 pages.

Application No. PCT/US2020/022766, International Search Report and Written Opinion, Mailed On Jul. 31, 2020, 17 pages.

Shifrut et al., "Genome-wide CRISPR Screens in Primary Human T Cells Reveal Key Regulators of Immune Function," Cell, vol. 175, No. 7, Dec. 13, 2018, pp. 1958-1971.

Shimatani et al., "Positive-Negative-Selection-Mediated Gene Targeting in Rice," Frontiers in Plant Science, vol. 5, Article 748, Jan. 5, 2015, pp. 1-7.

* cited by examiner

*Primary Examiner* — Neil P Hammell
*Assistant Examiner* — Lisa Horth
(74) *Attorney, Agent, or Firm* — Kilpatrick Townsend & Stockton LLP

(57) ABSTRACT

Provided herein are methods and compositions for identifying a targeted genomic insertion in a cell. Also provided are heterologous polypeptides that are co-expressed under the control of enodogenous loci and methods of using same.

18 Claims, 68 Drawing Sheets

Specification includes a Sequence Listing.

Checkpoint Inhibitors

Transcription Factors

Cytoskeletal Components

Additional Target Loci

Parameter gNRA Cut Distance (bps)

gRNA Cut Direction gRNA Predicted Cutting gRNA Observed Cutting

Target Gene RNA Expression (TPM, Day 0)
Donor 1
Donor 2
Donor 3
Donor 4
Donor 5
Donor 6
Donor Avg
Observed Knockin %
Parameter

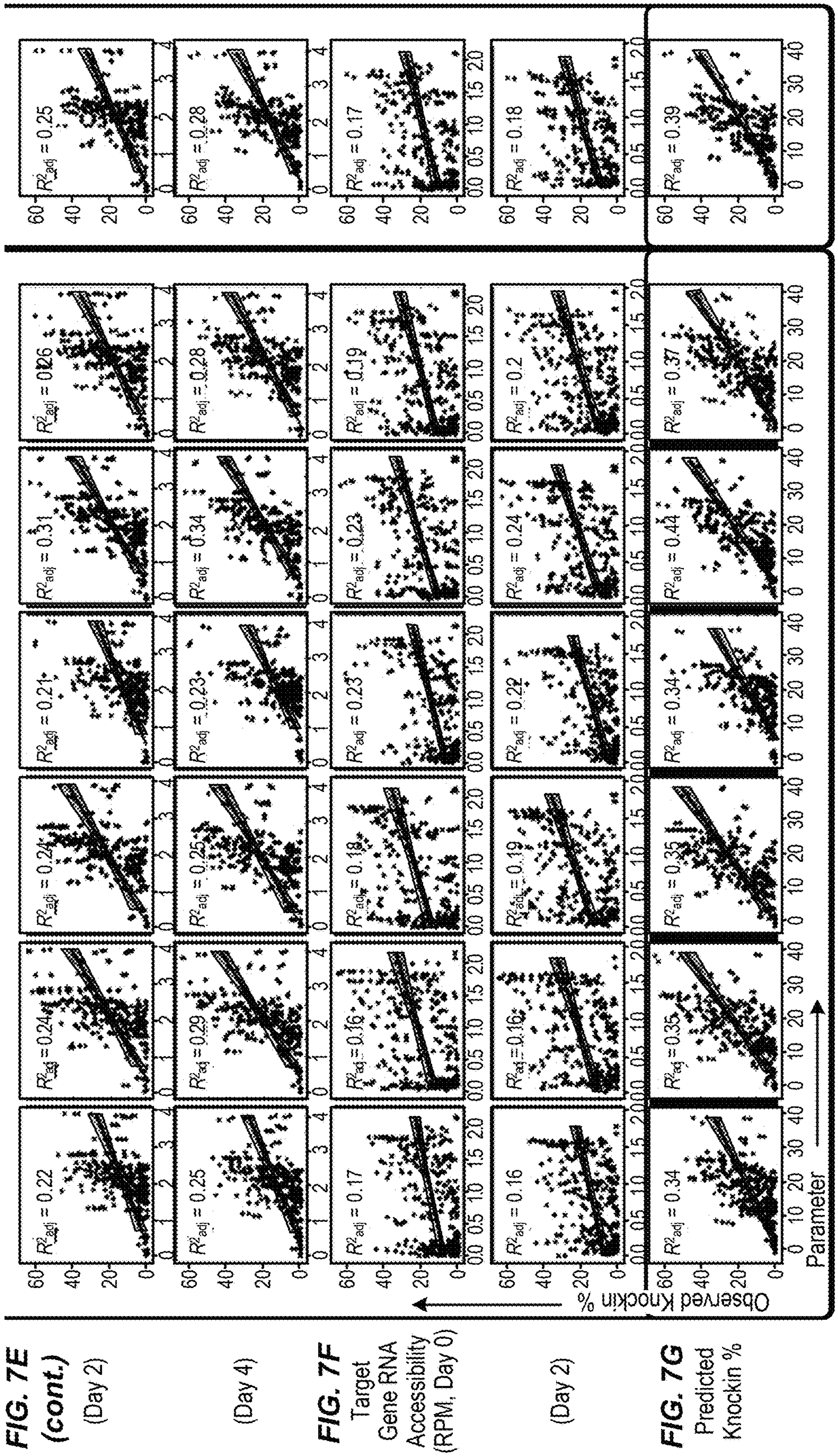
FIG. 7E (cont.) (Day 2)
(Day 4)
FIG. 7F Target Gene RNA Accessibility (RPM, Day 0)
(Day 2)
FIG. 7G Predicted Knockin %

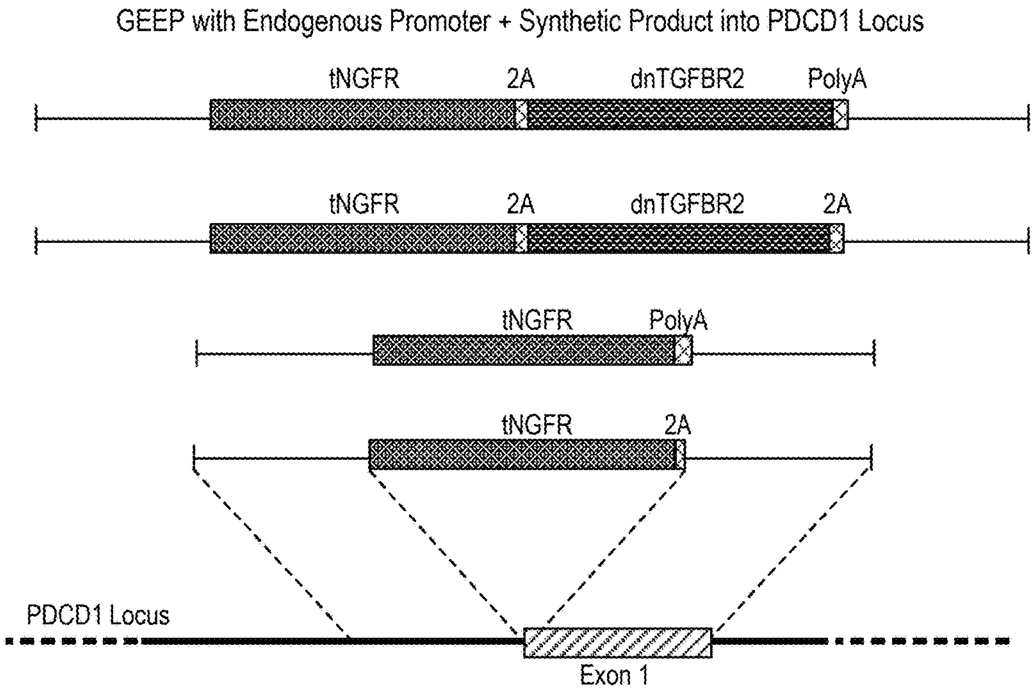
*FIG. 10A*
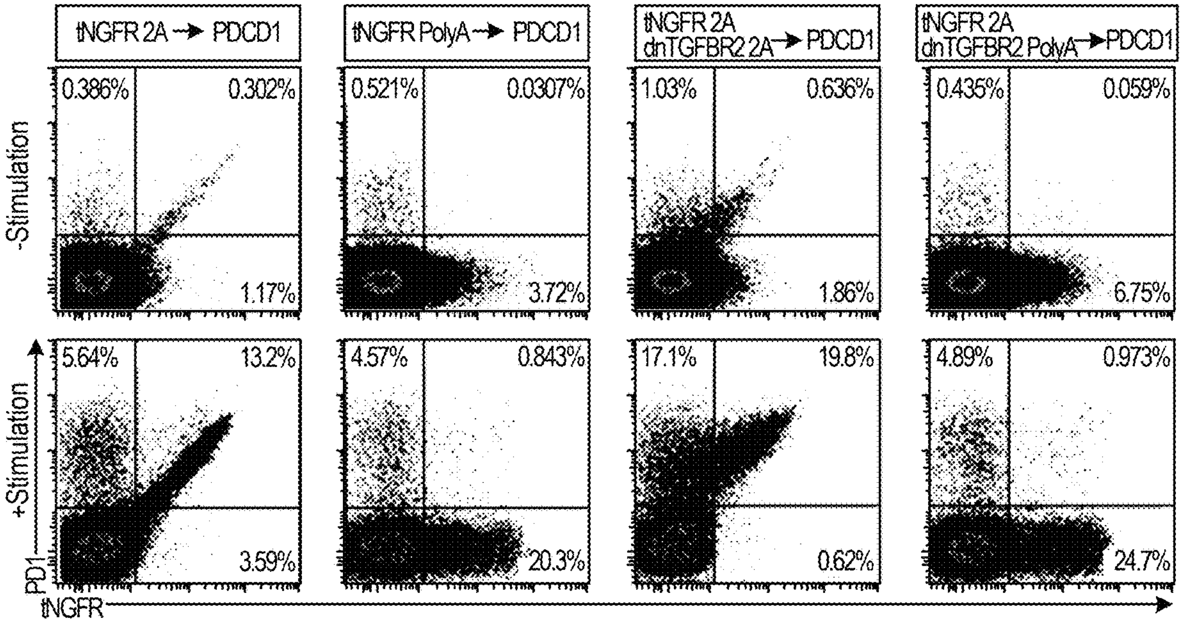
*FIG. 10B* *FIG. 10C* *FIG. 10D* *FIG. 10E*

Pooled Knock-ins with Multiplexed Barcoded Library

Sequenced Barcode Frequencies Match Observed Protein Expression

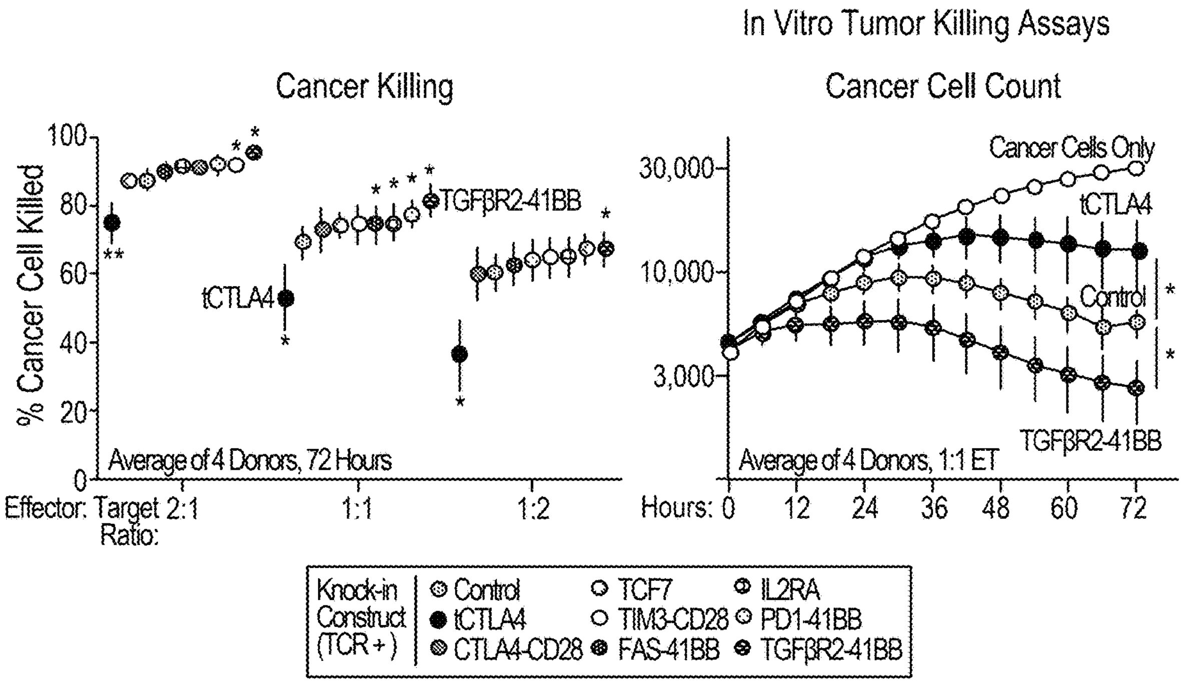
*FIG. 30D*
*FIG. 30E*
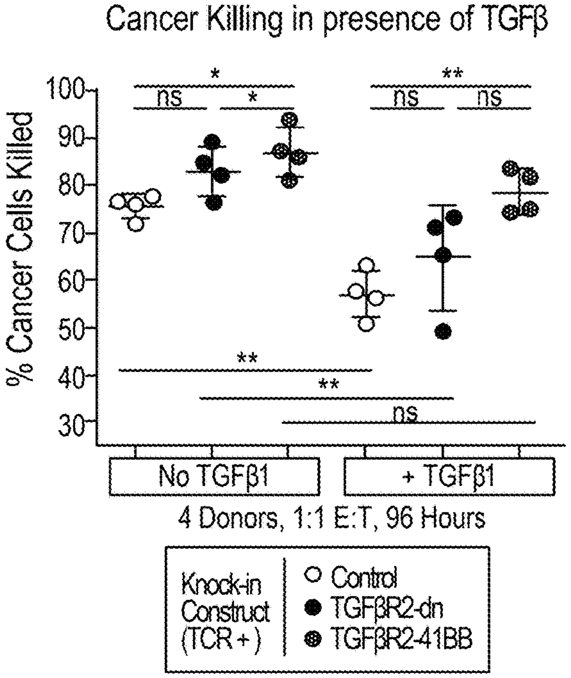
*FIG. 30F*

SEQUENCE LISTING

<160> NUMBER OF SEQ ID NOS: 118

<210> SEQ ID NO 1
<211> LENGTH: 603
<212> TYPE: DNA
<213> ORGANISM: Artificial Sequence
<220> FEATURE:
<223> OTHER INFORMATION: Synthetic Construct

<400> SEQUENCE: 1
atgcagatcc cacaggcgcc ctggccagtc gtctgggcgg tgctacaact gggctggcgg 60
ccaggatggt tcttagactc cccagacagg ccctggaacc ccccaacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggca 240
gcattccctg aggaccgtag ccagcctggc caggactgcc gtttccgtgt cacacaactg 300
cccaacgggc gtgacttcca catgagcgtg gtcagggccc ggcgcaatga cagcggcaca 360
tacctttgtg gggccatctc cctggccccc aaggcgcaga tcaaagagag cctgcgggca 420
gagctcaggg tgacagagag aagggcagaa gtgcccacag cccaccctag cccctcacct 480
agaccagccg gccagttcca aacactggtg gttggtgtcg tgggcggcct gctgggcagc 540
ctggtgctgc tagtctgggt cctggccgtc atctgctccc gggccgcacg tgggacaata 600
gga 603

<210> SEQ ID NO 2
<211> LENGTH: 708
<212> TYPE: DNA
<213> ORGANISM: Artificial Sequence
<220> FEATURE:
<223> OTHER INFORMATION: Synthetic Construct

<400> SEQUENCE: 2
atgcagatcc cacaggcgcc ctggccagtc gtctgggcgg tgctacaact gggctggcgg 60
ccaggatggt tcttagactc cccagacagg ccctggaacc ccccaacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggca 240
gcattccctg aggaccgtag ccagcctggc caggactgcc gtttccgtgt cacacaactg 300
cccaacgggc gtgacttcca catgagcgtg gtcagggccc ggcgcaatga cagcggcaca 360
tacctttgtg gggccatctc cctggccccc aaggcgcaga tcaaagagag cctgcgggca 420
gagctcaggg tgacagagag aagggcagaa gtgcccacag cccaccctgc ccctgcgaga 480
gagccaggac actctccgca gatcatctcc ttctttcttg cgctgacgtc gactgcgttg 540
ctcttcctgc tgttcttcct cacgctccgt ttctctgttg ttaaacgggg cagaaagaaa 600
ctcctgtata tattcaaaca accatttatg agaccagtac aaactactca agaggaagat 660
ggctgtagct gccgatttcc agaagaagaa gaaggaggat gtgaactg 708

<210> SEQ ID NO 3
<211> LENGTH: 900
<212> TYPE: DNA
<213> ORGANISM: Artificial Sequence
<220> FEATURE:
<223> OTHER INFORMATION: Synthetic Construct

<400> SEQUENCE: 3
atgcagatcc cacaggcgcc ctggccagtc gtctgggcgg tgctacaact gggctggcgg 60
ccaggatggt tcttagactc cccagacaga ccctggaacc ctcctacctt ctccccagcc 120
ctgcttgtgg tgaccgaagg ggacaacgcc accttcacct gcagcttctc caacacatcg 180
gagagcttcg tgctaaactg gtaccgcatg agccctagca accagacgga caagctggca 240
gcattccctg aggaccgtag ccagcctggc caggactgcc gtttccgtgt cacacaactg 300
cctaacgggc gtgacttcca catgagcgtg gtcagagccc ggcgcaatga cagcggcaca 360
tacctttgtg ggccatctc cctggcccct aaggcgcaga tcaaagagag cctgcgggca 420
gagcttaggg tgacagagag aagagcagaa gtgcctacag cccaccctag cccttcacct 480
agaccagccg gccagttcca aacactggtg gttggtgtcg tgggcggcct gctgggcagc 540
ctggtgctgc tagtctgggt cctggccgtc atctgctctc gggccgcacg aggaacacag 600
gtggcggctg actggaccgc gctggcggag gagatggatt ttgagtactt ggagatccgg 660
caactggaga cacaagcgga ccccactggc agactgctgg acgcctggca gggacgccct 720
ggcgcctctg taggccgact gcttgagctg cttaccaagc tgggccgcga cgacgtgctg 780
ctggagctgg gacccagcat tgaggaggat tgccaaaagt atatcttgaa gcagcagcag 840
gaggaggctg agaagccttt acaggtggcc gctgtagaca gtagtgtccc acggacagca 900

<210> SEQ ID NO 4
<211> LENGTH: 678
<212> TYPE: DNA
<213> ORGANISM: Artificial Sequence
<220> FEATURE:
<223> OTHER INFORMATION: Synthetic Construct

<400> SEQUENCE: 4
atgcagatcc cacaggcgcc ctggccagtc gtctgggcgg tgctacaact gggctggcgg 60
ccaggatggt tcttagactc cccagacagg ccctggaacc ccccaacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggca 240
gcattccctg aggaccgtag ccagcctggc caggactgcc gtttccgtgt cacacaactg 300
cccaacgggc gtgacttcca catgagcgtg gtcagggccc ggcgcaatga cagcggcaca 360
tacctttgtg ggccatctc cctggccccc aaggcgcaga tcaaagagag cctgcgggca 420
gagctcaggg tgacagagag aagggcagaa gtgcccacag cccaccatat ttatgaatca 480
caactttgtt gccagctgaa gttctggtta cccataggat gtgcagcctt tgttgtagtc 540
tgcattttgg gatgcatact tatttgttgg cttacaaaaa agaagtattc atccagtgtg 600
cacgacccta acggtgaata catgttcatg agagcagtga acacagccaa aaaatctaga 660
ctcacagatg tgaccta 678

<210> SEQ ID NO 5
<211> LENGTH: 567
<212> TYPE: DNA

<213> ORGANISM: Artificial Sequence
<220> FEATURE:
<223> OTHER INFORMATION: Synthetic Construct

<400> SEQUENCE: 5

```
atggcttgcc ttggatttca gcggcacaag gctcagctga acctggctac caggacctgg     60

ccctgcactc tcctgttttt tcttctcttc atccctgtct tctgcaaagc aatgcacgtg    120

gcccagcctg ctgtggtact ggccagcagc cgaggcatcg ccagctttgt gtgtgagtat    180

gcatctccag gcaaagccac tgaggtccgg gtgacagtgc ttcggcaggc tgacagccag    240

gtgactgaag tctgtgcggc aacctacatg atggggaatg agttgacctt cctagatgat    300

tccatctgca cgggcacctc cagtggaaat caagtgaacc tcactatcca aggactgagg    360

gccatggaca cgggactcta catctgcaag gtggagctca tgtacccacc gccatactac    420

ctgggcatag gcaacggaac ccagatttat gtaattgatc cagaaccgtg cccagattct    480

gacttcctcc tctggatcct tgcagcagtt agttcggggt tgttttttta tagctttctc    540

ctcacagctg tttctttgag caaaatg                                        567
```

<210> SEQ ID NO 6
<211> LENGTH: 690
<212> TYPE: DNA
<213> ORGANISM: Artificial Sequence
<220> FEATURE:
<223> OTHER INFORMATION: Synthetic Construct

<400> SEQUENCE: 6

```
atggcttgcc ttggatttca gcggcacaag gctcagctga acctggctac caggacctgg     60

ccctgcactc tcctgttttt tcttctcttc atccctgtct tctgcaaagc aatgcacgtg    120

gcccagcctg ctgtggtact ggccagcagc cgaggcatcg ccagctttgt gtgtgagtat    180

gcatctccag gcaaagccac tgaggtccgg gtgacagtgc ttcggcaggc tgacagccag    240

gtgactgaag tctgtgcggc aacctacatg atggggaatg agttgacctt cctagatgat    300

tccatctgca cgggcacctc cagtggaaat caagtgaacc tcactatcca aggactgagg    360

gccatggaca cgggactcta catctgcaag gtggagctca tgtacccacc gccatactac    420

ctgggcatag gcaacggaac ccagatttat gtaattgatc cagaaccgtg cccagattct    480

gacttcctcc tctggatcct tgcagcagtt agttcggggt tgttttttta tagctttctc    540

ctcacagctg tttctttgag caaaatgagg agtaagagga gcaggctcct gcacagtgac    600

tacatgaaca tgactccccg ccgccccggg cccacccgca agcattacca gccctatgcc    660

ccaccacgcg acttcgcagc ctatcgctcc                                     690
```

<210> SEQ ID NO 7
<211> LENGTH: 813
<212> TYPE: DNA
<213> ORGANISM: Artificial Sequence
<220> FEATURE:
<223> OTHER INFORMATION: Synthetic Construct

<400> SEQUENCE: 7

```
atgctctgcc cttggagaac tgctaaccta gggctactgt tgattttgac tatcttctta     60

gtggccgaag cggagggtgc tgctcaacca aacaactcat taatgctgca aactagcaag    120

gagaatcatg ctttagcttc aagcagttta tgtatggatg aaaaacagat tacacagaac    180

tactcgaaag tactcgcaga agttaacact tcatggcctg taaagatggc tacaaatgct    240

gtgctttgtt gccctcctat cgcattaaga aatttgatca taataacatg ggaaataatc    300
```

```
ctgagaggcc agccttcctg cacaaaagcc tacaagaaag aaacaaatga gaccaaggaa    360

accaactgta ctgatgagag aataacctgg gtctccagac ctgatcagaa ttcggacctt    420

cagattcgta ccgtggccat cactcatgac gggtattaca gatgcataat ggtaacacct    480

gatgggaatt tccatcgtgg atatcacctc caagtgttag ttacacctga agtgaccctg    540

tttcaaaaca ggaatagaac tgcagtatgc aaggcagttg cagggaagcc agctgcgcat    600

atctcctgga tcccagaggg cgattgtgcc actaagcaag aatactggag caatggcaca    660

gtgactgtta agagtacatg ccactgggag gtccacaatg tgtctaccgt gacctgccac    720

gtctcccatt tgactggcaa caagagtctg tacatagagc tacttcctgt tccaggtgcc    780

aaaaaatcag caaaattata tattccatat atc                                 813
```

<210> SEQ ID NO 8
<211> LENGTH: 555
<212> TYPE: DNA
<213> ORGANISM: Artificial Sequence
<220> FEATURE:
<223> OTHER INFORMATION: Synthetic Construct

<400> SEQUENCE: 8

```
atgaagacat tgcctgccat gcttggaact gggaaattat tttgggtctt cttcttaatc     60

ccatatctgg acatctggaa catccatggg aaagaatcat gtgatgtaca gctttatata    120

aagagacaat ctgaacactc catcttagca ggagatccct ttgaactaga atgccctgtg    180

aaatactgtg ctaacaggcc tcatgtgact tggtgcaagc tcaatggaac aacatgtgta    240

aaacttgaag atagacaaac aagttggaag gaagagaaga acatttcatt tttcattcta    300

cattttgaac cagtgcttcc taatgacaat gggtcatacc gctgttctgc aaattttcag    360

tctaatctca ttgaaagcca ctcaacaact ctttatgtga cagatgtaaa aagtgcctca    420

gaacgaccct ccaaggacga aatggcaagc agaccctggc tcctgtatcg tttacttcct    480

ttggggggat tgcctctact catcactacc tgtttctgcc tgttctgctg cctgagaagg    540

caccaaggaa agcaa                                                     555
```

<210> SEQ ID NO 9
<211> LENGTH: 684
<212> TYPE: DNA
<213> ORGANISM: Artificial Sequence
<220> FEATURE:
<223> OTHER INFORMATION: Synthetic Construct

<400> SEQUENCE: 9

```
atgaagacat tgcctgccat gcttggaact gggaaattat tttgggtctt cttcttaatc     60

ccatatctgg acatctggaa catccatggg aaagaatcat gtgatgtaca gctttatata    120

aagagacaat ctgaacactc catcttagca ggagatccct ttgaactaga atgccctgtg    180

aaatactgtg ctaacaggcc tcatgtgact tggtgcaagc tcaatggaac aacatgtgta    240

aaacttgaag atagacaaac aagttggaag gaagagaaga acatttcatt tttcattcta    300

cattttgaac cagtgcttcc taatgacaat gggtcatacc gctgttctgc aaattttcag    360

tctaatctca ttgaaagcca ctcaacaact ctttatgtga cagatgtaaa aagtgcctca    420

gaacgaccct ccaaggacga aatgtgtcca agtcccctat ttcccggacc ttctaagccc    480

ttttgggtgc tggtggtggt tggtggagtc ctggcttgct atagcttgct agtaacagtg    540

gcctttatta ttttctgggt gaggagtaag aggagcaggc tcctgcacag tgactacatg    600
```

```
aacatgactc cccgccgccc cggcccacc cgcaagcatt accagcccta tgccccacca    660

cgcgacttcg cagcctatcg ctcc                                          684


<210> SEQ ID NO 10
<211> LENGTH: 690
<212> TYPE: DNA
<213> ORGANISM: Artificial Sequence
<220> FEATURE:
<223> OTHER INFORMATION: Synthetic Construct

<400> SEQUENCE: 10

atgttttcac atcttccctt tgactgtgtc ctgctgctgc tgctgctact acttacaagg     60

tcctcagaag tggaatacag agcggaggtc ggtcagaatg cctatctgcc ctgcttctac    120

accccagccg ccccagggaa cctcgtgccc gtctgctggg gcaaaggagc ctgtcctgtg    180

tttgaatgtg gcaacgtggt gctcaggact gatgaaaggg atgtgaatta ttggacatcc    240

agatactggc taaatgggga tttccgcaaa ggagatgtgt ccctgaccat agagaatgtg    300

actctagcag acagtgggat ctactgctgc cggatccaaa tcccaggcat aatgaatgat    360

gaaaaattta acctgaagtt ggtcatcaaa ccagccaagg tcacccctgc accgactcgg    420

cagagagact tcactgcagc ctttccaagg atgcttacca ccaggggaca tggcccagca    480

gagacacaga cactggggag cctccctgat ataaatctaa cacaaatatc cacattggcc    540

aatgagttac gggactctag attggccaat gacttacggg actctggagc aaccatcaga    600

ataggcatct acatcggagc agggatctgt gctgggctgg ctctggctct tatcttcggc    660

gctttaattt tcaaatggta ttctcatagc                                    690


<210> SEQ ID NO 11
<211> LENGTH: 819
<212> TYPE: DNA
<213> ORGANISM: Artificial Sequence
<220> FEATURE:
<223> OTHER INFORMATION: Synthetic Construct

<400> SEQUENCE: 11

atgttttcac atcttccctt tgactgtgtc ctgctgctgc tgctgctact acttacaagg     60

tcctcagaag tggaatacag agcggaggtc ggtcagaatg cctatctgcc ctgcttctac    120

accccagccg ccccagggaa cctcgtgccc gtctgctggg gcaaaggagc ctgtcctgtg    180

tttgaatgtg gcaacgtggt gctcaggact gatgaaaggg atgtgaatta ttggacatcc    240

agatactggc taaatgggga tttccgcaaa ggagatgtgt ccctgaccat agagaatgtg    300

actctagcag acagtgggat ctactgctgc cggatccaaa tcccaggcat aatgaatgat    360

gaaaaattta acctgaagtt ggtcatcaaa ccagccaagg tcacccctgc accgactcgg    420

cagagagact tcactgcagc ctttccaagg atgcttacca ccaggggaca tggcccagca    480

gagacacaga cactggggag cctccctgat ataaatctaa cacaaatatc cacattggcc    540

aatgagttac gggactctag attggccaat gacttacggt gtccaagtcc cctatttccc    600

ggaccttcta agcccttttg ggtgctggtg gtggttggtg gagtcctggc ttgctatagc    660

ttgctagtaa cagtggcctt tattattttc tgggtgagga gtaagaggag caggctcctg    720

cacagtgact acatgaacat gactcctcgc cgccctgggc ccacccgcaa gcattaccag    780

ccctatgccc caccacgcga cttcgcagcc tatcgctcc                           819


<210> SEQ ID NO 12
<211> LENGTH: 507
```

<212> TYPE: DNA
<213> ORGANISM: Artificial Sequence
<220> FEATURE:
<223> OTHER INFORMATION: Synthetic Construct

<400> SEQUENCE: 12
atgcgctggt gtctcctcct gatctgggcc caggggctga ggcaggctcc cctcgcctca 60
ggaatgatga caggcacaat agaaacaacg gggaacattt ctgcagagaa aggtggctct 120
atcatcttac aatgtcacct ctcctccacc acggcacaag tgacccaggt caactgggag 180
cagcaggacc agcttctggc catttgtaat gctgacttgg ggtggcacat ctccccatcc 240
ttcaaggatc gagtggcccc aggtcccggc ctgggcctca ccctccagtc gctgaccgtg 300
aacgatacag gggagtactt ctgcatctat cacacctacc ctgatgggac gtacactggg 360
agaatcttcc tggaggtcct agaaagctca gtggctgagc acggtgccag gttccagatt 420
ccattgcttg gagccatggc cgcgacgctg gtggtcatct gcacagcagt catcgtggtg 480
gtcgcgttga ctagaaagaa gaaagcc 507

<210> SEQ ID NO 13
<211> LENGTH: 636
<212> TYPE: DNA
<213> ORGANISM: Artificial Sequence
<220> FEATURE:
<223> OTHER INFORMATION: Synthetic Construct

<400> SEQUENCE: 13
atgcgctggt gtctcctcct gatctgggcc caggggctga ggcaggctcc cctcgcctca 60
ggaatgatga caggcacaat agaaacaacg gggaacattt ctgcagagaa aggtggctct 120
atcatcttac aatgtcacct ctcctccacc acggcacaag tgacccaggt caactgggag 180
cagcaggacc agcttctggc catttgtaat gctgacttgg ggtggcacat ctccccatcc 240
ttcaaggatc gagtggcccc aggtcccggc ctgggcctca ccctccagtc gctgaccgtg 300
aacgatacag gggagtactt ctgcatctat cacacctacc ctgatgggac gtacactggg 360
agaatcttcc tggaggtcct agaaagctca gtggcttgtc caagtcccct atttcccgga 420
ccttctaagc ccttttgggt gctggtggtg gttggtggag tcctggcttg ctatagcttg 480
ctagtaacag tggcctttat tattttctgg gtgaggagta agaggagcag gctcctgcac 540
agtgactaca tgaacatgac tccccgccgc cccgggccca cccgcaagca ttaccagccc 600
tatgccccac cacgcgactt cgcagcctat cgctcc 636

<210> SEQ ID NO 14
<211> LENGTH: 603
<212> TYPE: DNA
<213> ORGANISM: Artificial Sequence
<220> FEATURE:
<223> OTHER INFORMATION: Synthetic Construct

<400> SEQUENCE: 14
atgggtcggg ggctgctcag ggcctgtgg ccgctgcaca tcgtcctgtg gacgcgtatc 60
gccagcacga tcccaccgca cgttcagaag tcggttaata acgacatgat agtcactgac 120
aacaacggtg cagtcaagtt tccacaactg tgtaaatttt gtgatgtgag attttccacc 180
tgtgacaacc agaaatcctg catgagcaac tgcagcatca cctccatctg tgagaagcca 240
caggaagtct gtgtggctgt atggagaaag aatgacgaga acataacact agagacagtt 300
tgccatgacc ccaagctccc ctaccatgac tttattctgg aagatgctgc ttctccaaag 360

```
tgcattatga aggaaaaaaa aaagcctggt gagactttct tcatgtgttc ctgtagctct    420

gatgagtgca atgacaacat catcttctca gaagaatata acaccagcaa tcctgacttg    480

ttgctagtca tatttcaagt gacaggcatc agcctcctgc caccactggg agttgccata    540

tctgtcatca tcatcttcta ctgctaccgc gttaaccggc agcagaagct gagttcatcc    600

gga                                                                  603
```

<210> SEQ ID NO 15
<211> LENGTH: 708
<212> TYPE: DNA
<213> ORGANISM: Artificial Sequence
<220> FEATURE:
<223> OTHER INFORMATION: Synthetic Construct

<400> SEQUENCE: 15

```
atgggtcggg ggctgctcag ggcctgtgg ccgctgcaca tcgtcctgtg gacgcgtatc      60

gccagcacga tcccaccgca cgttcagaag tcggttaata acgacatgat agtcactgac    120

aacaacggtg cagtcaagtt tccacaactg tgtaaatttt gtgatgtgag attttccacc    180

tgtgacaacc agaaatcctg catgagcaac tgcagcatca cctccatctg tgagaagcca    240

caggaagtct gtgtggctgt atggagaaag aatgacgaga acataacact agagacagtt    300

tgccatgacc ccaagctccc ctaccatgac tttattctgg aagatgctgc ttctccaaag    360

tgcattatga aggaaaaaaa aaagcctggt gagactttct tcatgtgttc ctgtagctct    420

gatgagtgca atgacaacat catcttctca gaagaatata acaccagcaa tcctgacttg    480

ttgctagtca tatttcaagt gacaggcatc agcctcctgc caccactggg agttgccata    540

tctgtcatca tcatcttcta ctgctaccgc gttaaccggc agaaacgggg cagaaagaaa    600

ctcctgtata tattcaaaca accatttatg agaccagtac aaactactca agaggaagat    660

ggctgtagct gccgatttcc agaagaagaa gaaggaggat gtgaactg                 708
```

<210> SEQ ID NO 16
<211> LENGTH: 888
<212> TYPE: DNA
<213> ORGANISM: Artificial Sequence
<220> FEATURE:
<223> OTHER INFORMATION: Synthetic Construct

<400> SEQUENCE: 16

```
atgggtcggg ggctgctcag ggcctgtgg ccgctgcaca tcgtcctgtg gacgcgtatc      60

gccagcacga tcccaccgca cgttcagaag tcggttaata acgacatgat agtcactgac    120

aacaacggtg cagtcaagtt tccacaactg tgtaaatttt gtgatgtgag attttccacc    180

tgtgacaacc agaaatcctg catgagcaac tgcagcatca cctccatctg tgagaagcca    240

caggaagtct gtgtggctgt atggagaaag aatgacgaga acataacact agagacagtt    300

tgccatgacc ccaagctccc ctaccatgac tttattctgg aagatgctgc ttctccaaag    360

tgcattatga aggaaaaaaa aaagcctggt gagactttct tcatgtgttc ctgtagctct    420

gatgagtgca atgacaacat catcttctca gaagaatata acaccagcaa tcctgacttg    480

ttgctagtca tatttcaagt gacaggcatc agcctcctgc caccactggg agttgccata    540

tctgtcatca tcatcttcta ctgctaccgc gttaaccggc agacacaggt ggcggccgac    600

tggaccgcgc tggcggagga gatggacttt gagtacttgg agatccggca actggagaca    660

caagcggacc ccactggcag gctgctggac gcctggcagg gacgccctgg cgcctctgta    720

ggccgactgc tcgagctgct taccaagctg ggccgcgacg acgtgctgct ggagctggga    780
```

cccagcattg aggaggattg ccaaaagtat atcttgaagc agcagcagga ggaggctgag 840
aagcctttac aggtggccgc tgtagacagc agtgtcccac ggacagca 888

<210> SEQ ID NO 17
<211> LENGTH: 789
<212> TYPE: DNA
<213> ORGANISM: Artificial Sequence
<220> FEATURE:
<223> OTHER INFORMATION: Synthetic Construct

<400> SEQUENCE: 17
atgctgccgt gcctcgtagt gctgctggcg gcgctcctca gcctccgtct tggctcagac 60
gctcatggga cagagctgcc cagccctccg tctgtgtggt ttgaagcaga atttttccac 120
cacatcctcc actggacacc catcccaaat cagtctgaaa gtacctgcta tgaagtggcg 180
ctcctgaggt atggaataga gtcctggaac tccatctcca actgtagcca gaccctgtcc 240
tatgacctta ccgcagtgac cttggacctg taccacagca atggctaccg ggccagagtg 300
cgggctgtgg acggcagccg gcactccaac tggaccgtca ccaacacccg cttctctgtg 360
gatgaagtga ctctgacagt tggcagtgtg aacctagaga tccacaatgg cttcatcctc 420
gggaagattc agctacccag gcccaagatg gcccccgcaa atgacacata tgaaagcatc 480
ttcagtcact tccgagagta tgagattgcc attcgcaagg tgccgggaaa cttcacgttc 540
acacacaaga aagtaaaaca tgaaaacttc agcctcctaa cctctggaga agtgggagag 600
ttctgtgtcc aggtgaaacc atctgtcgct tcccgaagta acaaggggat gtggtctaaa 660
gaggagtgca tctccctcac caggcagtat ttcaccgtga ccaacgtcat catcttcttt 720
gcctttgtcc tgctgctctc cggagccctc gcctactgcc tggccctcca gctgtatgtg 780
cggcgccga 789

<210> SEQ ID NO 18
<211> LENGTH: 1368
<212> TYPE: DNA
<213> ORGANISM: Artificial Sequence
<220> FEATURE:
<223> OTHER INFORMATION: Synthetic Construct

<400> SEQUENCE: 18
atgctgccgt gcctcgtagt gctgctggcg gcgctcctca gcctccgtct tggctcagac 60
gctcatggga cagagctgcc cagccctccg tctgtgtggt ttgaagcaga atttttccac 120
cacatcctcc actggacacc catcccaaat cagtctgaaa gtacctgcta tgaagtggcg 180
ctcctgaggt atggaataga gtcctggaac tccatctcca actgtagcca gaccctgtcc 240
tatgacctta ccgcagtgac cttggacctg taccacagca atggctaccg ggccagagtg 300
cgggctgtgg acggcagccg gcactccaac tggaccgtca ccaacacccg cttctctgtg 360
gatgaagtga ctctgacagt tggcagtgtg aacctagaga tccacaatgg cttcatcctc 420
gggaagattc agctacccag gcccaagatg gcccccgcaa atgacacata tgaaagcatc 480
ttcagtcact tccgagagta tgagattgcc attcgcaagg tgccgggaaa cttcacgttc 540
acacacaaga aagtaaaaca tgaaaacttc agcctcctaa cctctggaga agtgggagag 600
ttctgtgtcc aggtgaaacc atctgtcgct tcccgaagta acaaggggat gtggtctaaa 660
gaggagtgca tctccctcac caggcagtat ttcaccgtga ccaacgtccc tatcttacta 720
accatcagca ttttgagttt tttctctgtc gctctgttgg tcatcttggc ctgtgtgtta 780
tggaaaaaaa ggattaagcc tatcgtatgg cccagtctcc ccgatcataa gaagactctg 840
gaacatcttt gtaagaaacc aagaaaaaat ttaaatgtga gtttcaatcc tgaaagtttc 900
ctggactgcc agattcatag ggtggatgac attcaagcta gagatgaagt ggaaggtttt 960
ctgcaagata cgtttcctca gcaactagaa gaatctgaga agcagaggct tggaggggat 1020
gtgcagagcc ccaactgccc atctgaggat gtagtcatca ctccagaaag ctttggaaga 1080
gattcatccc tcacatgcct ggctgggaat gtcagtgcat gtgacgcccc tattctctcc 1140
tcttccaggt ccctagactg cagggagagt ggcaagaatg ggcctcatgt gtaccaggac 1200
ctcctgctta gccttgggac tacaaacagc acgctgcccc ctccattttc tctccaatct 1260
ggaatcctga cattgaaccc agttgctcag ggtcagccca ttcttacttc cctgggatca 1320
aatcaagaag aagcatatgt caccatgtcc agcttctacc aaaaccag 1368

<210> SEQ ID NO 19
<211> LENGTH: 1359
<212> TYPE: DNA
<213> ORGANISM: Artificial Sequence
<220> FEATURE:
<223> OTHER INFORMATION: Synthetic Construct

<400> SEQUENCE: 19
atggggtggc tttgctctgg gctcctgttc cctgtgagct gcctggtcct gctgcaggtg 60
gcaagctctg ggaacatgaa ggtcttgcag gagcccacct gcgtctccga ctacatgagc 120
atctctactt gcgagtggaa gatgaatggt cccaccaatt gcagcaccga gctccgcctg 180
ttgtaccagc tggtttttct gctctccgaa gcccacacgt gtatccctga gaacaacgga 240
ggcgcggggt gcgtgtgcca cctgctcatg gatgacgtgg tcagtgcgga taactataca 300
ctggacctgt gggctgggca gcagctgctg tggaagggct ccttcaagcc cagcgagcat 360
gtgaaaccca gggccccagg aaacctgaca gttcacacca atgtctccga cactctgctg 420
ctgacctgga gcaacccgta tccccctgac aattacctgt ataatcatct cacctatgca 480
gtcaacattt ggagtgaaaa cgacccggca gatttcagaa tctataacgt gacctaccta 540
gaaccctccc tccgcatcgc agccagcacc ctgaagtctg ggatttccta cagggcacgg 600
gtgagggcct gggctcagtg ctataacacc acctggagtg agtggagccc cagcaccaag 660
tggcacaact cctacaggga gcccttcgag cagcacctcc ctatcttact aaccatcagc 720
attttgagtt ttttctctgt cgctctgttg gtcatcttgg cctgtgtgtt atggaaaaaa 780
aggattaagc ctatcgtatg gcccagtctc cccgatcata agaagactct ggaacatctt 840
tgtaagaaac caagaaaaaa tttaaatgtg agtttcaatc ctgaaagttt cctggactgc 900
cagattcata gggtggatga cattcaagct agagatgaag tggaaggttt tctgcaagat 960
acgtttcctc agcaactaga agaatctgag aagcagaggc ttggagggga tgtgcagagc 1020
cccaactgcc catctgagga tgtagtcatc actccagaaa gctttggaag agattcatcc 1080
ctcacatgcc tggctgggaa tgtcagtgca tgtgacgccc ctattctctc ctcttccagg 1140
tccctagact gcagggagag tggcaagaat gggcctcatg tgtaccagga cctcctgctt 1200
agccttggga ctacaaacag cacgctgccc cctccatttt ctctccaatc tggaatcctg 1260
acattgaacc cagttgctca gggtcagccc attcttactt ccctgggatc aaatcaagaa 1320
gaagcatatg tcaccatgtc cagcttctac caaaaccag 1359

<210> SEQ ID NO 20
<211> LENGTH: 816

<212> TYPE: DNA
<213> ORGANISM: Artificial Sequence
<220> FEATURE:
<223> OTHER INFORMATION: Synthetic Construct

<400> SEQUENCE: 20
atggattcat acctgctgat gtggggactg ctcacgttca tcatggtgcc tggctgccag 60
gcagagctct gtgacgatga cccgccagag atcccacacg ccacattcaa agccatggcc 120
tacaaggaag gaaccatgtt gaactgtgaa tgcaagagag gtttccgcag aataaaaagc 180
gggtcactct atatgctctg tacaggaaac tctagccact cgtcctggga caaccaatgt 240
caatgcacaa gctctgccac tcggaacaca acgaaacaag tgacacctca acctgaagaa 300
cagaaagaaa ggaaaaccac agaaatgcaa agtccaatgc agccagtgga ccaagcgagc 360
cttccaggtc actgcaggga acctccacca tgggaaaatg aagccacaga gagaatttat 420
catttcgtgg tggggcagat ggtttattat cagtgcgtcc agggatacag ggctctacac 480
agaggtcctg ctgagagcgt ctgcaaaatg acccacggga agacaaggtg gacccagccc 540
cagctcatat gcacaggtga aatggagacc agtcagtttc caggtgaaga gaagcctcag 600
gcaagccccg aaggccgtcc tgagagtgag acttcctgcc tcgtcacaac aacagatttt 660
caaatacaga cagaaatggc tgcaaccatg gagacgtcca tatttacaac agagtaccag 720
gtagcagtgg ccggctgtgt tttcctgctg atcagcgtcc tcctcctgag tgggctcacc 780
tggcagcgga gacagaggaa gagtagaaga acaatc 816

<210> SEQ ID NO 21
<211> LENGTH: 1377
<212> TYPE: DNA
<213> ORGANISM: Artificial Sequence
<220> FEATURE:
<223> OTHER INFORMATION: Synthetic Construct

<400> SEQUENCE: 21
atgacaattc taggtacaac ttttggcatg gttttttctt tacttcaagt cgtttctgga 60
gaaagtggct atgctcaaaa tggagacttg gaagatgcag aactggatga ctactcattc 120
tcatgctata gccagttgga agtgaatgga tcgcagcact cactgacctg tgcttttgag 180
gacccagatg tcaacatcac caatctggaa tttgaaatat gtggggccct cgtggaggta 240
aagtgcctga atttcaggaa actacaagag atatatttca tcgagacaaa gaaattctta 300
ctgattggaa agagcaatat atgtgtgaag gttggagaaa agagtctaac ctgcaaaaaa 360
atagacctaa ccactatagt taaacctgag gctccttttg acctgagtgt cgtctatcgg 420
gaaggagcca atgactttgt ggtgacattt aatacatcac acttgcaaaa gaagtatgta 480
aaagttttaa tgcacgatgt agcttaccgc caggaaaagg atgaaaacaa atggacgcat 540
gtgaatttat ccagcacaaa gctgacactc ctgcagagaa agctccaacc ggcagcaatg 600
tatgagatta aagttcgatc catccctgat cactatttta aaggcttctg gagtgaatgg 660
agtccaagtt attacttcag aactccagag atcaataata gctcagggga gatggatcct 720
atcttactaa ccatcagcat tttgagtttt ttctctgtcg ctctgttggt catcttggcc 780
tgtgtgttat ggaaaaaaag gattaagcct atcgtatggc ccagtctccc cgatcataag 840
aagactctgg aacatctttg taagaaacca agaaaaaatt taaatgtgag tttcaatcct 900
gaaagtttcc tggactgcca gattcatagg gtggatgaca ttcaagctag agatgaagtg 960
gaaggttttc tgcaagatac gtttcctcag caactagaag aatctgagaa gcagaggctt 1020
ggaggggatg tgcagagccc caactgccca tctgaggatg tagtcatcac tccagaaagc 1080
tttggaagag attcatccct cacatgcctg gctgggaatg tcagtgcatg tgacgcccct 1140
attctctcct cttccaggtc cctagactgc agggagagtg gcaagaatgg gcctcatgtg 1200
taccaggacc tcctgcttag ccttgggact acaaacagca cgctgccccc tccattttct 1260
ctccaatctg gaatcctgac attgaaccca gttgctcagg gtcagcccat tcttacttcc 1320
ctgggatcaa atcaagaaga agcatatgtc accatgtcca gcttctacca aaaccag 1377

<210> SEQ ID NO 22
<211> LENGTH: 765
<212> TYPE: DNA
<213> ORGANISM: Artificial Sequence
<220> FEATURE:
<223> OTHER INFORMATION: Synthetic Construct

<400> SEQUENCE: 22
atgggaaaca gctgttacaa catagtagcc actctgttgc tggtcctcaa ctttgagagg 60
acaagatcat tgcaggatcc ttgtagtaac tgcccagctg gtacattctg tgataataac 120
aggaatcaga tttgcagtcc ctgtcctcca aatagtttct ccagcgcagg tggacaaagg 180
acctgtgaca tatgcaggca gtgtaaaggt gttttcagga ccaggaagga gtgttcctcc 240
accagcaatg cagagtgtga ctgcactcca gggtttcact gcctgggggc aggatgcagc 300
atgtgtgaac aggattgtaa acaaggtcaa gaactgacaa aaaaaggttg taaagactgt 360
tgctttggga catttaacga tcagaaacgt ggcatctgtc gaccctggac aaactgttct 420
ttggatggaa agtctgtgct tgtgaatggg acgaaggaga gggacgtggt ctgtggacca 480
tctccagccg acctctctcc gggagcatcc tctgtgaccc cgcctgcccc tgcgagagag 540
ccaggacact ctccgcagat catctccttc tttcttgcgc tgacgtcgac tgcgttgctc 600
ttcctgctgt tcttcctcac gctccgtttc tctgttgtta aacggggcag aaagaaactc 660
ctgtatatat tcaaacaacc atttatgaga ccagtacaaa ctactcaaga ggaagatggc 720
tgtagctgcc gatttccaga agaagaagaa ggaggatgtg aactg 765

<210> SEQ ID NO 23
<211> LENGTH: 591
<212> TYPE: DNA
<213> ORGANISM: Artificial Sequence
<220> FEATURE:
<223> OTHER INFORMATION: Synthetic Construct

<400> SEQUENCE: 23
atgctgggca tctggaccct cctacctctg gttcttacgt ctgttgctag attatcgtcc 60
aaaagtgtta atgcccaagt gactgacatc aactccaagg gattggaatt gaggaagact 120
gttactacag ttgagactca gaacttggaa ggcctgcatc atgatggcca attctgccat 180
aagccctgtc ctccaggtga aaggaaagct agggactgca cagtcaatgg ggatgaacca 240
gactgcgtgc cctgccaaga agggaaggag tacacagaca aagcccattt ttcttccaaa 300
tgcagaagat gtagattgtg tgatgaagga catggcttag aagtggaaat aaactgcacc 360
cggacccaga ataccaagtg cagatgtaaa ccaaactttt tttgtaactc tactgtatgt 420
gaacactgtg acccttgcac caaatgtgaa catggaatca tcaaggaatg cacactcacc 480
agcaacacca agtgcaaaga ggaaggatcc agatctaact tggggtggct ttgtcttctt 540
cttttgccaa ttccactaat tgtttgggtg aagagaaagg aagtacagaa a 591

<210> SEQ ID NO 24
<211> LENGTH: 714
<212> TYPE: DNA
<213> ORGANISM: Artificial Sequence
<220> FEATURE:
<223> OTHER INFORMATION: Synthetic Construct

<400> SEQUENCE: 24
atgctgggca tctggaccct cctacctctg gttcttacgt ctgttgctag attatcgtcc 60
aaaagtgtta atgcccaagt gactgacatc aactccaagg gattggaatt gaggaagact 120
gttactacag ttgagactca gaacttggaa ggcctgcatc atgatggcca attctgccat 180
aagccctgtc ctccaggtga aaggaaagct agggactgca cagtcaatgg ggatgaacca 240
gactgcgtgc cctgccaaga agggaaggag tacacagaca aagcccattt ttcttccaaa 300
tgcagaagat gtagattgtg tgatgaagga catggcttag aagtggaaat aaactgcacc 360
cggacccaga ataccaagtg cagatgtaaa ccaaactttt tttgtaactc tactgtatgt 420
gaacactgtg acccttgcac caaatgtgaa catggaatca tcaaggaatg cacactcacc 480
agcaacacca agtgcaaaga ggaaggatcc agatctaact tggggtggct ttgtcttctt 540
cttttgccaa ttccactaat tgtttgggtg aagagaaagg aagtacagaa aaggagtaag 600
aggagcaggc tcctgcacag tgactacatg aacatgactc ctcgccgccc tgggcctacc 660
cgcaagcatt accagcccta tgccccacca cgcgacttcg cagcctatcg ctcc 714

<210> SEQ ID NO 25
<211> LENGTH: 717
<212> TYPE: DNA
<213> ORGANISM: Artificial Sequence
<220> FEATURE:
<223> OTHER INFORMATION: Synthetic Construct

<400> SEQUENCE: 25
atgctgggca tctggaccct cctacctctg gttcttacgt ctgttgctag attatcgtcc 60
aaaagtgtta atgcccaagt gactgacatc aactccaagg gattggaatt gaggaagact 120
gttactacag ttgagactca gaacttggaa ggcctgcatc atgatggcca attctgccat 180
aagccctgtc ctccaggtga aaggaaagct agggactgca cagtcaatgg ggatgaacca 240
gactgcgtgc cctgccaaga agggaaggag tacacagaca aagcccattt ttcttccaaa 300
tgcagaagat gtagattgtg tgatgaagga catggcttag aagtggaaat aaactgcacc 360
cggacccaga ataccaagtg cagatgtaaa ccaaactttt tttgtaactc tactgtatgt 420
gaacactgtg acccttgcac caaatgtgaa catggaatca tcaaggaatg cacactcacc 480
agcaacacca agtgcaaaga ggaaggatcc agatctaact tggggtggct ttgtcttctt 540
cttttgccaa ttccactaat tgtttgggtg aagagaaagg aagtacagaa aaaacggggc 600
agaaagaaac tcctgtatat attcaaacaa ccatttatga gaccagtaca aactactcaa 660
gaggaagatg gctgtagctg ccgatttcca gaagaagaag aaggaggatg tgaactg 717

<210> SEQ ID NO 26
<211> LENGTH: 897
<212> TYPE: DNA
<213> ORGANISM: Artificial Sequence
<220> FEATURE:
<223> OTHER INFORMATION: Synthetic Construct

<400> SEQUENCE: 26
atgctgggca tctggaccct cctacctctg gttcttacgt ctgttgctag attatcgtcc 60

```
aaaagtgtta atgcccaagt gactgacatc aactccaagg gattggaatt gaggaagact    120

gttactacag ttgagactca gaacttggaa ggcctgcatc atgatggcca attctgccat    180

aagccctgtc ctccaggtga aaggaaagct agggactgca cagtcaatgg ggatgaacca    240

gactgcgtgc cctgccaaga agggaaggag tacacagaca aagcccattt ttcttccaaa    300

tgcagaagat gtagattgtg tgatgaagga catggcttag aagtggaaat aaactgcacc    360

cggacccaga ataccaagtg cagatgtaaa ccaaactttt tttgtaactc tactgtatgt    420

gaacactgtg acccttgcac caaatgtgaa catggaatca tcaaggaatg cacactcacc    480

agcaacacca agtgcaaaga ggaaggatcc agatctaact tggggtggct ttgtcttctt    540

cttttgccaa ttccactaat tgtttgggtg aagagaaagg aagtacagaa aacacaggtg    600

gcggccgact ggaccgcgct ggcggaggag atggactttg agtacttgga gatccggcaa    660

ctggagacac aagcggaccc cactggcagg ctgctggacg cctggcaggg acgccctggc    720

gcctctgtag gccgactgct cgagctgctt accaagctgg gccgcgacga cgtgctgctg    780

gagctgggac ccagcattga ggaggattgc caaaagtata tcttgaagca gcagcaggag    840

gaggctgaga agcctttaca ggtggccgct gtagacagca gtgtcccacg gacagca       897
```

```
<210> SEQ ID NO 27
<211> LENGTH: 705
<212> TYPE: DNA
<213> ORGANISM: Artificial Sequence
<220> FEATURE:
<223> OTHER INFORMATION: Synthetic Construct

<400> SEQUENCE: 27

atgctgggca tctggaccct cctacctctg gttcttacgt ctgttgctag attatcgtcc     60

aaaagtgtta atgcccaagt gactgacatc aactccaagg gattggaatt gaggaagact    120

gttactacag ttgagactca gaacttggaa ggcctgcatc atgatggcca attctgccat    180

aagccctgtc ctccaggtga aaggaaagct agggactgca cagtcaatgg ggatgaacca    240

gactgcgtgc cctgccaaga agggaaggag tacacagaca aagcccattt ttcttccaaa    300

tgcagaagat gtagattgtg tgatgaagga catggcttag aagtggaaat aaactgcacc    360

cggacccaga ataccaagtg cagatgtaaa ccaaactttt tttgtaactc tactgtatgt    420

gaacactgtg acccttgcac caaatgtgaa catggaatca tcaaggaatg cacactcacc    480

agcaacacca agtgcaaaga ggaaggatcc agatctaact tggggtggct ttgtcttctt    540

cttttgccaa ttccactaat tgtttgggtg aagagaaagg aagtacagaa atgttggctt    600

acaaaaaaga agtattcatc cagtgtgcac gaccctaacg gtgaatacat gttcatgaga    660

gcagtgaaca cagccaaaaa atctagactc acagatgtga cccta                   705
```

```
<210> SEQ ID NO 28
<211> LENGTH: 714
<212> TYPE: DNA
<213> ORGANISM: Artificial Sequence
<220> FEATURE:
<223> OTHER INFORMATION: Synthetic Construct

<400> SEQUENCE: 28

atggaacaac ggggacagaa tgccccggcc gcttcggggg cccggaaaag acacggccca     60

ggacctagag aggcgcgggg agccaggcct gggccccggg tccccaagac ccttgtgctc    120

gttgtcgccg cggtcctgct gttggtctca gctgagtctg ctctgatcac ccaacaagac    180

ctagctcccc agcagagagc ggccccacaa caaaagaggt ccagcccctc agagggattg    240
```

tgtccacctg gacaccatat ctcagaagac ggtagagatt gcatctcctg caaatatgga 300
caggactata gcactcactg gaatgacctc cttttctgct tgcgctgcac caggtgtgat 360
tcaggtgaag tggagctaag tccctgcacc acgaccagaa acacagtgtg tcagtgcgaa 420
gaaggcacct tccgggaaga agattctcct gagatgtgcc ggaagtgccg cacagggtgt 480
cccagaggga tggtcaaggt cggtgattgt acaccctgga gtgacatcga atgtgtccac 540
aaagaatcag gtacaaagca cagtggggaa gtcccagctg tggaggagac ggtgacctcc 600
agcccaggga ctcctgcctc tccctgttct ctctcaggca tcatcatagg agtcacagtt 660
gcagccgtag tcttgattgt ggctgtgttt gtttgcaagt ctttactgtg gaag 714

<210> SEQ ID NO 29
<211> LENGTH: 837
<212> TYPE: DNA
<213> ORGANISM: Artificial Sequence
<220> FEATURE:
<223> OTHER INFORMATION: Synthetic Construct

<400> SEQUENCE: 29
atggaacaac ggggacagaa tgccccggcc gcttcggggg cccggaaaag acacggccca 60
ggacctagag aggcgcgggg agccaggcct gggccccggg tccccaagac ccttgtgctc 120
gttgtcgccg cggtcctgct gttggtctca gctgagtctg ctctgatcac ccaacaagac 180
ctagctcccc agcagagagc ggccccacaa caaaagaggt ccagcccctc agagggattg 240
tgtccacctg gacaccatat ctcagaagac ggtagagatt gcatctcctg caaatatgga 300
caggactata gcactcactg gaatgacctc cttttctgct tgcgctgcac caggtgtgat 360
tcaggtgaag tggagctaag tccctgcacc acgaccagaa acacagtgtg tcagtgcgaa 420
gaaggcacct tccgggaaga agattctcct gagatgtgcc ggaagtgccg cacagggtgt 480
cccagaggga tggtcaaggt cggtgattgt acaccctgga gtgacatcga atgtgtccac 540
aaagaatcag gtacaaagca cagtggggaa gtcccagctg tggaggagac ggtgacctcc 600
agcccaggga ctcctgcctc tccctgttct ctctcaggca tcatcatagg agtcacagtt 660
gcagccgtag tcttgattgt ggctgtgttt gtttgcaagt ctttactgtg gaagaggagt 720
aagaggagca ggctcctgca cagtgactac atgaacatga ctcctcgccg ccctgggccc 780
acccgcaagc attaccagcc ctatgcccca ccacgcgact tcgcagccta tcgctcc 837

<210> SEQ ID NO 30
<211> LENGTH: 1086
<212> TYPE: DNA
<213> ORGANISM: Artificial Sequence
<220> FEATURE:
<223> OTHER INFORMATION: Synthetic Construct

<400> SEQUENCE: 30
atggggacca agcccacaga gcaggtctcc tggggacttt actccgggta cgatgaggag 60
gcctattcgg ttgggccgct gccagagctc tgttacaagg ctgatgtcca ggctttcagt 120
cgggccttcc aacccagtgt ctccctgatg gtggctgtac tgggtctggc tggcaatggc 180
ctagtcttgg ccacccatct ggctgctagg cgaactaccc gatctcccac ctccgttcac 240
ctgctccagt tggccctggc tgacctttta ttggccctga ctttgccttt tgctgcagca 300
ggggctcttc agggctggaa tctaggaagt accacctgcc gtgccatctc aggcctctac 360
tcggcctctt tccacgctgg cttcctcttc ctagcctgta tcagcgccga ccgctatgtg 420

```
gccatcgcac gagctctccc agccgggcag cggccctcaa cgcctagccg agcgcacttg    480

gtttcagtct tcgtgtggct gttgtcgctg tttctggctc tacctgcgct ccttttcagc    540

cgggacgggc cacgtgaagg ccaacgacgc tgtcggctca tttttcccga aagcctcacg    600

cagactgtga aaggagcaag cgcagtggcg caggtggtcc tcggcttcgc gctccctctg    660

ggcgtcatgg cagcctgtta tgcgcttctg ggccgaacgc ttctggctgc cagagggcca    720

gagcggcggc gtgcactgcg cgtcgtggtg gctttggtgg tggccttcgt ggtgctgcag    780

ttgccctaca gccttgccct gctgctggat acagccgatc tactggcagc ccgcgagcgg    840

agctgctcct ccagcaagcg caaggatcta gctttgctgg tcaccggcgg cttgaccctg    900

gtccgttgca gcctcaatcc ggtgctttat gccttttgg gcctgcgttt ccgacgggat    960

ctgcggagac tgctccaggg cggaggatgc agcccgaagc ctaaccctcg tggccgctgc   1020

cctcgtcgac tccgcctttc ttcctgttct gctcctactg agacccacag tctctcttgg   1080

gacaac                                                              1086
```

<210> SEQ ID NO 31
<211> LENGTH: 1395
<212> TYPE: DNA
<213> ORGANISM: Artificial Sequence
<220> FEATURE:
<223> OTHER INFORMATION: Synthetic Construct

<400> SEQUENCE: 31

```
atgggaggag ccgtggtgga tgagggacct acaggagtca aggcccctga tggaggatgg     60

ggatgggctg tgctcttcgg ctgtttcgtc atcactggct tctcctacgc cttccccaag    120

gccgtcagtg tcttcttcaa ggagctcata caggagtttg ggatcggcta cagcgacaca    180

gcctggatct cctccatcct gctggccatg ctctacggga caggtccgct ctgcagtgtg    240

tgcgtgaacc gctttggctg ccggcccgtc atgcttgtgg gaggtctctt tgcgtcgctg    300

ggcatggtgg ctgcgtcctt ttgccggagc atcatccagg tctacctcac cactggggtc    360

atcacggggt tgggtttggc actcaacttc cagccctcgc tcatcatgct gaaccgctac    420

ttcagcaagc ggcgccctat ggccaacgga ctggcggcag caggtagtcc tgtcttcctg    480

tgtgccctga gtccgctggg acagctgctg caggatcgct acggctggcg gggcggcttc    540

ctcatcctgg gcggcctgct gcttaactgt tgtgtgtgtg ccgcactcat gaggcctctg    600

gtggtcacgg cccagccggg ctcgggaccg ccgcgacctt cccgacgact gctagatctg    660

agtgtcttcc gagatcgcgg ctttgtgctt tacgccgtgg ccgcctcggt catggtgctg    720

ggactcttcg tcccgcccgt gttcgtggtg agctacgcca aggacctggg cgtgcccgac    780

accaaggccg ccttcctgct caccatcctg ggcttcattg acatcttcgc gcgaccggcc    840

gcaggcttcg tggcgggact tggaaaggtg cggccttact ccgtctacct cttcagcttc    900

tccatgttct tcaacggcct cgcggacctg gcgggttcta cggcgggcga ctacggcggc    960

ctcgtggtct tctgcatctt ctttggcatc tcctacggca tggtgggagc cctgcagttc   1020

gaggtgctca tggccatcgt gggcacccac aagttctcca gtgccattgg cctggtgctg   1080

ctgatggagg cggtggccgt gctcgtcggg cctccttcgg gaggcaaact cctggatgcg   1140

acccacgtct acatgtacgt gttcatcctg gcgggagccg aggtgctcac ctcctccctg   1200

attttgctgc tgggcaactt cttctgcatt aggaagaagc ccaaagagcc acagcctgag   1260

gtggcggccg cggaggagga gaagctccac aagcctcctg cagactcggg ggtggacttg   1320

cgggaggtgg agcatttcct gaaggctgag cctgagaaaa acggggaggt ggttcacacc   1380
```

```
ccggaaacaa gtgtc                                                   1395


<210> SEQ ID NO 32
<211> LENGTH: 462
<212> TYPE: DNA
<213> ORGANISM: Artificial Sequence
<220> FEATURE:
<223> OTHER INFORMATION: Synthetic Construct

<400> SEQUENCE: 32

atggcgacga aggccgtgtg cgtgctgaag ggcgacggcc cagtgcaggg catcatcaat     60

ttcgagcaga aggaaagtaa tggaccagtg aaggtgtggg gaagcattaa aggactgact    120

gaaggcctgc atggattcca tgttcatgag tttggagata atacagcagg ctgtaccagt    180

gcaggtcctc actttaatcc tctatccaga aaacacggtg ggccaaagga tgaagagagg    240

catgttggag acttgggcaa tgtgactgct gacaaagatg gtgtggccga tgtgtctatt    300

gaagattctg tgatctcact ctcaggagac cattgcatca ttggccgcac actggtggtc    360

catgaaaaag cagatgactt gggcaaaggt ggaaatgaag aaagtacaaa gacaggaaac    420

gctggaagtc gtttggcttg tggtgtaatt gggatcgccc aa                        462


<210> SEQ ID NO 33
<211> LENGTH: 1152
<212> TYPE: DNA
<213> ORGANISM: Artificial Sequence
<220> FEATURE:
<223> OTHER INFORMATION: Synthetic Construct

<400> SEQUENCE: 33

atgccgcagc tggattctgg cggaggagga gcgggcggag gagatgatct cggcgcgccg     60

gatgagctgc tggccttcca ggatgaaggc gaggagcagg atgacaagag ccgagatagc    120

gccgccggtc ctgagcgcga cctggccgag ctcaagtcgt cgcttgtgaa cgaatccgag    180

ggagcagccg gaggagcagg aatcccggga gttccgggag ccggcgccgg agcccgaggc    240

gaggccgaag ctcttggacg agaacacgct gcgcagagac tcttcccgga caaacttcca    300

gagcccctgg aggacggcct gaaggccccg gagtgcacca gcggcatgta caaagagacc    360

gtctactccg ccttcaatct gctcatgcat tacccacctc cttcgggagc aggacagcac    420

cctcagccgc agcctccgct gcacaaggcc aatcagcctc ctcacggtgt ccctcaactc    480

tctctctacg aacatttcaa cagcccacat cccacccctg cacctgcgga catcagccag    540

aagcaagttc acaggcctct gcagacccct gacctctctg gcttctactc cctgacctca    600

ggcagcatgg ggcagctccc ccacactgtg agctggttca cccacccatc cttgatgcta    660

ggttctggtg tacctggtca cccagcagcc atccctcacc cggccattgt gcctccttca    720

gggaagcagg agctgcagcc tttcgaccgc aacctgaaga cacaagcaga gtccaaggca    780

gagaaggagg ccaagaagcc aaccatcaag aagcccctca atgccttcat gctgtacatg    840

aaggagatga gagccaaggt cattgcagag tgcacactta aggagagcgc tgccatcaac    900

cagatcctgg gccgcaggtg gcacgcgctg tcgcgagaag agcaggccaa gtactatgag    960

ctggcccgca aggagaggca gctgcacatg cagctatacc caggctggtc agcgcgggac   1020

aactacggga agaagaagag gcggtcgagg gaaaagcacc aagaatccac cacaggagga   1080

aaaagaaatg cattcggtac ttacccggag aaggccgctg ccccagcccc gttccttccg   1140

atgacagtgc tc                                                       1152
```

<210> SEQ ID NO 34
<211> LENGTH: 831
<212> TYPE: DNA
<213> ORGANISM: Artificial Sequence
<220> FEATURE:
<223> OTHER INFORMATION: Synthetic Construct

<400> SEQUENCE: 34
atgggggcag gtgccactgg ccgcgccatg gacgggccgc gcctgctgct gttgctgctt 60
ctgggggtgt cccttggagg tgccaaggag gcatgcccca caggcctgta cacacacagc 120
ggtgagtgct gcaaagcctg caacctgggc gagggtgtgg cccagccttg tggagccaac 180
cagaccgtgt gtgagccctg cctggacagc gtgacgttct ccgacgtggt gagcgcgacc 240
gagccgtgca agccgtgcac cgagtgcgtg gggctccaga gcatgtcggc gccatgcgtg 300
gaggccgacg acgccgtgtg ccgctgcgcc tacggctact accaggatga gacgactggg 360
cgctgcgagg cgtgccgcgt gtgcgaggcg ggctcgggcc tcgtgttctc ctgccaggac 420
aagcagaaca ccgtgtgcga ggagtgcccc gacggcacgt attccgacga ggccaaccac 480
gtggacccgt gcctgccctg caccgtgtgc gaggacaccg agcgccagct ccgcgagtgc 540
acacgctggg ccgacgccga gtgcgaggag atccctggcc gttggattac acggtccaca 600
cccccagagg gctcggacag cacagccccc agcacccagg agcctgaggc acctccagaa 660
caagacctca tagccagcac ggtggcaggt gtggtgacca cagtgatggg cagctcccag 720
cccgtggtga cccgaggcac caccgacaac ctcatccctg tctattgctc catcctggct 780
gctgtggttg tgggtcttgt ggcctacata gccttcaaga ggtggaacag c 831

<210> SEQ ID NO 35
<211> LENGTH: 729
<212> TYPE: DNA
<213> ORGANISM: Artificial Sequence
<220> FEATURE:
<223> OTHER INFORMATION: Synthetic Construct

<400> SEQUENCE: 35
ggatcgggtg ggactagtgg cagcaagggc gaggagctgt tcaccggggt ggtgcccatc 60
ctggtcgagc tggacggcga cgtaaacggc cacaagttca gcgtgcgcgg cgagggcgag 120
ggcgatgcca ccaacggcaa gctgaccctg aagttcatct gcaccaccgg caagctgccc 180
gtgccctggc ccaccctcgt gaccaccctg acctacggcg tgcagtgctt cagccgctac 240
cccgaccaca tgaagcgcca cgacttcttc aagtccgcca tgcccgaagg ctacgtccag 300
gagcgcacca tcagcttcaa ggacgacggc acctacaaga cccgcgccga ggtgaagttc 360
gagggcgaca ccctggtgaa ccgcatcgag ctgaagggca tcgacttcaa ggaggacggc 420
aacatcctgg ggcacaagct ggagtacaac ttcaacagcc acaacgtcta tatcaccgcc 480
gacaagcaga agaacggcat caaggccaac ttcaagatcc gccacaacgt ggaggacggc 540
agcgtgcagc tcgccgacca ctaccagcag aacaccccca tcggcgacgg ccccgtgctg 600
ctgcccgaca accactacct gagcacccag tccgtgctga gcaaagaccc caacgagaag 660
cgcgatcaca tggtcctgct ggagttcgtg accgccgccg ggatcactgg aaccggtgct 720
ggaagtggt 729

<210> SEQ ID NO 36
<211> LENGTH: 747
<212> TYPE: DNA
<213> ORGANISM: Artificial Sequence

```
<220> FEATURE:
<223> OTHER INFORMATION: Synthetic Construct

<400> SEQUENCE: 36

ggatcgggtg ggactagtgg cgtgagcaag ggcgaggagg ataacatggc catcatcaag     60

gagttcatgc gcttcaaggt gcacatggag ggctccgtga acggccacga gttcgagatc    120

gagggcgagg gcgagggccg cccctacgag ggcacccaga ccgccaagct gaaggtgacc    180

aagggtggcc ccctgccctt cgcctgggac atcctgtccc ctcagttcat gtacggctcc    240

aaggcctacg tgaagcaccc cgccgacatc cccgactact tgaagctgtc cttccccgag    300

ggcttcaagt gggagcgcgt gatgaacttc gaggacggcg gcgtggtgac cgtgacccag    360

gactcctccc tgcaggacgg cgagttcatc tacaaggtga agctgcgcgg caccaacttc    420

cctccgacg gccccgtaat gcagaagaag accatgggct gggaggcctc ctccgagcgg    480

atgtaccccg aggacggcgc cctgaagggc gagatcaagc agaggctgaa gctgaaggac    540

ggcggccact acgacgctga ggtcaagacc acctacaagg ccaagaagcc cgtgcagctg    600

cccggcgcct acaacgtcaa catcaagttg gacatcacct cccacaacga ggactacacc    660

atcgtggaac agtacgaacg cgccgagggc cgccactcca ccggcggcat ggacgagctg    720

tacaagggaa ccggtgctgg aagtggt                                        747


<210> SEQ ID NO 37
<211> LENGTH: 201
<212> TYPE: PRT
<213> ORGANISM: Artificial Sequence
<220> FEATURE:
<223> OTHER INFORMATION: Synthetic Construct

<400> SEQUENCE: 37

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly
        195                 200
```

<210> SEQ ID NO 38
<211> LENGTH: 236
<212> TYPE: PRT
<213> ORGANISM: Artificial Sequence
<220> FEATURE:
<223> OTHER INFORMATION: Synthetic Construct

<400> SEQUENCE: 38

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ala Pro Ala Arg
145                 150                 155                 160

Glu Pro Gly His Ser Pro Gln Ile Ile Ser Phe Phe Leu Ala Leu Thr
                165                 170                 175

Ser Thr Ala Leu Leu Phe Leu Leu Phe Phe Leu Thr Leu Arg Phe Ser
            180                 185                 190

Val Val Lys Arg Gly Arg Lys Lys Leu Leu Tyr Ile Phe Lys Gln Pro
        195                 200                 205

Phe Met Arg Pro Val Gln Thr Thr Gln Glu Glu Asp Gly Cys Ser Cys
    210                 215                 220

Arg Phe Pro Glu Glu Glu Glu Gly Gly Cys Glu Leu
225                 230                 235
```

<210> SEQ ID NO 39
<211> LENGTH: 300
<212> TYPE: PRT
<213> ORGANISM: Artificial Sequence
<220> FEATURE:
<223> OTHER INFORMATION: Synthetic Construct

<400> SEQUENCE: 39

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
```

65 70 75 80

Ala Phe Pro Glu Asp Arg Ser Gln Pro Gly Gln Asp Cys Arg Phe Arg
85 90 95

Val Thr Gln Leu Pro Asn Gly Arg Asp Phe His Met Ser Val Val Arg
100 105 110

Ala Arg Arg Asn Asp Ser Gly Thr Tyr Leu Cys Gly Ala Ile Ser Leu
115 120 125

Ala Pro Lys Ala Gln Ile Lys Glu Ser Leu Arg Ala Glu Leu Arg Val
130 135 140

Thr Glu Arg Arg Ala Glu Val Pro Thr Ala His Pro Ser Pro Ser Pro
145 150 155 160

Arg Pro Ala Gly Gln Phe Gln Thr Leu Val Val Gly Val Val Gly Gly
165 170 175

Leu Leu Gly Ser Leu Val Leu Leu Val Trp Val Leu Ala Val Ile Cys
180 185 190

Ser Arg Ala Ala Arg Gly Thr Gln Val Ala Ala Asp Trp Thr Ala Leu
195 200 205

Ala Glu Glu Met Asp Phe Glu Tyr Leu Glu Ile Arg Gln Leu Glu Thr
210 215 220

Gln Ala Asp Pro Thr Gly Arg Leu Leu Asp Ala Trp Gln Gly Arg Pro
225 230 235 240

Gly Ala Ser Val Gly Arg Leu Leu Glu Leu Leu Thr Lys Leu Gly Arg
245 250 255

Asp Asp Val Leu Leu Glu Leu Gly Pro Ser Ile Glu Glu Asp Cys Gln
260 265 270

Lys Tyr Ile Leu Lys Gln Gln Gln Glu Glu Ala Glu Lys Pro Leu Gln
275 280 285

Val Ala Ala Val Asp Ser Ser Val Pro Arg Thr Ala
290 295 300

<210> SEQ ID NO 40
<211> LENGTH: 226
<212> TYPE: PRT
<213> ORGANISM: Artificial Sequence
<220> FEATURE:
<223> OTHER INFORMATION: Synthetic Construct

<400> SEQUENCE: 40

Met Gln Ile Pro Gln Ala Pro Trp Pro Val Val Trp Ala Val Leu Gln
1 5 10 15

Leu Gly Trp Arg Pro Gly Trp Phe Leu Asp Ser Pro Asp Arg Pro Trp
20 25 30

Asn Pro Pro Thr Phe Ser Pro Ala Leu Leu Val Val Thr Glu Gly Asp
35 40 45

Asn Ala Thr Phe Thr Cys Ser Phe Ser Asn Thr Ser Glu Ser Phe Val
50 55 60

Leu Asn Trp Tyr Arg Met Ser Pro Ser Asn Gln Thr Asp Lys Leu Ala
65 70 75 80

Ala Phe Pro Glu Asp Arg Ser Gln Pro Gly Gln Asp Cys Arg Phe Arg
85 90 95

Val Thr Gln Leu Pro Asn Gly Arg Asp Phe His Met Ser Val Val Arg
100 105 110

Ala Arg Arg Asn Asp Ser Gly Thr Tyr Leu Cys Gly Ala Ile Ser Leu
115 120 125

Ala Pro Lys Ala Gln Ile Lys Glu Ser Leu Arg Ala Glu Leu Arg Val

```
    130                 135                 140

Thr Glu Arg Arg Ala Glu Val Pro Thr Ala His His Ile Tyr Glu Ser
145                 150                 155                 160

Gln Leu Cys Cys Gln Leu Lys Phe Trp Leu Pro Ile Gly Cys Ala Ala
                165                 170                 175

Phe Val Val Val Cys Ile Leu Gly Cys Ile Leu Ile Cys Trp Leu Thr
            180                 185                 190

Lys Lys Lys Tyr Ser Ser Ser Val His Asp Pro Asn Gly Glu Tyr Met
        195                 200                 205

Phe Met Arg Ala Val Asn Thr Ala Lys Lys Ser Arg Leu Thr Asp Val
    210                 215                 220

Thr Leu
225


<210> SEQ ID NO 41
<211> LENGTH: 189
<212> TYPE: PRT
<213> ORGANISM: Artificial Sequence
<220> FEATURE:
<223> OTHER INFORMATION: Synthetic Construct

<400> SEQUENCE: 41

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met
            180                 185


<210> SEQ ID NO 42
<211> LENGTH: 230
<212> TYPE: PRT
<213> ORGANISM: Artificial Sequence
<220> FEATURE:
<223> OTHER INFORMATION: Synthetic Construct

<400> SEQUENCE: 42

Met Ala Cys Leu Gly Phe Gln Arg His Lys Ala Gln Leu Asn Leu Ala
1               5                   10                  15
```

Thr Arg Thr Trp Pro Cys Thr Leu Leu Phe Phe Leu Leu Phe Ile Pro
20 25 30

Val Phe Cys Lys Ala Met His Val Ala Gln Pro Ala Val Val Leu Ala
35 40 45

Ser Ser Arg Gly Ile Ala Ser Phe Val Cys Glu Tyr Ala Ser Pro Gly
50 55 60

Lys Ala Thr Glu Val Arg Val Thr Val Leu Arg Gln Ala Asp Ser Gln
65 70 75 80

Val Thr Glu Val Cys Ala Ala Thr Tyr Met Met Gly Asn Glu Leu Thr
85 90 95

Phe Leu Asp Asp Ser Ile Cys Thr Gly Thr Ser Ser Gly Asn Gln Val
100 105 110

Asn Leu Thr Ile Gln Gly Leu Arg Ala Met Asp Thr Gly Leu Tyr Ile
115 120 125

Cys Lys Val Glu Leu Met Tyr Pro Pro Pro Tyr Tyr Leu Gly Ile Gly
130 135 140

Asn Gly Thr Gln Ile Tyr Val Ile Asp Pro Glu Pro Cys Pro Asp Ser
145 150 155 160

Asp Phe Leu Leu Trp Ile Leu Ala Ala Val Ser Ser Gly Leu Phe Phe
165 170 175

Tyr Ser Phe Leu Leu Thr Ala Val Ser Leu Ser Lys Met Arg Ser Lys
180 185 190

Arg Ser Arg Leu Leu His Ser Asp Tyr Met Asn Met Thr Pro Arg Arg
195 200 205

Pro Gly Pro Thr Arg Lys His Tyr Gln Pro Tyr Ala Pro Pro Arg Asp
210 215 220

Phe Ala Ala Tyr Arg Ser
225 230

<210> SEQ ID NO 43
<211> LENGTH: 271
<212> TYPE: PRT
<213> ORGANISM: Artificial Sequence
<220> FEATURE:
<223> OTHER INFORMATION: Synthetic Construct

<400> SEQUENCE: 43

Met Leu Cys Pro Trp Arg Thr Ala Asn Leu Gly Leu Leu Leu Ile Leu
1 5 10 15

Thr Ile Phe Leu Val Ala Glu Ala Glu Gly Ala Ala Gln Pro Asn Asn
20 25 30

Ser Leu Met Leu Gln Thr Ser Lys Glu Asn His Ala Leu Ala Ser Ser
35 40 45

Ser Leu Cys Met Asp Glu Lys Gln Ile Thr Gln Asn Tyr Ser Lys Val
50 55 60

Leu Ala Glu Val Asn Thr Ser Trp Pro Val Lys Met Ala Thr Asn Ala
65 70 75 80

Val Leu Cys Cys Pro Pro Ile Ala Leu Arg Asn Leu Ile Ile Ile Thr
85 90 95

Trp Glu Ile Ile Leu Arg Gly Gln Pro Ser Cys Thr Lys Ala Tyr Lys
100 105 110

Lys Glu Thr Asn Glu Thr Lys Glu Thr Asn Cys Thr Asp Glu Arg Ile
115 120 125

Thr Trp Val Ser Arg Pro Asp Gln Asn Ser Asp Leu Gln Ile Arg Thr
130 135 140

```
Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
            180                 185                 190

Val Ala Gly Lys Pro Ala Ala His Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220

Ser Thr Cys His Trp Glu Val His Asn Val Ser Thr Val Thr Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ala Lys Leu Tyr Ile Pro Tyr Ile
            260                 265                 270


<210> SEQ ID NO 44
<211> LENGTH: 185
<212> TYPE: PRT
<213> ORGANISM: Artificial Sequence
<220> FEATURE:
<223> OTHER INFORMATION: Synthetic Construct

<400> SEQUENCE: 44

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln
            180                 185


<210> SEQ ID NO 45
<211> LENGTH: 228
<212> TYPE: PRT
<213> ORGANISM: Artificial Sequence
<220> FEATURE:
<223> OTHER INFORMATION: Synthetic Construct

<400> SEQUENCE: 45
```

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Cys Pro Ser Pro Leu Phe Pro Gly Pro Ser Lys Pro
145                 150                 155                 160

Phe Trp Val Leu Val Val Val Gly Gly Val Leu Ala Cys Tyr Ser Leu
                165                 170                 175

Leu Val Thr Val Ala Phe Ile Ile Phe Trp Val Arg Ser Lys Arg Ser
            180                 185                 190

Arg Leu Leu His Ser Asp Tyr Met Asn Met Thr Pro Arg Arg Pro Gly
        195                 200                 205

Pro Thr Arg Lys His Tyr Gln Pro Tyr Ala Pro Pro Arg Asp Phe Ala
    210                 215                 220

Ala Tyr Arg Ser
225


<210> SEQ ID NO 46
<211> LENGTH: 230
<212> TYPE: PRT
<213> ORGANISM: Artificial Sequence
<220> FEATURE:
<223> OTHER INFORMATION: Synthetic Construct

<400> SEQUENCE: 46

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125
```

```
Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser
225                 230


<210> SEQ ID NO 47
<211> LENGTH: 273
<212> TYPE: PRT
<213> ORGANISM: Artificial Sequence
<220> FEATURE:
<223> OTHER INFORMATION: Synthetic Construct

<400> SEQUENCE: 47

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Cys Pro Ser Pro Leu Phe Pro Gly Pro Ser Lys Pro Phe Trp Val
        195                 200                 205

Leu Val Val Val Gly Gly Val Leu Ala Cys Tyr Ser Leu Leu Val Thr
    210                 215                 220

Val Ala Phe Ile Ile Phe Trp Val Arg Ser Lys Arg Ser Arg Leu Leu
225                 230                 235                 240

His Ser Asp Tyr Met Asn Met Thr Pro Arg Arg Pro Gly Pro Thr Arg
                245                 250                 255
```

Lys His Tyr Gln Pro Tyr Ala Pro Pro Arg Asp Phe Ala Ala Tyr Arg
260 265 270

Ser

<210> SEQ ID NO 48
<211> LENGTH: 169
<212> TYPE: PRT
<213> ORGANISM: Artificial Sequence
<220> FEATURE:
<223> OTHER INFORMATION: Synthetic Construct

<400> SEQUENCE: 48

Met Arg Trp Cys Leu Leu Leu Ile Trp Ala Gln Gly Leu Arg Gln Ala
1 5 10 15

Pro Leu Ala Ser Gly Met Met Thr Gly Thr Ile Glu Thr Thr Gly Asn
20 25 30

Ile Ser Ala Glu Lys Gly Gly Ser Ile Ile Leu Gln Cys His Leu Ser
35 40 45

Ser Thr Thr Ala Gln Val Thr Gln Val Asn Trp Glu Gln Gln Asp Gln
50 55 60

Leu Leu Ala Ile Cys Asn Ala Asp Leu Gly Trp His Ile Ser Pro Ser
65 70 75 80

Phe Lys Asp Arg Val Ala Pro Gly Pro Gly Leu Gly Leu Thr Leu Gln
85 90 95

Ser Leu Thr Val Asn Asp Thr Gly Glu Tyr Phe Cys Ile Tyr His Thr
100 105 110

Tyr Pro Asp Gly Thr Tyr Thr Gly Arg Ile Phe Leu Glu Val Leu Glu
115 120 125

Ser Ser Val Ala Glu His Gly Ala Arg Phe Gln Ile Pro Leu Leu Gly
130 135 140

Ala Met Ala Ala Thr Leu Val Val Ile Cys Thr Ala Val Ile Val Val
145 150 155 160

Val Ala Leu Thr Arg Lys Lys Lys Ala
165

<210> SEQ ID NO 49
<211> LENGTH: 212
<212> TYPE: PRT
<213> ORGANISM: Artificial Sequence
<220> FEATURE:
<223> OTHER INFORMATION: Synthetic Construct

<400> SEQUENCE: 49

Met Arg Trp Cys Leu Leu Leu Ile Trp Ala Gln Gly Leu Arg Gln Ala
1 5 10 15

Pro Leu Ala Ser Gly Met Met Thr Gly Thr Ile Glu Thr Thr Gly Asn
20 25 30

Ile Ser Ala Glu Lys Gly Gly Ser Ile Ile Leu Gln Cys His Leu Ser
35 40 45

Ser Thr Thr Ala Gln Val Thr Gln Val Asn Trp Glu Gln Gln Asp Gln
50 55 60

Leu Leu Ala Ile Cys Asn Ala Asp Leu Gly Trp His Ile Ser Pro Ser
65 70 75 80

Phe Lys Asp Arg Val Ala Pro Gly Pro Gly Leu Gly Leu Thr Leu Gln
85 90 95

Ser Leu Thr Val Asn Asp Thr Gly Glu Tyr Phe Cys Ile Tyr His Thr
100 105 110

```
Tyr Pro Asp Gly Thr Tyr Thr Gly Arg Ile Phe Leu Glu Val Leu Glu
        115                 120                 125

Ser Ser Val Ala Cys Pro Ser Pro Leu Phe Pro Gly Pro Ser Lys Pro
    130                 135                 140

Phe Trp Val Leu Val Val Val Gly Gly Val Leu Ala Cys Tyr Ser Leu
145                 150                 155                 160

Leu Val Thr Val Ala Phe Ile Ile Phe Trp Val Arg Ser Lys Arg Ser
                165                 170                 175

Arg Leu Leu His Ser Asp Tyr Met Asn Met Thr Pro Arg Arg Pro Gly
            180                 185                 190

Pro Thr Arg Lys His Tyr Gln Pro Tyr Ala Pro Pro Arg Asp Phe Ala
        195                 200                 205

Ala Tyr Arg Ser
    210


<210> SEQ ID NO 50
<211> LENGTH: 201
<212> TYPE: PRT
<213> ORGANISM: Artificial Sequence
<220> FEATURE:
<223> OTHER INFORMATION: Synthetic Construct

<400> SEQUENCE: 50

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Ser Gly
        195                 200


<210> SEQ ID NO 51
<211> LENGTH: 236
<212> TYPE: PRT
<213> ORGANISM: Artificial Sequence
<220> FEATURE:
<223> OTHER INFORMATION: Synthetic Construct
```

<400> SEQUENCE: 51

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Lys Arg Gly Arg Lys Lys Leu Leu Tyr Ile Phe Lys Gln Pro
        195                 200                 205

Phe Met Arg Pro Val Gln Thr Thr Gln Glu Glu Asp Gly Cys Ser Cys
    210                 215                 220

Arg Phe Pro Glu Glu Glu Glu Gly Gly Cys Glu Leu
225                 230                 235

<210> SEQ ID NO 52
<211> LENGTH: 296
<212> TYPE: PRT
<213> ORGANISM: Artificial Sequence
<220> FEATURE:
<223> OTHER INFORMATION: Synthetic Construct

<400> SEQUENCE: 52

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys

```
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
            165                 170                 175

Gly Val Ala Ile Ser Val Ile Ile Ile Phe Tyr Cys Tyr Arg Val Asn
            180                 185                 190

Arg Gln Thr Gln Val Ala Ala Asp Trp Thr Ala Leu Ala Glu Glu Met
        195                 200                 205

Asp Phe Glu Tyr Leu Glu Ile Arg Gln Leu Glu Thr Gln Ala Asp Pro
    210                 215                 220

Thr Gly Arg Leu Leu Asp Ala Trp Gln Gly Arg Pro Gly Ala Ser Val
225                 230                 235                 240

Gly Arg Leu Leu Glu Leu Leu Thr Lys Leu Gly Arg Asp Asp Val Leu
            245                 250                 255

Leu Glu Leu Gly Pro Ser Ile Glu Glu Asp Cys Gln Lys Tyr Ile Leu
            260                 265                 270

Lys Gln Gln Gln Glu Glu Ala Glu Lys Pro Leu Gln Val Ala Ala Val
        275                 280                 285

Asp Ser Ser Val Pro Arg Thr Ala
    290                 295


<210> SEQ ID NO 53
<211> LENGTH: 263
<212> TYPE: PRT
<213> ORGANISM: Artificial Sequence
<220> FEATURE:
<223> OTHER INFORMATION: Synthetic Construct

<400> SEQUENCE: 53

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
            85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
            165                 170                 175

Asn Phe Thr Phe Thr His Lys Lys Val Lys His Glu Asn Phe Ser Leu
```

```
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg
            260


<210> SEQ ID NO 54
<211> LENGTH: 456
<212> TYPE: PRT
<213> ORGANISM: Artificial Sequence
<220> FEATURE:
<223> OTHER INFORMATION: Synthetic Construct

<400> SEQUENCE: 54

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Pro Ile Leu Leu
225                 230                 235                 240

Thr Ile Ser Ile Leu Ser Phe Phe Ser Val Ala Leu Leu Val Ile Leu
                245                 250                 255

Ala Cys Val Leu Trp Lys Lys Arg Ile Lys Pro Ile Val Trp Pro Ser
            260                 265                 270

Leu Pro Asp His Lys Lys Thr Leu Glu His Leu Cys Lys Lys Pro Arg
```

```
        275                 280                 285

Lys Asn Leu Asn Val Ser Phe Asn Pro Glu Ser Phe Leu Asp Cys Gln
    290                 295                 300

Ile His Arg Val Asp Asp Ile Gln Ala Arg Asp Glu Val Glu Gly Phe
305                 310                 315                 320

Leu Gln Asp Thr Phe Pro Gln Gln Leu Glu Glu Ser Glu Lys Gln Arg
                325                 330                 335

Leu Gly Gly Asp Val Gln Ser Pro Asn Cys Pro Ser Glu Asp Val Val
            340                 345                 350

Ile Thr Pro Glu Ser Phe Gly Arg Asp Ser Ser Leu Thr Cys Leu Ala
        355                 360                 365

Gly Asn Val Ser Ala Cys Asp Ala Pro Ile Leu Ser Ser Ser Arg Ser
    370                 375                 380

Leu Asp Cys Arg Glu Ser Gly Lys Asn Gly Pro His Val Tyr Gln Asp
385                 390                 395                 400

Leu Leu Leu Ser Leu Gly Thr Thr Asn Ser Thr Leu Pro Pro Pro Phe
                405                 410                 415

Ser Leu Gln Ser Gly Ile Leu Thr Leu Asn Pro Val Ala Gln Gly Gln
            420                 425                 430

Pro Ile Leu Thr Ser Leu Gly Ser Asn Gln Glu Glu Ala Tyr Val Thr
        435                 440                 445

Met Ser Ser Phe Tyr Gln Asn Gln
    450                 455


<210> SEQ ID NO 55
<211> LENGTH: 453
<212> TYPE: PRT
<213> ORGANISM: Artificial Sequence
<220> FEATURE:
<223> OTHER INFORMATION: Synthetic Construct

<400> SEQUENCE: 55

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
```

```
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln His Leu Pro Ile Leu Leu Thr Ile Ser
225                 230                 235                 240

Ile Leu Ser Phe Phe Ser Val Ala Leu Leu Val Ile Leu Ala Cys Val
                245                 250                 255

Leu Trp Lys Lys Arg Ile Lys Pro Ile Val Trp Pro Ser Leu Pro Asp
            260                 265                 270

His Lys Lys Thr Leu Glu His Leu Cys Lys Lys Pro Arg Lys Asn Leu
        275                 280                 285

Asn Val Ser Phe Asn Pro Glu Ser Phe Leu Asp Cys Gln Ile His Arg
    290                 295                 300

Val Asp Asp Ile Gln Ala Arg Asp Glu Val Glu Gly Phe Leu Gln Asp
305                 310                 315                 320

Thr Phe Pro Gln Gln Leu Glu Glu Ser Glu Lys Gln Arg Leu Gly Gly
                325                 330                 335

Asp Val Gln Ser Pro Asn Cys Pro Ser Glu Asp Val Val Ile Thr Pro
            340                 345                 350

Glu Ser Phe Gly Arg Asp Ser Ser Leu Thr Cys Leu Ala Gly Asn Val
        355                 360                 365

Ser Ala Cys Asp Ala Pro Ile Leu Ser Ser Ser Arg Ser Leu Asp Cys
    370                 375                 380

Arg Glu Ser Gly Lys Asn Gly Pro His Val Tyr Gln Asp Leu Leu Leu
385                 390                 395                 400

Ser Leu Gly Thr Thr Asn Ser Thr Leu Pro Pro Pro Phe Ser Leu Gln
                405                 410                 415

Ser Gly Ile Leu Thr Leu Asn Pro Val Ala Gln Gly Gln Pro Ile Leu
            420                 425                 430

Thr Ser Leu Gly Ser Asn Gln Glu Glu Ala Tyr Val Thr Met Ser Ser
        435                 440                 445

Phe Tyr Gln Asn Gln
    450


<210> SEQ ID NO 56
<211> LENGTH: 272
<212> TYPE: PRT
<213> ORGANISM: Artificial Sequence
<220> FEATURE:
<223> OTHER INFORMATION: Synthetic Construct

<400> SEQUENCE: 56

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
```

```
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270


<210> SEQ ID NO 57
<211> LENGTH: 459
<212> TYPE: PRT
<213> ORGANISM: Artificial Sequence
<220> FEATURE:
<223> OTHER INFORMATION: Synthetic Construct

<400> SEQUENCE: 57

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Ile Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Val Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
```

```
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
        355                 360                 365

Cys Leu Ala Gly Asn Val Ser Ala Cys Asp Ala Pro Ile Leu Ser Ser
    370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
    450                 455


<210> SEQ ID NO 58
<211> LENGTH: 255
<212> TYPE: PRT
<213> ORGANISM: Artificial Sequence
<220> FEATURE:
<223> OTHER INFORMATION: Synthetic Construct

<400> SEQUENCE: 58

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
```

```
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 59
<211> LENGTH: 197
<212> TYPE: PRT
<213> ORGANISM: Artificial Sequence
<220> FEATURE:
<223> OTHER INFORMATION: Synthetic Construct

<400> SEQUENCE: 59

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys
```

195

<210> SEQ ID NO 60
<211> LENGTH: 238
<212> TYPE: PRT
<213> ORGANISM: Artificial Sequence
<220> FEATURE:
<223> OTHER INFORMATION: Synthetic Construct

<400> SEQUENCE: 60

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Arg Ser Lys Arg Ser Arg Leu Leu His Ser Asp
        195                 200                 205

Tyr Met Asn Met Thr Pro Arg Arg Pro Gly Pro Thr Arg Lys His Tyr
    210                 215                 220

Gln Pro Tyr Ala Pro Pro Arg Asp Phe Ala Ala Tyr Arg Ser
225                 230                 235
```

<210> SEQ ID NO 61
<211> LENGTH: 239
<212> TYPE: PRT
<213> ORGANISM: Artificial Sequence
<220> FEATURE:
<223> OTHER INFORMATION: Synthetic Construct

<400> SEQUENCE: 61

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60
```

```
Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Lys Arg Gly Arg Lys Lys Leu Leu Tyr Ile Phe
        195                 200                 205

Lys Gln Pro Phe Met Arg Pro Val Gln Thr Thr Gln Glu Glu Asp Gly
    210                 215                 220

Cys Ser Cys Arg Phe Pro Glu Glu Glu Glu Gly Gly Cys Glu Leu
225                 230                 235
```

<210> SEQ ID NO 62
<211> LENGTH: 299
<212> TYPE: PRT
<213> ORGANISM: Artificial Sequence
<220> FEATURE:
<223> OTHER INFORMATION: Synthetic Construct

<400> SEQUENCE: 62

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190
```

Lys Glu Val Gln Lys Thr Gln Val Ala Ala Asp Trp Thr Ala Leu Ala
195 200 205

Glu Glu Met Asp Phe Glu Tyr Leu Glu Ile Arg Gln Leu Glu Thr Gln
210 215 220

Ala Asp Pro Thr Gly Arg Leu Leu Asp Ala Trp Gln Gly Arg Pro Gly
225 230 235 240

Ala Ser Val Gly Arg Leu Leu Glu Leu Leu Thr Lys Leu Gly Arg Asp
245 250 255

Asp Val Leu Leu Glu Leu Gly Pro Ser Ile Glu Glu Asp Cys Gln Lys
260 265 270

Tyr Ile Leu Lys Gln Gln Gln Glu Glu Ala Glu Lys Pro Leu Gln Val
275 280 285

Ala Ala Val Asp Ser Ser Val Pro Arg Thr Ala
290 295

<210> SEQ ID NO 63
<211> LENGTH: 235
<212> TYPE: PRT
<213> ORGANISM: Artificial Sequence
<220> FEATURE:
<223> OTHER INFORMATION: Synthetic Construct

<400> SEQUENCE: 63

Met Leu Gly Ile Trp Thr Leu Leu Pro Leu Val Leu Thr Ser Val Ala
1 5 10 15

Arg Leu Ser Ser Lys Ser Val Asn Ala Gln Val Thr Asp Ile Asn Ser
20 25 30

Lys Gly Leu Glu Leu Arg Lys Thr Val Thr Thr Val Glu Thr Gln Asn
35 40 45

Leu Glu Gly Leu His His Asp Gly Gln Phe Cys His Lys Pro Cys Pro
50 55 60

Pro Gly Glu Arg Lys Ala Arg Asp Cys Thr Val Asn Gly Asp Glu Pro
65 70 75 80

Asp Cys Val Pro Cys Gln Glu Gly Lys Glu Tyr Thr Asp Lys Ala His
85 90 95

Phe Ser Ser Lys Cys Arg Arg Cys Arg Leu Cys Asp Glu Gly His Gly
100 105 110

Leu Glu Val Glu Ile Asn Cys Thr Arg Thr Gln Asn Thr Lys Cys Arg
115 120 125

Cys Lys Pro Asn Phe Phe Cys Asn Ser Thr Val Cys Glu His Cys Asp
130 135 140

Pro Cys Thr Lys Cys Glu His Gly Ile Ile Lys Glu Cys Thr Leu Thr
145 150 155 160

Ser Asn Thr Lys Cys Lys Glu Glu Gly Ser Arg Ser Asn Leu Gly Trp
165 170 175

Leu Cys Leu Leu Leu Leu Pro Ile Pro Leu Ile Val Trp Val Lys Arg
180 185 190

Lys Glu Val Gln Lys Cys Trp Leu Thr Lys Lys Lys Tyr Ser Ser Ser
195 200 205

Val His Asp Pro Asn Gly Glu Tyr Met Phe Met Arg Ala Val Asn Thr
210 215 220

Ala Lys Lys Ser Arg Leu Thr Asp Val Thr Leu
225 230 235

<210> SEQ ID NO 64
<211> LENGTH: 238

<212> TYPE: PRT
<213> ORGANISM: Artificial Sequence
<220> FEATURE:
<223> OTHER INFORMATION: Synthetic Construct

<400> SEQUENCE: 64

```
Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys
225                 230                 235
```

<210> SEQ ID NO 65
<211> LENGTH: 279
<212> TYPE: PRT
<213> ORGANISM: Artificial Sequence
<220> FEATURE:
<223> OTHER INFORMATION: Synthetic Construct

<400> SEQUENCE: 65

```
Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95
```

-continued

```
Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Arg Ser
225                 230                 235                 240

Lys Arg Ser Arg Leu Leu His Ser Asp Tyr Met Asn Met Thr Pro Arg
                245                 250                 255

Arg Pro Gly Pro Thr Arg Lys His Tyr Gln Pro Tyr Ala Pro Pro Arg
            260                 265                 270

Asp Phe Ala Ala Tyr Arg Ser
        275
```

<210> SEQ ID NO 66
<211> LENGTH: 362
<212> TYPE: PRT
<213> ORGANISM: Artificial Sequence
<220> FEATURE:
<223> OTHER INFORMATION: Synthetic Construct

<400> SEQUENCE: 66

```
Met Gly Thr Lys Pro Thr Glu Gln Val Ser Trp Gly Leu Tyr Ser Gly
1               5                   10                  15

Tyr Asp Glu Glu Ala Tyr Ser Val Gly Pro Leu Pro Glu Leu Cys Tyr
            20                  25                  30

Lys Ala Asp Val Gln Ala Phe Ser Arg Ala Phe Gln Pro Ser Val Ser
        35                  40                  45

Leu Met Val Ala Val Leu Gly Leu Ala Gly Asn Gly Leu Val Leu Ala
    50                  55                  60

Thr His Leu Ala Ala Arg Arg Thr Thr Arg Ser Pro Thr Ser Val His
65                  70                  75                  80

Leu Leu Gln Leu Ala Leu Ala Asp Leu Leu Leu Ala Leu Thr Leu Pro
                85                  90                  95

Phe Ala Ala Ala Gly Ala Leu Gln Gly Trp Asn Leu Gly Ser Thr Thr
            100                 105                 110

Cys Arg Ala Ile Ser Gly Leu Tyr Ser Ala Ser Phe His Ala Gly Phe
        115                 120                 125

Leu Phe Leu Ala Cys Ile Ser Ala Asp Arg Tyr Val Ala Ile Ala Arg
    130                 135                 140

Ala Leu Pro Ala Gly Gln Arg Pro Ser Thr Pro Ser Arg Ala His Leu
145                 150                 155                 160

Val Ser Val Phe Val Trp Leu Leu Ser Leu Phe Leu Ala Leu Pro Ala
                165                 170                 175
```

```
Leu Leu Phe Ser Arg Asp Gly Pro Arg Glu Gly Gln Arg Arg Cys Arg
            180                 185                 190

Leu Ile Phe Pro Glu Ser Leu Thr Gln Thr Val Lys Gly Ala Ser Ala
        195                 200                 205

Val Ala Gln Val Val Leu Gly Phe Ala Leu Pro Leu Gly Val Met Ala
    210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Val Val Val Ala Leu Val Val Ala Phe
                245                 250                 255

Val Val Leu Gln Leu Pro Tyr Ser Leu Ala Leu Leu Leu Asp Thr Ala
            260                 265                 270

Asp Leu Leu Ala Ala Arg Glu Arg Ser Cys Ser Ser Ser Lys Arg Lys
        275                 280                 285

Asp Leu Ala Leu Leu Val Thr Gly Gly Leu Thr Leu Val Arg Cys Ser
    290                 295                 300

Leu Asn Pro Val Leu Tyr Ala Phe Leu Gly Leu Arg Phe Arg Arg Asp
305                 310                 315                 320

Leu Arg Arg Leu Leu Gln Gly Gly Gly Cys Ser Pro Lys Pro Asn Pro
                325                 330                 335

Arg Gly Arg Cys Pro Arg Arg Leu Arg Leu Ser Ser Cys Ser Ala Pro
            340                 345                 350

Thr Glu Thr His Ser Leu Ser Trp Asp Asn
        355                 360


<210> SEQ ID NO 67
<211> LENGTH: 465
<212> TYPE: PRT
<213> ORGANISM: Artificial Sequence
<220> FEATURE:
<223> OTHER INFORMATION: Synthetic Construct

<400> SEQUENCE: 67

Met Gly Gly Ala Val Val Asp Glu Gly Pro Thr Gly Val Lys Ala Pro
1               5                   10                  15

Asp Gly Gly Trp Gly Trp Ala Val Leu Phe Gly Cys Phe Val Ile Thr
            20                  25                  30

Gly Phe Ser Tyr Ala Phe Pro Lys Ala Val Ser Val Phe Phe Lys Glu
        35                  40                  45

Leu Ile Gln Glu Phe Gly Ile Gly Tyr Ser Asp Thr Ala Trp Ile Ser
    50                  55                  60

Ser Ile Leu Leu Ala Met Leu Tyr Gly Thr Gly Pro Leu Cys Ser Val
65                  70                  75                  80

Cys Val Asn Arg Phe Gly Cys Arg Pro Val Met Leu Val Gly Gly Leu
                85                  90                  95

Phe Ala Ser Leu Gly Met Val Ala Ala Ser Phe Cys Arg Ser Ile Ile
            100                 105                 110

Gln Val Tyr Leu Thr Thr Gly Val Ile Thr Gly Leu Gly Leu Ala Leu
        115                 120                 125

Asn Phe Gln Pro Ser Leu Ile Met Leu Asn Arg Tyr Phe Ser Lys Arg
    130                 135                 140

Arg Pro Met Ala Asn Gly Leu Ala Ala Ala Gly Ser Pro Val Phe Leu
145                 150                 155                 160

Cys Ala Leu Ser Pro Leu Gly Gln Leu Leu Gln Asp Arg Tyr Gly Trp
                165                 170                 175
```

```
Arg Gly Gly Phe Leu Ile Leu Gly Gly Leu Leu Leu Asn Cys Cys Val
            180                 185                 190

Cys Ala Ala Leu Met Arg Pro Leu Val Val Thr Ala Gln Pro Gly Ser
        195                 200                 205

Gly Pro Pro Arg Pro Ser Arg Arg Leu Leu Asp Leu Ser Val Phe Arg
    210                 215                 220

Asp Arg Gly Phe Val Leu Tyr Ala Val Ala Ala Ser Val Met Val Leu
225                 230                 235                 240

Gly Leu Phe Val Pro Pro Val Phe Val Val Ser Tyr Ala Lys Asp Leu
                245                 250                 255

Gly Val Pro Asp Thr Lys Ala Ala Phe Leu Leu Thr Ile Leu Gly Phe
            260                 265                 270

Ile Asp Ile Phe Ala Arg Pro Ala Ala Gly Phe Val Ala Gly Leu Gly
        275                 280                 285

Lys Val Arg Pro Tyr Ser Val Tyr Leu Phe Ser Phe Ser Met Phe Phe
    290                 295                 300

Asn Gly Leu Ala Asp Leu Ala Gly Ser Thr Ala Gly Asp Tyr Gly Gly
305                 310                 315                 320

Leu Val Val Phe Cys Ile Phe Phe Gly Ile Ser Tyr Gly Met Val Gly
                325                 330                 335

Ala Leu Gln Phe Glu Val Leu Met Ala Ile Val Gly Thr His Lys Phe
            340                 345                 350

Ser Ser Ala Ile Gly Leu Val Leu Leu Met Glu Ala Val Ala Val Leu
        355                 360                 365

Val Gly Pro Pro Ser Gly Gly Lys Leu Leu Asp Ala Thr His Val Tyr
    370                 375                 380

Met Tyr Val Phe Ile Leu Ala Gly Ala Glu Val Leu Thr Ser Ser Leu
385                 390                 395                 400

Ile Leu Leu Leu Gly Asn Phe Phe Cys Ile Arg Lys Lys Pro Lys Glu
                405                 410                 415

Pro Gln Pro Glu Val Ala Ala Ala Glu Glu Glu Lys Leu His Lys Pro
            420                 425                 430

Pro Ala Asp Ser Gly Val Asp Leu Arg Glu Val Glu His Phe Leu Lys
        435                 440                 445

Ala Glu Pro Glu Lys Asn Gly Glu Val Val His Thr Pro Glu Thr Ser
    450                 455                 460

Val
465
```

<210> SEQ ID NO 68
<211> LENGTH: 154
<212> TYPE: PRT
<213> ORGANISM: Artificial Sequence
<220> FEATURE:
<223> OTHER INFORMATION: Synthetic Construct

<400> SEQUENCE: 68

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60
```

Phe Asn Pro Leu Ser Arg Lys His Gly Gly Pro Lys Asp Glu Glu Arg
65 70 75 80

His Val Gly Asp Leu Gly Asn Val Thr Ala Asp Lys Asp Gly Val Ala
85 90 95

Asp Val Ser Ile Glu Asp Ser Val Ile Ser Leu Ser Gly Asp His Cys
100 105 110

Ile Ile Gly Arg Thr Leu Val Val His Glu Lys Ala Asp Asp Leu Gly
115 120 125

Lys Gly Gly Asn Glu Glu Ser Thr Lys Thr Gly Asn Ala Gly Ser Arg
130 135 140

Leu Ala Cys Gly Val Ile Gly Ile Ala Gln
145 150

<210> SEQ ID NO 69
<211> LENGTH: 384
<212> TYPE: PRT
<213> ORGANISM: Artificial Sequence
<220> FEATURE:
<223> OTHER INFORMATION: Synthetic Construct

<400> SEQUENCE: 69

Met Pro Gln Leu Asp Ser Gly Gly Gly Gly Ala Gly Gly Gly Asp Asp
1 5 10 15

Leu Gly Ala Pro Asp Glu Leu Leu Ala Phe Gln Asp Glu Gly Glu Glu
20 25 30

Gln Asp Asp Lys Ser Arg Asp Ser Ala Ala Gly Pro Glu Arg Asp Leu
35 40 45

Ala Glu Leu Lys Ser Ser Leu Val Asn Glu Ser Glu Gly Ala Ala Gly
50 55 60

Gly Ala Gly Ile Pro Gly Val Pro Gly Ala Gly Ala Gly Ala Arg Gly
65 70 75 80

Glu Ala Glu Ala Leu Gly Arg Glu His Ala Ala Gln Arg Leu Phe Pro
85 90 95

Asp Lys Leu Pro Glu Pro Leu Glu Asp Gly Leu Lys Ala Pro Glu Cys
100 105 110

Thr Ser Gly Met Tyr Lys Glu Thr Val Tyr Ser Ala Phe Asn Leu Leu
115 120 125

Met His Tyr Pro Pro Pro Ser Gly Ala Gly Gln His Pro Gln Pro Gln
130 135 140

Pro Pro Leu His Lys Ala Asn Gln Pro Pro His Gly Val Pro Gln Leu
145 150 155 160

Ser Leu Tyr Glu His Phe Asn Ser Pro His Pro Thr Pro Ala Pro Ala
165 170 175

Asp Ile Ser Gln Lys Gln Val His Arg Pro Leu Gln Thr Pro Asp Leu
180 185 190

Ser Gly Phe Tyr Ser Leu Thr Ser Gly Ser Met Gly Gln Leu Pro His
195 200 205

Thr Val Ser Trp Phe Thr His Pro Ser Leu Met Leu Gly Ser Gly Val
210 215 220

Pro Gly His Pro Ala Ala Ile Pro His Pro Ala Ile Val Pro Pro Ser
225 230 235 240

Gly Lys Gln Glu Leu Gln Pro Phe Asp Arg Asn Leu Lys Thr Gln Ala
245 250 255

Glu Ser Lys Ala Glu Lys Glu Ala Lys Lys Pro Thr Ile Lys Lys Pro
260 265 270

```
Leu Asn Ala Phe Met Leu Tyr Met Lys Glu Met Arg Ala Lys Val Ile
        275                 280                 285

Ala Glu Cys Thr Leu Lys Glu Ser Ala Ala Ile Asn Gln Ile Leu Gly
    290                 295                 300

Arg Arg Trp His Ala Leu Ser Arg Glu Glu Gln Ala Lys Tyr Tyr Glu
305                 310                 315                 320

Leu Ala Arg Lys Glu Arg Gln Leu His Met Gln Leu Tyr Pro Gly Trp
                325                 330                 335

Ser Ala Arg Asp Asn Tyr Gly Lys Lys Lys Arg Arg Ser Arg Glu Lys
            340                 345                 350

His Gln Glu Ser Thr Thr Gly Gly Lys Arg Asn Ala Phe Gly Thr Tyr
        355                 360                 365

Pro Glu Lys Ala Ala Ala Pro Ala Pro Phe Leu Pro Met Thr Val Leu
    370                 375                 380


<210> SEQ ID NO 70
<211> LENGTH: 277
<212> TYPE: PRT
<213> ORGANISM: Artificial Sequence
<220> FEATURE:
<223> OTHER INFORMATION: Synthetic Construct

<400> SEQUENCE: 70

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255
```

```
Ser Ile Leu Ala Ala Val Val Val Gly Leu Val Ala Tyr Ile Ala Phe
            260                 265                 270

Lys Arg Trp Asn Ser
        275


<210> SEQ ID NO 71
<211> LENGTH: 243
<212> TYPE: PRT
<213> ORGANISM: Artificial Sequence
<220> FEATURE:
<223> OTHER INFORMATION: Synthetic Construct

<400> SEQUENCE: 71

Gly Ser Gly Gly Thr Ser Gly Ser Lys Gly Glu Glu Leu Phe Thr Gly
1               5                   10                  15

Val Val Pro Ile Leu Val Glu Leu Asp Gly Asp Val Asn Gly His Lys
            20                  25                  30

Phe Ser Val Arg Gly Glu Gly Glu Gly Asp Ala Thr Asn Gly Lys Leu
        35                  40                  45

Thr Leu Lys Phe Ile Cys Thr Thr Gly Lys Leu Pro Val Pro Trp Pro
    50                  55                  60

Thr Leu Val Thr Thr Leu Thr Tyr Gly Val Gln Cys Phe Ser Arg Tyr
65                  70                  75                  80

Pro Asp His Met Lys Arg His Asp Phe Phe Lys Ser Ala Met Pro Glu
                85                  90                  95

Gly Tyr Val Gln Glu Arg Thr Ile Ser Phe Lys Asp Asp Gly Thr Tyr
            100                 105                 110

Lys Thr Arg Ala Glu Val Lys Phe Glu Gly Asp Thr Leu Val Asn Arg
        115                 120                 125

Ile Glu Leu Lys Gly Ile Asp Phe Lys Glu Asp Gly Asn Ile Leu Gly
    130                 135                 140

His Lys Leu Glu Tyr Asn Phe Asn Ser His Asn Val Tyr Ile Thr Ala
145                 150                 155                 160

Asp Lys Gln Lys Asn Gly Ile Lys Ala Asn Phe Lys Ile Arg His Asn
                165                 170                 175

Val Glu Asp Gly Ser Val Gln Leu Ala Asp His Tyr Gln Gln Asn Thr
            180                 185                 190

Pro Ile Gly Asp Gly Pro Val Leu Leu Pro Asp Asn His Tyr Leu Ser
        195                 200                 205

Thr Gln Ser Val Leu Ser Lys Asp Pro Asn Glu Lys Arg Asp His Met
    210                 215                 220

Val Leu Leu Glu Phe Val Thr Ala Ala Gly Ile Thr Gly Thr Gly Ala
225                 230                 235                 240

Gly Ser Gly


<210> SEQ ID NO 72
<211> LENGTH: 249
<212> TYPE: PRT
<213> ORGANISM: Artificial Sequence
<220> FEATURE:
<223> OTHER INFORMATION: Synthetic Construct

<400> SEQUENCE: 72

Gly Ser Gly Gly Thr Ser Gly Val Ser Lys Gly Glu Glu Asp Asn Met
1               5                   10                  15

Ala Ile Ile Lys Glu Phe Met Arg Phe Lys Val His Met Glu Gly Ser
            20                  25                  30
```

```
Val Asn Gly His Glu Phe Glu Ile Glu Gly Glu Gly Glu Gly Arg Pro
        35                  40                  45

Tyr Glu Gly Thr Gln Thr Ala Lys Leu Lys Val Thr Lys Gly Gly Pro
    50                  55                  60

Leu Pro Phe Ala Trp Asp Ile Leu Ser Pro Gln Phe Met Tyr Gly Ser
65                  70                  75                  80

Lys Ala Tyr Val Lys His Pro Ala Asp Ile Pro Asp Tyr Leu Lys Leu
                85                  90                  95

Ser Phe Pro Glu Gly Phe Lys Trp Glu Arg Val Met Asn Phe Glu Asp
            100                 105                 110

Gly Gly Val Val Thr Val Thr Gln Asp Ser Ser Leu Gln Asp Gly Glu
        115                 120                 125

Phe Ile Tyr Lys Val Lys Leu Arg Gly Thr Asn Phe Pro Ser Asp Gly
    130                 135                 140

Pro Val Met Gln Lys Lys Thr Met Gly Trp Glu Ala Ser Ser Glu Arg
145                 150                 155                 160

Met Tyr Pro Glu Asp Gly Ala Leu Lys Gly Glu Ile Lys Gln Arg Leu
                165                 170                 175

Lys Leu Lys Asp Gly Gly His Tyr Asp Ala Glu Val Lys Thr Thr Tyr
            180                 185                 190

Lys Ala Lys Lys Pro Val Gln Leu Pro Gly Ala Tyr Asn Val Asn Ile
        195                 200                 205

Lys Leu Asp Ile Thr Ser His Asn Glu Asp Tyr Thr Ile Val Glu Gln
    210                 215                 220

Tyr Glu Arg Ala Glu Gly Arg His Ser Thr Gly Gly Met Asp Glu Leu
225                 230                 235                 240

Tyr Lys Gly Thr Gly Ala Gly Ser Gly
                245


<210> SEQ ID NO 73
<211> LENGTH: 150
<212> TYPE: PRT
<213> ORGANISM: Artificial Sequence
<220> FEATURE:
<223> OTHER INFORMATION: Synthetic Construct

<400> SEQUENCE: 73

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140
```

```
Gln Phe Gln Thr Leu Val
145                 150


<210> SEQ ID NO 74
<211> LENGTH: 21
<212> TYPE: PRT
<213> ORGANISM: Artificial Sequence
<220> FEATURE:
<223> OTHER INFORMATION: Synthetic Construct

<400> SEQUENCE: 74

Val Gly Val Val Gly Gly Leu Leu Gly Ser Leu Val Leu Leu Val Trp
1               5                   10                  15

Val Leu Ala Val Ile
            20


<210> SEQ ID NO 75
<211> LENGTH: 97
<212> TYPE: PRT
<213> ORGANISM: Artificial Sequence
<220> FEATURE:
<223> OTHER INFORMATION: Synthetic Construct

<400> SEQUENCE: 75

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu


<210> SEQ ID NO 76
<211> LENGTH: 163
<212> TYPE: PRT
<213> ORGANISM: Artificial Sequence
<220> FEATURE:
<223> OTHER INFORMATION: Synthetic Construct

<400> SEQUENCE: 76

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
```

```
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln


<210> SEQ ID NO 77
<211> LENGTH: 27
<212> TYPE: PRT
<213> ORGANISM: Artificial Sequence
<220> FEATURE:
<223> OTHER INFORMATION: Synthetic Construct

<400> SEQUENCE: 77

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25


<210> SEQ ID NO 78
<211> LENGTH: 42
<212> TYPE: PRT
<213> ORGANISM: Artificial Sequence
<220> FEATURE:
<223> OTHER INFORMATION: Synthetic Construct

<400> SEQUENCE: 78

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 79
<211> LENGTH: 120
<212> TYPE: PRT
<213> ORGANISM: Artificial Sequence
<220> FEATURE:
<223> OTHER INFORMATION: Synthetic Construct

<400> SEQUENCE: 79

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110
```

```
Ser Gln Leu Cys Cys Gln Leu Lys
        115                 120


<210> SEQ ID NO 80
<211> LENGTH: 21
<212> TYPE: PRT
<213> ORGANISM: Artificial Sequence
<220> FEATURE:
<223> OTHER INFORMATION: Synthetic Construct

<400> SEQUENCE: 80

Phe Trp Leu Pro Ile Gly Cys Ala Ala Phe Val Val Val Cys Ile Leu
1               5                   10                  15

Gly Cys Ile Leu Ile
            20


<210> SEQ ID NO 81
<211> LENGTH: 38
<212> TYPE: PRT
<213> ORGANISM: Artificial Sequence
<220> FEATURE:
<223> OTHER INFORMATION: Synthetic Construct

<400> SEQUENCE: 81

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35


<210> SEQ ID NO 82
<211> LENGTH: 126
<212> TYPE: PRT
<213> ORGANISM: Artificial Sequence
<220> FEATURE:
<223> OTHER INFORMATION: Synthetic Construct

<400> SEQUENCE: 82

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125


<210> SEQ ID NO 83
<211> LENGTH: 21
<212> TYPE: PRT
<213> ORGANISM: Artificial Sequence
<220> FEATURE:
<223> OTHER INFORMATION: Synthetic Construct
```

<400> SEQUENCE: 83

```
Phe Leu Leu Trp Ile Leu Ala Ala Val Ser Ser Gly Leu Phe Phe Tyr
1               5                   10                  15

Ser Phe Leu Leu Thr
            20
```

<210> SEQ ID NO 84
<211> LENGTH: 41
<212> TYPE: PRT
<213> ORGANISM: Artificial Sequence
<220> FEATURE:
<223> OTHER INFORMATION: Synthetic Construct

<400> SEQUENCE: 84

```
Ala Val Ser Leu Ser Lys Met Leu Lys Lys Arg Ser Pro Leu Thr Thr
1               5                   10                  15

Gly Val Tyr Val Lys Met Pro Pro Thr Glu Pro Glu Cys Glu Lys Gln
            20                  25                  30

Phe Gln Pro Tyr Phe Ile Pro Ile Asn
        35                  40
```

<210> SEQ ID NO 85
<211> LENGTH: 134
<212> TYPE: PRT
<213> ORGANISM: Artificial Sequence
<220> FEATURE:
<223> OTHER INFORMATION: Synthetic Construct

<400> SEQUENCE: 85

```
Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130
```

<210> SEQ ID NO 86
<211> LENGTH: 27
<212> TYPE: PRT
<213> ORGANISM: Artificial Sequence
<220> FEATURE:
<223> OTHER INFORMATION: Synthetic Construct

<400> SEQUENCE: 86

```
Phe Trp Val Leu Val Val Val Gly Gly Val Leu Ala Cys Tyr Ser Leu
1               5                   10                  15

Leu Val Thr Val Ala Phe Ile Ile Phe Trp Val
```

20 25

<210> SEQ ID NO 87
<211> LENGTH: 41
<212> TYPE: PRT
<213> ORGANISM: Artificial Sequence
<220> FEATURE:
<223> OTHER INFORMATION: Synthetic Construct

<400> SEQUENCE: 87

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 88
<211> LENGTH: 215
<212> TYPE: PRT
<213> ORGANISM: Artificial Sequence
<220> FEATURE:
<223> OTHER INFORMATION: Synthetic Construct

<400> SEQUENCE: 88

Gln Pro Asn Asn Ser Leu Met Leu Gln Thr Ser Lys Glu Asn His Ala
1 5 10 15

Leu Ala Ser Ser Ser Leu Cys Met Asp Glu Lys Gln Ile Thr Gln Asn
20 25 30

Tyr Ser Lys Val Leu Ala Glu Val Asn Thr Ser Trp Pro Val Lys Met
35 40 45

Ala Thr Asn Ala Val Leu Cys Cys Pro Pro Ile Ala Leu Arg Asn Leu
50 55 60

Ile Ile Ile Thr Trp Glu Ile Ile Leu Arg Gly Gln Pro Ser Cys Thr
65 70 75 80

Lys Ala Tyr Lys Lys Glu Thr Asn Glu Thr Lys Glu Thr Asn Cys Thr
85 90 95

Asp Glu Arg Ile Thr Trp Val Ser Arg Pro Asp Gln Asn Ser Asp Leu
100 105 110

Gln Ile Arg Thr Val Ala Ile Thr His Asp Gly Tyr Tyr Arg Cys Ile
115 120 125

Met Val Thr Pro Asp Gly Asn Phe His Arg Gly Tyr His Leu Gln Val
130 135 140

Leu Val Thr Pro Glu Val Thr Leu Phe Gln Asn Arg Asn Arg Thr Ala
145 150 155 160

Val Cys Lys Ala Val Ala Gly Lys Pro Ala Ala His Ile Ser Trp Ile
165 170 175

Pro Glu Gly Asp Cys Ala Thr Lys Gln Glu Tyr Trp Ser Asn Gly Thr
180 185 190

Val Thr Val Lys Ser Thr Cys His Trp Glu Val His Asn Val Ser Thr
195 200 205

Val Thr Cys His Val Ser His
210 215

<210> SEQ ID NO 89
<211> LENGTH: 21
<212> TYPE: PRT
<213> ORGANISM: Artificial Sequence
<220> FEATURE:

<223> OTHER INFORMATION: Synthetic Construct

<400> SEQUENCE: 89

Leu Thr Gly Asn Lys Ser Leu Tyr Ile Glu Leu Leu Pro Val Pro Gly
1 5 10 15

Ala Lys Lys Ser Ala
20

<210> SEQ ID NO 90
<211> LENGTH: 61
<212> TYPE: PRT
<213> ORGANISM: Artificial Sequence
<220> FEATURE:
<223> OTHER INFORMATION: Synthetic Construct

<400> SEQUENCE: 90

Lys Val Asn Gly Cys Arg Lys Tyr Lys Leu Asn Lys Thr Glu Ser Thr
1 5 10 15

Pro Val Val Glu Glu Asp Glu Met Gln Pro Tyr Ala Ser Tyr Thr Glu
20 25 30

Lys Asn Asn Pro Leu Tyr Asp Thr Thr Asn Lys Val Lys Ala Ser Glu
35 40 45

Ala Leu Gln Ser Glu Val Asp Thr Asp Leu His Thr Leu
50 55 60

<210> SEQ ID NO 91
<211> LENGTH: 127
<212> TYPE: PRT
<213> ORGANISM: Artificial Sequence
<220> FEATURE:
<223> OTHER INFORMATION: Synthetic Construct

<400> SEQUENCE: 91

Lys Glu Ser Cys Asp Val Gln Leu Tyr Ile Lys Arg Gln Ser Glu His
1 5 10 15

Ser Ile Leu Ala Gly Asp Pro Phe Glu Leu Glu Cys Pro Val Lys Tyr
20 25 30

Cys Ala Asn Arg Pro His Val Thr Trp Cys Lys Leu Asn Gly Thr Thr
35 40 45

Cys Val Lys Leu Glu Asp Arg Gln Thr Ser Trp Lys Glu Glu Lys Asn
50 55 60

Ile Ser Phe Phe Ile Leu His Phe Glu Pro Val Leu Pro Asn Asp Asn
65 70 75 80

Gly Ser Tyr Arg Cys Ser Ala Asn Phe Gln Ser Asn Leu Ile Glu Ser
85 90 95

His Ser Thr Thr Leu Tyr Val Thr Asp Val Lys Ser Ala Ser Glu Arg
100 105 110

Pro Ser Lys Asp Glu Met Ala Ser Arg Pro Trp Leu Leu Tyr Arg
115 120 125

<210> SEQ ID NO 92
<211> LENGTH: 21
<212> TYPE: PRT
<213> ORGANISM: Artificial Sequence
<220> FEATURE:
<223> OTHER INFORMATION: Synthetic Construct

<400> SEQUENCE: 92

Leu Leu Pro Leu Gly Gly Leu Pro Leu Leu Ile Thr Thr Cys Phe Cys
1 5 10 15

```
Leu Phe Cys Cys Leu
            20


<210> SEQ ID NO 93
<211> LENGTH: 111
<212> TYPE: PRT
<213> ORGANISM: Artificial Sequence
<220> FEATURE:
<223> OTHER INFORMATION: Synthetic Construct

<400> SEQUENCE: 93

Arg Arg His Gln Gly Lys Gln Asn Glu Leu Ser Asp Thr Ala Gly Arg
1               5                   10                  15

Glu Ile Asn Leu Val Asp Ala His Leu Lys Ser Glu Gln Thr Glu Ala
            20                  25                  30

Ser Thr Arg Gln Asn Ser Gln Val Leu Leu Ser Glu Thr Gly Ile Tyr
        35                  40                  45

Asp Asn Asp Pro Asp Leu Cys Phe Arg Met Gln Glu Gly Ser Glu Val
    50                  55                  60

Tyr Ser Asn Pro Cys Leu Glu Glu Asn Lys Pro Gly Ile Val Tyr Ala
65                  70                  75                  80

Ser Leu Asn His Ser Val Ile Gly Pro Asn Ser Arg Leu Ala Arg Asn
                85                  90                  95

Val Lys Glu Ala Pro Thr Glu Tyr Ala Ser Ile Cys Val Arg Ser
            100                 105                 110


<210> SEQ ID NO 94
<211> LENGTH: 181
<212> TYPE: PRT
<213> ORGANISM: Artificial Sequence
<220> FEATURE:
<223> OTHER INFORMATION: Synthetic Construct

<400> SEQUENCE: 94

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180
```

<210> SEQ ID NO 95
<211> LENGTH: 21
<212> TYPE: PRT
<213> ORGANISM: Artificial Sequence
<220> FEATURE:
<223> OTHER INFORMATION: Synthetic Construct

<400> SEQUENCE: 95

```
Ile Tyr Ile Gly Ala Gly Ile Cys Ala Gly Leu Ala Leu Ala Leu Ile
1               5                   10                  15

Phe Gly Ala Leu Ile
            20
```

<210> SEQ ID NO 96
<211> LENGTH: 78
<212> TYPE: PRT
<213> ORGANISM: Artificial Sequence
<220> FEATURE:
<223> OTHER INFORMATION: Synthetic Construct

<400> SEQUENCE: 96

```
Phe Lys Trp Tyr Ser His Ser Lys Glu Lys Ile Gln Asn Leu Ser Leu
1               5                   10                  15

Ile Ser Leu Ala Asn Leu Pro Pro Ser Gly Leu Ala Asn Ala Val Ala
            20                  25                  30

Glu Gly Ile Arg Ser Glu Glu Asn Ile Tyr Thr Ile Glu Glu Asn Val
        35                  40                  45

Tyr Glu Val Glu Glu Pro Asn Glu Tyr Tyr Cys Tyr Val Ser Ser Arg
    50                  55                  60

Gln Gln Pro Ser Gln Pro Leu Gly Cys Arg Phe Ala Met Pro
65                  70                  75
```

<210> SEQ ID NO 97
<211> LENGTH: 120
<212> TYPE: PRT
<213> ORGANISM: Artificial Sequence
<220> FEATURE:
<223> OTHER INFORMATION: Synthetic Construct

<400> SEQUENCE: 97

```
Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120
```

<210> SEQ ID NO 98
<211> LENGTH: 21

<212> TYPE: PRT
<213> ORGANISM: Artificial Sequence
<220> FEATURE:
<223> OTHER INFORMATION: Synthetic Construct

<400> SEQUENCE: 98

```
Leu Leu Gly Ala Met Ala Ala Thr Leu Val Val Ile Cys Thr Ala Val
1               5                   10                  15

Ile Val Val Val Ala
            20
```

<210> SEQ ID NO 99
<211> LENGTH: 82
<212> TYPE: PRT
<213> ORGANISM: Artificial Sequence
<220> FEATURE:
<223> OTHER INFORMATION: Synthetic Construct

<400> SEQUENCE: 99

```
Leu Thr Arg Lys Lys Lys Ala Leu Arg Ile His Ser Val Glu Gly Asp
1               5                   10                  15

Leu Arg Arg Lys Ser Ala Gly Gln Glu Glu Trp Ser Pro Ser Ala Pro
            20                  25                  30

Ser Pro Pro Gly Ser Cys Val Gln Ala Glu Ala Ala Pro Ala Gly Leu
        35                  40                  45

Cys Gly Glu Gln Arg Gly Glu Asp Cys Ala Glu Leu His Asp Tyr Phe
    50                  55                  60

Asn Val Leu Ser Tyr Arg Ser Leu Gly Asn Cys Ser Phe Phe Thr Glu
65                  70                  75                  80

Thr Gly
```

<210> SEQ ID NO 100
<211> LENGTH: 144
<212> TYPE: PRT
<213> ORGANISM: Artificial Sequence
<220> FEATURE:
<223> OTHER INFORMATION: Synthetic Construct

<400> SEQUENCE: 100

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140
```

<210> SEQ ID NO 101

```
<211> LENGTH: 21
<212> TYPE: PRT
<213> ORGANISM: Artificial Sequence
<220> FEATURE:
<223> OTHER INFORMATION: Synthetic Construct

<400> SEQUENCE: 101

Val Thr Gly Ile Ser Leu Leu Pro Pro Leu Gly Val Ala Ile Ser Val
1               5                   10                  15

Ile Ile Ile Phe Tyr
            20


<210> SEQ ID NO 102
<211> LENGTH: 380
<212> TYPE: PRT
<213> ORGANISM: Artificial Sequence
<220> FEATURE:
<223> OTHER INFORMATION: Synthetic Construct

<400> SEQUENCE: 102

Cys Tyr Arg Val Asn Arg Gln Gln Lys Leu Ser Ser Thr Trp Glu Thr
1               5                   10                  15

Gly Lys Thr Arg Lys Leu Met Glu Phe Ser Glu His Cys Ala Ile Ile
            20                  25                  30

Leu Glu Asp Asp Arg Ser Asp Ile Ser Ser Thr Cys Ala Asn Asn Ile
        35                  40                  45

Asn His Asn Thr Glu Leu Leu Pro Ile Glu Leu Asp Thr Leu Val Gly
    50                  55                  60

Lys Gly Arg Phe Ala Glu Val Tyr Lys Ala Lys Leu Lys Gln Asn Thr
65                  70                  75                  80

Ser Glu Gln Phe Glu Thr Val Ala Val Lys Ile Phe Pro Tyr Glu Glu
                85                  90                  95

Tyr Ala Ser Trp Lys Thr Glu Lys Asp Ile Phe Ser Asp Ile Asn Leu
            100                 105                 110

Lys His Glu Asn Ile Leu Gln Phe Leu Thr Ala Glu Glu Arg Lys Thr
        115                 120                 125

Glu Leu Gly Lys Gln Tyr Trp Leu Ile Thr Ala Phe His Ala Lys Gly
    130                 135                 140

Asn Leu Gln Glu Tyr Leu Thr Arg His Val Ile Ser Trp Glu Asp Leu
145                 150                 155                 160

Arg Lys Leu Gly Ser Ser Leu Ala Arg Gly Ile Ala His Leu His Ser
                165                 170                 175

Asp His Thr Pro Cys Gly Arg Pro Lys Met Pro Ile Val His Arg Asp
            180                 185                 190

Leu Lys Ser Ser Asn Ile Leu Val Lys Asn Asp Leu Thr Cys Cys Leu
        195                 200                 205

Cys Asp Phe Gly Leu Ser Leu Arg Leu Asp Pro Thr Leu Ser Val Asp
    210                 215                 220

Asp Leu Ala Asn Ser Gly Gln Val Gly Thr Ala Arg Tyr Met Ala Pro
225                 230                 235                 240

Glu Val Leu Glu Ser Arg Met Asn Leu Glu Asn Val Glu Ser Phe Lys
                245                 250                 255

Gln Thr Asp Val Tyr Ser Met Ala Leu Val Leu Trp Glu Met Thr Ser
            260                 265                 270

Arg Cys Asn Ala Val Gly Glu Val Lys Asp Tyr Glu Pro Pro Phe Gly
        275                 280                 285

Ser Lys Val Arg Glu His Pro Cys Val Glu Ser Met Lys Asp Asn Val
```

290 295 300

Leu Arg Asp Arg Gly Arg Pro Glu Ile Pro Ser Phe Trp Leu Asn His
305 310 315 320

Gln Gly Ile Gln Met Val Cys Glu Thr Leu Thr Glu Cys Trp Asp His
325 330 335

Asp Pro Glu Ala Arg Leu Thr Ala Gln Cys Val Ala Glu Arg Phe Ser
340 345 350

Glu Leu Glu His Leu Asp Arg Leu Ser Gly Arg Ser Cys Ser Glu Glu
355 360 365

Lys Ile Pro Glu Asp Gly Ser Leu Asn Thr Thr Lys
370 375 380

<210> SEQ ID NO 103
<211> LENGTH: 214
<212> TYPE: PRT
<213> ORGANISM: Artificial Sequence
<220> FEATURE:
<223> OTHER INFORMATION: Synthetic Construct

<400> SEQUENCE: 103

His Gly Thr Glu Leu Pro Ser Pro Pro Ser Val Trp Phe Glu Ala Glu
1 5 10 15

Phe Phe His His Ile Leu His Trp Thr Pro Ile Pro Asn Gln Ser Glu
20 25 30

Ser Thr Cys Tyr Glu Val Ala Leu Leu Arg Tyr Gly Ile Glu Ser Trp
35 40 45

Asn Ser Ile Ser Asn Cys Ser Gln Thr Leu Ser Tyr Asp Leu Thr Ala
50 55 60

Val Thr Leu Asp Leu Tyr His Ser Asn Gly Tyr Arg Ala Arg Val Arg
65 70 75 80

Ala Val Asp Gly Ser Arg His Ser Asn Trp Thr Val Thr Asn Thr Arg
85 90 95

Phe Ser Val Asp Glu Val Thr Leu Thr Val Gly Ser Val Asn Leu Glu
100 105 110

Ile His Asn Gly Phe Ile Leu Gly Lys Ile Gln Leu Pro Arg Pro Lys
115 120 125

Met Ala Pro Ala Asn Asp Thr Tyr Glu Ser Ile Phe Ser His Phe Arg
130 135 140

Glu Tyr Glu Ile Ala Ile Arg Lys Val Pro Gly Asn Phe Thr Phe Thr
145 150 155 160

His Lys Lys Val Lys His Glu Asn Phe Ser Leu Leu Thr Ser Gly Glu
165 170 175

Val Gly Glu Phe Cys Val Gln Val Lys Pro Ser Val Ala Ser Arg Ser
180 185 190

Asn Lys Gly Met Trp Ser Lys Glu Glu Cys Ile Ser Leu Thr Arg Gln
195 200 205

Tyr Phe Thr Val Thr Asn
210

<210> SEQ ID NO 104
<211> LENGTH: 21
<212> TYPE: PRT
<213> ORGANISM: Artificial Sequence
<220> FEATURE:
<223> OTHER INFORMATION: Synthetic Construct

<400> SEQUENCE: 104

```
Val Ile Ile Phe Phe Ala Phe Val Leu Leu Leu Ser Gly Ala Leu Ala
1               5                   10                  15

Tyr Cys Leu Ala Leu
            20


<210> SEQ ID NO 105
<211> LENGTH: 322
<212> TYPE: PRT
<213> ORGANISM: Artificial Sequence
<220> FEATURE:
<223> OTHER INFORMATION: Synthetic Construct

<400> SEQUENCE: 105

Gln Leu Tyr Val Arg Arg Arg Lys Lys Leu Pro Ser Val Leu Leu Phe
1               5                   10                  15

Lys Lys Pro Ser Pro Phe Ile Phe Ile Ser Gln Arg Pro Ser Pro Glu
            20                  25                  30

Thr Gln Asp Thr Ile His Pro Leu Asp Glu Glu Ala Phe Leu Lys Val
        35                  40                  45

Ser Pro Glu Leu Lys Asn Leu Asp Leu His Gly Ser Thr Asp Ser Gly
    50                  55                  60

Phe Gly Ser Thr Lys Pro Ser Leu Gln Thr Glu Glu Pro Gln Phe Leu
65                  70                  75                  80

Leu Pro Asp Pro His Pro Gln Ala Asp Arg Thr Leu Gly Asn Arg Glu
                85                  90                  95

Pro Pro Val Leu Gly Asp Ser Cys Ser Ser Gly Ser Ser Asn Ser Thr
            100                 105                 110

Asp Ser Gly Ile Cys Leu Gln Glu Pro Ser Leu Ser Pro Ser Thr Gly
        115                 120                 125

Pro Thr Trp Glu Gln Gln Val Gly Ser Asn Ser Arg Gly Gln Asp Asp
    130                 135                 140

Ser Gly Ile Asp Leu Val Gln Asn Ser Glu Gly Arg Ala Gly Asp Thr
145                 150                 155                 160

Gln Gly Gly Ser Ala Leu Gly His His Ser Pro Pro Glu Pro Glu Val
                165                 170                 175

Pro Gly Glu Glu Asp Pro Ala Ala Val Ala Phe Gln Gly Tyr Leu Arg
            180                 185                 190

Gln Thr Arg Cys Ala Glu Glu Lys Ala Thr Lys Thr Gly Cys Leu Glu
        195                 200                 205

Glu Glu Ser Pro Leu Thr Asp Gly Leu Gly Pro Lys Phe Gly Arg Cys
    210                 215                 220

Leu Val Asp Glu Ala Gly Leu His Pro Pro Ala Leu Ala Lys Gly Tyr
225                 230                 235                 240

Leu Lys Gln Asp Pro Leu Glu Met Thr Leu Ala Ser Ser Gly Ala Pro
                245                 250                 255

Thr Gly Gln Trp Asn Gln Pro Thr Glu Glu Trp Ser Leu Leu Ala Leu
            260                 265                 270

Ser Ser Cys Ser Asp Leu Gly Ile Ser Asp Trp Ser Phe Ala His Asp
        275                 280                 285

Leu Ala Pro Leu Gly Cys Val Ala Ala Pro Gly Gly Leu Leu Gly Ser
    290                 295                 300

Phe Asn Ser Asp Leu Val Thr Leu Pro Leu Ile Ser Ser Leu Gln Ser
305                 310                 315                 320

Ser Glu
```

<210> SEQ ID NO 106
<211> LENGTH: 207
<212> TYPE: PRT
<213> ORGANISM: Artificial Sequence
<220> FEATURE:
<223> OTHER INFORMATION: Synthetic Construct

<400> SEQUENCE: 106

```
Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205
```

<210> SEQ ID NO 107
<211> LENGTH: 24
<212> TYPE: PRT
<213> ORGANISM: Artificial Sequence
<220> FEATURE:
<223> OTHER INFORMATION: Synthetic Construct

<400> SEQUENCE: 107

```
Leu Leu Leu Gly Val Ser Val Ser Cys Ile Val Ile Leu Ala Val Cys
1               5                   10                  15

Leu Leu Cys Tyr Val Ser Ile Thr
            20
```

<210> SEQ ID NO 108
<211> LENGTH: 569
<212> TYPE: PRT
<213> ORGANISM: Artificial Sequence
<220> FEATURE:
<223> OTHER INFORMATION: Synthetic Construct

<400> SEQUENCE: 108

```
Lys Ile Lys Lys Glu Trp Trp Asp Gln Ile Pro Asn Pro Ala Arg Ser
1               5                   10                  15

Arg Leu Val Ala Ile Ile Ile Gln Asp Ala Gln Gly Ser Gln Trp Glu
            20                  25                  30
```

```
Lys Arg Ser Arg Gly Gln Glu Pro Ala Lys Cys Pro His Trp Lys Asn
        35                  40                  45

Cys Leu Thr Lys Leu Leu Pro Cys Phe Leu Glu His Asn Met Lys Arg
    50                  55                  60

Asp Glu Asp Pro His Lys Ala Ala Lys Glu Met Pro Phe Gln Gly Ser
65                  70                  75                  80

Gly Lys Ser Ala Trp Cys Pro Val Glu Ile Ser Lys Thr Val Leu Trp
                85                  90                  95

Pro Glu Ser Ile Ser Val Val Arg Cys Val Glu Leu Phe Glu Ala Pro
            100                 105                 110

Val Glu Cys Glu Glu Glu Glu Glu Val Glu Glu Glu Lys Gly Ser Phe
        115                 120                 125

Cys Ala Ser Pro Glu Ser Ser Arg Asp Asp Phe Gln Glu Gly Arg Glu
    130                 135                 140

Gly Ile Val Ala Arg Leu Thr Glu Ser Leu Phe Leu Asp Leu Leu Gly
145                 150                 155                 160

Glu Glu Asn Gly Gly Phe Cys Gln Gln Asp Met Gly Glu Ser Cys Leu
                165                 170                 175

Leu Pro Pro Ser Gly Ser Thr Ser Ala His Met Pro Trp Asp Glu Phe
            180                 185                 190

Pro Ser Ala Gly Pro Lys Glu Ala Pro Pro Trp Gly Lys Glu Gln Pro
        195                 200                 205

Leu His Leu Glu Pro Ser Pro Pro Ala Ser Pro Thr Gln Ser Pro Asp
    210                 215                 220

Asn Leu Thr Cys Thr Glu Thr Pro Leu Val Ile Ala Gly Asn Pro Ala
225                 230                 235                 240

Tyr Arg Ser Phe Ser Asn Ser Leu Ser Gln Ser Pro Cys Pro Arg Glu
                245                 250                 255

Leu Gly Pro Asp Pro Leu Leu Ala Arg His Leu Glu Glu Val Glu Pro
            260                 265                 270

Glu Met Pro Cys Val Pro Gln Leu Ser Glu Pro Thr Thr Val Pro Gln
        275                 280                 285

Pro Glu Pro Glu Thr Trp Glu Gln Ile Leu Arg Arg Asn Val Leu Gln
    290                 295                 300

His Gly Ala Ala Ala Ala Pro Val Ser Ala Pro Thr Ser Gly Tyr Gln
305                 310                 315                 320

Glu Phe Val His Ala Val Glu Gln Gly Gly Thr Gln Ala Ser Ala Val
                325                 330                 335

Val Gly Leu Gly Pro Pro Gly Glu Ala Gly Tyr Lys Ala Phe Ser Ser
            340                 345                 350

Leu Leu Ala Ser Ser Ala Val Ser Pro Glu Lys Cys Gly Phe Gly Ala
        355                 360                 365

Ser Ser Gly Glu Glu Gly Tyr Lys Pro Phe Gln Asp Leu Ile Pro Gly
    370                 375                 380

Cys Pro Gly Asp Pro Ala Pro Val Pro Val Pro Leu Phe Thr Phe Gly
385                 390                 395                 400

Leu Asp Arg Glu Pro Pro Arg Ser Pro Gln Ser Ser His Leu Pro Ser
                405                 410                 415

Ser Ser Pro Glu His Leu Gly Leu Glu Pro Gly Glu Lys Val Glu Asp
            420                 425                 430

Met Pro Lys Pro Pro Leu Pro Gln Glu Gln Ala Thr Asp Pro Leu Val
        435                 440                 445
```

```
Asp Ser Leu Gly Ser Gly Ile Val Tyr Ser Ala Leu Thr Cys His Leu
    450                 455                 460

Cys Gly His Leu Lys Gln Cys His Gly Gln Glu Asp Gly Gly Gln Thr
465                 470                 475                 480

Pro Val Met Ala Ser Pro Cys Cys Gly Cys Cys Cys Gly Asp Arg Ser
                485                 490                 495

Ser Pro Pro Thr Thr Pro Leu Arg Ala Pro Asp Pro Ser Pro Gly Gly
            500                 505                 510

Val Pro Leu Glu Ala Ser Leu Cys Pro Ala Ser Leu Ala Pro Ser Gly
        515                 520                 525

Ile Ser Glu Lys Ser Lys Ser Ser Ser Ser Phe His Pro Ala Pro Gly
    530                 535                 540

Asn Ala Gln Ser Ser Ser Gln Thr Pro Lys Ile Val Asn Phe Val Ser
545                 550                 555                 560

Val Gly Pro Thr Tyr Met Arg Val Ser
                565
```

<210> SEQ ID NO 109
<211> LENGTH: 25
<212> TYPE: PRT
<213> ORGANISM: Artificial Sequence
<220> FEATURE:
<223> OTHER INFORMATION: Synthetic Construct

<400> SEQUENCE: 109

```
Pro Ile Leu Leu Thr Ile Ser Ile Leu Ser Phe Phe Ser Val Ala Leu
1               5                   10                  15

Leu Val Ile Leu Ala Cys Val Leu Trp
            20                  25
```

<210> SEQ ID NO 110
<211> LENGTH: 195
<212> TYPE: PRT
<213> ORGANISM: Artificial Sequence
<220> FEATURE:
<223> OTHER INFORMATION: Synthetic Construct

<400> SEQUENCE: 110

```
Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
        115                 120                 125

Ser Gly Lys Asn Gly Pro His Val Tyr Gln Asp Leu Leu Leu Ser Leu
    130                 135                 140

Gly Thr Thr Asn Ser Thr Leu Pro Pro Pro Phe Ser Leu Gln Ser Gly
145                 150                 155                 160
```

```
Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195


<210> SEQ ID NO 111
<211> LENGTH: 148
<212> TYPE: PRT
<213> ORGANISM: Artificial Sequence
<220> FEATURE:
<223> OTHER INFORMATION: Synthetic Construct

<400> SEQUENCE: 111

Gln Val Thr Asp Ile Asn Ser Lys Gly Leu Glu Leu Arg Lys Thr Val
1               5                   10                  15

Thr Thr Val Glu Thr Gln Asn Leu Glu Gly Leu His His Asp Gly Gln
            20                  25                  30

Phe Cys His Lys Pro Cys Pro Pro Gly Glu Arg Lys Ala Arg Asp Cys
        35                  40                  45

Thr Val Asn Gly Asp Glu Pro Asp Cys Val Pro Cys Gln Glu Gly Lys
    50                  55                  60

Glu Tyr Thr Asp Lys Ala His Phe Ser Ser Lys Cys Arg Arg Cys Arg
65                  70                  75                  80

Leu Cys Asp Glu Gly His Gly Leu Glu Val Glu Ile Asn Cys Thr Arg
                85                  90                  95

Thr Gln Asn Thr Lys Cys Arg Cys Lys Pro Asn Phe Phe Cys Asn Ser
            100                 105                 110

Thr Val Cys Glu His Cys Asp Pro Cys Thr Lys Cys Glu His Gly Ile
        115                 120                 125

Ile Lys Glu Cys Thr Leu Thr Ser Asn Thr Lys Cys Lys Glu Glu Gly
    130                 135                 140

Ser Arg Ser Asn
145


<210> SEQ ID NO 112
<211> LENGTH: 17
<212> TYPE: PRT
<213> ORGANISM: Artificial Sequence
<220> FEATURE:
<223> OTHER INFORMATION: Synthetic Construct

<400> SEQUENCE: 112

Leu Gly Trp Leu Cys Leu Leu Leu Leu Pro Ile Pro Leu Ile Val Trp
1               5                   10                  15

Val


<210> SEQ ID NO 113
<211> LENGTH: 145
<212> TYPE: PRT
<213> ORGANISM: Artificial Sequence
<220> FEATURE:
<223> OTHER INFORMATION: Synthetic Construct

<400> SEQUENCE: 113

Lys Arg Lys Glu Val Gln Lys Thr Cys Arg Lys His Arg Lys Glu Asn
1               5                   10                  15

Gln Gly Ser His Glu Ser Pro Thr Leu Asn Pro Glu Thr Val Ala Ile
```

```
            20                  25                  30

Asn Leu Ser Asp Val Asp Leu Ser Lys Tyr Ile Thr Thr Ile Ala Gly
        35                  40                  45

Val Met Thr Leu Ser Gln Val Lys Gly Phe Val Arg Lys Asn Gly Val
    50                  55                  60

Asn Glu Ala Lys Ile Asp Glu Ile Lys Asn Asp Asn Val Gln Asp Thr
65                  70                  75                  80

Ala Glu Gln Lys Val Gln Leu Leu Arg Asn Trp His Gln Leu His Gly
                85                  90                  95

Lys Lys Glu Ala Tyr Asp Thr Leu Ile Lys Asp Leu Lys Lys Ala Asn
            100                 105                 110

Leu Cys Thr Leu Ala Glu Lys Ile Gln Thr Ile Ile Leu Lys Asp Ile
        115                 120                 125

Thr Ser Asp Ser Glu Asn Ser Asn Phe Arg Asn Glu Ile Gln Ser Leu
    130                 135                 140

Val
145
```

<210> SEQ ID NO 114
<211> LENGTH: 155
<212> TYPE: PRT
<213> ORGANISM: Artificial Sequence
<220> FEATURE:
<223> OTHER INFORMATION: Synthetic Construct

<400> SEQUENCE: 114

```
Ile Thr Gln Gln Asp Leu Ala Pro Gln Gln Arg Ala Ala Pro Gln Gln
1               5                   10                  15

Lys Arg Ser Ser Pro Ser Glu Gly Leu Cys Pro Pro Gly His His Ile
            20                  25                  30

Ser Glu Asp Gly Arg Asp Cys Ile Ser Cys Lys Tyr Gly Gln Asp Tyr
        35                  40                  45

Ser Thr His Trp Asn Asp Leu Leu Phe Cys Leu Arg Cys Thr Arg Cys
    50                  55                  60

Asp Ser Gly Glu Val Glu Leu Ser Pro Cys Thr Thr Thr Arg Asn Thr
65                  70                  75                  80

Val Cys Gln Cys Glu Glu Gly Thr Phe Arg Glu Glu Asp Ser Pro Glu
                85                  90                  95

Met Cys Arg Lys Cys Arg Thr Gly Cys Pro Arg Gly Met Val Lys Val
            100                 105                 110

Gly Asp Cys Thr Pro Trp Ser Asp Ile Glu Cys Val His Lys Glu Ser
        115                 120                 125

Gly Thr Lys His Ser Gly Glu Val Pro Ala Val Glu Glu Thr Val Thr
    130                 135                 140

Ser Ser Pro Gly Thr Pro Ala Ser Pro Cys Ser
145                 150                 155
```

<210> SEQ ID NO 115
<211> LENGTH: 21
<212> TYPE: PRT
<213> ORGANISM: Artificial Sequence
<220> FEATURE:
<223> OTHER INFORMATION: Synthetic Construct

<400> SEQUENCE: 115

```
Leu Ser Gly Ile Ile Ile Gly Val Thr Val Ala Ala Val Val Leu Ile
1               5                   10                  15
```

Val Ala Val Phe Val
20

<210> SEQ ID NO 116
<211> LENGTH: 209
<212> TYPE: PRT
<213> ORGANISM: Artificial Sequence
<220> FEATURE:
<223> OTHER INFORMATION: Synthetic Construct

<400> SEQUENCE: 116

Cys Lys Ser Leu Leu Trp Lys Lys Val Leu Pro Tyr Leu Lys Gly Ile
1 5 10 15

Cys Ser Gly Gly Gly Gly Asp Pro Glu Arg Val Asp Arg Ser Ser Gln
20 25 30

Arg Pro Gly Ala Glu Asp Asn Val Leu Asn Glu Ile Val Ser Ile Leu
35 40 45

Gln Pro Thr Gln Val Pro Glu Gln Glu Met Glu Val Gln Glu Pro Ala
50 55 60

Glu Pro Thr Gly Val Asn Met Leu Ser Pro Gly Glu Ser Glu His Leu
65 70 75 80

Leu Glu Pro Ala Glu Ala Glu Arg Ser Gln Arg Arg Arg Leu Leu Val
85 90 95

Pro Ala Asn Glu Gly Asp Pro Thr Glu Thr Leu Arg Gln Cys Phe Asp
100 105 110

Asp Phe Ala Asp Leu Val Pro Phe Asp Ser Trp Glu Pro Leu Met Arg
115 120 125

Lys Leu Gly Leu Met Asp Asn Glu Ile Lys Val Ala Lys Ala Glu Ala
130 135 140

Ala Gly His Arg Asp Thr Leu Tyr Thr Met Leu Ile Lys Trp Val Asn
145 150 155 160

Lys Thr Gly Arg Asp Ala Ser Val His Thr Leu Leu Asp Ala Leu Glu
165 170 175

Thr Leu Gly Glu Arg Leu Ala Lys Gln Lys Ile Glu Asp His Leu Leu
180 185 190

Ser Ser Gly Lys Phe Met Tyr Leu Glu Gly Asn Ala Asp Ser Ala Met
195 200 205

Ser

<210> SEQ ID NO 117
<211> LENGTH: 49
<212> TYPE: DNA
<213> ORGANISM: Artificial sequence
<220> FEATURE:
<223> OTHER INFORMATION: Synthetic construct

<400> SEQUENCE: 117
aatgatacgg cgaccaccga gatctacact ctttccctac acgacgctc 49

<210> SEQ ID NO 118
<211> LENGTH: 62
<212> TYPE: DNA
<213> ORGANISM: Artificial sequence
<220> FEATURE:
<223> OTHER INFORMATION: Synthetic construct

<400> SEQUENCE: 118

```
gtgactggag ttcagacgtg tgctcttccg atctgaggaa ccagccttat tgttcatccg     60

ta                                                                   62
```

POOLED KNOCK-IN SCREENING AND HETEROLOGOUS POLYPEPTIDES CO-EXPRESSED UNDER THE CONTROL OF ENDOGENOUS LOCI

PRIOR RELATED APPLICATIONS

This application claims the benefit of U.S. Provisional Application No. 62/818,535, filed on Mar. 14, 2019, U.S. Provisional Application No. 62/818,578, filed on Mar. 14, 2019, U.S. Provisional Application No. 62/871,309, filed on Jul. 8, 2019, U.S. Provisional Application No. 62/871,467, filed on Jul. 8, 2019, all of which are hereby incorporated by reference in their entireties.

BACKGROUND OF THE INVENTION

Immune cellular therapies have been in development for over thirty years. The evolution from traditional randomly integrating viral gene modification methods to targeted non-viral integrations holds great promise for further unlocking the potential of cellular immunotherapies. However, crucial engineering challenges unique to targeted integrations remain, such as predicting efficiency across different target sites and developing high throughput screening platforms for rapid testing of pooled DNA sequences targeted for insertion into a genomic locus in a cell. There are limited options for rapidly identifying targeted genomic integrations in cells.

Further, current techniques for modification of ex vivo or intravitally gene edited cells for therapeutic use have focused on correction of an existing mutation, limiting therapeutic applicability to conditions caused by a single mutation resulting in a misfunctioning gene, or on integrating an entirely new synthetic gene, requiring extensive research and development into creating a new therapeutically useful synthetic DNA sequence. Therefore, there are limited options for genomic modifications. Given the importance of T cells in adoptive cellular therapeutics, the ability to obtain human T cells and modify them to produce edited T cells with desirable function(s) could be beneficial in the development and application of adoptive T cell therapies.

BRIEF SUMMARY OF THE INVENTION

Pooled Knock-In Screening

The present disclosure is directed to compositions and methods for identifying a targeted insertion in the genome of a cell. The inventors have discovered a pooled knockin screening method to rapidly assay many targeted knockins in a pooled cell population. Identification of targeted integrations is made possible by a DNA sequencing strategy that selectively amplifies on-target knockins (constructs, optionally encoding a heterologous polypeptide, that insert at the desired locus) while avoiding constructs that are not integrated into the cells' genome. Because the homology arms of an (homology-directed repair) HDR template are used for complementary base pairing with the target locus but are not themselves copied into the target site, a short region of DNA base pair mismatches with the target genomic locus can be introduced into one or both homology arms that flank an HDR template. The region of mismatches is not introduced into the target site upon HDR, creating a sequence easily detectable by amplification (e.g., PCR) that is unique to on-target knockins (those constructs not knocked in will contain the template mismatch and thus will not be amplified). See, for example, FIG. 15*a*. Sequencing of the resulting amplicons provides information regarding the abundance of different knockins (more sequence for a particular knockin indicates higher abundance of the cells having the knockin relative to other knockins, providing information about the effect of knockins in a biological system). In some embodiments, addition of a barcode unique for each HDR template enables a DNA readout of the abundance of each individual insert in the pooled population based on the identity of the barcode. The compositions and methods provided herein can be used to identify targeted genomic integrations in any cell, for example, a T cell. For example, as discussed below, in some embodiments, one can use the described methods to assay the effect of different heterologous knockins at a T-cell receptor (TCR) locus, optionally co-expressed as a single protein with an endogenous or heterologous TCR protein, which is subsequently self-cleaved to generate separate heterologous knockin polyopeptide and the endogenous or heterologous TCR protein. The same strategy can be applied to any desired locus in a cell.

Provided herein is a method for identifying a targeted insertion in the genome of a cell. In some embodiments, the method comprises (a) introducing into a population of cells (i) a targeted nuclease that cleaves a target region in the genome of the cell to create a target insertion site; and (ii) a plurality of DNA templates that are different by sequence from each other, wherein each DNA template comprises: i. a heterologous coding or noncoding nucleic acid sequence; ii. a unique barcode nucleotide sequence that indicates the identity of the heterologous coding or noncoding nucleic acid sequence; and iii. a common primer binding sequence, wherein the 5' and 3' ends of each DNA template comprise nucleotide sequences that are homologous to genomic sequences flanking the insertion site, and wherein one or both homologous nucleotide sequences comprise a mismatched nucleotide sequence compared to a homologous sequence in the genomic sequence, wherein the mismatched nucleotide sequence is not inserted into the target insertion site during recombination; (b) allowing recombination to occur, thereby creating a population of modified cells; (c) amplifying DNA from the cells with a pair of primers to form amplified DNA, wherein a first primer is complementary to the common primer binding sequence, and wherein a second primer binds to the homologous sequence in the genomic sequence flanking the insertion site and does not bind to the mismatched nucleotide sequence in the DNA template; or wherein a first primer binds to a first homologous sequence in a 5' genomic region flanking the insertion site and does not bind to a mismatched sequence in the DNA template at the same location as the first homologous sequence and a second primer binds to a 3' genomic region flanking the insertion site and does not bind to a mismatched nucleotide sequence in the DNA template at the same location as the second homologous sequence; and (f) sequencing the amplified DNA to identify a DNA template inserted into the target insertion site for a cell.

In some embodiments, the mismatched nucleotide sequence is about 3 to 40 nucleotides in length. In some embodiments, the barcode sequence is in the amplified DNA and is sequenced.

In some embodiments, the method further comprising determining the relative number of cells in the population having different DNA templates inserted in the target insertion site. In some embodiments, the method further comprises applying a selective pressure to the population of modified cells.

In some embodiments, the method further comprises comparing the relative number of cells in the population having different DNA templates inserted in the target insertion site before and after applying the selective pressure to the cells.

In some embodiment, the DNA template is inserted by introducing a viral vector comprising the DNA template into the cell.

In some embodiments, the population is a population of mammalian cells. In some embodiments, the mammalian cells are human cells. In some embodiments, the human cells are T cells, B cells, natural killer (NK) cells, myeoild cells or other immune cells. In some embodiments, the T cells are regulatory T cells, effector T cells or naïve T cells. In some embodiments, the effector T cells are CD8+ T cells or CD4+ T cells. In some embodiments, the effector T cells are CD8+ CD4+ T cells. In some embodiments, the cells are primary cells.

In some embodiments, the DNA template comprises a nucleic acid encoding a heterologous polypeptide. In some embodiments, the DNA template comprises any one of the nucleic acid constructs described herein.

In some embodiments, the target insertion site is in exon 1 of a TCR-alpha subunit constant gene (TRAC) or exon 1 of a TCR-beta subunit constant gene (TRBC). In some embodiments, the genomic sequences are human T-cell TCR locus sequences.

In some embodiments, the targeted nuclease is selected from the group consisting of an RNA-guided nuclease domain, a transcription activator-like effector nuclease (TALEN), a zinc finger nuclease (ZFN) and a megaTAL. In some embodiments, the targeted nuclease, a guide RNA and the DNA template are introduced into the cell as a ribonucleoprotein complex (RNP)-DNA template complex, wherein the RNP-DNA template complex comprises: (i) the RNP, wherein the RNP comprises the targeted nuclease and the guide RNA; and (ii) the DNA template.

Also provided herein is a nucleic acid construct comprising a coding nucleotide sequence that encodes a polypeptide, wherein the 5' and 3' ends of each DNA template comprise nucleotide sequences that are homologous to genomic sequences flanking the insertion site in the genome of a cell, wherein one or both homologous nucleotide sequences comprise a mismatched nucleotide sequence compared to a homologous genomic sequence in the cell; and wherein the length of the mismatched nucleotide sequence is sufficient to prevent binding of a primer that specifically binds to the genomic sequence corresponding to the mismatched nucleotide sequence.

In some embodiments, the coding nucleotide sequence comprises two heterologous coding sequences joined by a coding sequence for a coding sequence for a self-cleaving peptide. In some embodiments, the length of the mismatched nucleotide sequence is about 3 to about 40 nucleotides. In some embodiments, the nucleic acid construct encodes, in the following order, (i) a first self-cleaving peptide sequence; (ii) a first heterologous TCR subunit chain, wherein the TCR subunit chain comprises the variable region and the constant region of the TCR subunit; (iii) a second self-cleaving peptide sequence; (iv) a polypeptide; (v) a third self-cleaving peptide sequence; (vi) a variable region of a second heterologous TCR subunit chain; and (vii) a portion of the N-terminus of an endogenous TCR subunit, wherein the nucleic acid construct comprises a barcode sequence, wherein the insertion sequence is a TCR locus of a T-cell, wherein one or both homologous nucleotide sequence comprise a mismatched nucleotide sequence, and wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct encodes, in the following order, (i) a first self-cleaving peptide sequence; (ii) a polypeptide; (iii) a second self-cleaving peptide sequence; (iv) a first heterologous TCR subunit chain, wherein the TCR subunit chain comprises the variable region and the constant region of the TCR subunit; (v) a third self-cleaving peptide sequence; (vi) a variable region of a second heterologous TCR subunit chain; and (vii) a portion of the N-terminus of an endogenous TCR subunit, wherein the nucleic acid construct comprises a barcode sequence, wherein the insertion sequence is a TCR locus of a human T-cell, wherein one or both homologous nucleotide sequence comprise a mismatched nucleotide sequence, and wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct encodes, in the following order, (i) a first self-cleaving peptide sequence; (ii) a first heterologous TCR subunit chain, wherein the TCR subunit chain comprises the variable region and the constant region of the TCR subunit; (iii) a second self-cleaving peptide sequence; (iv) a second heterologous TCR subunit chain, wherein the TCR subunit chain comprises the variable region and the constant region of the TCR subunit; (v) a third self-cleaving peptide sequence; (vi) a polypeptide; and (vii) a fourth self-cleaving peptide sequence or a poly A sequence, wherein the nucleic acid construct comprises a barcode sequence, insertion sequence is a TCR locus of a human T-cell, wherein one or both homologous nucleotide sequence comprise a mismatched nucleotide sequence, and wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct encodes, in the following order, (i) a first self-cleaving peptide sequence; (ii) a synthetic antigen receptor; (iii) a second self-cleaving peptide sequence; (iv) a heterologous polypeptide; and (v) a third self-cleaving peptide sequence or a polyA sequence, wherein the nucleic acid construct comprises a barcode sequence, wherein the insertion sequence is a TCR locus of a human T-cell.

In some embodiments, the nucleic acid construct encodes, in the following order, (i) a first self-cleaving peptide sequence; (ii) a polypeptide; (iii) a second self-cleaving peptide sequence; (iv) a synthetic antigen receptor; and (v) a third self-cleaving peptide sequence or a polyA sequence, wherein the nucleic acid construct comprises a barcode sequence, wherein the insertion sequence is a TCR locus of a human T-cell.

In some embodiments, the nucleic acid construct encodes, in the following order, (i) a first self-cleaving peptide sequence; (ii) a first TCR β or α subunit chain, wherein the TCR subunit chain comprises the variable region and the constant region of the TCR subunit chain; (iii) a second self-cleaving peptide sequence; (iv) a second TCR β or α subunit chain, wherein the second TCR subunit chain is different from the first TCR subunit chain, wherein the TCR subunit chain comprises the variable region and the constant region of the TCR subunit; or the TCR subunit comprises the variable region of the subunit; and (v) a third self-cleaving peptide sequence or a polyA sequence, wherein the nucleic acid construct comprises a barcode sequence, wherein the insertion sequence is a TCR locus of a human T-cell.

In some embodiments, the nucleic acid construct encodes, in the following order, (i) a first self-cleaving peptide sequence; (ii) a synthetic antigen receptor; and (v) a second self-cleaving peptide sequence or a polyA sequence, wherein the nucleic acid construct comprises a barcode sequence, wherein the insertion sequence is a TCR locus of a human T-cell.

In some embodiments, the nucleic acid construct encodes a synthetic antigen receptor, wherein the synthetic antigen receptor is a chimeric antigen receptor (CAR) or a SynNotch receptor.

In some embodiments, any one of the nucleic acid constructs described herein comprises a barcode sequence indicating the identity of the polypeptide. In some embodiments, the nucleic acid construct comprises a pair of unique barcodes that flank the nucleotide sequence encoding the polypeptide (i.e., a barcode sequence is located on either side of the nucleotide sequence encoding the polypepide, wherein each barcode has a different sequence). In some embodiments, the one or more barcodes are located before, after or in the self-cleaving peptide sequence or a polyA sequence.

In some embodiments, the nucleic acid construct comprises one or more linker sequences separate the components of the nucleic acid construct. In some embodiments, the one or more linker sequences have the same sequence.

Also provided is a library comprising two or more nucleic acid constructs described herein, wherein each construct encodes a different polypeptide.

Also provided is a population of cells comprising any of the libraries described herein. Further provided is a cell comprising one or more of the nucleic constructs described herein. In some embodiments, the cell is a human T-cell.

Also provided is a method for determining a transcriptome of cells having a specific DNA template comprising:

(a) introducing into a population of cells (i) a targeted nuclease that cleaves a target region in the genome of the cell to create a target insertion site; and (ii) a plurality of DNA templates that are different by sequence from each other, wherein each DNA template comprises:

i. a heterologous coding or noncoding nucleic acid sequence;

ii. a unique barcode nucleotide sequence that indicates the identity of the heterologous coding or noncoding nucleic acid sequence; and iii. a common primer binding sequence, wherein the 5' and 3' ends of each DNA template comprise nucleotide sequences that are homologous to genomic sequences flanking the target insertion site, and wherein neither, one or both homologous nucleotide sequences comprise a mismatched nucleotide sequence compared to a homologous sequence in the genomic sequence, wherein the mismatched nucleotide sequence is not inserted into the target insertion site during recombination;

(b) allowing recombination to occur, thereby creating a population of modified cells;

(c) before or after the introducing, the allowing, or both, partitioning the cells into partitions, wherein at least a majority of the partitions contain a single cell;

(d) in the partitions, generating cDNA from mRNA in the cells by extending an oligonucleotide that is complementary to the mRNA, wherein the oligonucleotide comprises a partition-specific barcode, thereby forming a pool of cDNAs linked to a partition-specific barcode;

(e) combining contents of the partitions to form a mixture of cDNAs from multiple cells;

(f) from a first aliquot of the mixture of cDNAs, amplifying at least a dual barcode portion of the cDNA that comprises the unique barcode and the partition-specific barcode;

(g) performing nucleotide sequencing of the dual barcode portion to generate sequencing reads comprising the unique barcode and the partition-specific barcode;

(h) from the first aliquot or a second aliquot of the pool of cDNAs, performing nucleotide sequencing of cDNAs in the pool, thereby generating sequencing reads comprising partition-specific barcodes and sequences from a plurality of cDNAs, (i) correlating unique barcode sequences with partition-specific barcode sequences based on the dual barcode portion sequencing reads, thereby forming an association of a specific DNA template with a partition-specific barcode; and (j) correlating sequencing reads from the second aliquot to specific templates using the association of (i), thereby providing a transcriptome of cells having a specific DNA template.

In some embodiments, contents of the partitions are combined before the performing and before or after the amplifying.

In some embodiments, the method further comprises determining the relative number of cells in the population having different DNA templates inserted in the target insertion site.

In some embodiments, the method further comprises applying a selective pressure to the population of modified cells.

In some embodiments, the method further comprises comparing the relative number of cells in the population having different DNA templates inserted in the target insertion site before and after applying the selective pressure to the cells.

In some embodiments, the DNA template is inserted by introducing a viral vector comprising the DNA template into the cell.

In some embodiments, the population is a population of mammalian cells. In some embodiments, the mammalian cells are human cells.

In some embodiments, the human cells are T cells, B cells, natural killer (NK) cells, myeoild cells or other immune cells.

In some embodiments, the T cells are regulatory T cells, effector T cells or naïve T cells.

In some embodiments, the effector T cells are CD8+ T cells or CD4+ T cells.

In some embodiments, the effector T cells are CD8+ CD4+ T cells.

In some embodiments, the cells are primary cells.

In some embodiments, the DNA template comprises a nucleic acid encoding a heterologous polypeptide.

In some embodiments, the target insertion site is in exon 1 of a TCR-alpha subunit constant gene (TRAC) or exon 1 of a TCR-beta subunit constant gene (TRBC).

In some embodiments, the genomic sequences are human T-cell TCR locus sequences.

In some embodiments, the targeted nuclease is selected from the group consisting of an RNA-guided nuclease domain, a transcription activator-like effector nuclease (TALEN), a zinc finger nuclease (ZFN) and a megaTAL.

In some embodiments, the targeted nuclease, a guide RNA and the DNA template are introduced into the cell as a ribonucleoprotein complex (RNP)-DNA template complex, wherein the RNP-DNA template complex comprises: (i) the RNP, wherein the RNP comprises the targeted nuclease and the guide RNA; and (ii) the DNA template.

Heterologous Polypeptides Co-Expressed Under the Control of Endogenous Loci

The present disclosure is also directed to compositions and methods for modifying the genome of a T cell. The inventors have discovered that human T cells can be modified to alter T cell specificity and function. By inserting a nucleic acid encoding a polypeptide and a heterologous T cell receptor (TCR) or a synthetic antigen receptor (e.g., a chimeric antigen receptor (CAR)) into a specific endogenous site in the genome of the T cell, (e.g., a TCR locus), human T cells having the desired antigen specificity of the TCR or CAR and the function of the polypeptide can be made. Further, the compositions and methods described herein can be used to generate human T cells with altered specificity and functionality, while limiting the side effects associated with T cell therapies.

Provided herein is a human T cell that heterologously expresses a polypeptide, wherein the polypeptide is encoded by a nucleic acid construct inserted into the TCR locus of the cell. In some embodiments, the polypeptide is a truncated human PD-1 protein comprising the human PD-1 extracellular domain and transmembrane domain and lacking 80-90 (e.g., 87) carboxyl terminal PD-1 amino acids.

In some embodiments, the polypeptide comprises a human PD-1 extracellular domain or portion thereof of at least 120 or 130 amino acids (and optionally 1-20 (e.g., 11) amino acids of the 4-1BB extracellular domain) linked to a human 4-1BB intracellular domain via a transmembrane domain. In some embodiments, the polypeptide comprises a human PD-1 extracellular domain linked to a human MyD88 intracellular domain or a portion thereof of at least 90 or 100 amino acids (and optionally 1-10 amino acids of the PD-1 intracellular domain) via a transmembrane domain.

In some embodiments, the polypeptide comprises a human PD-1 extracellular domain linked to a human ICOS intracellular domain via a transmembrane domain. In some embodiments, the transmembrane domain is a human ICOS or PD-1 transmembrane domain.

In some embodiments, the polypeptide is a truncated human CTLA4 protein comprising the human CTLA4 extracellular domain and transmembrane domain and lacking 30-40 (e.g., 34) carboxyl terminal CTLA4 amino acids. In some embodiments, the truncated human CTLA4 protein comprises the first 1-12 (e.g., 6) amino acids of the human CTLA4 intracellular domain but lacks the remaining human CTLA4 protein intracellular domain.

In some embodiments, the polypeptide comprises a human CTLA4 extracellular domain linked to a human CD28 intracellular domain or a portion thereof of at least 30 or 40 amino acids (and optionally 1-10 amino acids of the CTLA4 intracellular domain) via a transmembrane domain.

In some embodiments, the polypeptide is a truncated human CD200R protein comprising the human CD200R extracellular domain and transmembrane domain and lacking 50-60 carboxyl terminal CD200R amino acids. In some embodiments, the truncated human CD200R protein comprises the first 1-12 (e.g., 6) amino acids of the human CD200R intracellular domain but lacks the remaining human CD200R protein intracellular domain.

In some embodiments, the polypeptide is a truncated human BTLA protein comprising the human BTLA extracellular domain and transmembrane domain and lacking 100-110 (e.g., 104) carboxyl terminal BTLA amino acids. In some embodiments, the truncated human BTLA protein comprises the first 1-12 (e.g., 6) amino acids of the human BTLA intracellular domain but lacks the remaining human BTLA protein intracellular domain.

In some embodiments, the polypeptide comprises a human BTLA extracellular domain or a portion thereof of at least 110 or 120 amino acids (and optionally 1-20 amino acids of the CD28 extracellular domain) linked to a human CD28 intracellular domain via a transmembrane domain.

In some embodiments, the polypeptide is a truncated human TIM-3 protein comprising the human TIM-3 extracellular domain and transmembrane domain and lacking 65-75 (e.g., 71) carboxyl terminal TIM-3 amino acids. In some embodiments, the truncated human TIM-3 protein comprises the first 1-12 (e.g., 6) amino acids of the human TIM-3 intracellular domain but lacks the remaining human TIM-3 protein intracellular domain.

In some embodiments, the polypeptide comprises a human TIM-3 extracellular domain or a portion thereof of at least 160 or 170 amino acids (and optionally 1-20 amino acids of the CD28 extracellular domain) linked to a human CD28 intracellular domain via a transmembrane domain.

In some embodiments, the polypeptide is a truncated human TIGIT protein comprising the human TIGIT extracellular domain and transmembrane domain and lacking 70-80 (e.g., 75) carboxyl terminal TIGIT amino acids. In some embodiments, the truncated human TIGIT protein comprises the first 1-12 (e.g., 6) amino acids of the human TIGIT intracellular domain but lacks the remaining human TIGIT protein intracellular domain.

In some embodiments, the polypeptide comprises a human TIGIT extracellular domain or a portion thereof of at least 100 or 110 amino acids (and optionally 1-20 amino acids of the CD28 extracellular domain) linked to a human CD28 intracellular domain via a transmembrane domain. In some embodiments, the transmembrane domain is a human CD28 or TIGIT transmembrane domain.

In some embodiments, the polypeptide is a truncated human TGFβR2 protein comprising the human TGFβR2 extracellular domain and transmembrane domain and lacking 360-370 (e.g., 366) carboxyl terminal TGFβR2 amino acids. In some embodiments, the truncated human TGFβR2 protein comprises the first 1-20 (e.g., 13) amino acids of the human TGFβR2 intracellular domain but lacks the remaining human TGFβR2 protein intracellular domain.

In some embodiments, the polypeptide comprises a human TGFβR2 extracellular domain or a portion thereof of at least 130 or 140 amino acids (and optionally 1-20 amino acids of the 4-1BB extracellular domain) linked to a human 4-1BB intracellular domain via a transmembrane domain. In some embodiments, the transmembrane domain is a human 4-1BB or TGFβR2 transmembrane domain.

In some embodiments, the polypeptide comprises a human TGFβR2 extracellular domain linked to a human Myd88 intracellular domain or a portion thereof of at least 90 or 100 amino acids (and optionally 1-20 amino acids of the TGFβR2 intracellular domain) via a transmembrane domain.

In some embodiments, the polypeptide comprises a truncated human IL-10RA protein comprising the human IL-10RA extracellular domain and transmembrane domain and lacking 310-320 (e.g., 315) carboxyl terminal IL-10RA amino acids. In some embodiments, the truncated human IL-10RA protein comprises the first 1-20 (e.g., 13) amino acids of the human IL-10RA intracellular domain but lacks the remaining human IL-10RA protein intracellular domain.

In some embodiments, the polypeptide comprises a human IL-10RA extracellular domain linked to a human IL-7RA intracellular domain via a transmembrane domain. In some embodiments, the transmembrane domain comprises a human IL-7RA or IL-10RA transmembrane domain or a portion thereof at least 20 amino acids long.

In some embodiments, the polypeptide comprises a human IL-4RA extracellular domain linked to a human IL-7RA intracellular domain via a transmembrane domain. In some embodiments, the transmembrane domain comprises a human IL-7RA or IL-4RA transmembrane domain or a portion thereof at least 20 amino acids long.

In some embodiments, the polypeptide is a truncated human Fas protein comprising the human Fas extracellular domain and transmembrane domain and lacking 132-142 (e.g., 138) carboxyl terminal Fas amino acids. In some embodiments, the truncated human Fas protein comprises the first 1-12 (e.g., 6) amino acids of the human Fas intracellular domain but lacks the remaining human Fas protein intracellular domain.

In some embodiments, the polypeptide comprises a human Fas extracellular domain linked to a human CD28 intracellular domain or a portion thereof of at least 30 or 40 amino acids (and optionally 1-20 amino acids of the Fas intracellular domain) via a transmembrane domain. In some embodiments, the transmembrane domain is a human Fas or CD28 transmembrane domain.

In some embodiments, the polypeptide comprises a human Fas extracellular domain linked to a human 41BB intracellular domain or a portion thereof of at least 30 or 40 amino acids (and optionally 1-20 amino acids of the Fas intracellular domain) via a transmembrane domain.

In some embodiments, the polypeptide comprises a human Fas extracellular domain linked to a human MyD88 intracellular domain or a portion thereof of at least 90 or 100 amino acids (and optionally 1-20 amino acids of the Fas intracellular domain) via a transmembrane domain. In some embodiments the polypeptide comprises or consists of SEQ ID NO: 62. In some embodiments, the transmembrane domain is a human Fas or MyD88 transmembrane domain.

In some embodiments, the polypeptide comprises a human Fas extracellular domain linked to a human ICOS intracellular domain or a portion thereof of at least 25 or 35 amino acids (and optionally 1-20 amino acid of the Fas intracellular domain) via a transmembrane domain. In some embodiments, the transmembrane domain is a human Fas or ICOS transmembrane domain.

In some embodiments, the polypeptide is a truncated human TRAIL-R2 protein comprising the human TRAIL-R2 extracellular domain and transmembrane domain and lacking 196-206 (e.g., 202) carboxyl terminal TRAIL-R2 amino acids. In some embodiments, the truncated human TRAIL-R2 protein comprises the first 1-12 (e.g., 6) amino acids of the human TRAIL-R2 intracellular domain but lacks the remaining human TRAIL-R2 protein intracellular domain.

In some embodiments, the polypeptide comprises a human TRAIL-R2 extracellular domain linked to a human CD28 intracellular domain or a portion thereof of at least 30 or 40 amino acids (and optionally 1-20 amino acids of the TRAIL-R2 intracellular domain) via a transmembrane domain. In some embodiments, the transmembrane domain is a human TRAIL-R2 or CD28 transmembrane domain. In some embodiments, the polypeptide comprises a full-length CCR10, MCT4, SOD1, TCF7, IL-2RA, IL-7RA or 41BB protein.

In some embodiments, the T cell heterologously expresses a polypeptide comprising an amino acid sequence that is at least 95% identical to an amino acid sequence selected from the group consisting of SEQ ID NO: 42, SEQ ID NO: 45, SEQ ID NO: 47, SEQ ID NO: 50, SEQ ID NO: 51, SEQ ID NO: 52, SEQ ID NO: 56, SEQ ID NO: 57, SEQ ID NO: 59, SEQ ID NO: 61, SEQ ID NO: 62, SEQ ID NO: 63, SEQ ID NO: 67, and SEQ ID NO: 69, set forth in Table 3.

In some embodiments, the target insertion site is in exon 1 of a TCR-alpha subunit constant gene (TRAC). In some embodiments, the target insertion site is in exon 1 of a TCR-beta subunit constant gene (TRBC).

In some embodiments, the heterologous nucleic acid construct comprises a nucleic acid sequence that is at least 95% identical to a nucleic acid sequence selected from the consisting of SEQ ID NO: 6, SEQ ID NO: 9, SEQ ID NO: 11, SEQ ID NO: 14, SEQ ID NO: 15, SEQ ID NO: 16, SEQ ID NO: 20, SEQ ID NO: 21, SEQ ID NO: 23, SEQ ID NO: 25, SEQ ID NO: 26, SEQ ID NO: 27, SEQ ID NO: 31 and SEQ ID NO: 33, set forth in Table 3.

In some embodiments, the T cell expresses an antigen-specific T-cell receptor (TCR) that recognizes a target antigen. In some embodiments, the T cell is a regulatory T cell, effector T cell or naïve T cell. In some embodiments, the effector T cell is a CD8+ T cells or a CD4+ T cell. In some embodiments, the effector T cell is a CD8+ CD4+ T cell. In some embodiments, the T cell is a primary cell.

In some embodiments, the heterologous nucleic acid construct encodes (i) a first self-cleaving peptide sequence; (ii) a first heterologous TCR subunit chain, wherein the TCR subunit chain comprises a variable region and a constant region of the TCR subunit; (iii) a second self-cleaving peptide sequence; (iv) any of the polypeptides described herein; (v) a third self-cleaving peptide sequence; (vi) a variable region of a second heterologous TCR subunit chain; and (vii) a portion of the N-terminus of the endogenous TCR subunit, wherein, if the endogenous TCR subunit of the cell is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit of the cell is a TCR-β subunit, the first heterologous TCR subunit chain is a heterologous TCR-α subunit chain and the second heterologous TCR subunit chain is a heterologous TCR-β subunit chain.

In some embodiments, the polypeptide sequence encoded by the nucleic acid construct is at least 95% identical to an amino acid sequence selected from the group consisting of SEQ ID NO: 42, SEQ ID NO: 45, SEQ ID NO: 47, SEQ ID NO: 50, SEQ ID NO: 51, SEQ ID NO: 52, SEQ ID NO: 56, SEQ ID NO: 57, SEQ ID NO: 59, SEQ ID NO: 61, SEQ ID NO: 62, SEQ ID NO: 63, SEQ ID NO: 67, and SEQ ID NO: 69.

Also provided is nucleic acid comprising a nucleic acid sequence encoding a polypeptide comprising an amino acid sequence at least 95% identical to a protein selected from the group consisting of: SEQ ID NO: 38, SEQ ID NO: 40, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 60, SEQ ID NO: 61 and SEQ ID NO: 62, SEQ ID NO: 63, SEQ ID NO: 64 and SEQ ID NO: 65.

In some embodiments, the nucleic acid construct comprises flanking homology arm sequences having homology to a human TCR locus.

Also provided are T cells comprising any of the nucleic acid constructs described herein.

Further provided is a nucleic acid construct that encodes in the following order, (i) a first self-cleaving peptide sequence; (ii) a first heterologous TCR subunit chain, wherein the TCR subunit chain comprises a variable region and a constant region of the TCR subunit; (iii) a second self-cleaving peptide sequence; (iv) a polypeptide sequence that is at least 95% identical to an amino acid sequence selected from the group consisting of SEQ ID NO: 42, SEQ ID NO: 45, SEQ ID NO: 47, SEQ ID NO: 50, SEQ ID NO: 51, SEQ ID NO: 52, SEQ ID NO: 56, SEQ ID NO: 57, SEQ ID NO: 59, SEQ ID NO: 61, SEQ ID NO: 62, SEQ ID NO: 63, SEQ ID NO: 67, and SEQ ID NO: 69; (v) a third self-cleaving peptide sequence; (vi) a variable region of a second heterologous TCR subunit chain; and (vii) a portion of the N-terminus of an endogenous T-cell TCR subunit, wherein, if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct comprises a nucleic acid sequence that is at least 95% identical to a nucleic acid sequence selected from the group consisting of SEQ ID NO: 42, SEQ ID NO: 45, SEQ ID NO: 47, SEQ ID NO: 50, SEQ ID NO: 51, SEQ ID NO: 52, SEQ ID NO: 56, SEQ ID NO: 57, SEQ ID NO: 59, SEQ ID NO: 61, SEQ ID NO: 62, SEQ ID NO: 63, SEQ ID NO: 67, and SEQ ID NO: 69.

Also provided is a method of modifying a human T cell comprising (a) introducing into the human T cell (i) a targeted nuclease that cleaves a target region in the TCR locus of a human T cell to create a target insertion site in the genome of the cell; and (ii) a nucleic acid construct encoding a polypeptide a polypeptide selected from the group consisting of: a truncated human PD-1 protein comprising the human PD-1 extracellular domain and transmembrane domain and lacking 80-90 (e.g., 87) carboxyl terminal PD-1 amino acids; a polypeptide comprising a human PD-1 extracellular domain or portion thereof of at least 120 or 130 amino acids (and optionally 1-20 (e.g., 11) amino acids of the 4-1BB extracellular domain) linked to a human 4-1BB intracellular domain via a transmembrane domain; a polypeptide comprising a human PD-1 extracellular domain linked to a human MyD88 intracellular domain or a portion thereof of at least 90 or 100 amino acids (and optionally 1-10 amino acids of the PD-1 intracellular domain) via a transmembrane domain; a polypeptide comprising a human PD-1 extracellular domain linked to a human ICOS intracellular domain via a transmembrane domain; a truncated human CTLA4 protein comprising the human CTLA4 extracellular domain and transmembrane domain and lacking 30-40 (e.g., 34) carboxyl terminal CTLA4 amino acids; a polypeptide comprising a human CTLA4 extracellular domain linked to a human CD28 intracellular domain or a portion thereof of at least 30 or 40 amino acids (and optionally 1-10 amino acids of the CTLA4 intracellular domain) via a transmembrane domain; a truncated human CD200R protein comprising the human CD200R extracellular domain and transmembrane domain and lacking 50-60 carboxyl terminal CD200R amino acids; a truncated human BTLA protein comprising the human BTLA extracellular domain and transmembrane domain and lacking 100-110 (e.g., 104) carboxyl terminal BTLA amino acids. In some embodiments, the truncated human BTLA protein comprises the first 1-12 (e.g., 6) amino acids of the human BTLA intracellular domain but lacks the remaining human BTLA protein intracellular domain; a polypeptide comprising a human BTLA extracellular domain or a portion thereof of at least 110 or 120 amino acids (and optionally 1-20 amino acids of the CD28 extracellular domain) linked to a human CD28 intracellular domain via a transmembrane domain; a truncated human TIM-3 protein comprising the human TIM-3 extracellular domain and transmembrane domain and lacking 65-75 (e.g., 71) carboxyl terminal TIM-3 amino acids; a polypeptide comprising a human TIM-3 extracellular domain or a portion thereof of at least 160 or 170 amino acids (and optionally 1-20 amino acids of the CD28 extracellular domain) linked to a human CD28 intracellular domain via a transmembrane domain; a truncated human TIGIT protein comprising the human TIGIT extracellular domain and transmembrane domain and lacking 70-80 (e.g., 75) carboxyl terminal TIGIT amino acids; a polypeptide comprising a human TIGIT extracellular domain or a portion thereof of at least 100 or 110 amino acids (and optionally 1-20 amino acids of the CD28 extracellular domain) linked to a human CD28 intracellular domain via a transmembrane domain; a truncated human TGFβR2 protein comprising the human TGFβR2 extracellular domain and transmembrane domain and lacking 360-370 (e.g., 366) carboxyl terminal TGFβR2 amino acids; a polypeptide comprising a human TGFβR2 extracellular domain or a portion thereof of at least 130 or 140 amino acids (and optionally 1-20 amino acids of the 4-1BB extracellular domain) linked to a human 4-1BB intracellular domain via a transmembrane domain; a polypeptide comprising a human TGFβR2 extracellular domain linked to a human Myd88 intracellular domain or a portion thereof of at least 90 or 100 amino acids (and optionally 1-20 amino acids of the TGFβR2 intracellular domain) via a transmembrane domain; a truncated human IL-10RA protein comprising the human IL-10RA extracellular domain and transmembrane domain and lacking 310-320 (e.g., 315) carboxyl terminal IL-10RA amino acids; a polypeptide comprising a human IL-10RA extracellular domain linked to a human IL-7RA intracellular domain via a transmembrane domain; a polypeptide comprising a human IL-4RA extracellular domain linked to a human IL-7RA intracellular domain via a transmembrane domain; a truncated human Fas protein comprising the human Fas extracellular domain and transmembrane domain and lacking 132-142 (e.g., 138) carboxyl terminal Fas amino acids; a polypeptide comprising a human Fas extracellular domain linked to a human CD28 intracellular domain or a portion thereof of at least 30 or 40 amino acids (and optionally 1-20 amino acids of the Fas intracellular domain) via a transmembrane domain; a polypeptide comprising a human Fas extracellular domain linked to a human 4-1BB intracellular domain or a portion thereof of at least 30 or 40 amino acids (and optionally 1-20 amino acids of the Fas intracellular domain) via a transmembrane domain; a polypeptide comprising a human Fas extracellular domain linked to a human MyD88 intracellular domain or a portion thereof of at least 90 or 100 amino acids (and optionally 1-20 amino acids of the Fas intracellular domain) via a transmembrane domain; a polypeptide comprising a human Fas extracellular domain linked to a human ICOS intracellular domain or a portion thereof of at least 25 or 35 amino acids (and optionally 1-20 amino acid of the Fas intracellular domain) via a transmembrane domain; a truncated human TRAIL-R2 protein comprising the human TRAIL-R2 extracellular domain and transmembrane domain and lacking 196-206 (e.g., 202) carboxyl terminal TRAIL-R2 amino acids; a polypeptide comprising a human TRAIL-R2 extracellular domain linked to a human CD28 intracellular domain or a portion thereof of at least 30 or 40 amino acids (and optionally 1-20 amino acids of the TRAIL-R2 intracellular domain) via a transmembrane domain; and a polypeptide comprising an IL2RA protein, an IL7RA protein, an MCT4 protein or a TCF7 protein; and (b) allowing recombination to occur, thereby inserting the nucleic acid construct in the target insertion site to generate a modified human T cell.

In some methods, the target insertion site is in exon 1 of a TCR-alpha subunit constant gene (TRAC) or in exon 1 of a TCR-beta subunit constant gene (TRBC). In some methods, the nucleic acid construct is inserted by introducing a viral vector comprising the nucleic acid construct into the cell. In some methods, the targeted nuclease is selected from the group consisting of an RNA-guided nuclease domain, a transcription activator-like effector nuclease (TALEN), a zinc finger nuclease (ZFN) and a megaTAL. In some methods, the targeted nuclease, a guide RNA and the DNA template are introduced into the cell as a ribonucleoprotein complex (RNP)-DNA template complex, wherein the RNP-DNA template complex comprises: (i) the RNP, wherein the RNP comprises the targeted nuclease and the guide RNA; and (ii) the nucleic acid construct.

In some methods, the T cell expresses an antigen-specific T-cell receptor (TCR) that recognizes a target antigen. In some embodiments, the T cell is a regulatory T cell, effector T cell or naïve T cell. In some embodiments, the effector T cell is a CD8+ T cells or a CD4+ T cell. In some embodiments, the effector T cell is a CD8+ CD4+ T cell. In some embodiments, the T cell is a primary cell.

Also provided is a modified T cell produced by any of the methods described herein.

Further provided is a method of enhancing an immune response in a human subject comprising administering any of the T cells described herein. In some embodiments, T cell expresses an antigen-specific TCR that recognizes a target antigen in the subject. In some embodiments, the human subject has cancer and the target antigen is a cancer-specific antigen. In some embodiments, the human subject has an autoimmune disorder and the antigen is an antigen associated with the autoimmune disorder. In some embodiments, the subject has an infection and the target antigen is an antigen associated with the infection. In some embodiments, the T-cell is autologous. In some embodiments, the T-cell is allogenic.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIGS. **1*a*-1*f*** show that arrayed knockins across endogenous loci reveal rules for efficient non-viral gene targeting in primary human T cells. (a) An arrayed knockin screen was performed targeting integration of a large DNA template (either GFP or tNGFR, ~800 bps) to 91 unique genomic sites. Two gRNAs were chosen for each site, and differences across cell types and biologic donor were assayed by performing the arrayed knockins in both CD4 and CD8 T cells from 6 unique healthy human blood donors. (b) Arrayed knockin screen timeline and readouts for target gene expression, target site accessibility, gRNA cutting efficiency, and observed knockin percentages. RNA-Seq was performed at day 0 (prior to activation), day 2 (time of electroporation), and day 4 (during expansion). ATAC-Seq was performed at days 0 and 2. Amplicon sequencing to determine the actual cutting efficiency of each guide was performed at day 6 (using separate RNP only plates where no HDR template was electroporated). Actual knockin percentages were analyzed at the cellular level by flow cytometry for GFP or tNGFR expression, either at day 6 for samples without a second stimulation ("– Stim") or at day 7 for samples 24 hours after a second stimulation ("+ Stim"). (c) Observed knockin percentages for knockin of a large HDR template across 90 unique genomic target sites, testing two gRNAs per site. A wide range of knockin efficiencies were observed, from below detectable levels at genes such CX3CR1 and ELOB to averages across donors of ~50% at B2M, IL2RA, RAB11A, and STAT1. Across tested sites, observed knockin was much higher with an on-target RNP than with a scrambled RNP not specific for any human genomic sequence. (d) Correlation of gRNA and target genomic site parameters with observed knockin percentage. The relative distance between cut site and integration site ("Cut Distance") or the orientation of Cas9 relative to the integration site ("Cut Direction") were minimally correlative (although only gRNAs with Cut Distance <~25 bps were predominantly used). Actual observed NHEJ % cutting of each gRNA (in the absence of HDRT) was more correlative with observed knockin % (when including HDRT) than predicted gRNA cut scores. RNA expression of the target gene was more correlative with knockin %, especially at days closer to the protein level readout (note that as expression of the knocked-in GFP or tNGFR was driven by each genes endogenous promoter, the actual knockin % may be higher than the observed knockin % for low-expression genes). DNA accessibility at the gRNA cut site was similarly correlated with observed knockin percentage. (e) Multivariate linear regression across gRNA and target genomic site parameters is more predictive of observed knockin % than any individual parameter. The predicted knockin % for each combination of genomic site, gRNA, and cell type (CD4 or CD8) is graphed relative to the average observed knockin % (average of n=6 unique donors). (f) Examination of the multivariate linear regression model's weighting of individual parameters revealed large independent contributions to observed knockin % from gRNA observed cutting efficiency, RNA expression levels of the target gene, and DNA accessibility at the gRNA target site. An ideal target genomic locus for large knockin in primary T cells is thus highly expressed, accessible at the time of electroporation, and contains a target sequence for a gRNA that cuts efficiently.

FIGS. 4*a-h* show targeted pooled knockin screens in primary human T cells.

Figure 1A:
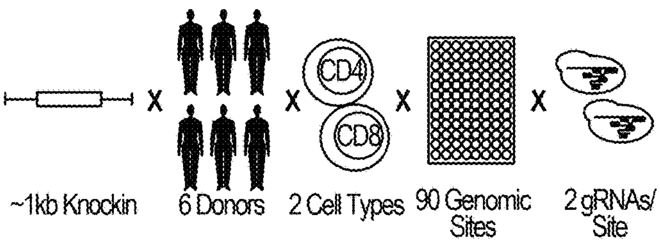

(a) Generalizable method for targeted pooled knockin screens using non-viral genome targeting. A library of HDR templates each containing a unique insert sequence are electroporated into primary human T cells to produce a modified T cell library. After applying a selective pressure to the T cell library, a barcode unique to each insert can be simply sequences by PCR, taking advantage of a constant short altered sequence in the HDRT 3' homology arm that is not integrated during homology directed repair.

(b) A 36 member pooled knockin library was designed containing previously described and novel chimeric and therapeutic genes and targeted to the TCR alpha locus in primary human T cells along with a new TCR specificity (for NY-ESO-1, total insert sizes ~2-3 kB). Comparison of the modified T cell library after TCR stimulation with CD3/CD38 magnetic beads revealed dramatic relative expansion of four chimeric proteins derived from the apoptosis mediator FAS that was highly reproducible across human donors.

(c) Application of diverse in vitro selective pressures to the therapeutic T cell pooled knockin library. Individual functional genes within the library showed greater relative proliferation in specific selective contexts rather than across all conditions. Comparison to stimulation only further elucidated the unique functional contribution of individual therapeutic knockin constructs. Two novel TGFBR2 derived chimeric proteins, along with the previously described dnTGFBR2, increased proliferation selectively in the presence of exogenous TGFB. The transcription factor TCF7 selectively enriched in the presence of excessive amounts of TCR stimulus (5× more anti-CD3/CD28 stimulation than stimulation only condition). Novel and described CD28 chimeric switch receptors with various immune checkpoints selectively increased proliferation in the context of CD3 stimulation only. Averages of n=4 independent healthy donors are displayed for each condition.

(d) In vivo pooled knockin screen in a solid tumor xenograft model of human melanoma. The A375 human melanoma line expresses the target NY-ESO-1 peptide/MHC recognized by the new TCR specificity knocked into the TRAC locus along with the therapeutic construct library. After expansion, a bulk population of 10 million T cells, containing ~2 million knockin positive NY-ESO-1 TCR expressing cells, were transferred I.V. into tumour bearing mice, and an input control T cell population saved. Four days post transfer tumours were harvested, and the modified T cell library post in vivo selection was sorted out and analyzed relative to input control.

(e) A variety of hits identified in in vitro pooled knockin screens validated in the in vivo melanoma xenografts model, including the TGFBR2 derived constructs and the transcription factor TCF7. Averages of n=2 independent healthy donors are displayed.

(f) Knockin of a single HDRT to the TRAC locus allows replacement of the endogenous TCR with a new specificity as well expression of a new gene modifying function. Pooled targeted knockin screening allowed rapid identification of new constructs that modified T cell function in specific contexts. Additional individual validation of hits from in vitro pooled knockin screens. A chimeric protein with TGFBR2's extracellular domain and a 41BB intraceulluar domain showed greater antigen specific cancer cell killing compared to a dnTGFBR2 construct or TCR knockin with a control tNGFR insert, both in the absence of presence of exogenous TGFB.

(g) Individual knockin of a new TCR specificity plus a FAS extracellular 41BB intercellular chimera or the transcription factor TCF7 similarly showed greater antigen specific killing compared to TCR knockin with a control GFP insert.

Figure 1B:
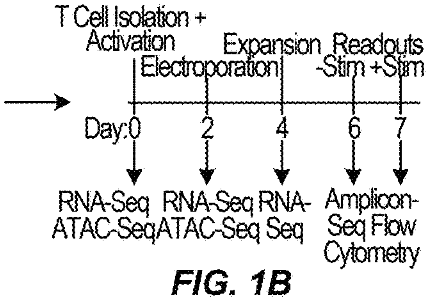

FIGS. 5*a*-5*f* show the results of large non-viral knockins at 91 unique genomic loci in primary human T cells.

a) A non-viral arrayed knockin screen was performed across 91 unique genomic loci. Efficient knockin of a GFP fusion protein to the C terminus of TCR-α and the four members of the CD3 complex were all achieved. No HDR template control showed minimal background levels of fluorescence in the GFP channel.

b) For additional targets, a tNGFR-2A multicistronic cassette was knocked in to the N-terminus of the target gene. Efficient knockin was achieved at many of an additional 24 surface receptors targeted. In both GFP fusion constructs and tNGFR-2A targeted constructs the observed GFP or tNGFR expression was driven by each gene's endogenous promoter, yielding diverse expression levels across target loci. For example, note the extremely high expression of tNGFR targeted to the B2M or CD45 loci, and the comparatively lower expression at CXCR4. No knockin was observed at some target sites, such as CX3CR1 and LTK, whereas at other sites over 50% of cells were successfully targeted, such as IL2RA and CD28.

c) Targeting of various checkpoint inhibitors showed greater observed knockin percentages upon stimulation than in unstimulated cells. Note all cells received an initial CD3/CD28 activation upon isolation and two days prior to electroporation in order to achieve efficient non-viral genome targeting, and flow cytometry was performed either four days after electroporation without additional stimulation ("No stim" or "unstimulated") or five days after electroporation following 24 hours of CD3/CD28 bead stimulation (FIG. 1*b*).

d) Non-viral genome targeting at 16 different transcription factors. Some target loci, such as JunD, showed low observed knockin percentages but high expression levels of the knocked in gene, whereas other sites, such as NCOA3, showed high percentages of observed knockin but low overall expression levels.

e) Efficient targeting of seven unique cytoskeletal elements. Again not the variable expression levels of the integrated target genes under diverse endogenous promoters.

f) Large knockins at an additional 32 target genes. All displays are from the same healthy blood donor, and are representative of n=6 total donors tested during the arrayed knockin screen. Displays show the more efficient of the two gRNAs tested for each loci. Unless significant differences in observed knockin % were seen between CD8 and CD4 T cells or between stimulated and unstimulated conditions (FIG. 6), the unstimulated CD8 T cell condition is shown. In all panels the X-axis is either GFP fluorescence or tNGFR staining, and the Y-axis shows cell size (FSC-A).

FIGS. 6*a-e* show analysis of observed knockin percentages across 91 target loci in multiple cell types and stimulation conditions.

a) Relative observed knockin percentages in CD8 vs CD4 T cells. The highest divergence in observed knockin in both cell types was their hallmark surface receptor, CD8A and CD4 respectively. Knockin at 41BB (TNFRSF9) and LAG3 was much higher in CD8 T cells, while observed knockin at the cytokine IL2 was higher in CD4 T cells. The vast majority of targeted sites did not show large difference between the two cell types. Observed knockin % for n=6 donors across 91 target genomic loci with 2 gRNAs per locus.

b) Relative observed knockin percentages in stimulated vs unstimulated CD8 T cells (FIG. 1*b*). The amount of knockin observed by flow cytometry at various activation/exhaustion markers, such as PD1, 41BB, and OX40 (TNFRSF4) was higher after a second stimulation four days following electroporation. In comparison, observed knockin at other sites, such as FBL, CCR2, and IL7R, was higher without a second stimulation ("Unstimulated"). n=6 donors across 91 target genomic loci with 2 gRNAs per locus.

c) Analysis of the observed off-target knockin % for each of the 91 unique HDR templates containing a GFP or tNGFR knockin sequence along with homology arms specific for their target genomic locus. In all 6 donors in the arrayed knockin screen, all 91 HDR templates were electroporated with a scrambled gRNA (forming an RNP that is not specific for any site in the human genome). While the vast majority of HDR templates showed minimal to no observed off-target knockin, a handful of HDR templates (targeting the genes FBL, IL2RG, and STAT2) showed higher amounts. Future analysis of the DNA sequences of these templates could yield further insights into patterns of off-target integration.

d) Observed MFI of knockin positive cells across all templates, donors, and cell types, was correlated with the RNA-Seq expression values recorded for each combination of target gene, donor, and cell type. Aggregated data from n=6 unique human blood donors.

e) Correlation of predicted cut score for each gRNA used in the arrayed knockin screen (91 target sites×2 gRNA per site=182 total gRNAs) with the observed cutting efficiency in each of the 6 donors that the arrayed knockin screen was performed in. All 182 gRNAs were individually electroporated into bulk CD3+ T cells in all 6 donors in the absence of an HDR template, and the % editing at each target locus was analyzed by amplicon sequencing. Likely due to the high efficiency of RNP based knock outs in primary human T cells (vast majority of gRNAs showed >95% NHEJ editing by amplicon sequencing), the predicted cut score was not observed to be correlated with observed cutting in these conditions.

FIGS. 7*a*-7*g* show the Correlation of gRNA and target DNA locus parameters with observed knockin efficiency.

a) The distance between the cut site of the tested gRNAs and the integration site of their associated HDR template in bps ("Cut Distance") was correlated with observed knockin efficiency across all donors. The utility of short distances between a cut site and integration site has been well described, but within the window of a cut distance less than approximately 25 bps there was a low correlation with observed knockin.

b) A gRNA can recognize a DNA sequence and cut in either the 5' or 3' direction relative to the integration site. A cut towards the 5' direction was defined as when the gRNA's NGG PAM faced towards the integration site in a 5' to 3' direction, and was assigned a value of −1. A cut towards the 3' direction was defined as when the gRNA's NGG PAM faced away from the integration site in a 5' to 3' direction, and was assigned a value of 1. No correlation was observed across the 91 targeted loci in regards to the directionality of the cut.

c) The predicted on-target cut score for each guide was not correlated with observed on-target knockin percentage.

d) The observed NHEJ efficiency of each gRNA in each of the 6 donors tested (FIG. 6*e*) showed a positive correlation with observed knockin efficiency. X-axis displays proportion of alleles with NHEJ edit.

e) Bulk RNA-Seq was performed in all combinations of the 6 tested healthy donors tested, 2 cell types (CD4 and CD8) and three time points. Expression levels of the 91 target genes at the time of T cell isolation and prior to activation ("Day 0"), at the time of electroporation two days after CD3/CD28 stimulation ("Day 2"), or during the expansion phase after electroporation ("Day 4") were determined. RNA expression levels at all three time points were correlated with observed knockin %, with the highest correlation being the time point (Day 4) closest to the time of the protein level flow cytometry readout. Note that the actual knockin efficiency at each loci may be higher than the observed efficiency, since the expression of each construct in the arrayed knockin screen is driven by the target gene's endogenous promoter. Genes that are expressed at levels below the detection limit of the flow cytometric readout could potentially have higher actual knockin percentages that are not seen due to a low level of protein expression. X-axis displays log 10 transcripts per million (TPM).

f) ATAC-Seq was performed in all combinations of the 6 tested healthy donors, 2 cell types (CD4 and CD8), and two time points (Day 0 before activation and Day 2 prior to electroporation). DNA accessibility was determined for a 1 kb window centered on the cut site of each gRNA at the 91 target loci. At both timepoints, the accessibility of the target locus was correlated with observed knockin efficiency. X-axis displays log 10 reads per million (RPM).

g) A multivariate linear regression model (FIG. 1*e, f*) incorporating each of the gRNA parameters (except predicted cutting), RNA expression, and DNA accessibility shows greater correlation than any individual parameter in isolation.

FIGS. 8*a*-8*e* show the results of examination of knockin target sites with divergent predicted and observed knockin efficiencies.

a) Analysis of difference between the predicted knockin efficiencies by a multivariate linear regression model and the actual observed knockin efficiencies for each of the 91 unique genomic target sites with 2 gRNAs per site in 2 cell types (CD4 and CD8). The vast majority of genes had predicted knockin efficiencies within a one fold change of the actual observed amount, but a handful of genes had much higher predicted knockin efficiencies than were actually observed (ELOB, JUND), while some genes had much lower predicted knockin values than were observed (DDX20, STAT4, ITGB1).

b) Top 6 gene targets with higher predicted knockin % than observed. The two tested gRNAs are colored, and the two lines for each guide represent CD4 and CD8 T cells.

c) Bottom 6 gene targets with lower predicted knockin % than observed. As these sites showed higher knockin efficiencies than would otherwise be predicted, further examination of these targets and their sequence context may reveal design features that could improve overall knockin efficiencies across target sites.

d) 6 target loci with the highest variance in prediction accuracy between the two gRNAs tested at that site. For at least two of these sites (SATB1, CCR7) the gRNA that showed much higher predicted knockin than was actually observed was found to actually cut its associated HDR template due to design errors in the DNA HDRT sequence (the gRNA binding sequence and/or PAM site for all gRNAs was disrupted in their respective HDR template to prevent cutting of the HDR template either episomally prior to integration or in a second round of cutting after homology directed repair).

e) The top 6 target loci with the highest variance in prediction accuracy between the two cell types tested (CD4 and CD8 T cells). Averages from n=6 unique healthy donors are displayed (a-e).

FIGS. 9*a*-9*d* show schematics and results for Genetically Engineered Endogenous Proteins with synthetic regulation of endogenous products.

a) Schematic describing our knock-in strategy for targeting a novel promoter to the N-terminus of a gene of interest with or without an additional selection marker.

b) Representative flow data for our knock-in strategy wherein we integrate (in 5' to 3' order) a SFFV promoter, a selection marker tNGFR, and a 2A sequence such that a multicistronic mRNA that produces two proteins, tNGFR and the endogenous protein, is being expressed off an SFFV promoter at defined endogenous gene locus. We targeted the N-terminus of three immune receptors, PD1, Lag3, and IL2RA, whose expression are highly upregulated upon T-cell activation. In the top row, we observe that expression levels of each respective immune receptor in cells that have been cultured for 7 days post electroporation without restimulation. Consistently, we observe that in control conditions (Scrambled RNP+HDR DNA Template) expression levels or immune receptor are relatively low. In the on target conditions (On-target RNP+HDR DNA Template), we see that tNGFR+ cells, which also have the SFFV promoter knocked in, have high levels of expression of each of the immune receptors while the tNGFR− cells have expression levels similar or lower than the control, the latter most likely attributed to KO occurring with the on-target RNP in the absence of HDR DNA Template integration. When we restimulated these cells, we see that the expression levels of each of the immune receptors increase in the control samples. In the restimulated on-target samples, the tNGFR+ cells retain high expression levels of each respective immune receptor whereas the tNGFR− cells upregulate expression levels, although to a lesser extent.

c) When we compare tNGFR expression levels against expression levels of the respective immune receptor in control and on-Target edited cells that have not been restimulated, we see that on-target cells have high expression levels of both tNGFR and their respective immune receptor (demonstrated by the linear relationship) while the control cells have lower expression levels of the respective immune receptor and negligible tNGFR expression.

d) Having validated our knock-in strategy for integrating a novel/synthetic promoter along with a selection marker, we applied our knock-in strategy to an array of transcription factors whose overexpression may be beneficial for T-cell proliferation and long-term function. To readout successful integration of our construct, we examined tNGFR expression levels in on-target samples for four different transcription factors and found that we were able to achieve 10-25% knock-in efficiency. This strategy has implications for being able to efficiently modulate transcription factor expression and subsequent T-cell function.

FIGS. 10*a*-10*e* show schematics and results for Genetically Engineered Endogenous Proteins with endogenous regulation of synthetic products at PDCD1 locus.

a) Schematic describing our knock-in strategy for targeting novel protein(s) to the N-terminus of a gene of interest for coordinated expression of the novel protein (s) and the endogenous protein or expression of the novel protein(s) with knock out of the endogenous protein under endogenous gene regulation.

b) Representative flow plots validating our strategy for coordinated expression of a novel protein and PD1 under the endogenous gene regulation of PD1. In rested cells (top row), there is minimal PD1 and tNGFR expression. However, by 48 hours after restimulation with CD3/CD28 Dynabeads, we see a coordinated upregulation of tNGFR and PD1.

c) Representative flow plots validating our strategy for simultaneous expression of a novel protein and knock out of PD1 under the endogenous gene regulation of PDCD. In rested cells (top row), there is minimal PD1 and tNGFR expression. However, by 48 hours after restimulation with CD3/CD28 Dynabeads, we see upregulation of tNGFR and without upregulation of PD1.

d) Representative flow plots validating our strategy for coordinated expression of multiple novel proteins and PD1 under the endogenous gene regulation of PDCD1. Based on tNGFR readout, we were able to successfully integrate our novel construct at the PDCD1 gene locus.

e) Representative flow plots validating our strategy for simultaneous expression of multiple novel proteins and knock-out of PD1 under the endogenous gene regulation of PDCD1. Based on tNGFR readout, we were able to successfully integrate our novel construct at the PDCD1 gene locus.

FIGS. 11*a*-11*d* show schematics and results for Genetically Engineered Endogenous Proteins with endogenous regulation of synthetic products.

a) Schematic describing our knock-in strategy for targeting a novel protein to the N-terminus of a gene of interest for coordinated expression of the novel protein and the endogenous protein under endogenous gene regulation.

b) Representative flow data from experiments wherein we integrate a tNGFR-2A construct at the N-terminus of IL2RA. We demonstrate tNGFR expression levels differ depending integration site, time, and cell culture conditions and, importantly, mirror that of that of the endogenous protein whose promoter is controlling expression. In cells where the target site was IL2RA, we see a linear IL2RA high, tNGFR high population at Day 3 post-electroporation, indicative of coordinated expression of the two. At Day 7 post-electroporation, cells that were cultured without restimulation see a gradual and coordinated decreased expression of both IL2RA and tNGFR whereas in cells that were restimulated, we see the maintenance of an IL2RA high, tNGFR high population.

c) Representative flow data from experiments wherein we integrate a tNGFR-2A construct at the N-terminus of CD28. We similarly observe a linear CD28 high tNGFR high population at Day 3. CD28 expression levels remain high without restimulation and that is reflected in our Day 7 analyses. In cells that were cultured without restimulation, we see a sustained CD28 high tNGFR high population where as in restimulated cells, we see a simultaneous modulation of CD28 and tNGFR expression. The more drastic decrease of CD28 expression could be due to the combination of gene expression modulation and internalization of the protein whereas tNGFR is not being internalized.

d) Representative flow data from experiments wherein we integrate a tNGFR-2A construct at the N-terminus of Lag3. At Day 3, Lag3 and tNGFR expression were neglible and both levels of expression remained low without restimulation at Day 7. However, when we restimulated the cells and analyzed them on Day 7, we saw the simultaneous upregulation of Lag3 and tNGFR.

Figure 12A:
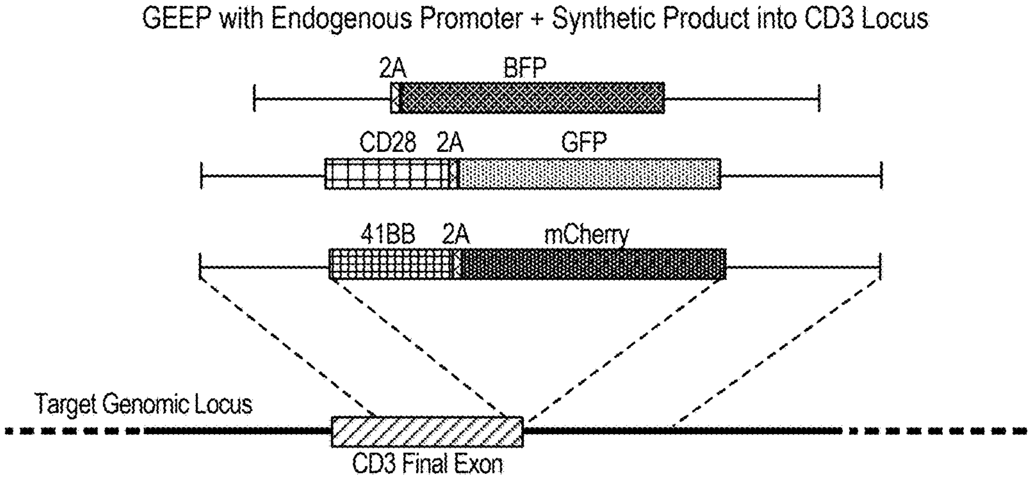
Figure 12B:
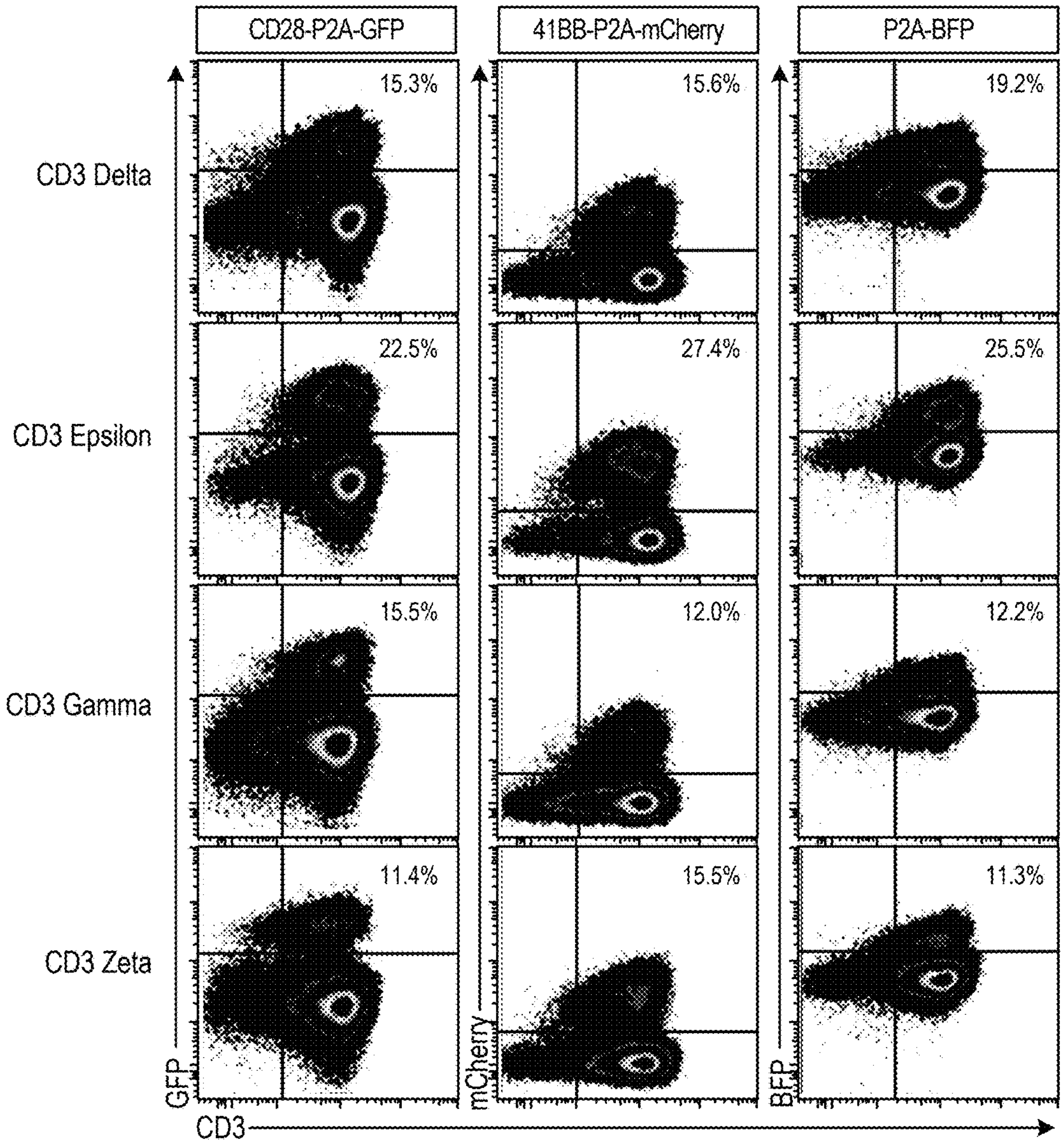

FIGS. 12*a*-12*b* show schematics and results for Genetically Engineered Endogenous Proteins with endogenous specificity and synthetic signaling in CD3 complex members.

a) Schematic describing the three different constructs we designed to modify the C-terminus of each of the different CD3 subunits in the TCR complex, which include the CD3δ chain, CD3ε chain, CD3γ chain, and CD3ζ chain. For initial tests, we designed a construct that would knock-in a 2A-BFP at the C-terminus of each of the different CD3 subunits. The 2A-BFP integration would create a multicistronic mRNA that produces two separate proteins: an unmodified CD3 chain and BFP. Once the 2A-BFP integration was validated, we modified the construct to include a cytoplasmic domain of an activating immune receptor before the 2A sequence such that the C-terminus of the CD3 subunit chain now contains an additional signaling domain/motif.

b) To readout successful integration of the signaling domain, we analyzed the percentage of fluorescent protein expressing T-cells by flow cytometry. The addition of an extra signaling domain did not have a significant/consistent effect on knock-in efficiency. The positioning of the additional signaling domain relative to endogenous CD3 signaling motifs was not optimized, but the ability to modify the intracellular domains of individual CD3 subunits provides a promising platform for tuning TCR signaling.

Figure 13A:
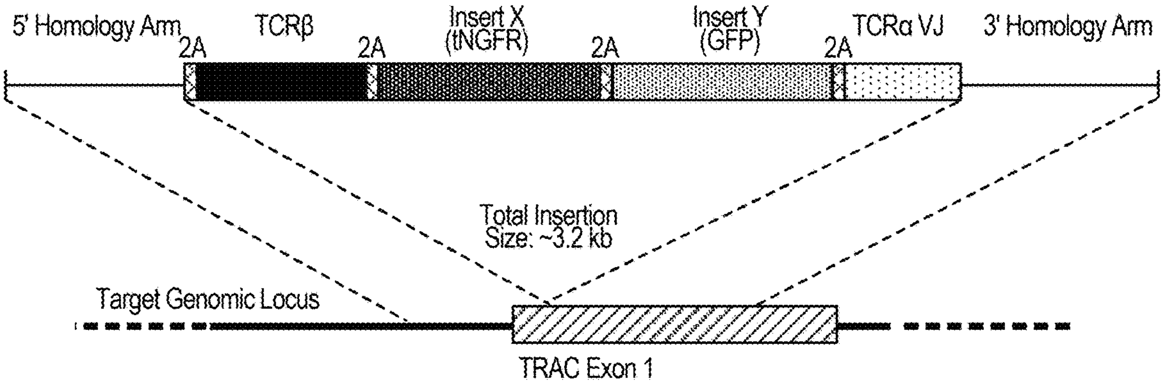
Figure 13B:
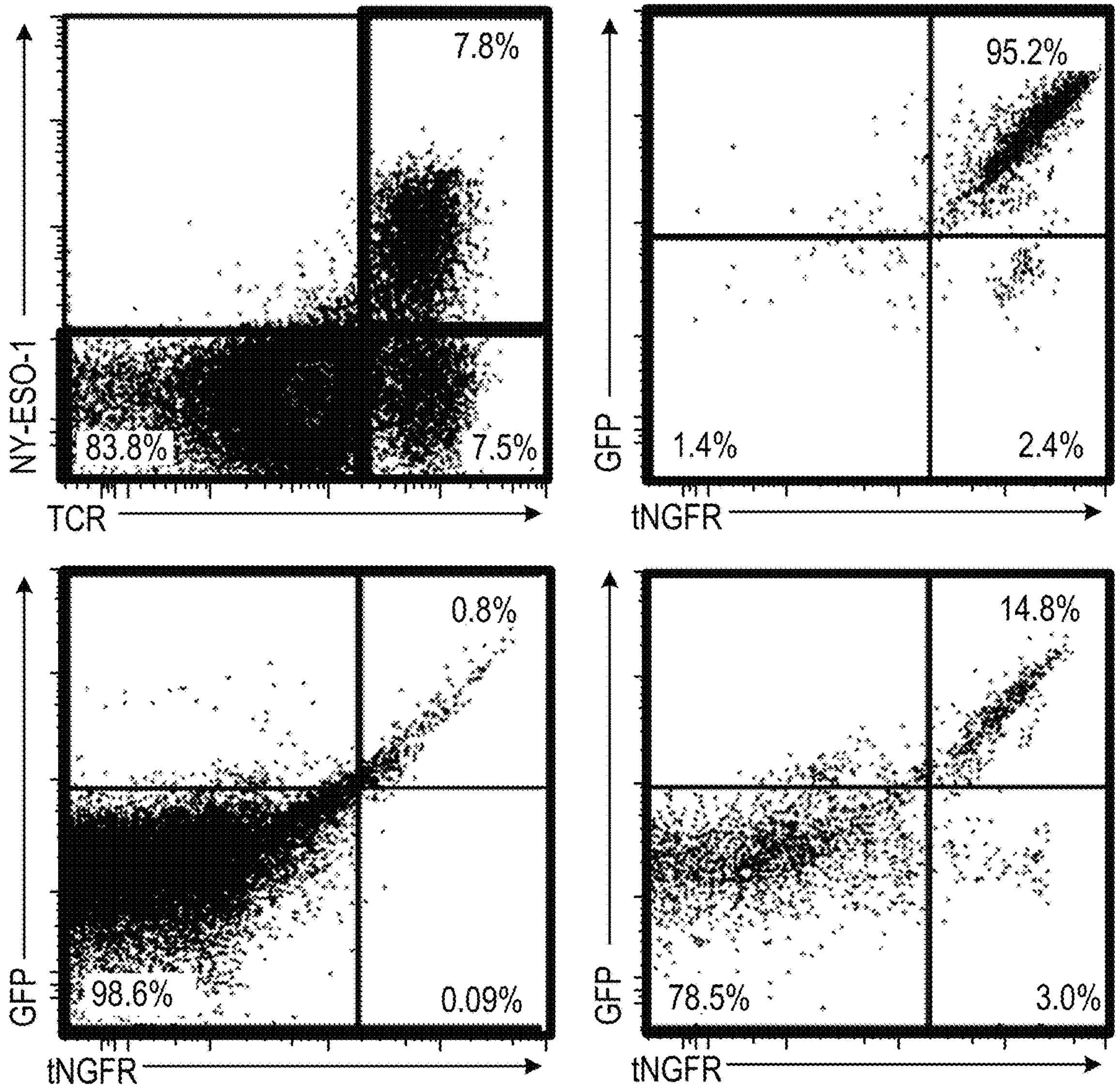
Figure 14A:
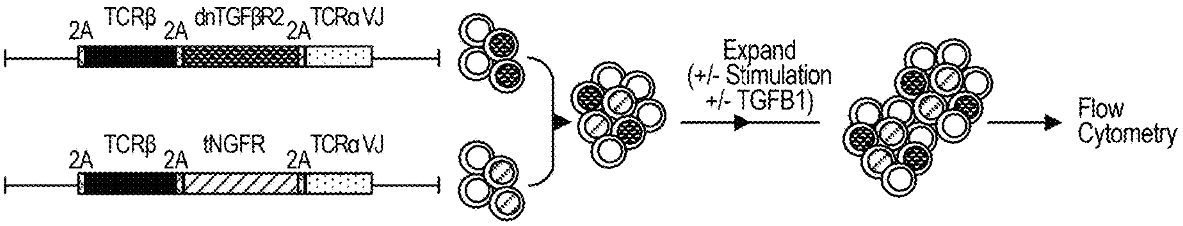
Figure 14B:
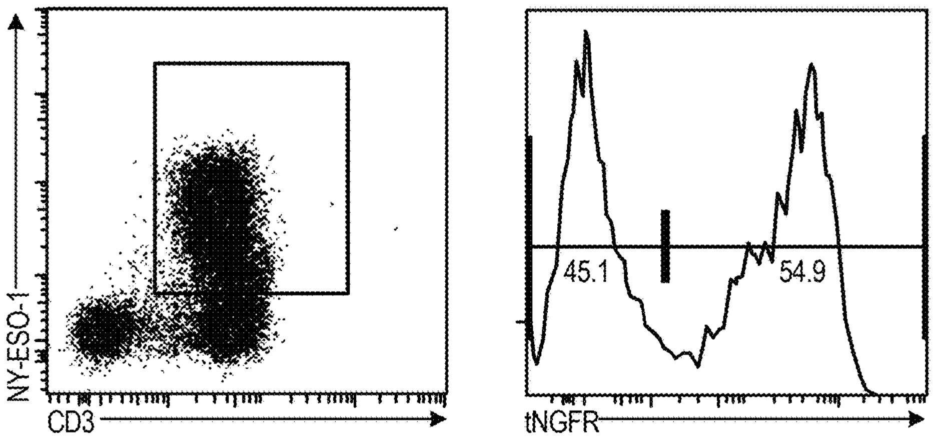
Figure 14C:
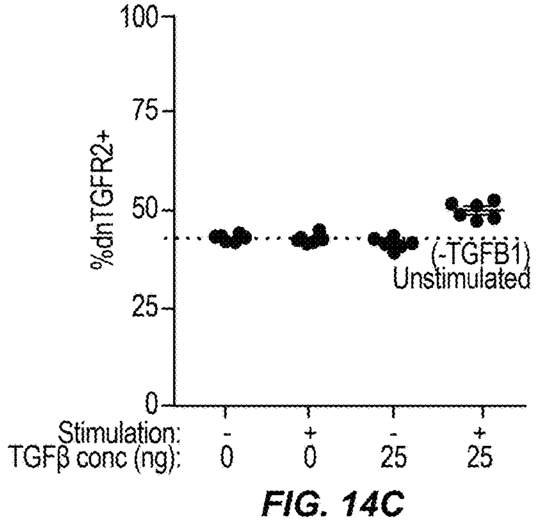
Figure 14D:
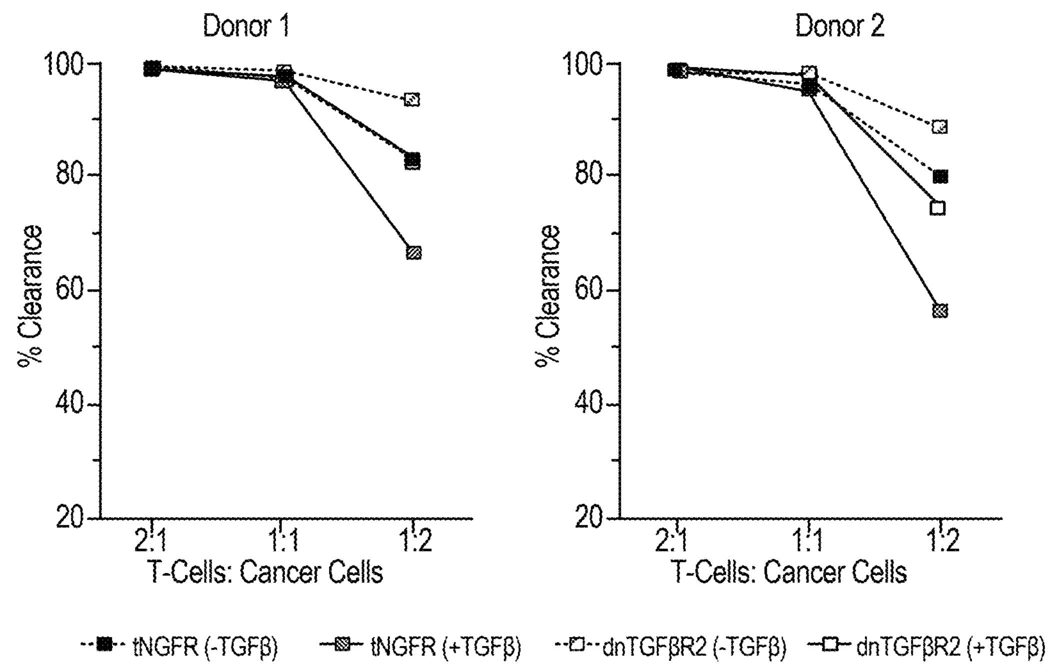
Figure 14E:
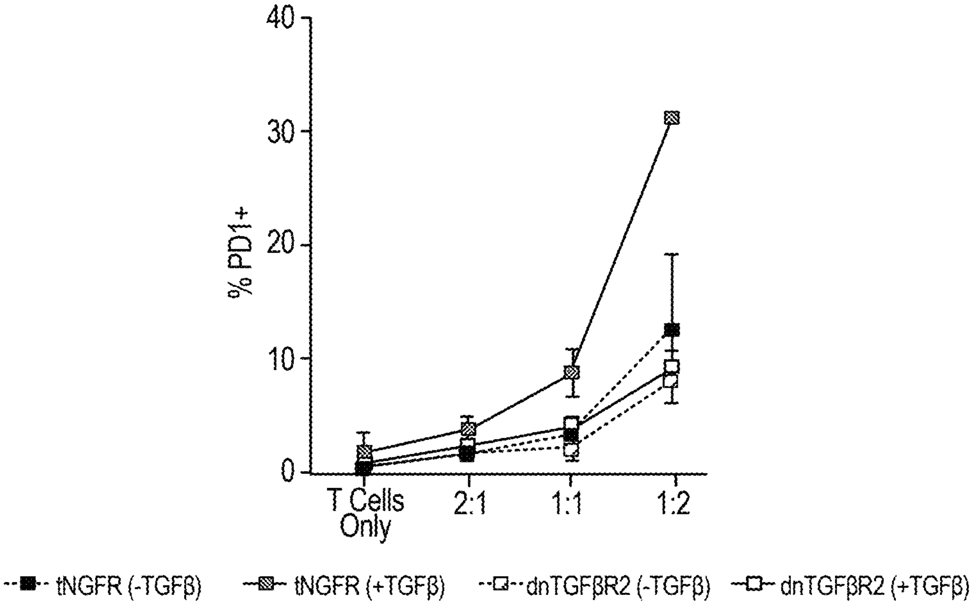

FIGS. 13*a*-13*b* show knockin of a four-component multicistronic or polycistronic cassette to the human TCR-α locus.

a) Schematic description of our strategy for simultaneous in-frame integration of a new replacement TCR and two additional proteins of interest at the endogenous TCR-α locus. We designed a single HDR DNA Template that included (in order) a Furin-Spacer-T2A sequence, the sequence for a new full-length TCR-β chain, a Furin-Spacer-E2A sequence, the sequence for our first protein of interest, a Furin-Spacer-F2A sequence, the sequence for our second protein of interest, a Furin-Spacer-P2A sequence, and the sequence of the new variable region of the TCR-α chain. These exogenous sequences were flanked by homology arms homologous to the endogenous TCR-α locus Exon 1 region. Successful knock-in would yield a multi-cistronic mRNA that expresses four separate proteins.

b) Representative data from a flow cytometry readout of our knock-in strategy. For initial tests, our TCR replacement was the 1G4 TCR and our additional proteins of interest were tNGFR and GFP. Proper integration of this construct at the endogenous TCR-α locus would yield NY-ESO-1 TCR+ tNGFR+GFP+ T-cells. The flow plot in the top left illustrates the knock-in efficiency, determined by the percentage T-cells staining positive with a NY-ESO-1 dextramer. NY-ESO-1+ cells all express GFP and tNGFR concordantly (top right flow plot) whereas NY-ESO-1-TCR− cells do not (bottom left flow plot). A relatively small percentage of TCR+NY-ESO-1− cells express both GFP and tNGFR, but not either alone (bottom right flow plot). This observation can most likely be explained by off-target integration of our construct at a locus with active expression or an on-target integration of our construct with improper expression of either the 1G4 TCR-α chain, TCR-β chain, or both.

Figure 3A:
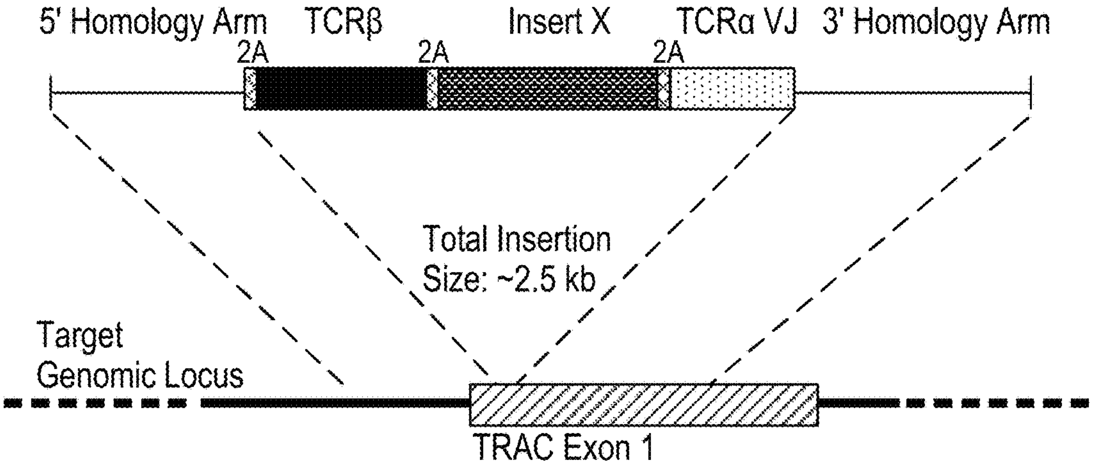
FIGS. 3*a*-3*e* show simultaneous engineering of T cell specificity and function. (a) Schematic description of our strategy for simultaneous in-frame integration of a new replacement TCR and an additional protein of interest at the endogenous TCR-α locus. We designed a single HDR DNA Template that included (in order) a Furin-Spacer-T2A sequence, the sequence for a new full-length TCR-β chain, a Furin-Spacer-E2A sequence, the sequence for a protein of interest, a Furin-Spacer-P2A sequence, and the sequence of the new variable region of the TCR-α chain. These exogenous sequences were flanked by homology arms homologous to the endogenous TCR-α locus Exon 1 region. Successful knock-in yields a multi-cistronic mRNA that expresses three separate proteins. (b) Representative data from a flow cytometry readout of our TCR+Payload knock-in. For initial tests, our TCR replacement was the 1G4 TCR, which targets the NY-ESO-1 cancer-testis antigen, and our additional protein of interest was a truncated Nerve Growth Factor Receptor (tNGFR). Proper integration of this construct at the endogenous TCR-α locus would yield NY-ESO-1 TCR+ tNGFR+ T-cells. The flow plot on the left illustrates the knock-in efficiency, determined by the percentage T-cells staining positive with a NY-ESO-1 dextramer. The histogram on the right demonstrates that the NY-ESO-1 TCR+ population expresses tNGFR concordantly. (c) Our TCR+Payload knock-in strategy at the endogenous TRAC locus leads to coordinated gene expression of a novel TCR-β chain, a TCR-α chain, and a protein of interest. The three proteins, however, should retain independent protein level regulation. To test this, we sorted NYESO-1+tNGFR+CD4/CD8 T-cells and compared NY-ESO-1 TCR expression levels with tNGFR expression levels at steady state versus after TCR stimulation. TCR stimulation is known to cause TCR internalization, and after 24 hours of stimulation, we observed decreased NY-ESO-1 TCR expression by dextramer staining. In contrast, tNGFR protein expression remained high after 24 hours of stimulation. (d) After validating our TCR+Payload knock-in strategy, we designed a second construct that replaced tNGFR with a dominant negative TGFβ receptor 2 (dnTGFβR2) as our additional protein of interest. We hypothesized that the addition of a dnTGFβR2 would not only enable us to target T-cells to a specific cancer antigen but also provide the T-cells a functional advantage in an immunosuppressive tumor microenvironment mediated by TGFβ1. To test this, we pooled two unsorted, edited T-cell populations containing either NY-ESO-1 TCR+ dnTGFβR2+ T-cells or NY-ESO-1 TCR+ tNGFR+ T-cells and expanded this mixed population under various culture conditions (+/−stimulation+/−TGFβ1). Our observations in FIGS. 3*b* and 3*c* enabled us to distinguish our two populations of interest within a pooled sample and determine their relative expansion by flow cytometry. After 5 days, we found that stimulated pooled samples cultured in 25 ng/mL of TGFβ1 saw a significant expansion of the NY-ESO-1 TCR+ dnTGFβR2+ T-cells over the NY-ESO-1 TCR+ tNGFR+ T-cells. (e) To validate both reprogrammed T-cell specificity and enhanced function, we utilized a killing assay where melanoma cell lines expressing the NY-ESO-1 antigen were co-cultured with NY-ESO-1 TCR+ dnTGFβR2+ T-cells or NY-ESO-1 TCR+ tNGFR+ T-cells in the presence or absence of additional TGFβ1 at various effector to target ratios. We found that NY-ESO-1 TCR+ tNGFR+ performed relatively poorly in the presence of TGFβ1 but that the NY-ESO-1 TCR+ dnTGFBR2+ T-cells were able to overcome the suppressive force of TGFβ1. Cancer cell growth/killing was monitored on the Incucyte and quantified using an image analysis software. The % Clearance was calculated as the (% Confluence of Cancer Cells Only−% Confluence of Co-Culture Condition)/(% Confluence of Cancer Cells Only) and all values were taken from images taken 96 hours of co-culture.
Figure 3B:
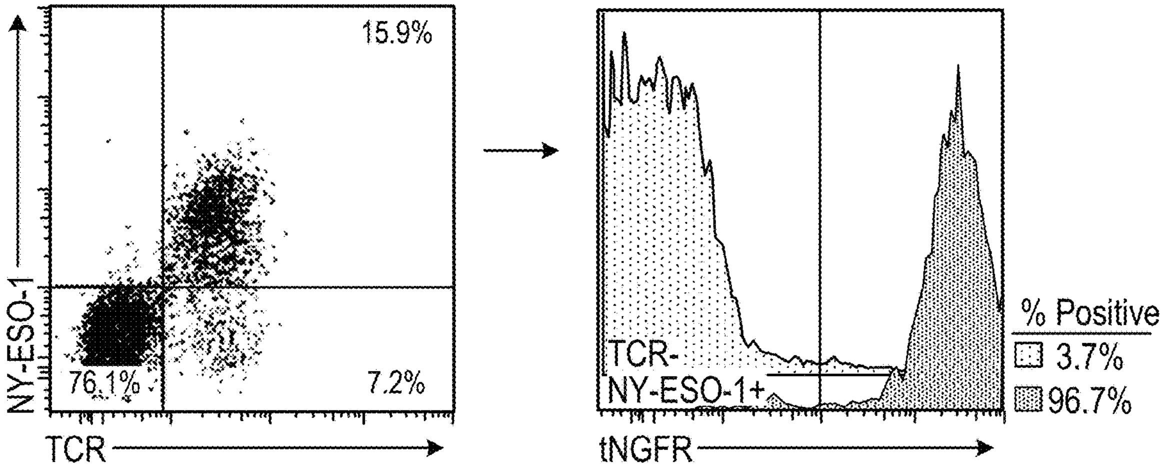
Figure 3C:
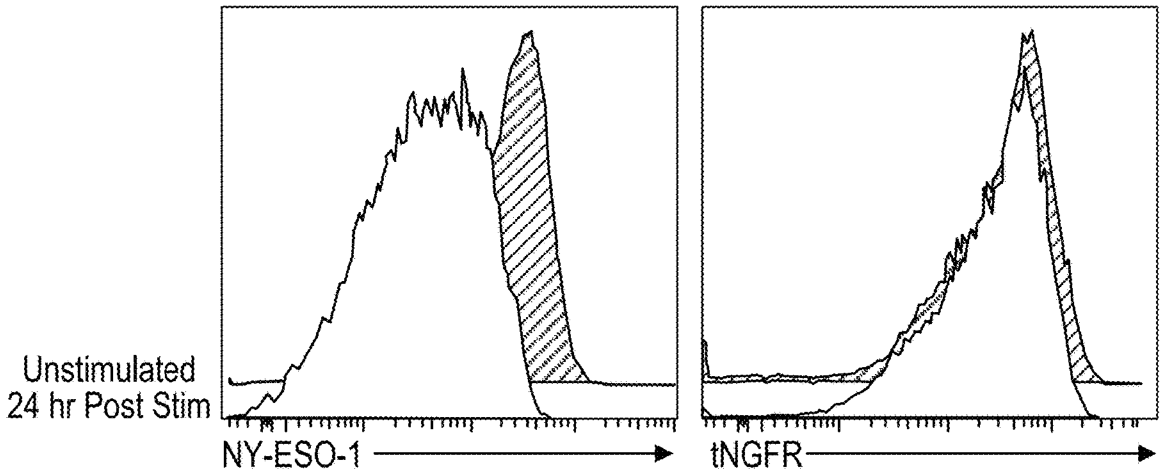
Figure 3D:
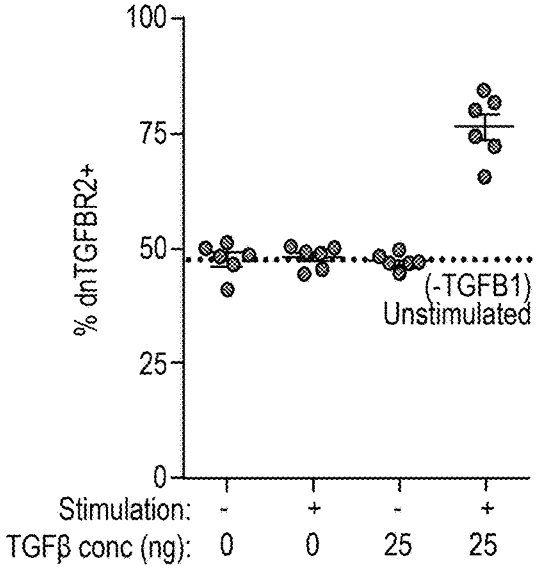
Figure 3E:
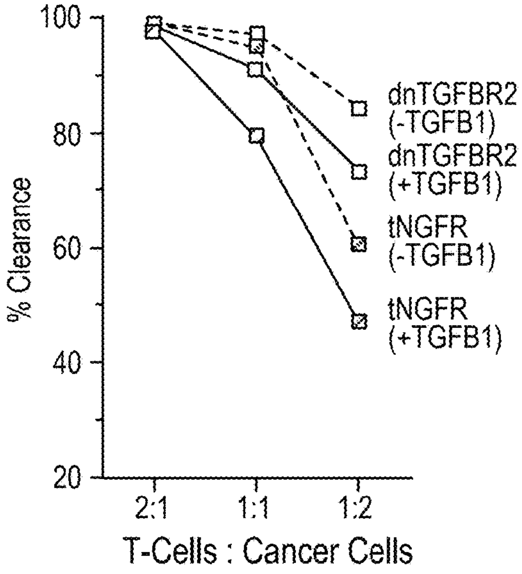

FIGS. 14*a*-14*e* show the results of characterization of T cell function after knockin of a new TCR specity along with a dnTGFβR2 functional gene.

a) Schematic description of construct designs and experimental set up for FIG. 3*d* (pooled proliferation assay). NY-ESO-1 TCR+ dnTGFβR2+ T-cells and NY-ESO-1 TCR+tNGFR+ T-cells were edited and expanded independently. After expansion, the two bulk edited samples were pooled together. The pooled population included a heterogenous population of NY-ESO-1 TCR+ dnTGFβR2+ T-cells, NY-ESO-1 TCR+ tNGFR+, TCR KO T-cells, and NY-ESO-1-TCR+ T-cells. Input numbers of NY-ESO-1 TCR+ dnTGFβR2+ T-cells and NY-ESO-1 TCR+ tNGFR+ were approximately normalized based on observed knock-in percentages. Replicates of the pooled populations were further expanded with or without Immunocult stimulation and in the presence or absence of TGFβ1.

b) Gating strategy to determine relative expansion of NY-ESO-1 TCR+ dnTGFβR2+ T-cells over NY-ESO-1 TCR+ tNGFR+. The majority of T-cells at this stage of the experiment (19 days after initial isolation, 2 rounds of stimulation, continuous culture in 500 U/mL of IL-2) were CD8+ T-cells. Thus, we completed our flow analysis on CD8+ T-cells. Gating on NY-ESO-I+CD3+ CD8+ T-cells, we see a bimodal distribution of cells when examining tNGFR expression. The proportion of tNGFR− NY-ESO-I+CD3+ CD8+ T-cells represents the NY-ESO-1 TCR+ dnTGFβR2+ T-cells and was used for downstream analysis.

c) The results of a replicate pooled proliferation assay in another independent healthy donor. After 5 days, we again found that stimulated pooled samples cultured in 25 ng/mL of TGFβ1 saw a significant expansion of the NY-ESO-1 TCR+ dnTGFβR2+ T-cells over the NY-ESO-1 TCR+ tNGFR+ T-cells.

d) The results of a replicate killing assay in two additional independent healthy donors. Again, we found that NY-ESO-1 TCR+ tNGFR+ performed relatively poorly in the presence of TGFβ1 but that the NY-ESO-1 TCR+ dnTGFBR2+ T-cells were able to overcome the suppressive force of TGFβ1 and performed the best in this assay.

e) After co-culture for 108 hours, T-cells were recovered from the killing assay in the previous figure and analyzed by flow cytometry for activation markers/checkpoint molecules on CD8+ T-cells. In samples with only T-cells and no cancer cells, there was a negligible PD1 high population, which suggests that the T-cells at steady state are not in an activated or exhausted state. At decreasing effector to target ratio, we see a general increase in the PD1 high population across all variants and culture conditions, which suggests either sustained activation from the continual clearance of cancer cells or the beginnings of exhaustion due to an inability to effectively clear the cancer cells. At the 1:2 effector to target ratio, the NY-ESO-1 TCR+ dnTGFBR2+ T-cells had significantly lower percentages of PD1 high T-cells, an observation that was independent of TGFβ1 addition. This could be because NY-ESO-1 TCR+ dnTGFBR2+ T-cells were more effective at clearing cancer cells in general. TGFβ1 has been shown to increase antigen induced PD1 expression. Thus, the lower percentage of PD1 high T-cells among NY-ESO-1 TCR+ dnTGFBR2+ T-cells could also be attributed to the direct downstream effects of the dominant negative receptor.

Figure 15A:
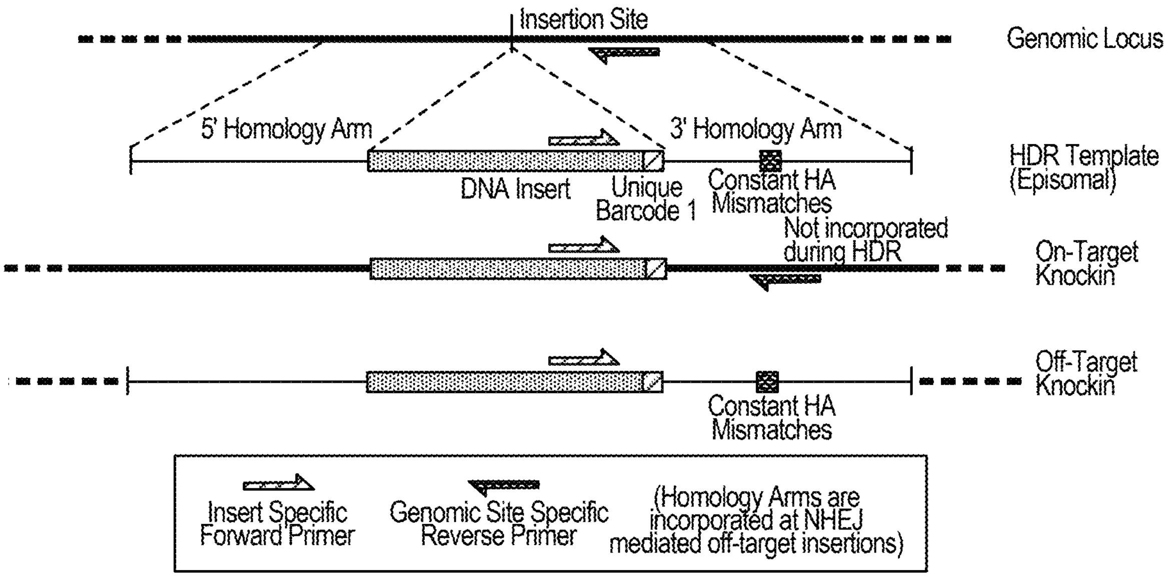
Figure 15B:
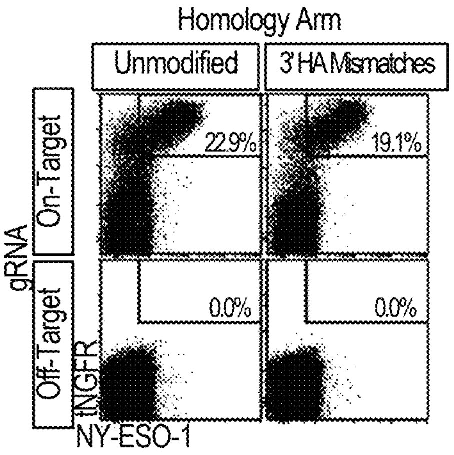
Figure 15C:
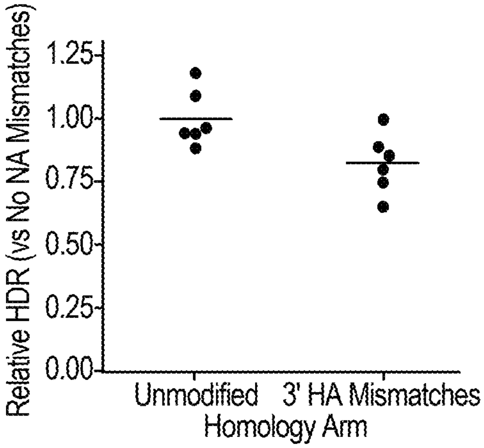

FIGS. 15*a*-15*c* depict a DNA sequencing strategy to selectively detect on-target knockins.

a) DNA sequencing of homology directed repair outcomes is complicated by the large amount of HDRT introduces into the cell and which remains episomal. A successful on-target knockin can be distinguished from the wild type or NHEJ modified genomic locus, non-integrates episomal template, and nhej mediated off-target integrations. To overcome this challenge, two aspects of homology directed repair can be used to create a unique amplifyable sequence at on-target knockins exclusively. First, only a short region of the homology arms of an HDRT are copied into the genome during homology directed repair (along with the entire length of the inserted region), while the majority of the homology arm is used for complementary base pairing when the genomic locus crosses over. Second, small mismatches in the homology arm can be tolerated during crossing over, as long as the vast majority of homology arm remains complementary to the genomic target site. This enables a strategy where a short stretch of mismatches is introduced to the homology arm (~10 bp of mismatches to the 3' HA in this case), and will thus be included in any episomal template. These mismatches will also be included in any off-target integrations, as the entire homology arms are integrated during NHEJ mediated integrations at off-target sites of random dsDNA breaks. However, at the on-target locus, the mismatches are not copied into the genome. This enables a simple PCR to amplify off of the on-target locus by using one primer contained within the inserted region (and thus unable to prime off of the non-integrated genomic locus), and a second primer binding to the genomic sequence overlapping with the site of the homology arm mismatches introduced into the HDRT. Only the on-target knockin possesses both primer binding sites.

b) Knockin of a tri-cistronic HDRT to the TRAC locus replacing the endogenous TCR with a new specificity (NY-ESO-1) along with an additional gene (tNGFR) with standard unaltered homology arms, as well as with a 3' HA containing ~10 bp of mismatches to the target genomic site at ~100 bps into the homology arm sequence.

c) Knockin of ~2.5 kb NY-ESO-1 TCR+ tNGFR was slightly less efficient with the homology arm mismatches compared to unaltered homology arms, but still easily detectable.

Figure 16A:
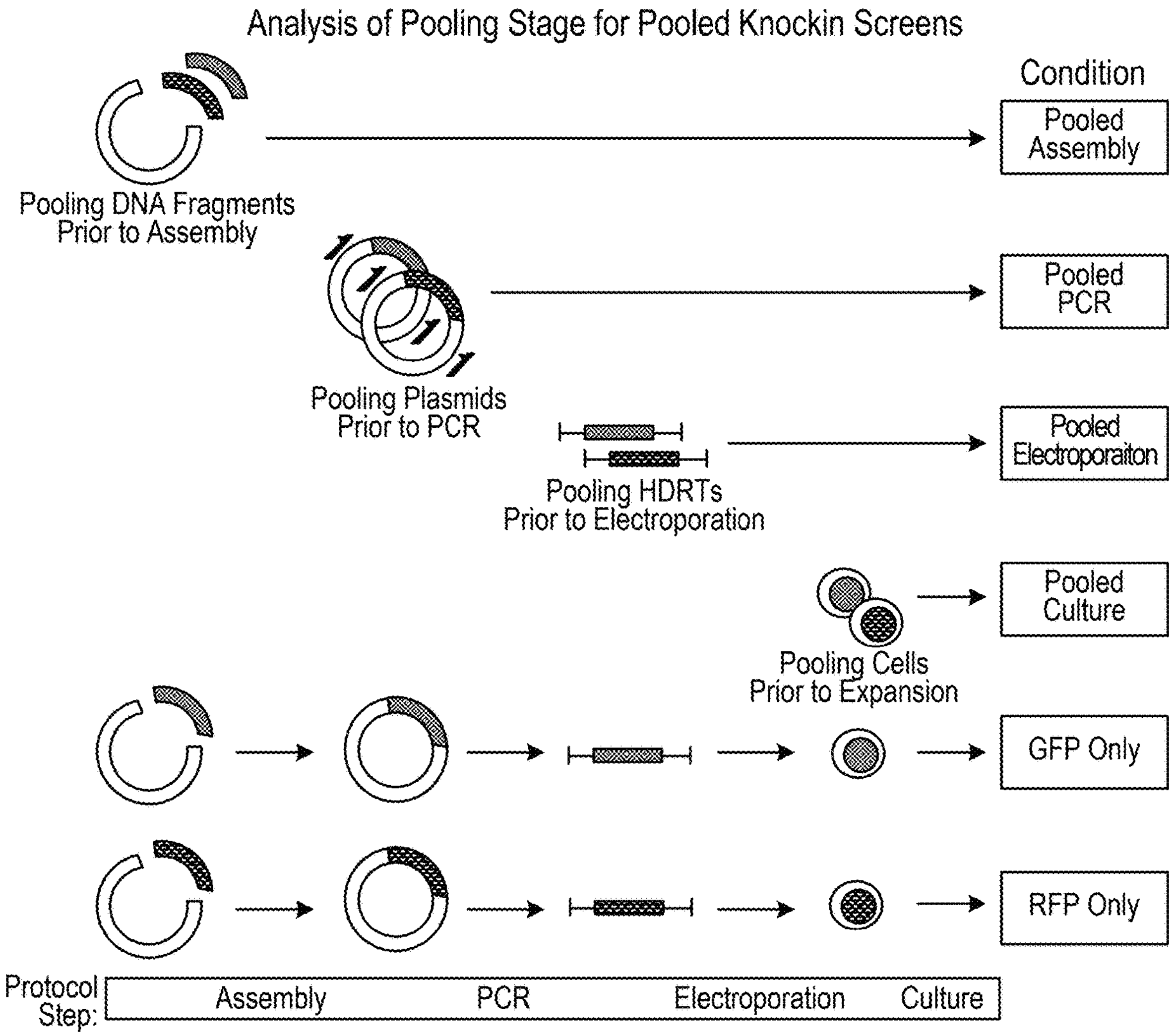
Figures 16B, 16C:
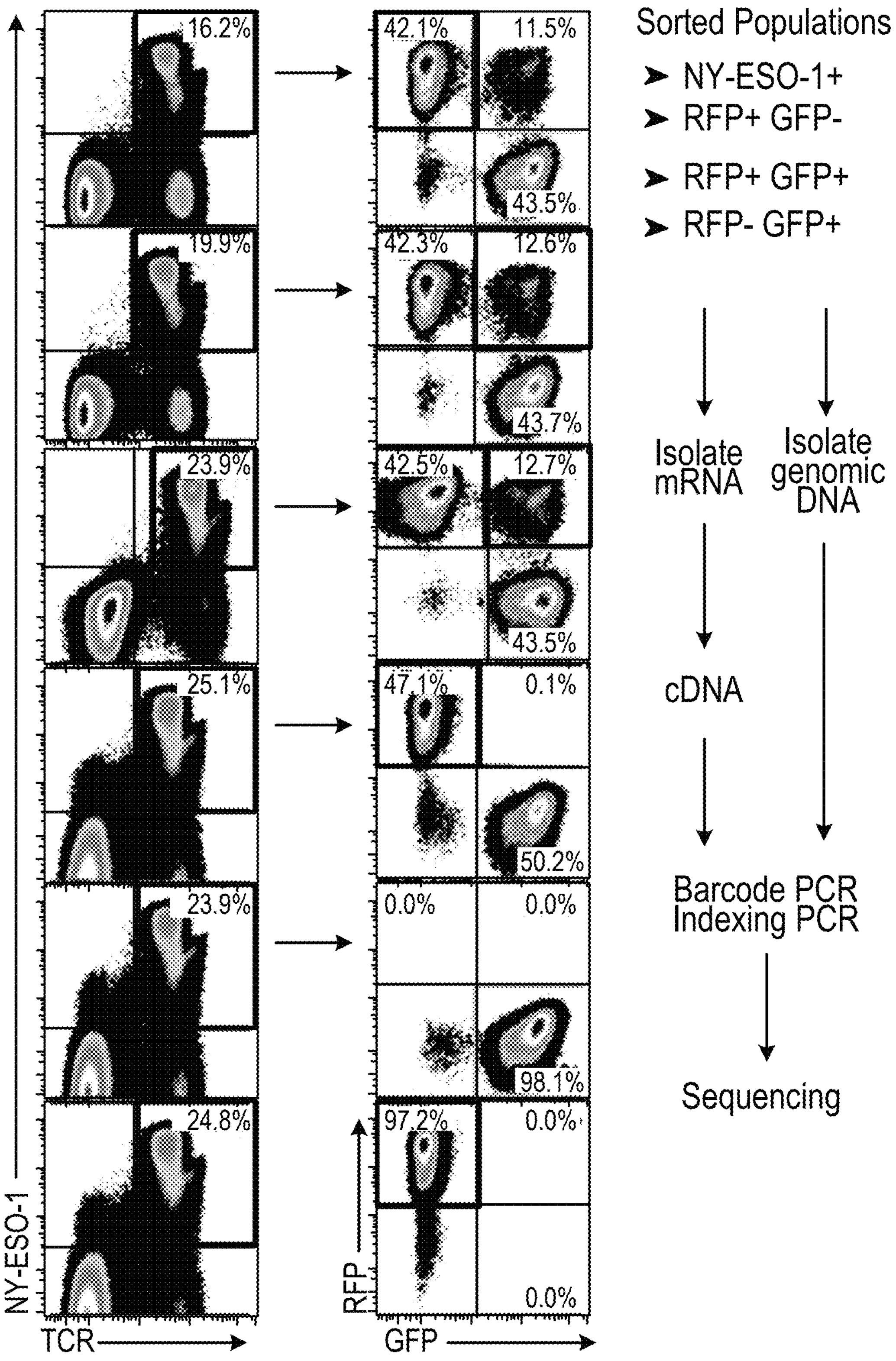
Figure 16D:
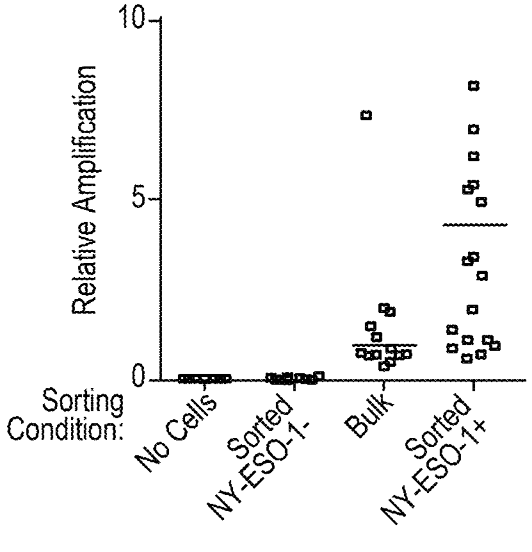
Figure 16E:
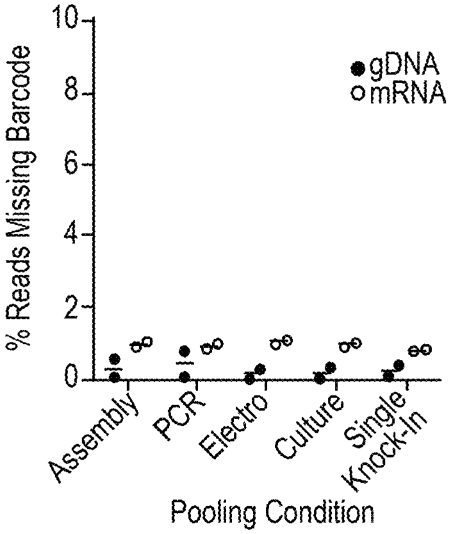
Figure 16F:
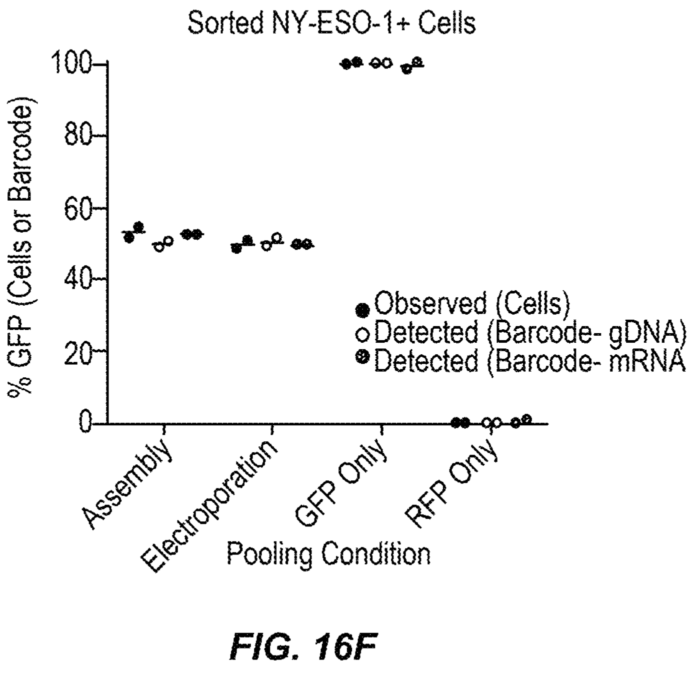
Figure 16G:
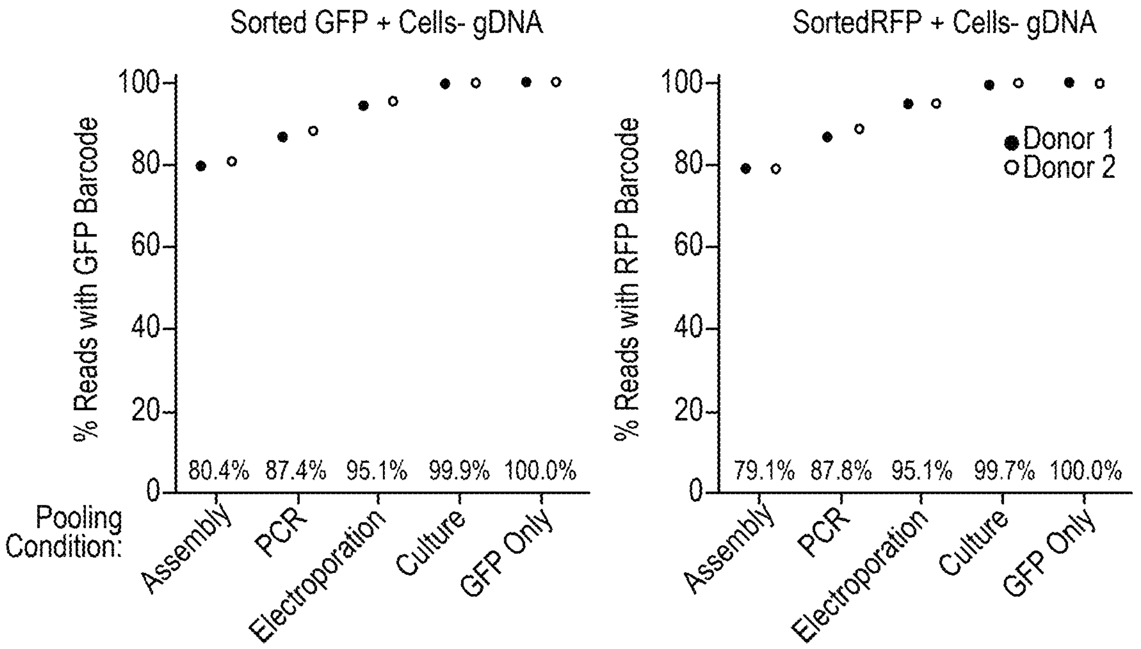

FIGS. 16*a*-6*h* show the results of an analysis of template switching with varying pooling stages in pooled knockin screens.

a) Pooling of samples can occur at each distinct step of a non-viral genome targeting protocol: dsDNA fragments containing the unique members of a pooled knockin library can be pooled prior to assembly into DNA plasmids already containing constant elements such as homology arms ("Pooled Assembly"); DNA plasmids containing the entire HDRT sequence for each unique library member can be pooled prior to a PCR reaction to generate large amounts of dsDNA HDR template ("Pooled PCR"); dsDNA HDR templates for each unique library member can be pooled prior to electroporation into the final cells ("Pooled Electroporation"); or, cells separately electroporated with each unique library member can be pooled following electroporation but before a final readout ("Pooled Culture").

b) A library of two members, either a GFP or RFP template each contained within a knockin cassette encoding a new TCR specificity (NY-ESO-1 specific 1G4 clone) to TRAC exon 1, was used for the analysis of pooling stage. Knockin positive primary human T cell could be identified based on expression of the new TCR specificity (TCR+NY-ESO-1+).

c) Knockin positive cells were analyzed for GFP and RFP expression. Cells with either GFP or RFP templates alone only showed expression of each respective fluor, while the Pooled Culture condition showed equal populations of GFP and RFP positive cells exclusively, without any dual GFP+RFP+ cells. Pooling conditions prior to the electroporation step (Pooled Assembly, Pooled PCR, or Pooled Electroporation) all showed both single GFP+ or RFP+cells, as well as dual GFP+ RFP+ cells, potentially due to bi-allelic knockin at both TRAC loci, as T cells often express functional TCR-α chains off of both alleles. Multiple populations were sorted for barcode sequencing, including bulk knockin negative cells (NY-ESO-1−), bulk knockin positive cells (NY-ESO-1+), and individual populations of RFP+GFP− or RFP−GFP+ cells. Next-generation DNA sequencing of on-target knockins was performed using either isolated mRNA converted to cDNA, or isolated genomic DNA using a 2 step PCR. An initial PCR amplified the barcode region using a reverse primer overlapping mismatches in the 3' HA of the HDR template (FIG. 15) and a constant forward primer within the insert sequence (total amplified region ~140 bp). A second indexing PCR was then performed prior to pooling of samples for sequencing.

d) To analyze the selectivity of the selective on-target knockin PCR sequencing strategy, the total amount of amplification off of sorted knockin positive (NY-ESO-1+) vs knockin negative (NY-ESO-1−) cells was analyzed relative to the bulk population of edited cells using a constant amount of input genomic DNA prior to the first PCR and reading out the total relative number of reads sequenced (no concentration normalizations were used between samples at any protocol steps). Knockin positive cells showed enhanced amplification of the region of the knocked in HDRT containing the barcode relative to the bulk edited population, while knockin negative cells showed little to no successful amplification, demonstrating the selectivity for amplifying and sequencing on-target knockins relative to non-integrated episomal HDRT or off-target integrations (FIG. 15).

e) The degree to which the endogenous genomic locus was amplified during the barcode sequencing PCR was analyzed across pooling stages and comparing isolated mRNA vs genomic DNA. All conditions showed low amounts of reads without a barcode sequence (e.g. containing the wild-type sequence at the genomic locus), although when sequencing off of mRNA the amount was consistently slightly higher (~1% of total reads). Sequencing off of mRNA has the advantage of amplifying the number of sequencable barcodes from each individual cell, but requires the pooled knockin screen be performed in a coding region that is expressed (such as the TCR α locus) and that the barcode be integrated into degenerate bases in a coding sequence. In contrast, sequencing off of genomic DNA has the advantage of generalizability to any genomic locus where a successful knockin can be performed (FIG. 1), but has potentially lower signal to noise compared to sequencing off of mRNA (converted to cDNA) when using low numbers of cells.

f) The percentage of sequenced reads containing the GFP HDR template's barcode corresponded with the observed percentage of cells expressing GFP protein by flow cytometry across pooling conditions and was constant when sequencing off of both genomic DNA or mRNA, demonstrating the ability of the pooled knockin screening sequencing strategy to accurately assess the cellular population frequencies by sequencing of their DNA barcodes.

g) The percentage of sequenced barcodes in sorted GFP+ or RFP+ cells that contained the correct barcode is displayed across pooling conditions when sequencing off of genomic DNA. Knockin of GFP or RFP templates only yielded 100% of reads containing the correct barcode, and pooled culture of cells after electroporation yielded >99% correct barcodes. However, pooling at earlier experimental stages produced a highly consistent increasing amount of template switching across donors and whether sorted GFP+ or RFP+ cells were analyzed.

h) Quantification of the amount of template switching using the homology arm mismatch priming strategy for pooled knockin screening that was observed across pooling stages. The amount of template switching observed was highly consistent between sequencing off of genomic DNA or mRNA. The earliest pooling stage, Pooled Assembly, showed the greatest amount of template switching, but a consistent amount of template switching was observed with Pooled PCR and Pooled Electroporation conditions, indicating that crossing over or template switching events likely occurred during both the Gibson Assembly reaction, the PCR to produce the HDR templates, and even potentially within the cell during homology directed repair. Given that in a pooled knockin library with two members (GFP and RFP) approximately half of the actual amount of template switching will yield a barcode with an identical sequence, the predicted amount of template switching in an arbitrarily large library will be higher. Given the parameters of the current pooled knockin library design (~400 bps between unique library insert and its corresponding barcode, separated by the new knocked in TCR-α specificity), the amount of predicted template switching with pooled assembly reactions was ~50%, whereas with a pooled electroporation was only ~10%. All experiments display one representative donor (b, c) or one or more technical replicates (d-h) from n=2 unique healthy donors.

FIGS. 17*a*-17*e* show the design of a 36 member pooled knockin library to alter T cell function and results after screening same.

a) A pooled knockin library of 36 potentially therapeutic genes was constructed that could be integrated along with a new TCR specificity (NY-ESO-1) using a single HDR template. The library was designed to contain both previously published and novel members that potentially modified immuno-therapeutic T cell function in a variety of broad classes: immune checkpoints with their intracellular domains either truncated ("tPD1" or "tCTLA4") or replaced with an activated domain (chimeric switch receptors, "CTLA4-CD28"); apoptotic mediators similarly truncated or with intracellular domains switched; genes involved in cell proliferation; chemokines; transcription factors; genes involved in metabolic pathways associated with survival in tumor environments; and suppressive cytokine receptors either as truncated/dominant negative receptors ("dnTGFβR2") or with switched intracellular domains.

b) All 36 constructs were synthesized and placed into a TCR insertion cassette that would replace the endogenous T cell receptor with a new specificity (NY-ESO-1 TCR) as well as drive expression of the new gene that potentially modifies T cell function off of the endogenous TCR-α promoter. Each library member was individually tested in an arrayed knockin screen and assayed for the percent knockin as well MFI of the surface expressed TCR to assay any potential effects of the individual inserts on TCR expression.

c) All 36 constructs successfully showed functional TCR expression as analyzed by surface dextramer staining for the new NY-ESO-1 TCR.

d) The total insert sizes ranged from ~2,000-3,000 bps (not including the homology arm sequences), and little correlation was observed between template size and knockin efficiency.

e) Observed MFI of NY-ESO-1 TCR expression following knockin of all 36 library members individually. Highly consistent TCR expression levels were observed across library members.

Figure 16H:
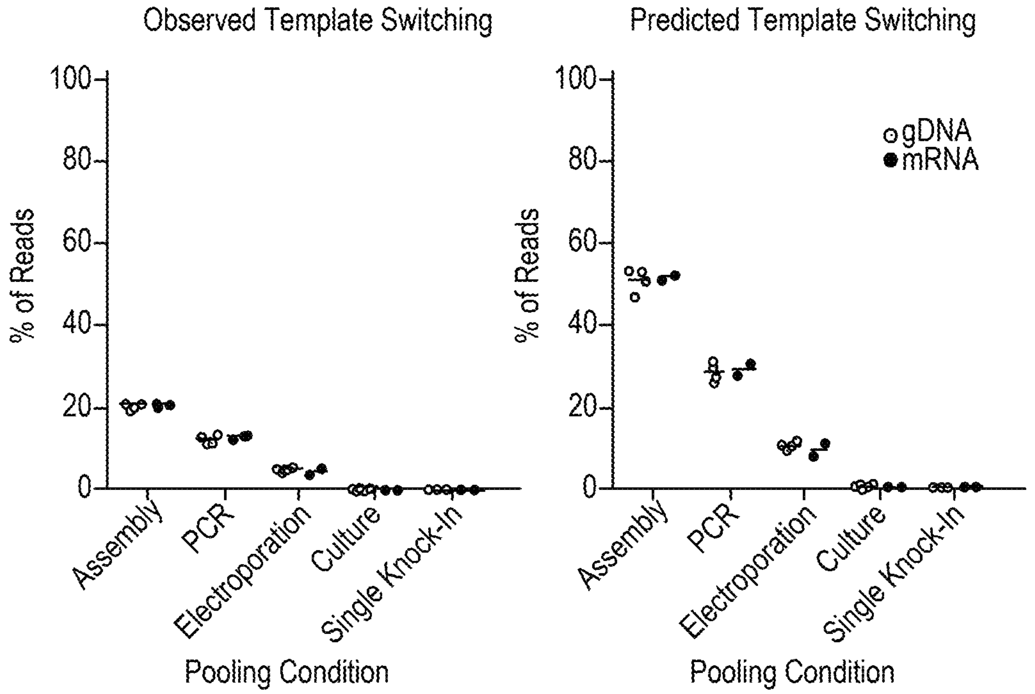
Figure 17A:
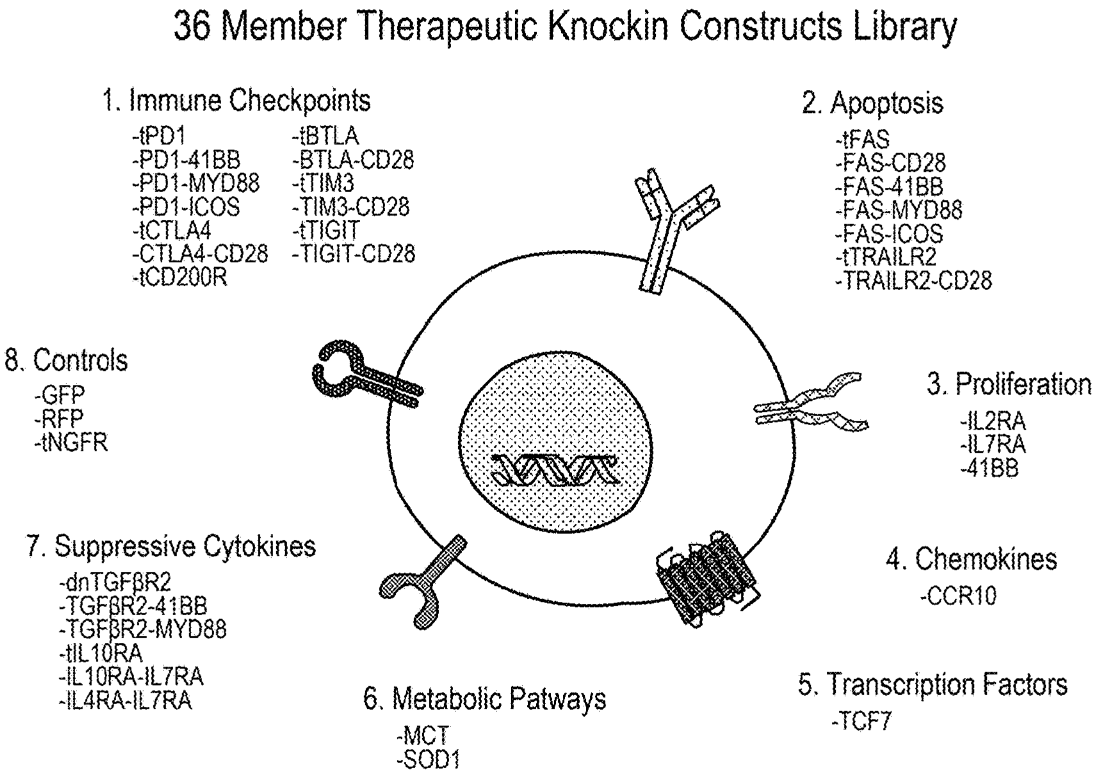
Figure 17B:
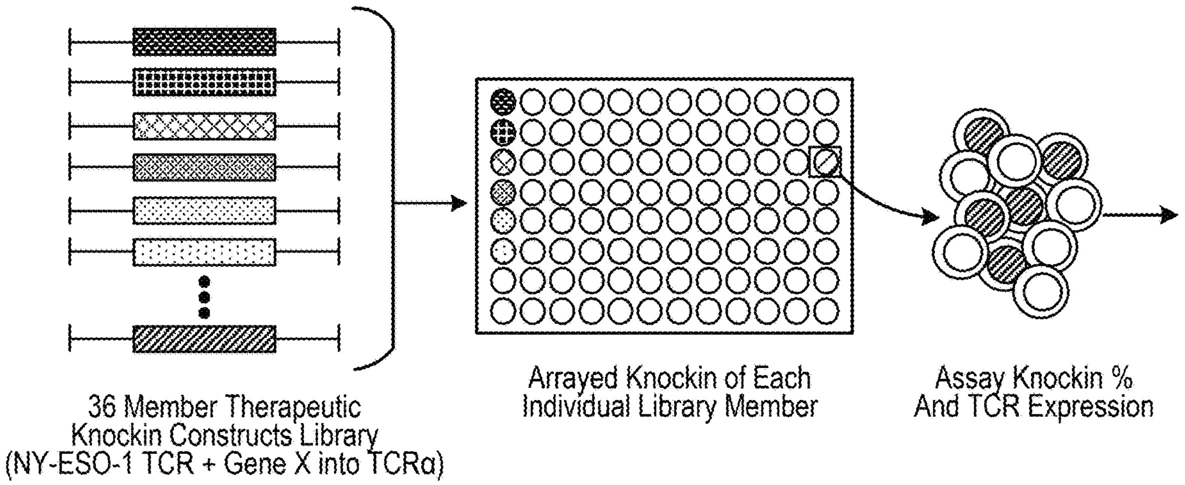
Figure 17C:
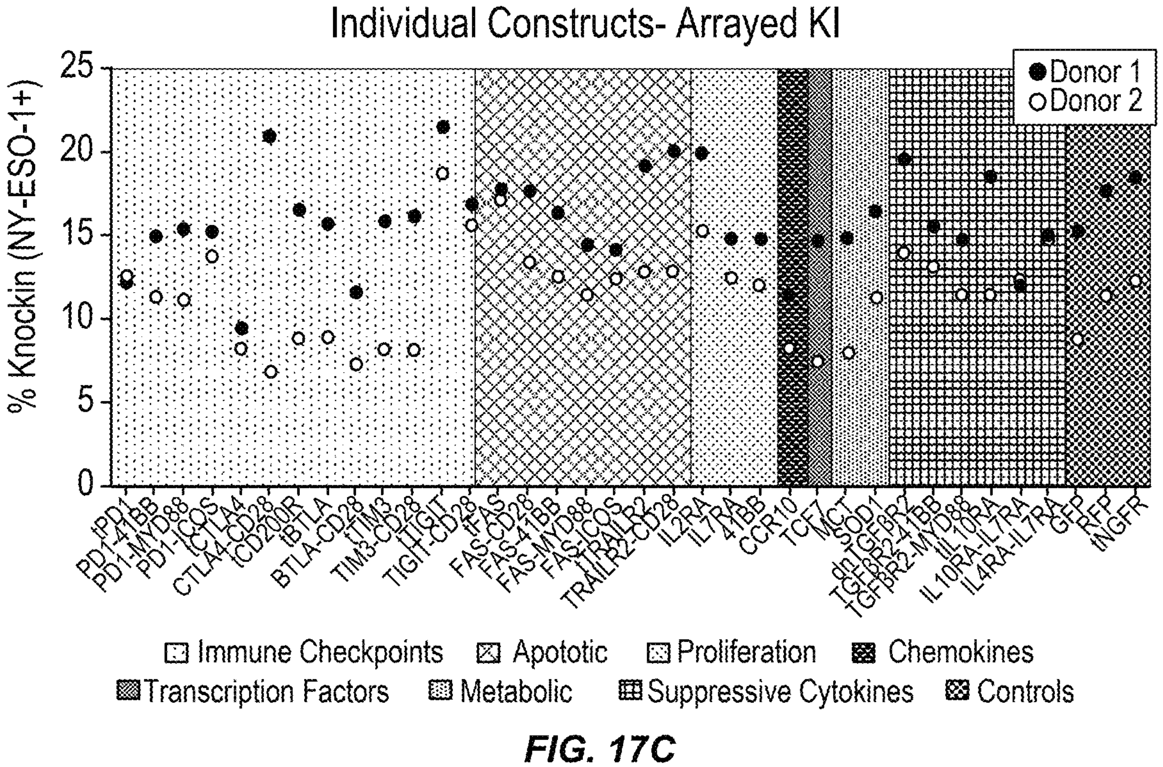
Figure 17D:
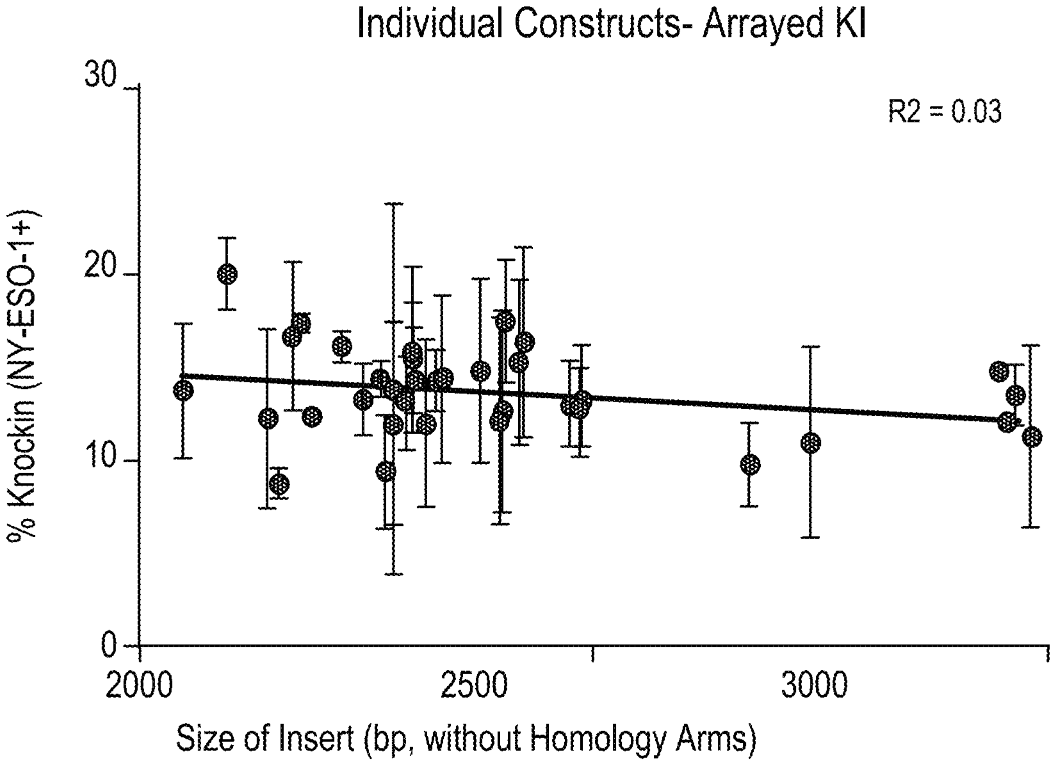
Figure 17E:
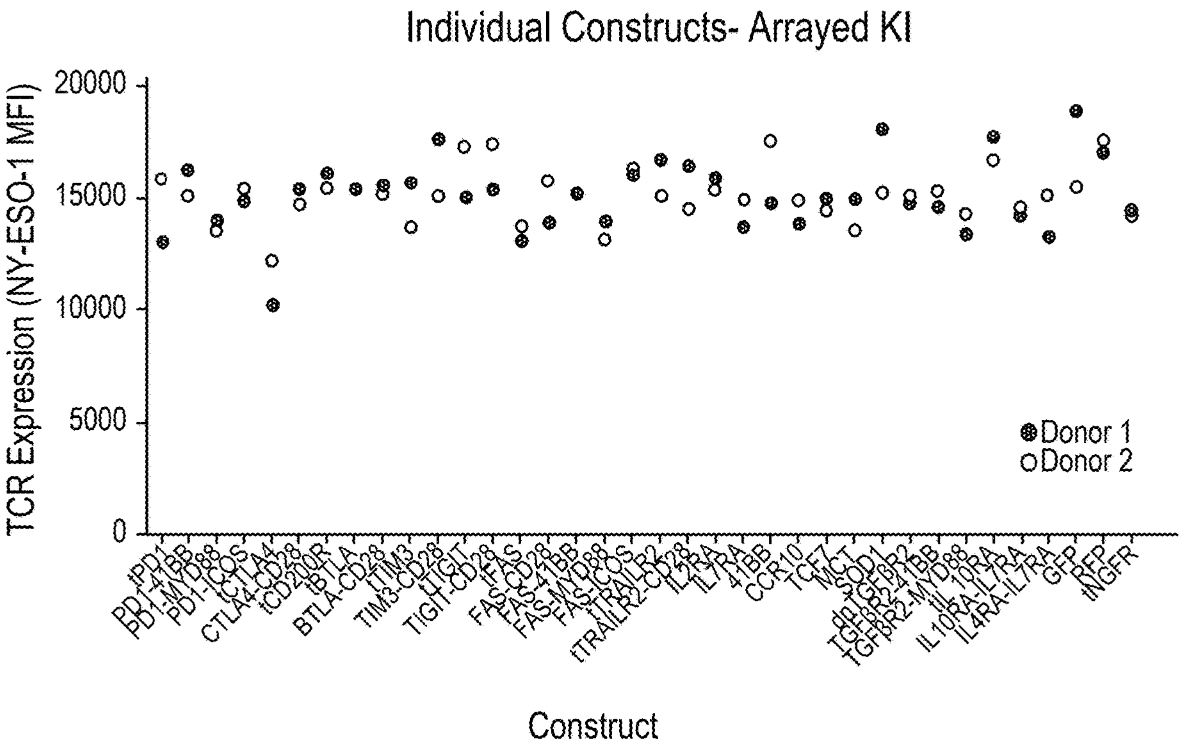
Figure 18A:
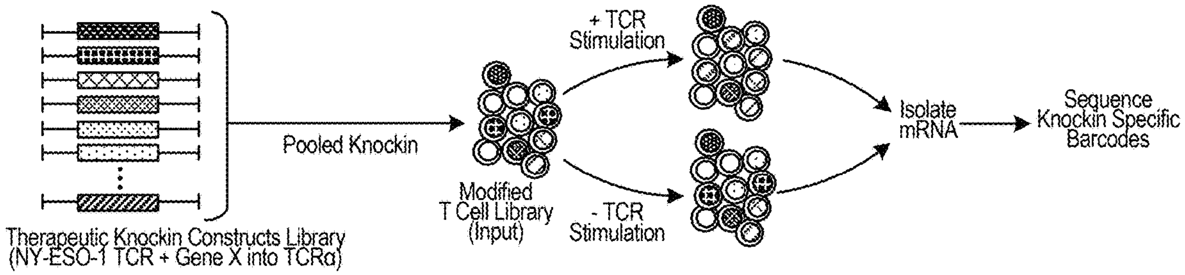
Figure 18B:
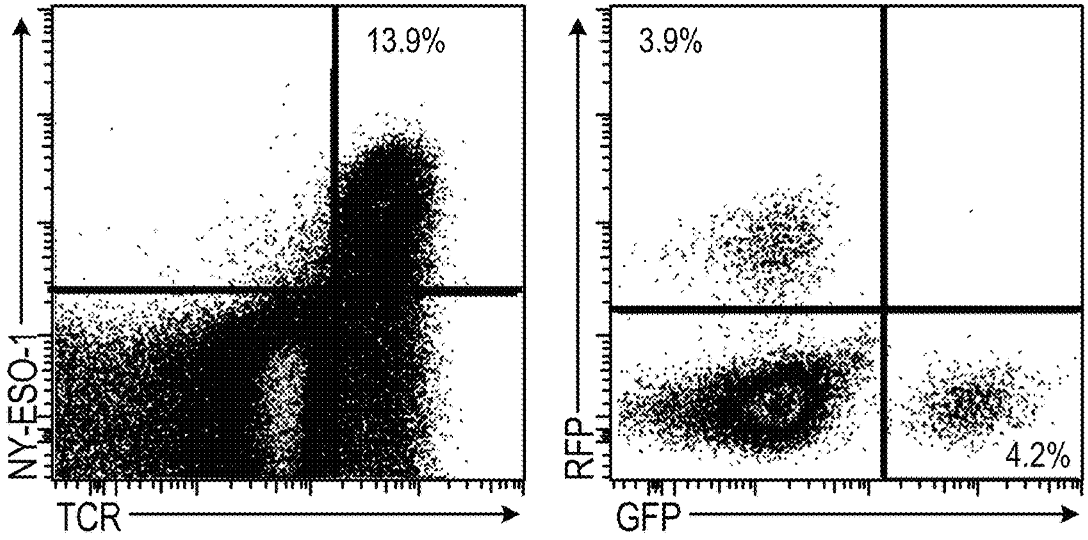
Figure 18C:
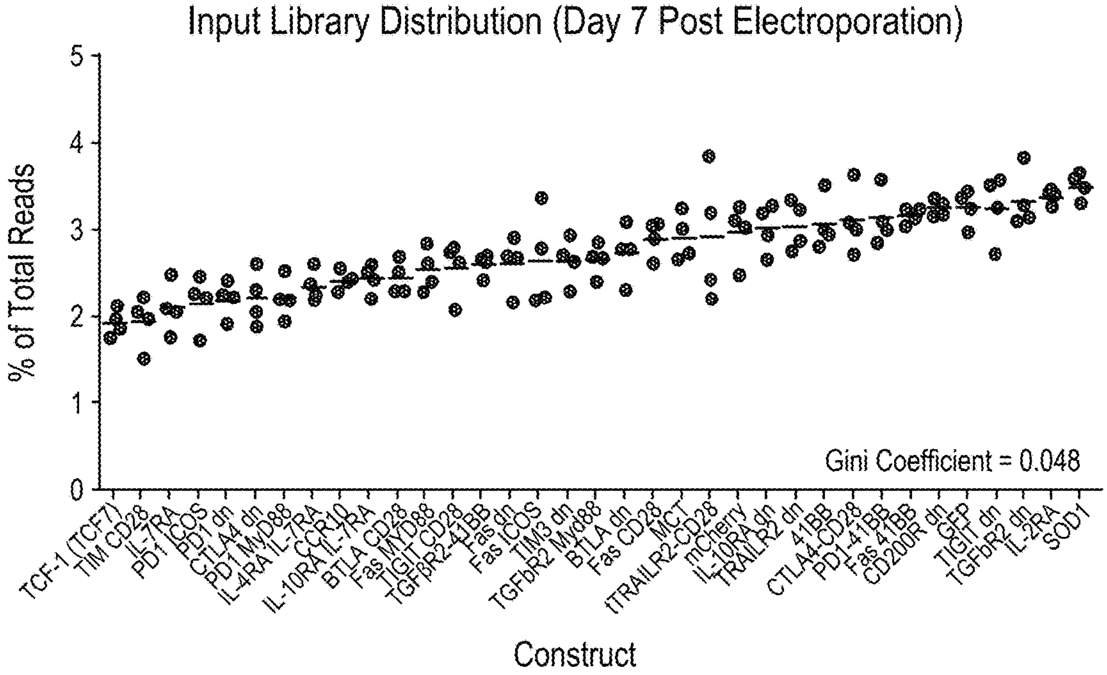
Figure 18D:
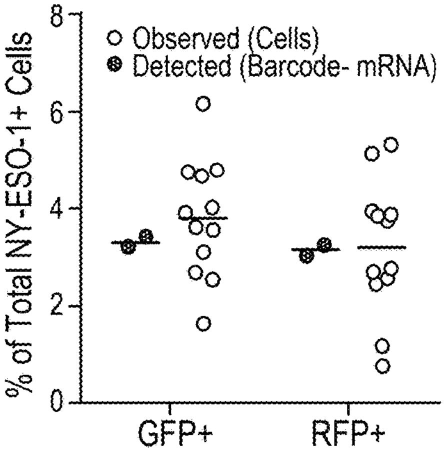
Figure 18E:
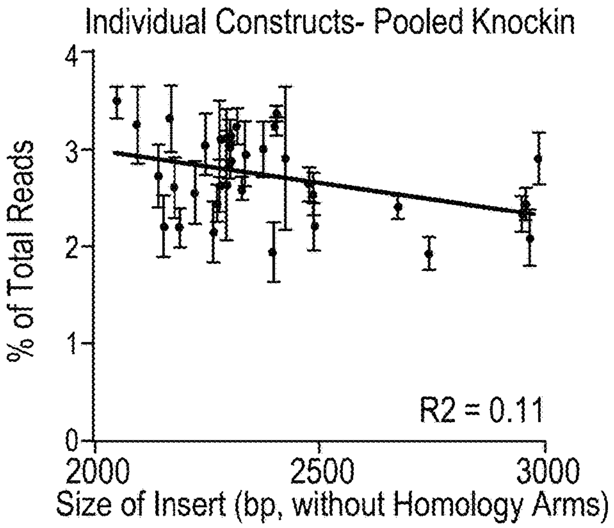

FIGS. 18*a*-18*k* show the results of technical validations of pooled knockin screening in primary human T cells.

a) Pooled knockin screening of a 36 member HDR template library where each member contains a constant new specificity (NY-ESO-1 specific TCR) as well as a unique gene with barcode that potentially modifies T cell function all targeted for integration at the TCR-α locus (TRAC exon 1). After electroporation, a modified T cell library is generated that can then be assayed, for instance by addition of a second TCR stimulation (an initial stimulation is used to knockin the constructs). The frequency of the unique barcodes for each library member is then determined by DNA sequencing. Barcode frequencies can then be compared to the input population to see the relative effects of each library member on T cell behavior in that assay.

b) Two genes in the 36 member library were easily detectable by flow cytometry, control knockins of GFP and RFP. Gating on knockin positive cells that has acquired the new NY-ESO-1 specific TCR revealed that the proportion of cells that were also GFP+ or RFP+ was roughly equivalent.

c) Distribution of barcodes in the modified T cell library seven days after pooled electroporation of the 36 member library. The percentage of total reads for each library member was consistent across four unique healthy human T cell donors, and the library showed a relatively even distribution (Gini coefficient=0.048).

d) Correspondence between observed population frequencies at the protein level by flow cytometry and detected barcode frequencies at the DNA level through the pooled knockin sequencing approach. For the proteins GFP and RFP easily observable by flow cytometry, the proportion of cells positive at the protein level was similar to the proportion of reads with corresponding GFP and RFP barcodes.

e) Relationship between the size of the inserted sequence and the detected frequency in the modified T cell library. The NY-ESO-1-β and NY-ESO-1-α VJ segments along with their associated 2A elements are ~1.5 kb, while the size of the additional functional gene knocked in in the same construct varied from ~0.5-1.5 kb, yielding a total insert size of between 2-3 kb. A slight correlation was observed with larger inserts present in the library at slightly lower frequencies ($R^2$=0.11).

f) Seven days after pooled electroporation of the 36 pooled knockin constructs, the modified T cell library was either stimulated 1:1 CD3/CD28 beads:cells ratio or isolated as an input population. The log 2 fold change in barcode frequency over the input population after 5 days of in-vitro TCR stimulation is displayed. Constructs derived from the apoptotic mediator FAS cell surface protein showed remarkable increases in relative proliferation across four unique healthy T cell donors.

g) The reproducibility of pooled knockin screen results was examined across technical replicates and for different pooling stages (FIG. 16*a*). Technical replicates of the TCR stimulation screen in the same biologic donor showed high correlation ($R^2$=0.99). The correlation between Pooled Assembly and Pooled Electroporation conditions was lower ($R^2$=0.88). This was likely due to greater variation between technical replicates in the Pooled Assembly condition due to the higher amounts of template switching observed when the library pooling occurs at earlier stages (FIG. 16*h*), as the correlation between technical replicates of Pooled Assembly conditions was similarly slightly lower ($R^2$=0.89).

h) The number of knockin positive viable cells is important for performing large pooled screens. The expansion of primary human T cells after pooled knockin was assayed for 10 days poste electroporation. Given 1 million primary human T cells at isolation, an average of ~0.5 million knockin positive cells were recovered by four days post electroporation (average knockin efficiencies were 10%-20%), and these cells continued to expand robustly over additional days in culture across four healthy human donors.

i) Knockin experiments generate mixed populations of cells, some with alleles containing the desired knockin, some with knockout alleles, and some with unedited alleles (FIG. 18*b*). Pooled knockin screening can be performed on both sorted knockin positive cells (here sorted on NY-ESO-1 dextramer staining) as well as an unsorted bulk population of edited cells when sorting is not practical or feasible. The sequenced barcode frequencies after pooled knockins were highly correlated between both sorted and unsorted bulk populations ($R^2$=0.87).

j-k) For the majority of pooled knockin experiments, T cells were expanded for 7-10 days after electroporation prior to application of a selective pressure. Expansion in culture (containing media+IL-2 only) over this time period did not show any large changes in abundance of library members, except for a large relative increase in abundance of IL2RA.

Experiments display or are representative of n=2 (d, g, i) or n=4 (c, e-f, h, j-k) unique healthy human T cell donors. Dotted lines represent max and min abundance of non-functional control library members.

FIGS. 19*a*-19*d* show that pooled knockin screening identifies distinct functional sequences under varying in vitro selective pressures mimicking tumour environments.

a) Pooled electroporation of a 36 member library of DNA sequences encoding potential function modifying proteins along with a constant new TCR specificity (NY-ESO-1) generates a pooled library of modified primary human T cells. Various In vitro Selective pressures mimicking the tumour environment can then be applied and the distribution of unique barcodes in the pool of modified T cells can be compared to the input population of T cells or between the given selective pressures, revealing library sequences that impart changes in T cell proliferation in each specific context.

b) Distribution of library members after in vitro culture for 5 days in TGFB, represented as a ranked list of log 2 fold changes over the input population. Input cells were taken at 7 days post electroporation and 1:1 CD3/CD28 beads:cells stimulation was applied with 25 ng/mL of exogenous TGFB in the culture media. Relative to input, multiple FAS derived anti-apoptotic receptors as well as TGFBR2 derived anti-suppressive receptors increased relative proliferation. When compared to bead based stimulation only though, FAS derived receptors showed a relative decrease in abundance (but still an absolute increase) demonstrating potentially enhanced susceptibility to TGFB mediated suppression. TGFBR2 derived receptors in contrast showed by far the greatest relative proliferation in the presence of TGFB. The previously published dominant negative TGFBR2 receptor was only by a novel chimeric TGFBR2 extracellular-41BB intracellular construct.

c) In the context of excessive amounts of TCR stimulation (5:1 CD3/CD28 bead:cell ratio instead of a standard 1:1 ratio), again FAS derived constructs showed increased relative abundance when compared to the input population prior to stimulation. When comparing the suppressive excessive stimulation population to standard stimulation, the FAS constructs again showed greater relative inhibition in the suppressive condition, whereas a construct expressing the transcription factor TCF7 in all four donors showed greater relative proliferation with excessive stimulation when compared to standard amounts of CD3/CD28 stimulation.

d) Stimulation of the modified T cell library through the TCR only (through incubation with an NY-ESO-1 specific dextramer) without the presence of a CD28 engaging co-stimulatory signal showed selective increase of some, but not all, CD28 chimeric switch receptors. The extracellular domain of various immune checkpoint proteins, such as CTLA4, TIM3, and BTLA were fused with the intracellular domain of CD28. In comparison to CD3/CD28 stimulation, stimulation only through the TCR (CD3) showed relative increases in proliferation among CTLA4-CD28, TIM3-CD28, and BTLA-CD28 constructs. All graphs display log 2 fold change compared to modified T cell library input, or relative log 2 fold change compared to CD3/CD28 stimulation. Mean of n=4 unique healthy donors is displayed and was used to rank the constructs. Dotted lines represent max and min abundance of non-functional control library members.

Figure 18F:
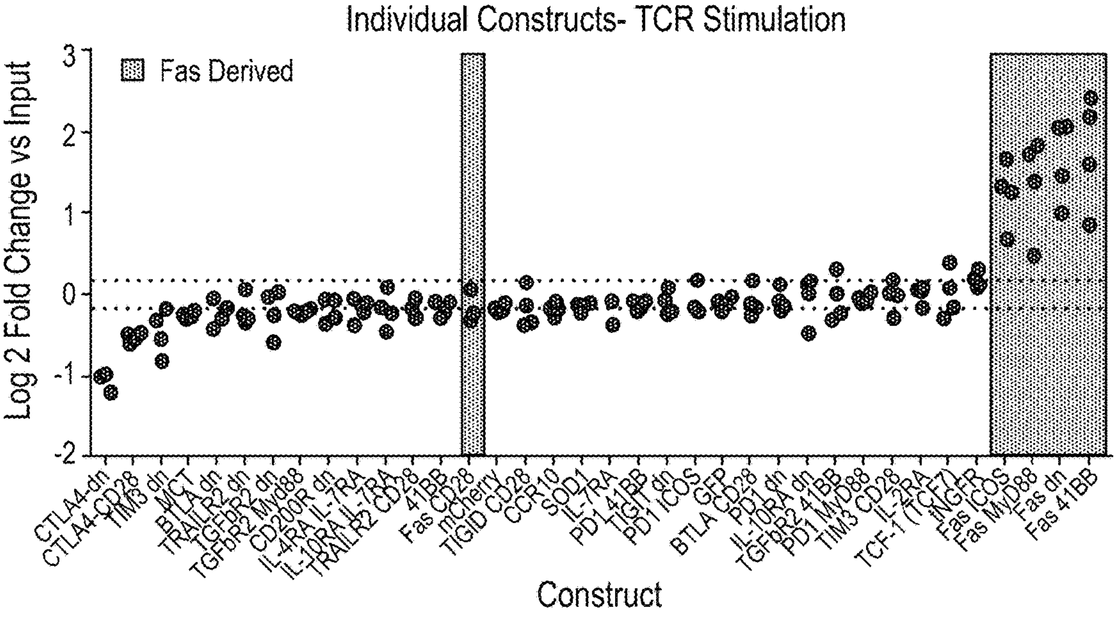
Figure 18G:
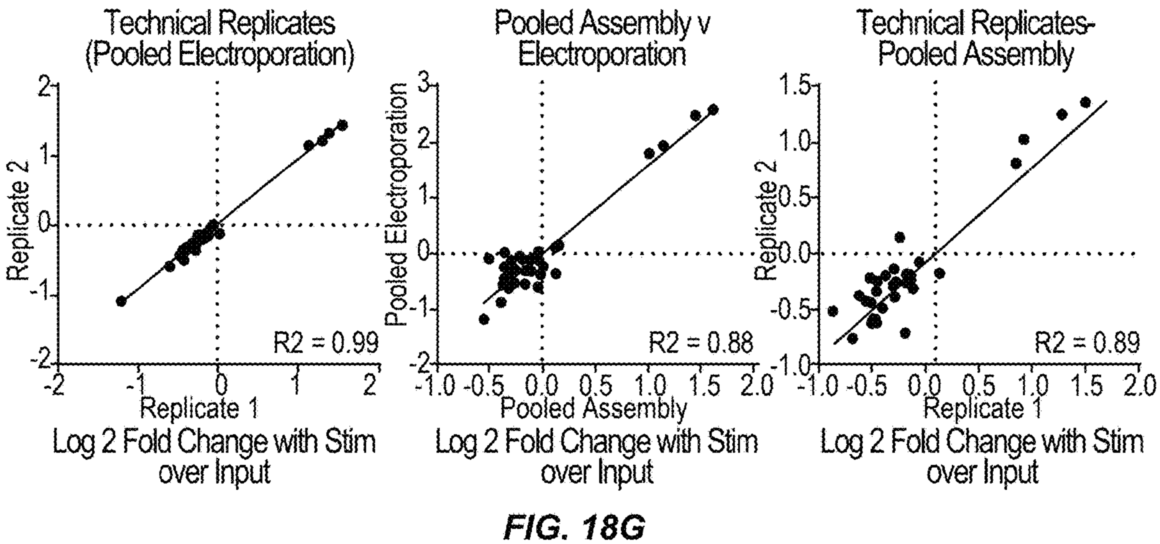
Figure 18H:
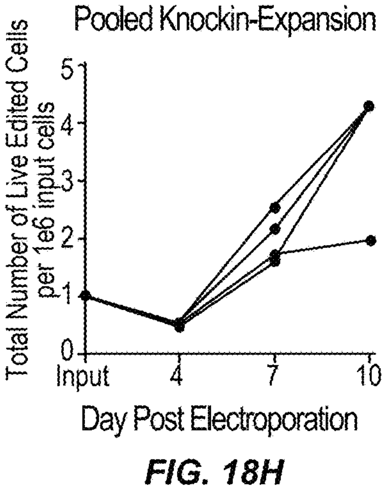
Figure 18I:
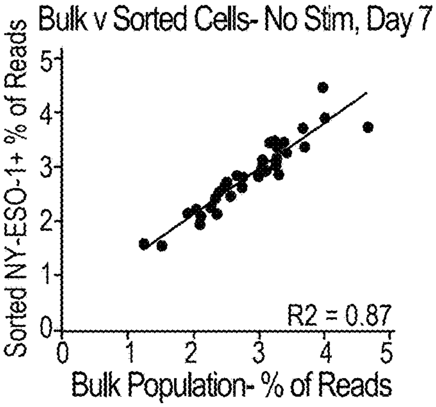
Figure 18J:
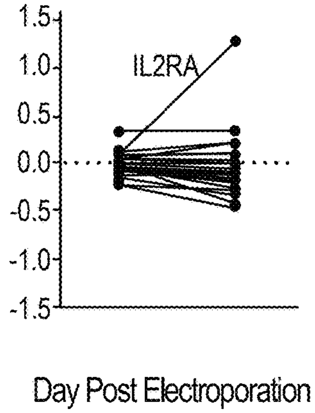
Figure 18K:
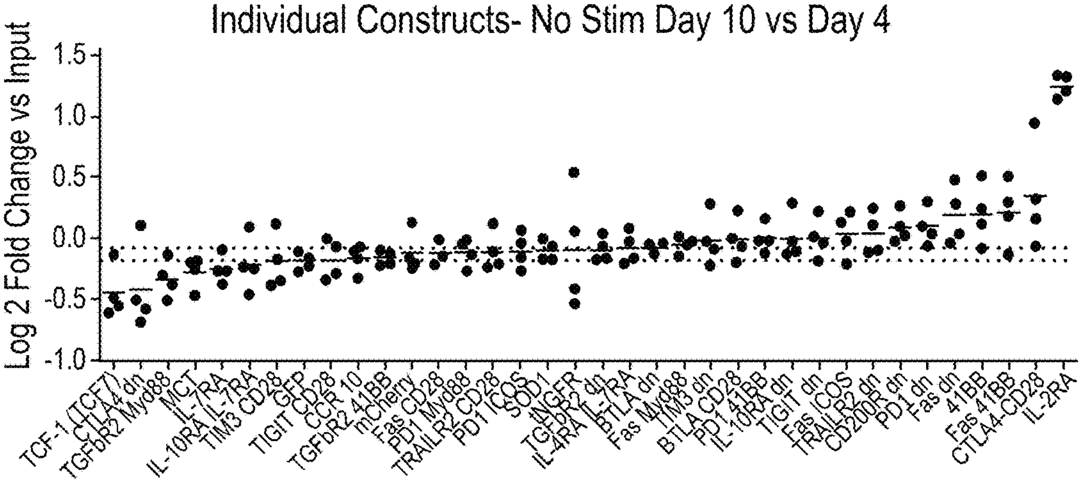

FIGS. 20*a*-20*d* show the results of an in vivo pooled knockin screen in solid tumour xenograft model.

a) Pooled knockin of a 36 member potential therapeutic knockin constructs library that imparts a new unique function modifying protein as well as a constant new TCR specificity (NY-ESO-1 specific TCR, 1G4 clone). After generation and expansion for 10 days, a modified T cell library (2.5e6 NY-ESO-1+ T cells) was adoptively transferred into immunodeficient NSG mice bearing a solid human melanoma tumour xenograft (A375 melanoma cells expressing the target peptide/MHC for the NY-ESO-1 TCR) injected sub-cutaneously 7 days before transfer. After 5 days of in vivo selective pressure in the solid tumour environment the tumours were dissected, T cells sorted, and the relative abundance of barcodes analyzed by DNA sequencing.

b) Biologic replicates of the in vivo solid tumor pooled knockin screen showed greater variance across the library than in vitro pooled knockin screens (FIG. 4*b*), but consistently showed the same top library hits.

c) Technical replicates of the in vivo pooled knockin screen within the same donor similarly showed greater variance than in vitro pooled knockin screens (FIG. 18*g*).

d) Multiple hits from in vitro pooled knockin screens similarly showed increased proliferation and/or persistence in the solid tumour xenograft environment. Both the transcription factor TCF7, as well as TGFβR2 derived chimeric receptors, showed robust and reproducible increases in relative abundance. Additional library members not identified in any of the in vitro screens performed, such as the metabolite transporter MCT4, showed strong relative enrichment in the in vivo tumour environment. Experiments display or are representative of n=2 (b-d) unique healthy human T cell donors. Dotted lines represent max and min abundance of non-functional control library members.

Figure 4A:
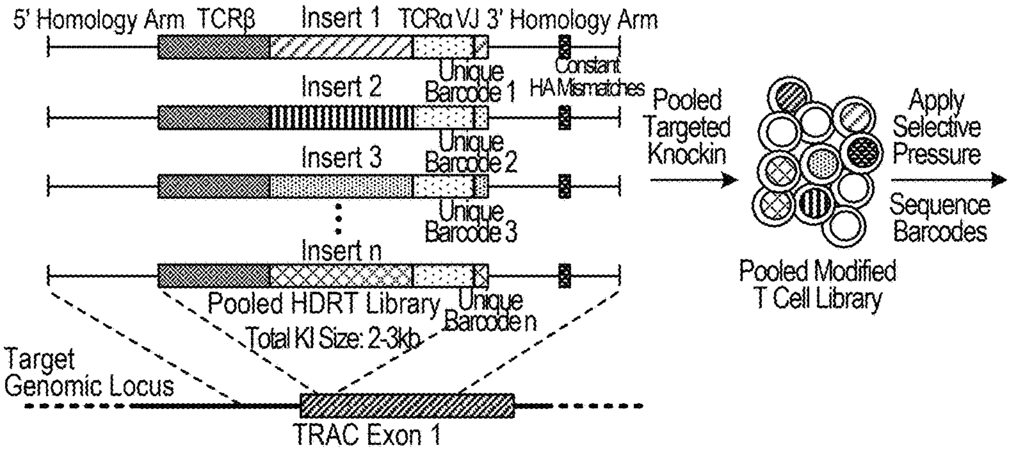
Figure 4B:
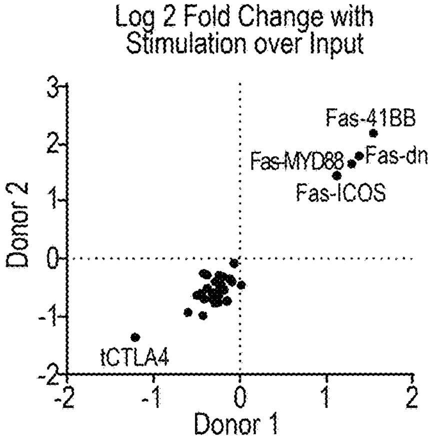
Figure 4C:
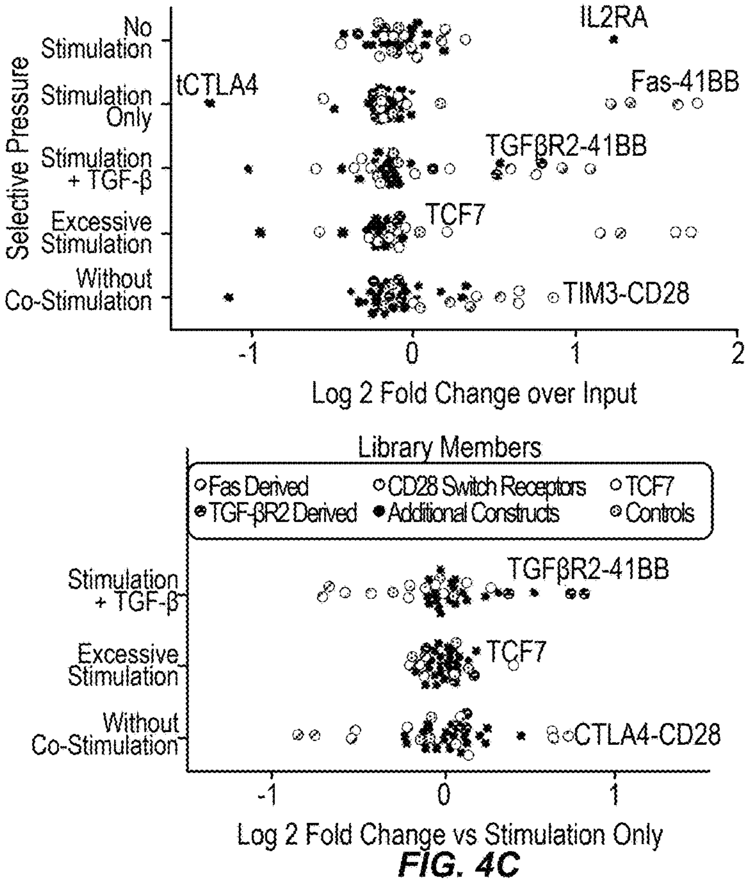

FIGS. 21*a*-21*h* show data for individual validation of hits from pooled knockin screening.

a) Individual functional validation of a TGFβR2-41BB chimeric receptor bearing the extracellular domain of the suppressive cytokine receptor TGFβR2 and the intracellular domain of the proliferative receptor 41BB. With a single HDR template, primary human T cells were engineered to express both a new TCR specificity (NY-ESO-1) as well as the anti-suppressive TGFβR2-41BB receptor.

b) In the presence of TGFβ, the TGFβR2-41BB modified cells recapitulated the observed phenotype of greater relative proliferation compared to stimulation only (FIG. 19). Sorted NY-ESO-1+ T cells also expressing either TGFβR2-41BB or a GFP control were stimulated with CD3/CD28 beads (1:1 bead to cell ratio) 7 days after electroporation and proliferation was assayed by absolute cell counts at each indicated day. Surface staining for activation and exhaustion markers was performed 6 days after the stimulation.

c) TGFβR2-41BB modified cells showed greater antigen specific tumour killing in vitro than GFP controls, and comparable if not greater killing than expression of the dnTGFβR2, when co-cultured with A375 human melanoma cells with the addition of exogenous TGF-β across the indicated range of T cell to cancer cell ratios. At 5 days after beginning the co-culture killing assay, T cells were removed and stained for surface expression of PD1.

d) Individual functional validation of a FAS-41BB chimeric receptor bearing the extracellular domain of the apoptotic receptor FAS and the intracellular domain of the proliferative receptor 41BB. With a single HDR template, primary human T cells were engineered to express both a new TCR specificity (NY-ESO-1) as well as the anti-apoptotic FAS-41BB receptor.

e) Expression of a FAS-41BB chimeric receptor greatly increased relative proliferation compared to expression of a GFP control receptor (both along with the new TCR specificity) in an antigen-independent proliferation assay (CD3/CD28 bead stimulation 7 days post electroporation), validating the observed increased proliferation seen with stimulation in the pooled screens (FIG. 4*c*). Crucially, increased proliferation with the FAS-41BB receptor was only seen upon stimulation, whereas continued expansion in IL-2 without stimulation showed no relative proliferative advantage compared to control. Decreased surface expression of activation and exhaustion markers was also observed 6 days after bead stimulation.

f) FAS-41BB modified T cells showed greater antigen specific tumor killing in vitro.

g) Individual functional validation of the TCF7 expression construct. With a single HDR template, primary human T cells were engineered to express both a new TCR specificity (NY-ESO-1) as well as an altered transcriptional program through expression of TCF7 off of the TCR-α promoter.

h) Expression of TCF7 recapitulated the higher observed relative proliferation compared to TCR+GFP control knockin in an excessive stimulation condition (5:1 CD3/CD28 bead to cell ratio) compared to standard stimulation (1:1 bead to cell ratio). Expression of the indicated activation and exhaustion markers was unchanged between the conditions. Note that in these individual validation experiments the effect size of the alteration in relative proliferation with TCF7 expression compared to the proliferative effect of the FAS-41BB chimera similarly recapitulated the observed effect sizes in the pooled knockin screens (FIG. 4*c*).

i) TCF7 expressing modified T cells showed greater antigen specific tumor killing in vitro. Experiments display or are representative of n=2 (b-c, e-f, h-i) unique healthy human T cell donors.

Figure 22:
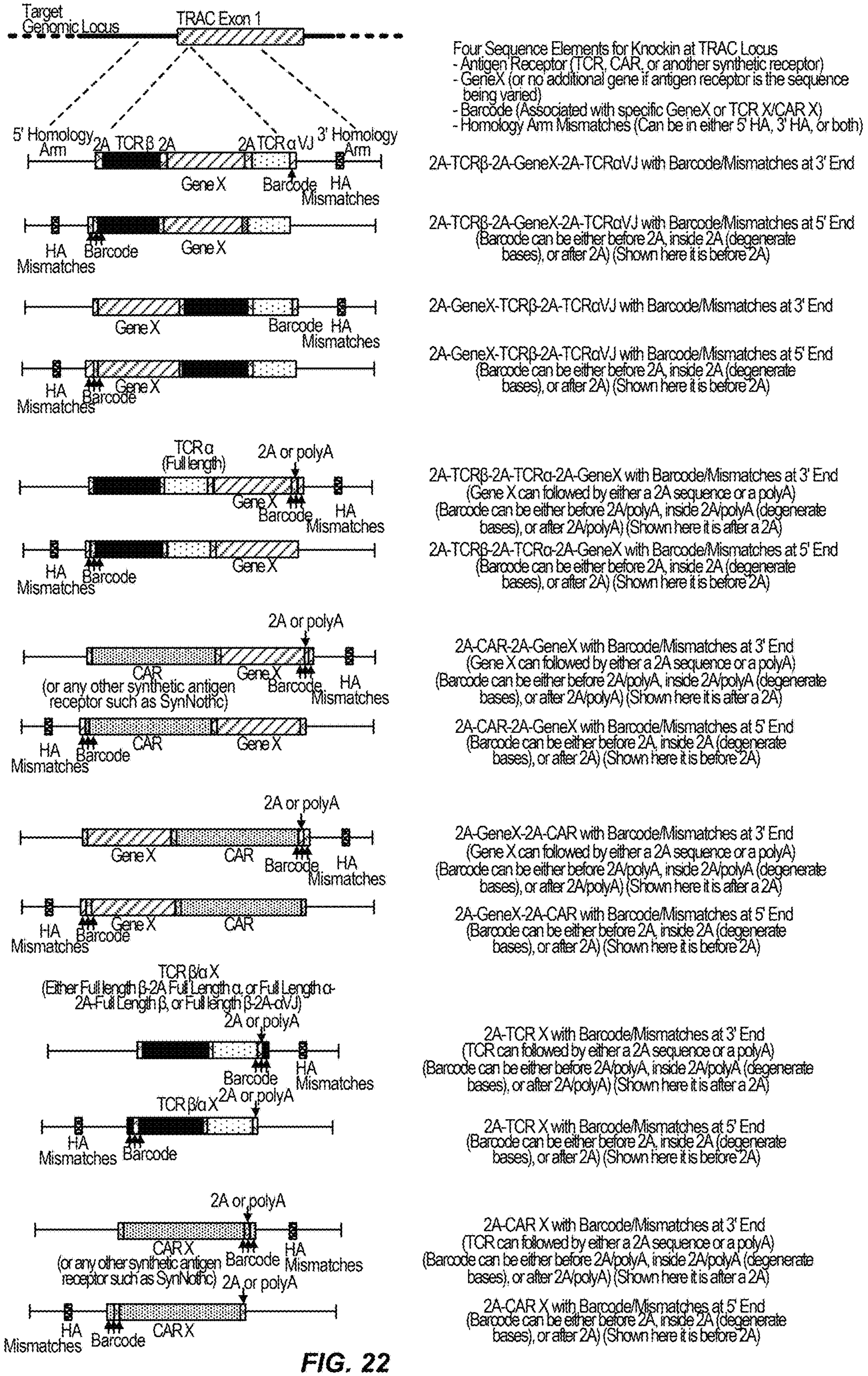

FIG. 22 shows exemplary schematic diagrams of nucleic acid constructs that can be used in the screening methods described herein. In any one of the constructs shown in FIG. 22, one or more barcodes can be included either before the 2A sequence, inside the 2A sequence, optionally, with degenerate bases, or after the 2A sequence. In any one of the constructs shwon in FIG. 22, a pair of unique barcodes, i.e., barcodes having different sequences, can flank Gene X, i.e., a gene of interest, on either side.

FIGS. 23*a-e* show pooled knock-in screening paired with single cell RNA sequencing for rapid phenotyping of therapeutic primary T cell modifications.

a) A 36 member library of control and potentially therapeutic constructs was knocked into the TCRα locus of primary human T cells along with replacing their endogenous TCR with an NY-ESO-1 cancer antigen specific TCR. After either in vitro expansion only (Input) or four days after adoptive transfer into an in vivo antigen specific melanoma xenograft model, live T cells were sorted and single cell droplets generated. The specific knock-in construct for each cell was determined by amplicon sequencing (FIG. 24*a-e*) and associated with each single cell's transcriptome.

b) UMAP representation of all single cells identified from two donors in a pooled knock-in screen combined with single cell RNA sequencing in two donors.

c) Normalized gene expression (Z-Score) on the UMAP representation reveal differences in expression between input and in vivo populations in markers of activation status (CCR7 and MK167) and effector function (GZWB and IFNG).

d) Correlation in in vivo abundance of each library member in the bulk cell pooled knock-in screen (FIG. 4*d*) and the single-cell pooled knock-in screen.

e) In vivo phenotypic signatures of NY-ESO-1 TCR plus control, TCF7, or TGFβR2-41BB polycistronic constructs. Relative gene expression heatmap of genes differentially expressed in vivo between the three knock-in constructs revealed distinct gene signatures.

FIGS. 24*a-e*: Molecular and analytic pipeline for single-cell RNAseq combined with pooled knock-in screening.

a) Molecular diagram of sequencing pipeline to associate a cell with the gene knocked in during a combined pooled knock-in plus single cell RNAseq experiment. The barcode for the specific knock-in construct ("Knock-in Barcode") the cell expresses is integrated into the cells genomic DNA during HDR (FIG. 4*a*) and is present in degenerate bases of the coding region of the integrated TCRαVJ region. After transcription and single cell isolation in droplets, the TCR+Gene X mRNA transcripts from the individual cell are bound to a bead containing poly(dT) primers along with a unique cell barcode. Following reverse transcription, a primer binding immediately upstream of the knock-in barcode creates an amplicon containing both the knock-in barcode as well as the cell-barcode. Next-generation sequencing from both ends of this amplicon yields a matched pair of knock-in barcode and cell-barcode, along with an universal molecular identifier (UMI). Note that only a portion of cDNA isolated during the droplet-based polyA pulldown is used for sequencing of the barcodes, and a separate portion of the cDNA can be used to generate single-cell transcriptomes.

b) Computational analysis pipeline for associating knock-in barcodes with individual cells in combined pooled knock-in plus single cell RNAseq experiments.

c) Histogram of the number of unique molecular identifiers (UMIs) associated with each sequenced combination of knock-in barcode and cell barcode. UMIs are added during the reverse transcription step (a) and each represents a unique mRNA transcript. Knock-in barcode/cell barcode combinations with only a single UMI were filtered from further analysis.

d) Histogram of the number of knock-in barcodes associated with each sequenced cell barcode. As expected, the vast majority of cell barcodes had only a single knock-in barcode associated with them. Cell barcodes that had two associated knock-in barcodes could represent real biallelic knock-ins or results from template switching during library preparation. Cells barcodes with greater than two associated knock-in barcodes were rare, and likely represent template switching events. The minority of cell barcodes with two or more associated knock-in were filtered from further analysis.

e) Over 75% of cell barcodes that were assigned a knock-in barcode also had single cell transcriptomes that passed quality filters (see Examples) A larger number of cell barcodes that had sequenced transcriptomes but did not have a knock-in barcode assigned could be due to inefficiencies in the library preparation process, cells with biallelic knock-ins being filtered out, or cells without an on-target knock-in being present the sorted and sequenced samples.

FIGS. 25*a-e* provides data showing that pooled knock-in screening reveals therapeutic knock-in cassettes that improve antigen specific tumour control in vitro and in vivo.

(a) Knock-in of a single polycistron to the TRAC locus allowed simultaneous replacement of the endogenous antigen specificity and co-expression of natural or synthetic gene-product to modify cell function. Complementary in vitro and in vivo pooled knock-in screening allowed rapid identification of new constructs that enhanced context-specific T cell functions, including polycistrons encoding novel TGFβR2-41BB and FAS-41BB chimeric receptors or the TCF7 transcription factor.

(b) Polycistrons encoding NY-ESO-1 antigen specificity plus a FAS extracellular 41BB switch receptor or the transcription factor TCF7 similarly, identified as hits in the expansion screens, showed enhanced in vitro NY-ESO-1+ cancer cell killing compared to TCR knock-in with a control GFP insert.

(c) Polycistrons with TGFβR2 switch receptor or dnTGFβR2 identified as hits in in vitro and in vivo expansion screens, enhanced NY-ESO-1+ cancer cell killing in vitro. A chimeric protein with TGFβR2's extracellular domain and a 41BB intracellular domain showed greater antigen specific cancer cell killing compared to a dnTGFβR2 construct or TCR knock-in with a control tNGFR insert, both in the absence or presence of exogenous TGFβ1. Representative of n=2 independent healthy donors (b, c).

(d), Melanoma tumour mouse xenograft model. NSG mice, non-obese diabetic (NOD)/severe combined immunodeficiency (SCID)/Il2rg$^{-/-}$ mice.

(e) Tumour sizing after adoptive transfer of vehicle alone (saline, Grey) or NY-ESO-1 TCR cells with an additional polycistronic construct: tNGFR control (Black), the transcription factor TCF7 (Orange), or the chimeric TGFβR2-41BB receptor (Red). The three polycistronic NY-ESO-1 TCR constructs showed statistically significant reductions in tumour size compared to vehicle alone, but only the TGFβR2-41BB construct resulted in tumour clearance. One representative donor with n=8+ mice per condition shown out of n=2 (TCF7, FIG. 25) or n=4 (tNGFR, TGFβR2-41BB, FIG. 26) unique healthy human donors. P<0.01, *P<0.001, ****P<0.0001 (two-way analysis of variance (ANOVA) with Holm-Sidak's multiple comparisons test).

FIGS. 26*a-e* show in vitro validation of FAS-41BB chimeric receptor hit from pooled knock-in screening.

(a) Individual functional validation of a Fas-41BB chimeric receptor bearing the extracellular domain of the apoptotic receptor FAS and an intracellular domain of the proliferative receptor 41BB. With a polycistronic HDR template, primary human T cells were engineered to express both a new TCR specificity (NY-ESO-1 antigen) as well as the chimeric Fas-41BB receptor. (b) Antigen-independent validation assays. Expression of a Fas-41BB chimeric receptor increased relative expansion compared to expression of a GFP control receptor (both along with the new TCR specificity) in an antigen-independent proliferation assay (anti-CD3/CD28 bead re-stimulation 7 days post electroporation), validating the observed increased expansion seen with stimulation in pooled screens. Similarly to the pooled screens, increased expansion with the Fas-41BB receptor was only seen upon re-stimulation, whereas continued expansion in IL-2 without re-stimulation showed no relative expansion advantage compared to control. Decreased surface expression of some activation and exhaustion markers was also observed after bead stimulation. (c) Antigen specific validation assays. T cells targeted with the NY-ESO-1 TCR/Fas-41BB construct showed greater NY-ESO-1+ cancer cell killing in vitro than those targeted with control NY-ESO-1 TCR construct across T cell to cancer cell ratios. Increased antigen specific in vitro killing was observed across multiple biologic donors % hours after co-culture at 1:4 T cell to cancer cell ratio (n=5 unique healthy human T cell donors with 2 technical replicates each). **P<0.01, Wilcoxon matched-pairs signed-rank test. 5 days after beginning the co-culture killing assay, T cells were removed and stained for surface expression of activation and exhaustion markers. (d) Pooled knock-in plus single-cell RNAseq data reveals changes in abundance of different FAS derived chimeric proteins after in vitro expansion. (e) Gene expression analysis of five different FAS derived chimeric proteins reveals distinct gene expression signatures. Note the enriched expression of genes associated with proliferation in the FAS-41BB construct, which showed the greatest relative proliferative potential in pooled stimulation screens. Experiments display or are representative of n=2 (b-c) unique healthy human T cell donors unless otherwise noted.

FIGS. 27*a-d* show in vitro validation of the pooled knock-in screen hit TCF7 and in vivo tumour control experiment.

(a) Individual functional validation of the TCF7 expression construct. With a polycistronic HDR template, primary human T cells were engineered to express both a new TCR specificity (NY-ESO-1 antigen) as well as an altered transcriptional program through TCF7 controlled by endogenous TCR-α gene regulation.

(b) Antigen-independent validation assays. Expression of TCF7 recapitulated the higher observed relative expansion compared to NY-ESO-1 TCR+ GFP+ control knock-in under excessive stimulation conditions (5:1 anti-CD3/CD28 bead to cell ratio) relative to standard stimulation (1:1 bead to cell ratio). Expression of the indicated activation and exhaustion markers did not appear changed between the modifications.

(c) Antigen specific validation assays. T cells targeted with the NY-ESO-1 TCR/TCF7 construct showed greater NY-ESO-1+ cancer cell killing in vitro than those targeted with control NY-ESO-1 TCR construct across T cell to cancer cell ratios. Increased antigen specific in vitro killing was observed across multiple biologic donors 96 hours after co-culture at 1:4 T cell to cancer cell ratio, although the magnitude of effect was strongly donor dependent (n=5 unique healthy human T cell donors with 2 technical replicates each; **P<0.01, Wilcoxon matched-pairs signed-rank test). 5 days after beginning the co-culture killing assay, T cells were removed and stained for surface expression of activation and exhaustion markers.

(d) Individual tumour tracings for in vivo tumour growth in A375 melanoma xenograft model. At day 9 after tumour seeding, 1.5 e6 sorted NY-ESO-1 TCR/tNGFR control T cells (Black) or NY-ESO-1 TCR/TCF7 T cells (Orange), or no T cells (Grey, Vehicle Only) were adoptively transferred. While both the tNGFR control and TCF7 cells showed statistically significant reductions in tumour size relative to vehicle only (FIG. 23*e*), TCF7 expression did not show statistically significant improvements relative to tNGFR control T cells. Experiments display or are representative of n=2 (b-c) unique healthy human T cell donors unless otherwise noted.

FIGS. 28*a-e* show in vitro and in vivo validation of TGFβR2-41BB chimeric receptor.

(a) Individual functional validation of a TGFβR2-41BB chimeric receptor bearing the extracellular domain of the suppressive cytokine receptor TGFβR2 and the intracellular domain of the proliferative receptor 41BB. With a polycistronic HDR template, primary human T cells were engineered to express both a new TCR specificity (NY-ESO-1) as well as the TGFβR2-41BB chimeric switch receptor.

b) Antigen independent validation assay. In the presence of TGFβ, the TGFβR2-41BB modified cells recapitulated the observed phenotype of greater relative expansion compared to stimulation only. Sorted NY-ESO-1+ T cells also expressing either TGFβR2-41BB or a GFP control were re-stimulated with anti-CD3/CD28 beads (1:1 bead to cell ratio) 7 days after electroporation and expansion was assayed by quantifying absolute cell counts at each indicated day. Surface staining for activation and exhaustion markers was performed 6 days after the stimulation.

(c), Increased production of the cytokines IFNγ, IL-2, and TNFα 24 hours after in vitro antigen independent TCR stimulation in the presence of exogenous TGFβ. *P<0.05, **P<0.01 (one-way analysis of variance (ANOVA) with Holm-Sidak's multiple comparisons test).

(d) Antigen specific validation assays. TGFβR2-41BB modified cells showed greater NY-ESO-1+ cancer cell killing in vitro than tNGFR controls, and similar killing to dnTGFβR2 modified cells, when co-cultured with A375 human melanoma cells with the addition of exogenous TGFβ across the indicated range of T cell to cancer cell ratios. Increased antigen specific in vitro killing was observed across multiple biologic donors 72 hours after co-culture at 1:1 T cell to cancer cell ratio in the presence of exogenous TGFβ (n=4 unique healthy human T cell donors with 2 technical replicates each; **P<0.01, Wilcoxon matched-pairs signed-rank test). At 5 days after beginning the co-culture killing assay, T cells were removed and stained for surface expression of PD1.

(e) Individual tumour tracings for in vivo tumour growth in A375 melanoma xenograft model. At day 9 after tumour seeding, 1.5 e6 sorted NY-ESO-1 TCR/tNGFR control T cells (Black) or NY-ESO-1 TCR/TGFβR2-41BB T cells (Red), or no T cells (Grey, Vehicle Only) were adoptively transferred. While variability was observed across the four donors tested, TGFβR2-41BB cells showed statistically significant reductions in tumour burdon (FIG. 25*e*, summarized data from Donor 1). In many cases across multiple donors TGFβR2-41BB cells cleared the tumour, which was not observed in any control mice. Separate cohorts of vehicle only control mice were examined concurrently with either the first (Donor 1 and 2) or second (Donor 3 and 4) pairs of unique healthy human donors. Note Donor 1 and Donor 2 tNGFR and vehicle only control traces are reproduced from FIG. 25*d*. Experiments display or are representative of n=2 (b-d) unique healthy human T cell donors unless otherwise noted.

FIGS. 29A-G show pooled knock-in screening of a multiplexed library of large DNA inserts.

(A) Non-viral targeted pooled knock-in of a 36-member construct library into the TRAC locus in primary human T cells and subsequent sequencing of knock-in barcodes 7 days post-electroporation. All construct barcodes in the 36-member library were consistently well-represented with even library distribution (n=4, independent human donors, Gini coefficient=0.048).

(B) A weak negative correlation between knock-in efficiency and insert size was observed (R2=0.11), but even the largest library members (~3 kb inserts) were well represented with less than two-fold differences in abundance between the least and most abundant constructs.

(C) Flow cytometry identified all knock-in positive cells that stained for the NY-ESO-1 TCR (introduced to the TRAC locus; off-target integrations should not yield NY-ESO-1 TCR+ cells). The percentage of knock-in positive cells that expressed GFP (NY-ESO-1 TCR+GFP+) or RFP protein (NY-ESO-1 TCR+RFP+) could be assessed and these cells could be FACS sorted.

(D) The percentages of knock-in cells that expressed GFP (NY-ESO-1 TCR+GFP+) or RFP protein (NY-ESO-1 TCR+RFP+) corresponded closely with frequencies of corresponding GFP or RFP template barcodes in experiments across four blood donors. ns=not significant (Paired two-way T test).

(E) Validation of homology arm (HA) mismatch priming strategy with a 36-member large knock-in library. Knock-in positive cells were sorted based on NY-ESO-1 TCR expression as well as either GFP+, RFP+ or neither. When sequencing on-target knock-ins using primer matching the genomic sequence (and lacking the mismatches introduced into the homology arms), the percent of sequenced reads with a GFP or RFP barcode in their respective populations closely matched the predicted percentage after correction for expected template switching and biallelic integrations. However, as expected, sequencing with a primer binding the template homology arm (containing the mismatch sequences) did not strongly enrich the on-target knock-ins for either GFP+ or RFP+ sorted populations.

(F-G) Distribution of library members (based on barcode frequencies) was largely consistent throughout T cell expansion over 10 days of ex vivo culture in IL2 post-electroporation. IL2RA-encoding construct showed an increased abundance over input, owing to the culture condition. Dotted lines represent maximum and minimum abundance of control library members (encoding GFP, RFP and tNGFR). *P<0.05, ****P<0.0001 (two-way analysis of variance (ANOVA) with Holm-Sidak's multiple comparisons test). Unless otherwise indicated, all experiments were analyzed seven days after electroporation of primary T cells from n=4 (B-D, F-G) or n=2 (E) individual healthy human donors.

FIGS. 30A-F show functional validation and improved in vitro cancer cell killing with novel gene constructs identified by pooled knock-in screens.

(A) Arrayed knock-in experiments validated the improved context-dependent fitness in pooled knock-in screens for selected library members (FAS-41BB, TGFBR2-41BB, IL2RA, TIM3-CD28, CTLA-CD28). Control constructs (tNGFR), neutral constructs that did not cause statistically-significant fitness improvements in the contexts tested (TCF7, PD1-41BB, tBTLA), and a negative hit from the screens (truncated CTLA4; tCTLA4) were also included in arrayed experiments.

Figure 32A:
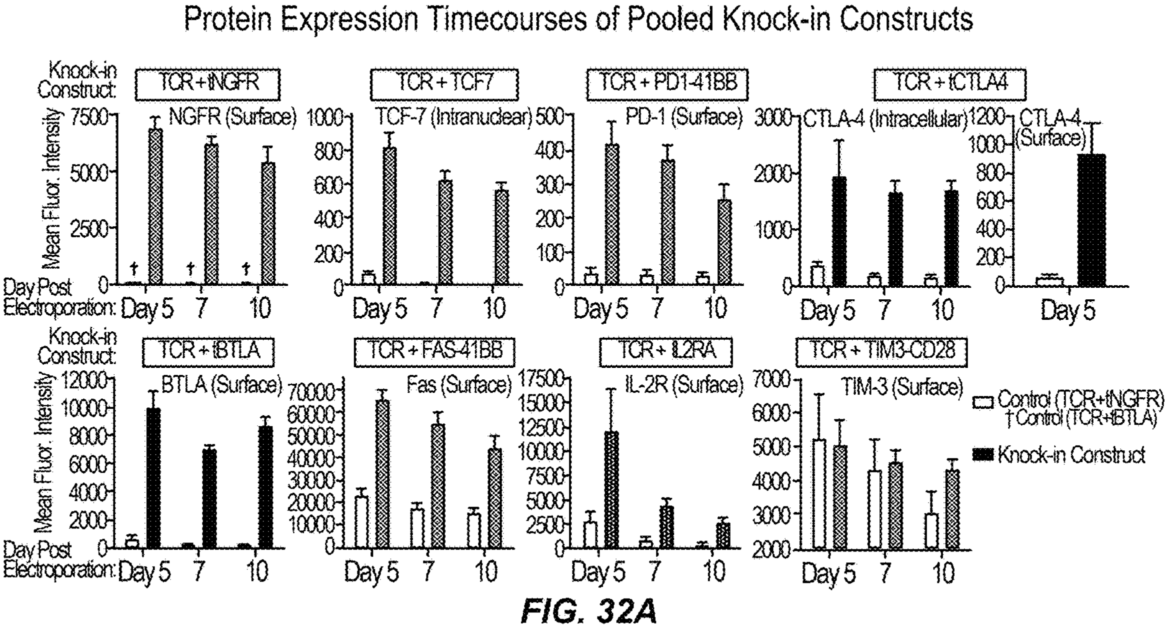

(B) Flow cytometry confirmed overexpression of expected protein product encoded in knock-in constructs relative to control cells treated with the same stimulation conditions. In knock-in positive cells (gated on NY-ESO-1 TCR+), all eight constructs tested showed increased expression of the expected transgene protein product compared to control cells seven days post-electroporation (TIM3-CD28 measured at 10 days). Time courses of protein expression are shown in FIG. 32A.

(C) Expansion, viability and proliferation effects were assayed for eight individual knock-in constructs under multiple conditions. The FAS-41BB knock-in construct increased expansion following stimulation, whereas the TGFβR2-41BB construct showed the greatest relative increase in both expansion and proliferation (by CFSE dilution) when exogenous TGFβ was added to the assay.

(D) In vitro cancer cell killing assays were performed with eight selected individual knock-in constructs. At 72 hours post co-culture of sorted NY-ESO-1+ T cells with each indicated knock-in construct, the percentage of A375 human melanoma target cells is shown (y-axis) across varying T effector (E) to cancer cell target (T) ratios (x-axis). TGFβR2-41BB(Red), significantly improved target cell killing compared to control cells (tNGFR, Green). In contrast, tCTLA4 (Black), impaired killing. At higher E:T ratios additional constructs showed more moderate improvements in cell killing (See also FIG. 32C).

(E) Time course data for cancer cell killing data in D, averaged across experiments performed in cells from four independent healthy blood donors.

(F) The TGFβR2-41BB knock-in construct enhanced NY-ESO-1+ cancer cell killing in vitro both in the absence and presence of exogenous TGFβ1 compared to knock-in cells with a control tNGFR construct. n=4 independent healthy blood donors. Experiments performed in n=4 (B-F) independent healthy human donors. *P<0.05, P<0.01, *P<0.001, **P<0.0001 (paired two-tailed T test). See also FIG. 32**.

FIGS. 31A-I show PoKI-Seq pooled knock-in screening combined with single-cell RNA sequencing.

(A) Design of pooled knock-in experiments paired with single cell RNA-sequencing, termed PoKI-seq. This platform provides high-dimensional assessment of cell phenotypes caused by each knock-in construct (See also FIG. 33A for details). Knock-in constructs integrated in each cell could then be associated with effects on the cell's transcriptome.

(B) To validate the molecular assignment of knock-in template barcodes to each individual cell, bulk knock-in positive cells expressing the integrated NY-ESO-1 TCR (All TCR+) were sorted, as were NY-ESO-1 positive cells that also expressed either GFP+ or RFP+. In the sorted NY-ESO-1 TCR+GFP+ and NY-ESO-1 TCR+RFP+ populations, the vast majority of template barcodes corresponded to the expression of the expected protein product.

(C) PoKI-seq also accurately identified cells with biallelic integrations. The frequency of observed cells with biallelic knock-in constructs closely matched those predicted based on 2-member GFP/RFP library knock-in experiments. As expected, in sorted GFP+ and RFP+ cells with biallelic integrations, one of the barcodes corresponded to GFP or RFP respectively. Of note, biallelic integration of the same knock-in construct (1/36 of total biallelic integrations) cannot be distinguished from monoallelic integration.

(D) UMAP representation of all single cell states identified in vitro with pooled knock-in T cell populations from two human blood donors. Seven days following pooled knock-in editing, sorted knock-in positive T cells (NY-ESO-1 TCR+) were stimulated at a 1:1 ratio with CD3/CD28 beads in the presence or absence of exogenous TGFβ.

(E) Nearest neighbor clustering (Louvain) overlaid on the UMAP representation revealed single cell populations corresponding to distinct cell states. Hallmark genes that showed enrichment or depletion in select clusters are displayed.

Figure 33A:
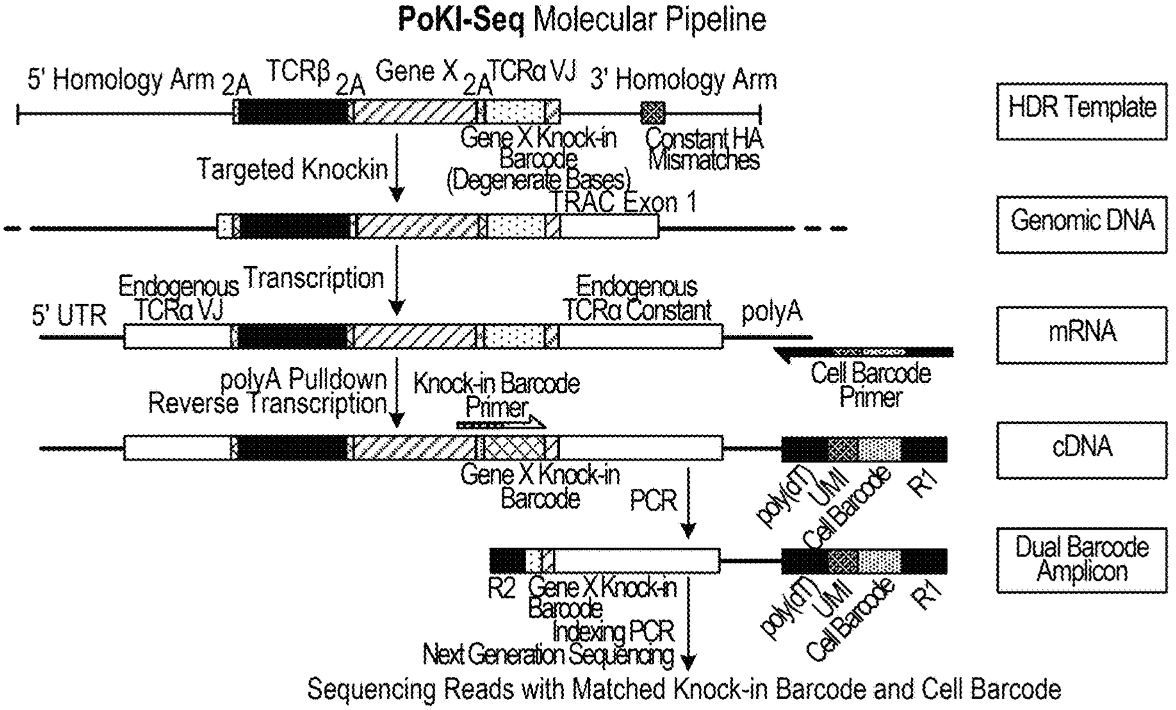
Figure 33B:
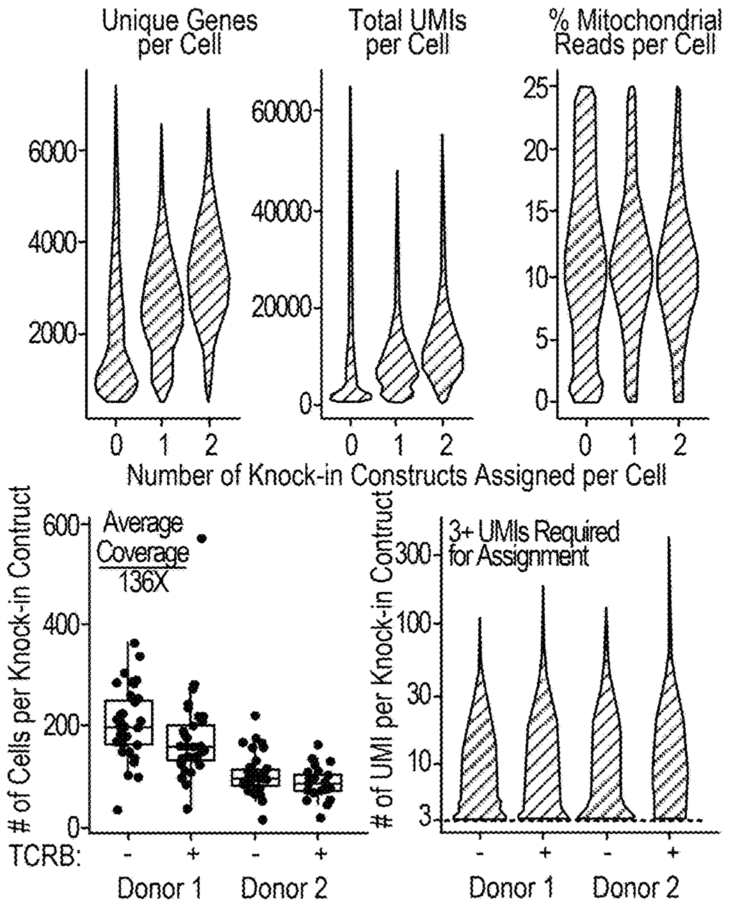

(F) Assignment of knock-in constructs for each single cell in D. Over 58% of cells were assigned a knock-in construct. Approximately 3.4% of cells were assigned 3 or greater knock-in barcodes, potentially due to sequencing cell doublets, rare imperfect integration of multiple templates or template switching. Cells that could not be assigned a knock-in construct barcode tended to be lower quality, with fewer genes called and unique UMIs, than transcriptomes of cells successfully assigned barcodes (FIG. 33B).

(G) Density plots (in the UMAP representation of single cell states) for cells with indicated knock-in constructs in TGFβ-treated conditions. Distinct differences were observed for the TGFβR2-derived constructs compared to controls and other knock-in constructs.

(H) Over-representation analysis for cells with select knock-in constructs in defined single cell clusters as measured by observed vs. expected Chi-square residuals. In the context of stimulation only (top row), the FAS-41BB construct enriched in the proliferative cluster 8. With the addition of exogenous suppressive cytokine TGFβ, cells with TGFβR2-derived knock-in constructs showed strong enrichment in clusters corresponding to proliferative (cluster 8) and effector states (cluster 12), and depletion from the clusters associated with response to TGFβ (clusters 2, 4, 6).

(I) Gene expression heatmap for select knock-in constructs in PoKI-seq experiment. Gene list was generated from genes in the clusters examined in H with absolute log fold change of >0.8 compared to all other clusters. Transcriptional effects of TGFβR2-derived constructs strongly correlated with each other in the presence of exogenous TGFβ but not in the stimulation-only condition. TGFβR2-derived constructs altered the transcriptional response to TGFB, maintaining expression of genes otherwise associated with the stimulation-only condition, such as proliferative markers MKI67 and TOP2A. See also FIG. 33.

Figure 32B:
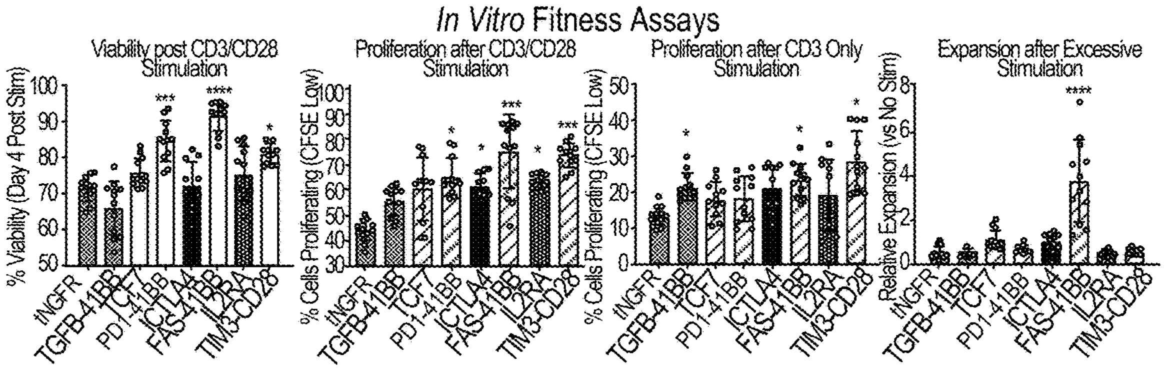
Figure 32C:
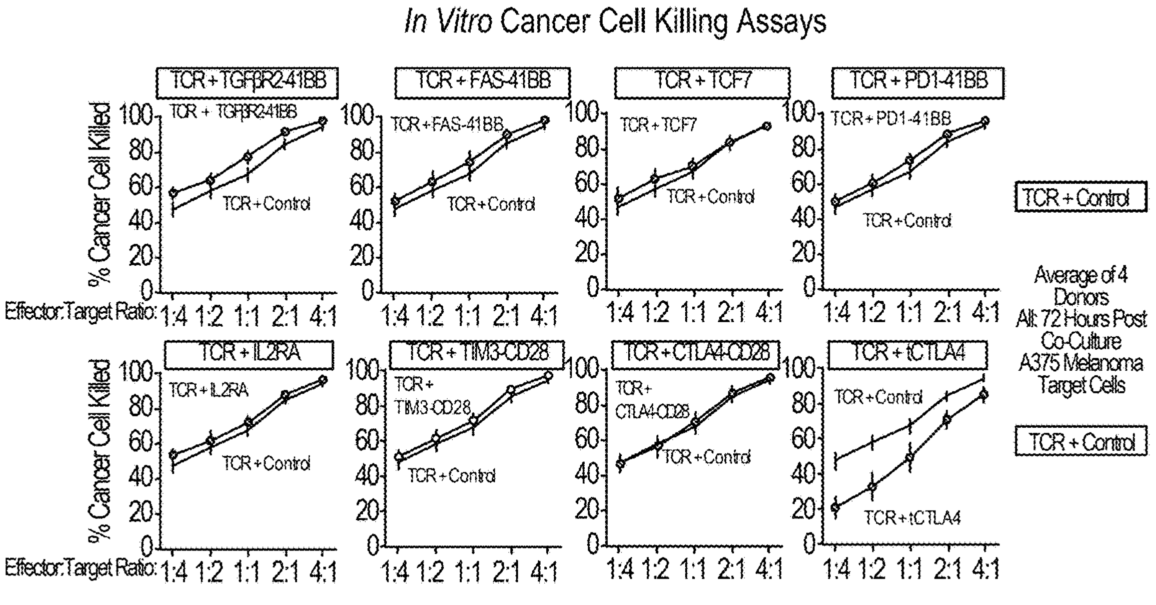

FIGS. 32A-C show arrayed in vitro validation of pooled knock-in screen hits, related to FIG. 30.

(A) Time course of protein expression for each indicated knock-in construct at 5, 7 and 10 days post-electroporation compared to control knock-in (NY-ESO-1 TCR+ tNGFR for all constructs except tNGFR itself, where a TCR+ tBTLA construct was used as a control) in gated NY-ESO-ITCR+ cells. Expression of some endogenous gene products (Fas, IL2RA, Tim-3) was detected, but increased expression was observed with the addition of the knock-in constructs at all time points except day 5 and 7 for TIM3-CD28. At day 10, TIM3-CD28 construct expression was observed above endogenous levels, likely due to consistent high expression off of the TCR promoter relative to activation dependent expression of endogenous Tim-3.

Figures 30A, 30B, 30C:
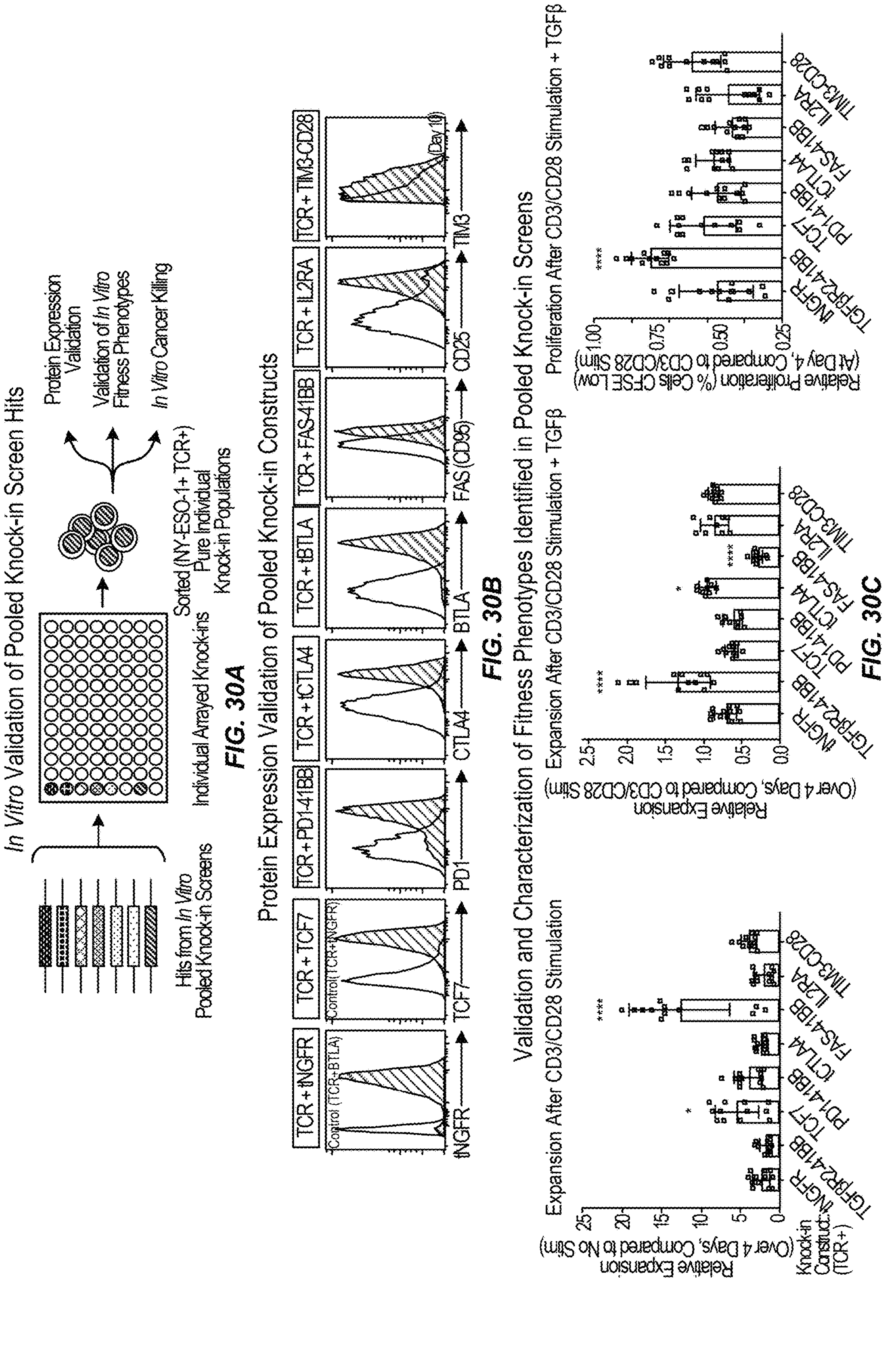

(B) Additional viability (% live cell staining in total lymphocyte population), proliferation (% CFSE Low), and expansion (total cell number compared to input) assays with individual knock-in constructs in sorted cells as in FIG. 30C. The Fas-41BB chimeric receptor showed the highest viability following stimulation, as well as the greatest amount of proliferation as measured by CFSE dilution staining 4 days after stimulation. When only CD3 stimulation was provided, a TIM3-CD28 chimeric receptor showed the greatest amount of proliferation, similar to the pooled knock-in screen. In the context of excessive stimulation (5:1 CD3/CD28 bead to cell ratio), the Fas-41BB chimeric receptor again showed the greatest relative expansion. Three technical replicates in n=4 independent healthy donors shown.

(C) Sorted NY-ESO-1 TCR+ T cells were co-cultured with target RFP+ A375 melanoma at the indicated effector to target cell ratios beginning 9 days after electroporation and imaged for 72 hours by Incucyte timelapse microscopy. The percentage of target cell killing for each of eight individual knock-in constructs tested is shown against control (average of TCR+ tNGFR and TCR+GFP constructs similarly tested). The average+SEM for three technical replicates in each of n=4 independent healthy donors is shown.

FIGS. 33A-F show a PoKI-Seq molecular pipeline, quality control metrics, and single cell phenotypes of pooled knock-in constructs, related to FIG. 31.

(A) Diagram of molecular sequencing pipeline to associate a cell's transcriptome with its knock-in construct using PoKI-Seq. The barcode for the specific knock-in construct ("Knock-in Barcode") in a cell is encoded in degenerate bases of the coding region of the integrated TCRαVJ region. After transcription and single cell isolation in droplets, the TCR+Gene X mRNA transcripts from the individual cell are bound to a bead containing poly(dT) primers along with a unique cell barcode. Following reverse transcription, a primer binding immediately upstream of the knock-in barcode creates an amplicon containing both the knock-in barcode as well as the cell-barcode. Next-generation sequencing from both ends of this amplicon yields a matched pair of knock-in barcode and cell-barcode, along with a universal molecular identifier (UMI). Only a portion of cDNA isolated during the droplet-based polyA pulldown is used to generate single-cell transcriptomes (25%) and the remainder of the cDNA (75%) can be used for sequencing of the knock-in barcodes.

(B) Quality control metrics from PoKI-Seq in ex vivo primary human T cells. A large number of unique genes and unique UMIs were called per cell. Notably single cells with transcriptomes assigned through Cell Ranger (10×) for which a knock-in construct was not assigned ("0") showed markedly poorer QC metrics. Within each of the two donors and two conditions tested (Stim+/−TGFβ), the average coverage (number of individual cells with a monoallelic integration of each knock-in construct) was ~136×. At least 3 UMIs all containing the same knock-in barcode were used to assign a cell to a specific knock-in construct, with the majority of cells possessing many more than 3.

(C) Heatmap of normalized gene expression values of transcripts containing the knocked-in sequence for selected knock-in constructs. The knock-in constructs are driven by the endogenous TCR promoter, generating a higher expression level than the endogenous genes containing portions of the knock-in construct's sequence (e.g., Fas-41BB driven off the TCR promoter is expressed at higher levels than endogenous Fas, see FIG. 30B and FIG. 32A). Transcripts are fragmented during 10× library preparation making it impossible to discriminate transcripts from endogenous genes from those produced from the knock-in constructs. Increased abundance of the expected mRNA associated was observed for many of the knock-in constructs, similar to was seen for expected protein products in FIG. 30B and FIG. 32A, (D) Enrichment (Chi-square residual) of each knock-in construct examined using PoKI-Seq within the indicated single cell clusters. TGFβR2 switch receptors or dominant negative receptor showed strong enrichment in specific clusters in the presence of exogenous TGFβ, consistent with their context-dependent specific biological effects on cell states. Color indicates the chi-square residual value and size indicates the chi-square residual's magnitude.

(E) GO term enrichment analysis within each defined single cell cluster. GO terms further supported the functional interpretation of individual cell-state clusters. The color is the average log fold change for the gene set associated with the indicated GO term within the specified cluster compared to all other clusters. Size is the p-value of the hypergeometric enrichment test.

(F) Pairwise Pearson correlation of the average expression for all differentially expressed genes identified in any of the single cell clusters, calculated for the indicated knock-in constructs and control in both stimulation only and stimulation+ TGFβ in vitro conditions. The dominant transcriptional differences were driven by exposure to TGFβ, but within the stimulation condition the knock-in constructs that promoted the greatest proliferative advantages (Fas switch receptors and IL2RA, but notably not the Fas-CD28 construct) showed the most similar transcriptional profiles. In contrast, in the presence of TGFβ, all three TGFβR2-derived receptors showed more correlated transcriptional changes with each other than with the other knock-in constructs.

Figure 34:
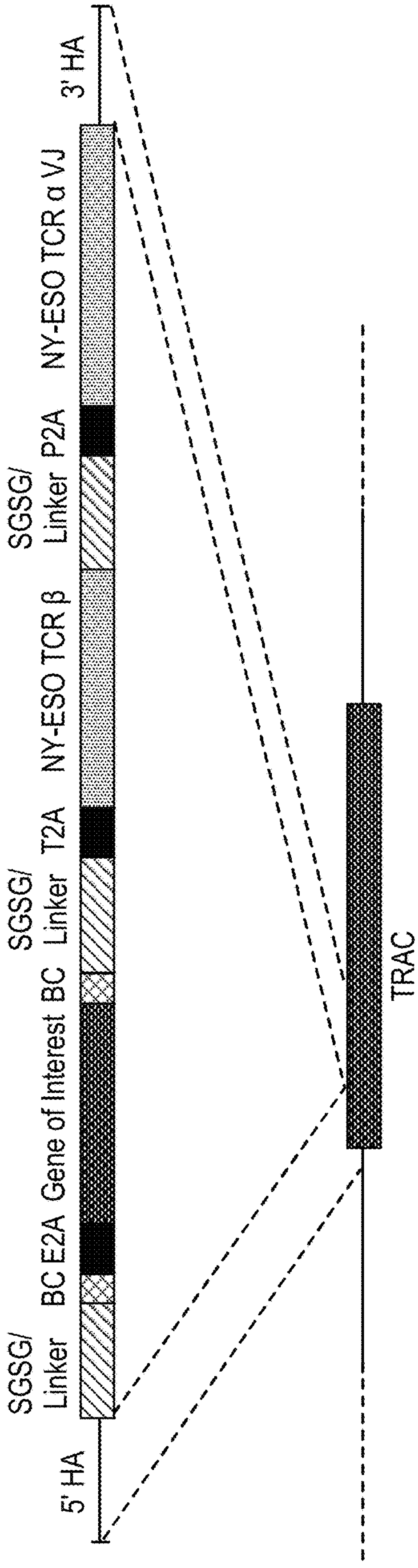

FIG. 34 is a diagram of an exemplary construct for pooled knock-in screening. The polycistronic construct includes three 2A fragments, the gene of interest (library of transcription factors and therapeutic constructs), and the NY-ESO specific T cell receptor (TCR) chains. To prevent incorrect barcode/gene assignments due to template switching, the barcode for construct identification was transferred from the 3' end of the TRAV region to close proximity of the gene of interest (5' and 3' end). Inserting one unique barcode at each side of the gene and addition of constant linker sequences allow for combinatorial strategies (combination of two different genes of interest in one polycistronic construct).

Figure 35A:
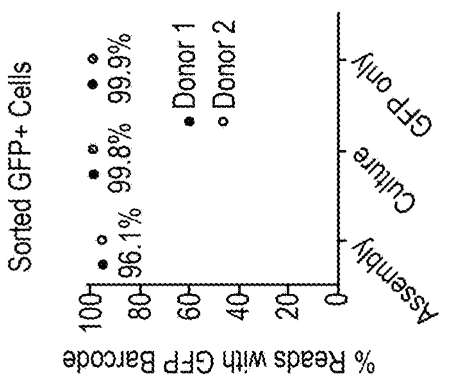
Figure 35B:
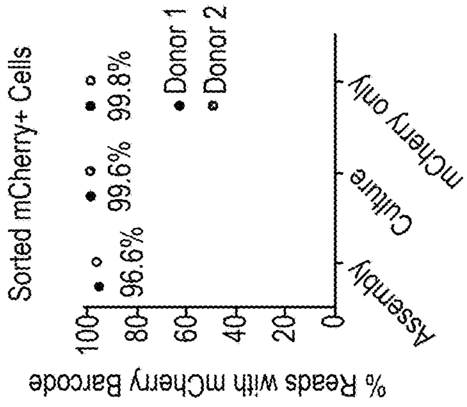

FIGS. 35*a-d* shows the results for template switching using the construct depicted in FIG. 34. Template switching was evaluated using two example constructs (mCherry vs GFP in the polycistronic cassette described above). A plasmid pool (n=2) was built by pooled assembly. HDR template was generated from the plasmid pool and electroporated into primary T cells of two individual healthy donors. Cells were sorted based on NY-ESO-1 TCR and GFP or mCherry expression. Number of correct barcode reads was analyzed by amplicon sequencing of cDNA. Percentage of correctly assigned reads was compared to T cells which were electroporated separately with mCherry/GFP templates and pooled during culture and T cells electroporated with only one of the constructs (FIGS. 35*a* and *b*). Template switching was calculated for the 2-member library (FIG. 35*c*) and predicted for an N-member library (FIG. 2*d*). Using the new barcoding strategy, the predicted template switching for an N-member library was decreased from 50% in the previous design to a mean of 7.6% in the improved pooled knock-in library design. Observed and predicted template switching for improved pooled knock-in library design (a) The percentage of sequenced reads that contained the GFP or (b) mCherry HDR template's barcode corresponded with the observed percentage of cells expressing GFP or mCherry protein by flow cytometry across pooling conditions. (c) Amount of observed template switching for the 2-member library and (d) predicted template switching for an N-member library were calculated. Predicted template switching of the new library design at the pooled assembly stage was 7.6%. All experiments performed in n=2 unique healthy donors.

DEFINITIONS

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA (e.g., a single guide RNA), or micro RNA.

As used herein, the term "endogenous" with reference to anucleic acid, for example, a gene, or a protein in a cell is a nucleic acid or protein that occurs in that particular cell as it is found in nature, for example, at its natural genomic location or locus. Moreover, a cell "endogenously expressing" a nucleic acid or protein expresses that nucleic acid or protein as it is found in nature.

A "promoter" is defined as one or more a nucleic acid control sequences that direct transcription of a nucleic acid. As used herein, a promoter includes nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. Complementary nucleotides are, generally, A and T (or A and U), and G and C. The guide RNAs described herein can comprise sequences, for example, DNA targeting sequences that are perfectly complementary or substantially complementary (e.g., having 1-4 mismatches) to a genomic sequence.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, for example, Cas9, in complex with guide and activating RNA to recognize and cleave foreign nucleic acid. Guide RNAs having the activity of both a guide RNA and an activating RNA are also known in the art. In some cases, such dual activity guide RNAs are referred to as a single guide RNA (sgRNA).

Cas9 homologs are found in a wide variety of eubacteria, including, but not limited to bacteria of the following taxonomic groups: Actinobacteria, Aqufícae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9;497(7448):254-7; and Jinek, et al., Science. 2012 Aug. 17; 337(6096):816-21. Variants of any of the Cas9 nucleases provided herein can be optimized for efficient activity or enhanced stability in the host cell. Thus, engineered Cas9 nucleases are also contemplated. See, for example, "Slaymaker et al., "Rationally engineered Cas9 nucleases with improved specificity," Science 351 (6268): 84-88 (2016)).

As used herein, the term "Cas9" refers to an RNA-mediated nuclease (e.g., of bacterial or archeal orgin, or derived therefrom). Exemplary RNA-mediated nucleases include the foregoing Cas9 proteins and homologs thereof. Other RNA-mediated nucleases include Cpf1 (See, e.g., Zetsche et al., Cell, Volume 163, Issue 3, p759-771, 22 Oct. 2015) and homologs thereof.

As used herein, the term "ribonucleoprotein" complex and the like refers to a mixture of a targeted nuclease, for example, Cas9, and a crRNA (e.g., guide RNA or single guide RNA), the Cas9 protein and a trans-activating crRNA (tracrRNA), the Cas9 protein and a guide RNA, or a combination thereof(e.g., the Cas9 protein, a tracrRNA, and a crRNA guide RNA are mixed together). It is understood that in any of the embodiments described herein, a Cas9 nuclease can be subsittuted with a Cpf1 nuclease or any other guided nuclease.

As used herein, the phrase "modifying" in the context of modifying a genome of a cell refers to inducing a structural change in the sequence of the genome at a target genomic region. For example, the modifying can take the form of inserting a nucleotide sequence into the genome of the cell. For example, a nucleotide sequence encoding a polypeptide can be inserted into the genomic sequence the TCR locus of a T cell. As used throughout a "TCR locus" is a location in the genome where the gene encoding a TCRα subunit, a TCRβ subunit, a TCRγ subunit, or a TCRδ subunit is located. Such modifying can be performed, for example, by inducing a double stranded break within a target genomic region, or a pair of single stranded nicks on opposite strands and flanking the target genomic region. Methods for inducing single or double stranded breaks at or within a target genomic region include the use of a Cas9 nuclease domain, or a derivative thereof, and a guide RNA, or pair of guide RNAs, directed to the target genomic region.

As used herein, the phrase "introducing" in the context of introducing a nucleic acid or a complex comprising a nucleic acid, for example, an RNP-DNA template complex, refers to the translocation of the nucleic acid sequence or the RNP-DNA template complex from outside a cell to inside the cell. In some cases, introducing refers to translocation of the nucleic acid or the complex from outside the cell to inside the nucleus of the cell. Various methods of such translocation are contemplated, including but not limited to, electroporation, contact with nanowires or nanotubes, receptor mediated internalization, translocation via cell penetrating peptides, liposome mediated translocation, and the like.

As used herein the phrase "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein, a "cell" can be a eukaryotic cell, a prokaryotic cell, an animal cell, a plant cell, a fungal cell, and the like. Optionally, the cell is a mammalian cell, for example, a human cell. In some cases, the cell is a human T cell or a cell capable of differentiating into a T cell that expresses a TCR receptor molecule. These include hematopoietic stem cells and cells derived from hematopoietic stem cells.

As used herein, the term "selectable marker" refers to a gene which allows selection of a host cell, for example, a T cell, comprising a marker. The selectable markers may include, but are not limited to: fluorescent markers, luminescent markers and drug selectable markers, cell surface receptors, and the like. In some embodiments, the selection can be positive selection; that is, the cells expressing the marker are isolated from a population, e.g. to create an enriched population of cells expressing the selectable marker. Separation can be by any convenient separation technique appropriate for the selectable marker used. For example, if a fluorescent marker is used, cells can be separated by fluorescence activated cell sorting, whereas if a cell surface marker has been inserted, cells can be separated from the heterogeneous population by affinity separation techniques, e.g. magnetic separation, affinity chromatography, "panning" with an affinity reagent attached to a solid matrix, fluorescence activated cell sorting or other convenient technique.

As used herein, the phrase "hematopoietic stem cell" refers to a type of stem cell that can give rise to a blood cell. Hematopoietic stem cells can give rise to cells of the myeloid or lymphoid lineages, or a combination thereof. Hematopoietic stem cells are predominantly found in the bone marrow, although they can be isolated from peripheral blood, or a fraction thereof. Various cell surface markers can be used to identify, sort, or purify hematopoietic stem cells. In some cases, hematopoietic stem cells are identified as c-kit$^+$ and lin$^-$. In some cases, human hematopoietic stem cells are identified as CD34$^+$, CD59$^+$, Thyl/CD90$^+$, CD38$^{lo/-}$, C-kit/CD117$^+$, lin$^-$. In some cases, human hematopoietic stem cells are identified as CD34$^-$, CD59$^+$, Thyl/CD90$^+$, CD38$^{lo/-}$, C-kit/CD117$^+$, lin$^-$. In some cases, human hematopoietic stem cells are identified as CD133$^+$, CD59$^+$, Thyl/CD90$^+$, CD38$^{lo/-}$, C-kit/CD117$^+$, lin$^-$. In some cases, mouse hematopoietic stem cells are identified as CD34$^{lo/-}$, SCA-1$^+$, Thyl$^{+/lo}$, CD38$^+$, C-kit$^+$, lin$^-$. In some cases, the hematopoietic stem cells are CD150$^+$CD48$^-$CD244$^-$.

As used herein, the phrase "hematopoietic cell" refers to a cell derived from a hematopoietic stem cell. The hematopoietic cell may be obtained or provided by isolation from an organism, system, organ, or tissue (e.g., blood, or a fraction thereof). Alternatively, an hematopoietic stem cell can be isolated and the hematopoietic cell obtained or provided by differentiating the stem cell. Hematopoietic cells include cells with limited potential to differentiate into further cell types. Such hematopoietic cells include, but are not limited to, multipotent progenitor cells, lineage-restricted progenitor cells, common myeloid progenitor cells, granulocyte-macrophage progenitor cells, or megakaryocyte-erythroid progenitor cells. Hematopoietic cells include cells of the lymphoid and myeloid lineages, such as lymphocytes, erythrocytes, granulocytes, monocytes, and thrombocytes. In some embodiments, the hematopoietic cell is an immune cell, such as a T cell, B cell, macrophage, a natural killer (NK) cell or dendritic cell. In some embodiments the cell is an innate immune cell.

As used herein, the phrase "T cell" refers to a lymphoid cell that expresses a T cell receptor molecule. T cells include human alpha beta (αβ) T cells and human gamma delta (γδ) T cells. T cells include, but are not limited to, naïve T cells, stimulated T cells, primary T cells (e.g., uncultured), cultured T cells, immortalized T cells, helper T cells, cytotoxic T cells, memory T cells, regulatory T cells, natural killer T cells, combinations thereof, or sub-populations thereof. T cells can be CD4$^+$, CD8$^+$, or CD4$^+$ and CD8$^+$. T cells can also be CD4$^-$, CD8$^-$, or CD4$^-$ and CD8$^-$ T cells can be helper cells, for example helper cells of type $T_H1$, $T_H2$, $T_H3$, $T_H9$, $T_H17$, or $T_{FH}$. T cells can be cytotoxic T cells. Regulatory T cells can be FOXP3$^+$ or FOXP3$^-$. T cells can be alpha/beta T cells or gamma/delta T cells. In some cases, the T cell is a CD4$^+$CD25$^{hi}$CD127$^{lo}$ regulatory T cell. In some cases, the T cell is a regulatory T cell selected from the group consisting of type 1 regulatory (Tr1), $T_H3$, CD8+ CD28−, Treg17, and Qa-1 restricted T cells, or a combination or sub-population thereof. In some cases, the T cell is a FOXP3$^+$ T cell. In some cases, the T cell is a CD4$^+$ CD25$^{lo}$CD127$^{hi}$ effector T cell. In some cases, the T cell is a CD4$^+$CD25$^{lo}$CD127$^{hi}$CD45RA$^{hi}$CD45RO$^-$ naïve T cell. A T cell can be a recombinant T cell that has been genetically manipulated.

As used herein, the phrase "primary" in the context of a primary cell is a cell that has not been transformed or immortalized. Such primary cells can be cultured, subcultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized directly without culturing or sub-culturing. In some cases, the primary cells are stimulated, activated, or differentiated. For example, primary T cells can be activated by contact with (e.g., culturing in the presence of) CD3, CD28 agonists, IL-2, IFN-γ, or a combination thereof.

As used herein, the term "homology directed repair" or HDR refers to a cellular process in which cut or nicked ends of a DNA strand are repaired by polymerization from a homologous template nucleic acid. Thus, the original sequence is replaced with the sequence of the template. In some cases, an exogenous template nucleic acid, for example, a DNA template, can be introduced to obtain a specific HDR-induced change of the sequence at a target site. In this way, specific mutations can be introduced at a cut site, for example, a cut site created by a targeted nuclease. A single-stranded DNA template or a double-stranded DNA template can be used by a cell as a template for editing or modifying the genome of a cell, for example, by HDR Generally, the single-stranded DNA template or a double-stranded DNA template has at least one region of homology to a target site. In some cases, the single-stranded DNA template or double-stranded DNA template has two homologous regions, for example, a 5' end and a 3' end, flanking a region that contains the DNA template to be inserted at a target cut or insertion site.

The term "substantial identity" or "substantially identical," as used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA.*) 85: 2444 (1988), by computerized implementations of these algorithms (e.g., BLAST), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977)*Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see. e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 10', and most preferably less than about 10'.

DETAILED DESCRIPTION OF THE INVENTION

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Pooled Knockin Screening

The present disclosure is directed to compositions and methods for identifying a targeted insertion in the genome of a cell. The inventors have discovered a pooled knockin screening method to rapidly assay many targeted knockins in a pooled cell population.

Screening Methods

Methods for identifying a targeted insertion in the genome of a cell are provided herein. In the methods provided herein, (i) a targeted nuclease that cleaves a target region in the genome of the cell to create a target insertion site; and (ii) a plurality of DNA templates that are different by sequence from each other are introduced into a population of cells. The DNA template can comprise: i. a heterologous coding or noncoding nucleic acid sequence; ii. optionally a unique barcode nucleotide sequence that indicates the identity of the heterologous coding or noncoding nucleic acid sequence; and iii. a common primer binding sequence, wherein the 5' and 3' ends of each DNA template comprise nucleotide sequences that are homologous to genomic sequences flanking the insertion site, and wherein one or both homologous nucleotide sequences comprise a mismatched nucleotide sequence compared to a homologous sequence in the genomic sequence, wherein the mismatched nucleotide sequence is not inserted into the target insertion site during recombination.

As used herein, a "plurality of DNA templates" refers to two or more DNA templates that differ by sequence. In some embodiments, the plurality includes at least 10, 20, 30, 40, 50. 60, 70, 80, 90, or 100 DNA templates that differ by sequence. In some embodiments, multiple copies of one or more DNA templates that differ by sequence are present in the plurality.

In the compositions and methods described herein, the length of one or both homologous sequences is at least about 50, 100, 150, 200, 250, 300, 350, 400 or 450 nucleotides. In some cases, a nucleotide sequence that is homologous to a genomic sequence is at least 80%, 90%, 95%, 99% or 100% complementary to the genomic sequence. In some embodiments, the homologous sequences are homologous to genomic sequences in a human T-cell TCR locus. As used throughout a "TCR locus" is a location in the genome where the gene encoding a TCRα subunit, a TCRβ subunit, a TCRγ subunit, or a TCRδ subunit is located.

In the compositions and methods described herein, the mismatched nucleotide sequence is designed to be non-complementary with a corresponding sequence in the genomic sequence of the cell. See, e.g., FIG. 4*a*. The mismatched sequence is sufficiently non-complementary to minimize or eliminate base-pairing between the mismatched nucleotide sequence and the corresponding sequence in the genomic sequence of the cell during a subsequent amplification. Thus, when amplification is performed with a primer as described herein that "binds the genomic sequence flanking the insertion site but does not bind the mismatched nucleotide in the template" this means that the primer is sufficiently complementary to the genomic sequence to initiate amplification from the genomic sequence but is not sufficiently complementary to the mismatched sequence in the template to initiate amplification of the template when both the genomic sequence and the template are present in the same amplification reaction. The primer is targeted to the portion of the genomic sequence that is at the same location as the mismatched sequence in the template. That is, when the homology "arms" sequence of the template are aligned (e.g., by BLAST) with the genomic DNA in the target cell, the sequence in the genomic DNA to which the primer binds will correspond to the position of the mismatched sequence in the template, there being aligned sequences between the template and genomic sequence on either side of the mismatched sequence.

In the compositions and methods described herein, the length of the mismatched nucleotide sequence in one or both homologous sequences (arms) flanking the DNA template is sufficient to allow the majority of the homologous sequence to remain complementary to the genomic sequence flanking the insertion site in the genome. In some embodiments, the homologous sequences (arms) are each 50-500, e.g., 200-400, e.g., 250-350, e.g., 300 nucleotides in length. The length of the homologous arms can be selected to optimize homologous rcombination at the target genomic site. The length of the mismatched nucleotide sequence is selected sufficient to prevent binding of a primer that specifically binds to the genomic sequence corresponding to the mismatched nucleotide sequence, such that when recombination occurs, a pair of primers (a primer that binds to the genomic sequence corresponding to the mismatched nucleotide sequence and a primer that binds to the common primer binding site in the DNA template), can be used to selective amplify an on-target insertion as compared to a wild type loci, a non-homologous end joing (NHEJ)-modified genomic loci, a non-integrated episomal template or an NHEJ-mediated off-target integration. In some embodiments, the length of the mismatched nucleotide sequence is from about 3 to about 50 nucleotides in length, for example, about 5, 10, 15, 20, 25, 30, 35, 40, 45 or 50 nucleotides in length.

In the compositions and methods provided herein, the mismatched nucleotide sequence is inserted at a location in the homologous sequence such that when homologous recombination occurs, the mismatched nucleotide sequence is not inserted into the genome with the DNA template. In some embodiments, the mismatched nucleotide sequence is inserted about 25, 50, 75, 100, 125 or more nucleotides from either end of the DNA template or homologous arm sequence. In some embodiments, a mismatched nucleotide sequence is inserted about 25, 50, 75, 100, 125 or from each end of the DNA template or homologous arm sequence. In some embodiments, the mismatched sequence can be inserted about 25, 50, 75, 100, 125 or more nucleotides downstream of the 3' end of the DNA template or homologous arm sequence. In some embodiments, the mismatched sequence can be inserted about 25, 50, 75, 100, 125 or more nucleotides upstream of the 5' end of the DNA template or homologous arm sequence. In some embodiments, a mismatched sequence is inserted about 25, 50, 75, 100, 125 or more nucleotides upstream of the 5' end of the DNA template or homologous arm sequence and a mismatched sequence is inserted about 25, 50, 75, 100, 125 or more nucleotides downstream of the 3' end of the DNA template or homologous arm sequence. Since the mismatched sequence is not incorporated into the genome of the cell upon recombination, on-target insertions that do not include the mismatched sequence can be selectively amplified and identified. See, for example, FIG. 15*a*.

After introducing the targeted nuclease and plurality of DNA templates into population of cells, recombination is allowed to occur, thereby creating a population of modified cells. Once the cells have been modified, DNA is amplified from the cells with a pair of primers, for example, by polymerase chain reaction (PCR) or other amplification method. In some embodiments, a first primer is complementary to the common primer binding sequence, and a second primer binds to a genomic sequence flanking the insertion site and does not bind to the mismatched nucleotide sequence in the DNA template. In another embodiment, a first primer binds to a 5' genomic region flanking the insertion site and does not bind to a corresponding first mismatched sequence in the DNA template and a second primer binds to a 3' genomic region flanking the insertion site and does not bind to a corresponding second mismatched nucleotide sequence in the DNA template.

In some embodiments, the common primer binding site in the DNA template is in a nucleic acid sequence in the DNA template relative to the barcode sequence, such that when DNA from the cell is amplified with a first primer that binds the common primer binding site and a second primer that binds to a genomic region flanking the insertion site, the barcode sequence is also amplified. Primer sequences can be designed to target either end of the template as desired. Thus in some cases for example, the mismatch sequence is at the 5' end of the DNA template and alternatively it is at the 3' end of the DNA template (or both) and the primers are designed accordingly to amplify the barcode sequence in combination with a primer to an appropriately positioned common primer binding sequence internal to the DNA template relative to the mismatch.

In embodiments where a first primer binds to a 5' genomic region flanking the insertion site and does not bind to a mismatched sequence in the DNA template and a second primer binds to a 3' genomic region flanking the insertion site and does not bind to a mismatched nucleotide sequence in the DNA template, the entire DNA template, including a barcode can be amplified.

After amplification, the DNA is sequenced to identify a DNA template inserted into the target insertion site for a cell. In some embodiments, the DNA template is sequenced to identify the DNA template. In some embodiments, the barcode sequence is sequenced to identify the DNA template (that is based on the barcode sequence, the DNA template sequence can be predicted based on a known correlation of the template sequence and the barcode sequence).

In general sequencing methods will be used such that the absolute or relative quantity of different sequences can be determined. Sequencing methods include, but are not limited to, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, CA), ion semiconductor sequencing, ligation sequencing, sequencing by synthesis (Illumina®, San Diego, Ca), Polony sequencing, 454 sequencing, solid phase sequencing, DNA nanoball sequencing, heliscope single molecule sequencing, mass spectroscopy sequencing, pyrosequencing, Supported Oligo Ligation Detection (SOLiD) sequencing, DNA microarray sequencing, RNAP sequencing, and tunneling currents DNA sequencing, to name a few. One or more of the sequencing methods described herein can be used in high throughput sequencing methods. As used herein, the term "high throughput sequencing" refers to all methods related to sequencing nucleic acids where more than one nucleic acid sequence is sequenced at a given time.

In some embodiments, the modified cells are cultured under conditions that allow expression of a heterologous polypeptide. In other embodiments, the cells are cultured under conditions effective for expanding the population of modified cells.

In some embodiments, the method further comprises determining the relative number of cells in the population having different DNA templates inserted in the target insertion site.

In some embodiments, a selective pressure is applied to the population of modified cells prior to determining the relative number of cells in the population having different DNA templates inserted in the target insertion site. By applying a selective pressure on the cells, coding or noncoding sequences that impart a desired function on the cell, for example, a T cell, can be identified. In some embodiments, a DNA template encoding a polypeptide that imparts a desired function on a cell, in the presence or absence of selective pressure is identified. In some embodiments, the relative number of cells in the population having different DNA templates inserted in the target insertion site is compared before and after applying a selective pressure on the modified cells. In this way, the abundance of each individual insert in a pooled population, including those that are enriched under specific conditions, can be identified. In some embodiments, the selective pressure is cell stimulation. In some embodiments, the selective pressure can be, but is not limited to, contacting the cells with an immunosuppressive cytokine, culture the cells in adverse metabolic conditions, excessive stimulation of the cells, partial stimulation of the cells (e.g., CD3 or CD28 stimulation only.

In some embodiments, the cells are subjected to in vitro or in vivo phenotypic selection or enrichment to associate modifications with desired phenotypes. Any of the screening methods described herein can be performed in in vitro, ex vivo or in vivo. In some embodiments, FACS-based selections using markers of cell state in various conditions can be made. It is understood that cell populations can be tested in various in vitro and in vivo contexts.

In some embodiments, after modification of the cells, one or more subpopulations of the cells expressing a detectable phenotype can be analyzed to determine the relative number of cells in the subpopulation having different DNA templates inserted in the target insertion site. In some embodiments, the DNA template optionally encodes a selectable marker that can be used to separate or isolate subpopulations of modified cells.

In some embodiments, in combination with monitoring cell proliferation as described above, or instead of monitoring cell proliferation, one can monitor mRNA of cells as a function of template insert. See, e.g., FIG. 24*a*. This can be performed, for example, using single cell RNA-seq, i.e., in partitions, which can include droplets or other types of partitions. The resulting cDNA reads from cells can be correlated with a specific cell based on the partition-specific barcode. To associate each partition-specific barcode with a specific template insertion, a portion of the cDNAs can be amplified in a reaction to form a dual barcode amplicon that comprises the partition-specific barcode linked to the cDNAs as well as the unique barcode that indicates the identity of the template insert. By sequencing these amplicons, one can associate partition-specific barcodes (representing specific cells) with a unique barcode indicating the template inserted into those same cells. Thus, cDNA reads from the RNA-seq can be sorted based upon the partition-specific barcode into reads from cells that contain the same template insert (as determined by the association of unique barcode and partition-specific barcode in the dual barcode amplicon). See, e.g., FIG. 24*b* and Example 2. Accordingly in some embodiments the method comprises generating the dual barcode amplicon that comprises the partition-specific barcode linked to the cDNAs as well as the unique barcode that indicates the identity of the template insert from the cDNAs comprising the partition-specific barcodes as described herein.

In some embodiments, the DNA template library is inserted by introducing a viral vector comprising the DNA template into the cell. Examples of viral vectors include, but are not limited to, adeno-associated viral (AAV) vectors, retroviral vectors or lentiviral vectors. In some embodiments, the lentiviral vector is an integrase-deficient lentiviral vector.

In some embodiments, the DNA template library is inserted by introducing a non-viral vector comprising the nucleic acid into the cell. In non-viral delivery methods, the nucleic acid can be naked DNA, or in a non-viral plasmid or vector. For non-viral delivery methods, the DNA template can be inserted using a non-viral genome targeting protocol based on a Cas9 'shuttle' system and an anionic polymer. A transposon delivery system can also be used to insert the DNA template library into cells.

In some embodiments, the nucleic acid is inserted into a T cell by introducing into the T cell, (a) a targeted nuclease that cleaves a target region in exon 1 of a TCR-α subunit constant gene (TRAC) to create an insertion site in the genome of the T cell; and (b) the DNA template, wherein the nucleic acid sequence is incorporated into the insertion site by homology directed repair (HDR). In some embodiments, the nucleic acid is inserted into a T cell by introducing into the T cell, (a) a targeted nuclease that cleaves a target region in exon 1 of a TCR-β subunit constant gene (TRBC) to create an insertion site in the genome of the T cell; and (b) the DNA template, wherein the nucleic acid sequence is incorporated into the insertion site by homology directed repair (HDR). In some embodiments the nucleic acid is inserted into TRAC Exon 2, TRAC Exon 3, TRAC Exon 4, TRBC1 Exon 1, TRBC1 Exon 2, TRBC1 Exon 3, TRBC1 Exon 4, TRBC2 Exon 1, TRBC2 Exon 2, TRBC2 Exon 3, or TRBC2 Exon4 of aT cell.

In some cases, the nucleic acid sequence is introduced into the cell as a linear DNA template. In some cases, the nucleic acid sequence is introduced into the cell as a double-stranded DNA template. In some cases, the DNA template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA. In some cases, the DNA template is a double-stranded or single-stranded plasmid or mini-circle.

In some embodiments, the targeted nuclease is selected from the group consisting of an RNA-guided nuclease domain, a transcription activator-like effector nuclease (TALEN), a zinc finger nuclease (ZFN) and a megaTAL (See, for example, Merkert and Martin "Site-Specific Genome Engineering in Human Pluripotent Stem Cells," *Int. J. Mol. Sci.* 18(7): 1000 (2016)). In some embodiments, the RNA-guided nuclease is a Cas9 nuclease and the method further comprises introducing into the cell a guide RNA that specifically hybridizes to a target region in the genome of the cell, for example, a target region in exon 1 of the TRAC gene in a T cell. In other embodiments, the RNA-guided nuclease is a Cas9 nuclease and the method further comprises introducing into the cell a guide RNA that specifically hybridizes to a target region in exon 1 of the TRBC gene.

As used throughout, a guide RNA (gRNA) sequence is a sequence that interacts with a site-specific or targeted nuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence or protospacer sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%). In some embodiments, the Cas9 protein can be in an active endonuclease form, such that when bound to target nucleic acid as part of a complex with a guide RNA or part of a complex with a DNA template, a double strand break is introduced into the target nucleic acid. In the methods provided herein, a Cas9 polypeptide or a nucleic acid encoding a Cas9 polypeptide can be introduced into the cell. The double strand break can be repaired by HDR to insert the DNA template into the genome of the cell. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to, for example, a region in exon 1 of the TRAC or exon 1 of the TRAB that contains an NGG sequence. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to those described in Esvelt et al., Nature Methods 10: 1116-1121 (2013).

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region, for example exon 1 of a TRAC gene or exon 1 of a TRBC gene. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," *Cell* 154(6): 1380-1389 (2013)).

In some embodiments, the Cas9 nuclease, the guide RNA and the nucleic acid sequence are introduced into the cell as a ribonucleoprotein complex (RNP)-DNA template complex, wherein the RNP-DNA template complex comprises: (i) the RNP, wherein the RNP comprises the Cas9 nuclease and the guide RNA; and (ii) the DNA template.

In some embodiments, the molar ratio of RNP to DNA template can be from about 3:1 to about 100:1. For example, the molar ratio can be from about 5:1 to 10:1, from about 5:1 to about 15:1, 5:1 to about 20:1; 5:1 to about 25:1; from about 8:1 to about 12:1; from about 8:1 to about 15:1, from about 8:1 to about 20:1, or from about 8:1 to about 25:1.

In some embodiments, the DNA template in the RNP-DNA template complex is at a concentration of about 2.5 μM to about 25 μM. In some embodiments, the amount of DNA template is about 1 μg to about 10 μg.

In some cases, the RNP-DNA template complex is formed by incubating the RNP with the DNA template for less than about one minute to about thirty minutes, at a temperature of about 20° C. to about 25° C. In some embodiments, the RNP-DNA template complex and the cell are mixed prior to introducing the RNP-DNA template complex into the cell.

In some embodiments the nucleic acid sequence or the RNP-DNA template complex is introduced into the cells by electroporation. Methods, compositions, and devices for electroporating cells to introduce a RNP-DNA template complex can include those described in the examples herein. Additional or alternative methods, compositions, and devices for electroporating cells to introduce a RNP-DNA template complex can include those described in WO/2006/001614 or Kim, J. A. et al. Biosens. Bioelectron. 23, 1353-1360 (2008). Additional or alternative methods, compositions, and devices for electroporating cells to introduce a RNP-DNA template complex can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186,559; 7,771,984; 7,991,559; 6,485,961; 7,029,916; and U.S. Patent Appl. Pub. Nos: 2014/0017213; and 2012/0088842. Additional or alternative methods, compositions, and devices for electroporating cells to introduce a RNP-DNA template complex can include those described in Geng, T. et al., J. Control Release 144, 91-100 (2010); and Wang, J., et al. Lab. Chip 10, 2057-2061 (2010).

In some embodiments, the RNP is delivered to the cells in the presence of an anionic polymer. In some embodiments, the anionic polymer is an anionic polypeptide or an anionic polysaccharide. In some embodiments, the anionic polymer is an anionic polypeptide (e.g., a polyglutamic acid (PGA), a polyaspartic acid, or polycarboxyglutamic acid). In some embodiments, the anionic polymer is an anionic polysaccharide (e.g., hyaluronic acid (HA), heparin, heparin sulfate, or glycosaminoglycan). In some embodiments, the anionic polymer is poly(acrylic acid) (PAA), poly(methacrylic acid) (PMAA), poly(styrene sulfonate), or polyphosphate. In some embodiments, the anionic polymer has a molecular weight of at least 15 kDa (e.g., between 15 kDa and 50 kDa). In some embodiments, the anionic polymer and the Cas protein are in a molar ratio of between 10:1 and 120:1, respectively (e.g., 10:1, 20:1, 30:1, 40:1, 50:1, 60:1, 70:1, 80:1, 90:1, 100:1, 110:1, or, 120:1). In some embodiments of this aspect, the molar ratio of sgRNA:Cas protein is between 0.25:1 and 4:1 (e.g., 0.25:1, 0.5:1, 1:1, 1.2:1, 1.4:1, 1.6:1, 1.8:1, 2:1, 2.2:1, 2.4:1, 2.6:1, 2.8:1, 3:1, 3.2:1, 3.4:1, 3.6:1, 3.8:1, or4:1).

In some embodiments, the donor template comprising a homology directed repair (HDR) template and one or more DNA-binding protein target sequences. In some embodiments, the donor template has one DNA-binding protein target sequence and one or more protospacer adjacent motif (PAM). The complex containing the DNA-binding protein (e.g., a RNA-guided nuclease), the donor gRNA, and the donor template can shuttle the donor template, without cleavage of the DNA-binding protein target sequence, to the desired intracellular location (e.g., the nucleus) such that the HDR template can integrate into the cleaved target nucleic acid. In some embodiments, the DNA-binding protein target sequence and the PAM are located at the 5' terminus of the HDR template. Particularly, in some embodiments, the PAM can be located at the 5' terminus of the DNA-binding protein target sequence. In other embodiments, the PAM can be located at the 3' terminus of the DNA-binding protein target sequence. In some embodiments, the DNA-binding protein target sequence and the PAM are located at the 3' terminus of the HDR template. Particularly, in some embodiments, the PAM can be located at the 5' terminus of the DNA-binding protein target sequence. In other embodiments, the PAM is located at the 3' terminus of the DNA-binding protein target sequence. In some embodiments, the donor template has two DNA-binding protein target sequences and two PAMs. Particularly, in some embodiments, a first DNA-binding protein target sequence and a first PAM are located at the 5' terminus of the HDR template and a second DNA-binding protein target sequence and a second PAM are located at the 3' terminus of the HDR template. In some embodiments, the first PAM is located at the 5' terminus of the first DNA-binding protein target sequence and the second PAM is located at the 5' of the second DNA-binding protein target sequence. In other embodiments, the first PAM is located at the 5' terminus of the first DNA-binding protein target sequence and the second PAM is located at the 3' of the second DNA-binding protein target sequence. In yet other embodiments, the first PAM is located at the 3' terminus of the first DNA-binding protein target sequence and the second PAM is located at the 5' of the second DNA-binding protein target sequence. In yet other embodiments, the first PAM is located at the 3' terminus of the first DNA-binding protein target sequence and the second PAM is located at the 3' of the second DNA-binding protein target sequence.

In some embodiments, the nucleic acid sequence or RNP-DNA template complex are introduced into about $1\times10^5$ to about $100\times10^6$ cells T cells. For example, the nucleic acid sequence or RNP-DNA template complex can be introduced into about $1\times10^5$ cells to about $5\times10^5$ cells, about $1\times10^5$ cells to about $1\times10^6$ cells, $1\times10^5$ cells to about $1.5\times10^6$ cells, $1\times10^5$ cells to about $2\times10^6$ cells, about $1\times10^6$ cells to about $1.5\times10^6$ cells or about $1\times10^6$ cells to about $2\times10^6$ cells.

In some embodiments, the cells are mammalian cells, for example, human cells. The cells can also be a cell line. In some embodiments, the human cell is a hematopoietic cell, for example, an immune cell, such as a hematopoietic stem cells, a T cell, a B cell, a macrophage, a natural killer (NK) cell or dendritic cell.

In the methods and compositions provided herein, the human T cells can be primary T cells. In some embodiments, the T cell is a regulatory T cell, an effector T cell, or a naïve T cell. In some embodiments, the effector T cell is a $CD8^+$ T cell. In some embodiments, the T cell is an CD4+ cell. In some embodiments, the T cell is a $CD4^+CD8^+$ T cell. In some embodiments, the T cell is a $CD4^-CD8^-$T cell. In some embodiments, the T cell is a T cell that expresses a TCR receptor or differentiates into a T cell that expresses a TCR receptor.

Compositions

Also provided herein is a nucleic acid construct comprising a coding nucleotide sequence that encodes a polypeptide, wherein the 5' and 3' ends of each DNA template comprise nucleotide sequences that are homologous to genomic sequences flanking the insertion site in the genome of a cell, wherein one or both homologous nucleotide sequences comprise a mismatched nucleotide sequence compared to a homologous genomic sequence in the cell; and wherein the length of the mismatched nucleotide sequence is sufficient to prevent binding of a primer that specifically binds to the genomic sequence corresponding to the mismatched nucleotide sequence. Exemplary genomic sequences for insertion sites in cells can include, for example, a sequence within the human TCR locus.

In some embodiments, the coding nucleotide sequence comprises two heterologous coding sequences joined by a coding sequence for a self-cleaving peptide. Examples of self-cleaving peptides include, but are not limited to, self-cleaving viral 2A peptides, for example, a porcine teschovirus-1 (P2A) peptide, aThosea asigna virus (T2A) peptide, an equine rhinitis A virus (E2A) peptide, or a foot-and-mouth disease virus (F2A) peptide. Self-cleaving 2A peptides allow expression of multiple gene products from a single construct. (See, for example, Chng et al. "Cleavage efficient 2A peptides for high level monoclonal antibody expression in CHO cells," *MAbs* 7(2): 403-412 (2015)). In some embodiments, the nucleic acid construct comprises two or more self-cleaving peptides. In some embodiments, the two or more self-cleaving peptides are all the same. In other embodiments, a least one of the two or more self-cleaving peptides is different.

In some embodiments, one or more linker sequences separate the components of the nucleic acid construct. The linker sequence can be two, three, four, five, six, seven, eight, nine, ten amino acids or greater in length. In some embodiments, the one or more linker sequences in the construct have the sequence. In some embodiments, the one or more linker sequences in the construct have different sequences. In some embodiments, the linker is a GSG linker or a SGSG linker.

In some embodiments, the length of the mismatched nucleotide sequence is about 3 to about 40 nucleotides. In some embodiments, the nucleic acid construct is a construct set forth in FIG. 22.

In some embodiments, the nucleic acid construct encodes, in the following order, (i) a first self-cleaving peptide sequence; (ii) a first heterologous TCR subunit chain, wherein the TCR subunit chain comprises the variable region and the constant region of the TCR subunit; (iii) a second self-cleaving peptide sequence; (iv) a polypeptide; (v) a third self-cleaving peptide sequence; (vi) a variable region of a second heterologous TCR subunit chain; and (vii) a portion of the N-terminus of an endogenous TCR subunit, wherein the nucleic acid construct comprises a barcode sequence, wherein the insertion sequence is a TCR locus of a T-cell, wherein one or both homologous nucleotide sequence comprise a mismatched nucleotide sequence, and wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain. As used throughout, the term "endogenous TCR subunit" is the TCR subunit, for example, TCR-α or TCR-β that is endogenously expressed by the cell that the nucleic acid construct is introduced into. In some embodiments, upon insertion of the nucleic acid construct into the TCR locus of a cell, the construct is under the control of an endogenous TCR promoter, for example a TRAC1 promoter or a TRBC promoter. Once the construct is incorporated into the genome of the T cell by HDR, and under the control of the endogenous promoter the T cells can be cultured under conditions that allow transcription of the inserted construct into a single mRNA sequence encoding a fusion polypeptide. Insertion of any of the nucleic acid constructs described herein encoding the components of a heterologous T cell receptor and a heterologous polypeptide will produce a T cell with the specificity of the heterologous TCR receptor and the function of the heterologous polypeptide. Similarly, insertion of any of the nucleic acid constructs described herein encoding a synthetic antigen receptor and a heterologous polypeptide will produce a T cell with the specificity of the heterologous TCR receptor and the function of the heterologous polypeptide.

In some embodiments, the barcode can be inserted in, before or after the nucleic acid sequence encoding a portion of the N-terminus of an endogenous TCR subunit. In some embodiments, the barcode can be inserted in, before or after the nucleic acid sequence encoding the first self cleaving peptide.

In some embodiments, the nucleic acid construct encodes, in the following order, (i) a first self-cleaving peptide sequence; (ii) a polypeptide; (iii) a second self-cleaving peptide sequence; (iv) a first heterologous TCR subunit chain, wherein the TCR subunit chain comprises the variable region and the constant region of the TCR subunit; (v) a third self-cleaving peptide sequence; (vi) a variable region of a second heterologous TCR subunit chain; and (vii) a portion of the N-terminus of an endogenous TCR subunit, wherein the nucleic acid construct comprises a barcode sequence, wherein the insertion sequence is a TCR locus of a human T-cell, wherein one or both homologous nucleotide sequence comprise a mismatched nucleotide sequence, and wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the barcode can be inserted in, before or after the nucleic acid sequence encoding a portion of the N-terminus of an endogenous TCR subunit. In some embodiments, the barcode can be inserted in, before or after the nucleic acid sequence encoding the first self cleaving peptide.

In some embodiments, the nucleic acid construct encodes, in the following order, (i) a first self-cleaving peptide sequence; (ii) a first heterologous TCR subunit chain, wherein the TCR subunit chain comprises the variable region and the constant region of the TCR subunit; (iii) a second self-cleaving peptide sequence; (iv) a second heterologous TCR subunit chain, wherein the TCR subunit chain comprises the variable region and the constant region of the TCR subunit; (v) a third self-cleaving peptide sequence; (vi) a polypeptide; and (vii) a fourth self-cleaving peptide sequence or a poly A sequence, wherein the nucleic acid construct comprises a barcode sequence, wherein the insertion sequence is a TCR locus of a human T-cell, wherein one or both homologous nucleotide sequence comprise a mismatched nucleotide sequence, and wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the barcode can be inserted in, before or after the nucleic acid sequence encoding the fourth self-cleaving peptide or polyA sequence. In some embodiments, the barcode can be inserted in, before or after the nucleic acid sequence encoding the first self cleaving peptide.

In some embodiments, the nucleic acid construct encodes, in the following order, (i) a first self-cleaving peptide sequence; (ii) a synthetic antigen receptor; (iii) a second self-cleaving peptide sequence; (iv) a heterologous polypeptide; and (v) a third self-cleaving peptide sequence or a polyA sequence, wherein the nucleic acid construct comprises a barcode sequence, wherein the insertion sequence is a TCR locus of a human T-cell.

In some embodiments, the barcode can be inserted in, before or after the nucleic acid sequence encoding the third self-cleaving peptide or polyA sequence. In some embodiments, the barcode can be inserted in, before or after the nucleic acid sequence encoding the first self cleaving peptide.

In some embodiments, the nucleic acid construct encodes, in the following order, (i) a first self-cleaving peptide sequence; (ii) a polypeptide; (iii) a second self-cleaving peptide sequence; (iv) a synthetic antigen receptor; and (v) a third self-cleaving peptide sequence or a polyA sequence, wherein the nucleic acid construct comprises a barcode sequence, wherein the insertion sequence is a TCR locus of a human T-cell.

In some embodiments, the barcode can be inserted in, before or after the nucleic acid sequence encoding the third self-cleaving peptide or polyA sequence. In some embodiments, the barcode can be inserted in, before or after the nucleic acid sequence encoding the first self cleaving peptide.

In some embodiments, the nucleic acid construct encodes, in the following order, (i) a first self-cleaving peptide sequence; (ii) a first TCR β or α subunit chain, wherein the TCR subunit chain comprises the variable region and the constant region of the TCR subunit chain; (iii) a second self-cleaving peptide sequence; (iv) a second TCR β or α subunit chain, wherein the second TCR subunit chain is different from the first TCR subunit chain, wherein the TCR subunit chain comprises the variable region and the constant region of the TCR subunit; or the TCR subunit comprises the variable region of the subunit; and (v) a third self-cleaving peptide sequence or a polyA sequence, wherein the nucleic acid construct comprises a barcode sequence, wherein the insertion sequence is a TCR locus of a human T-cell.

In some embodiments, the barcode can be inserted in, before or after the nucleic acid sequence encoding the third self-cleaving peptide or polyA sequence. In some embodiments, the barcode can be inserted in, before or after the nucleic acid sequence encoding the first self cleaving peptide.

In some embodiments, the nucleic acid construct encodes, in the following order, (i) a first self-cleaving peptide sequence; (ii) a synthetic antigen receptor; and (v) a second self-cleaving peptide sequence or a polyA sequence, wherein the nucleic acid construct comprises a barcode sequence, wherein the insertion sequence is a TCR locus of a human T-cell.

In some embodiments, the barcode can be inserted in, before or after the nucleic acid sequence encoding the third self-cleaving peptide or polyA sequence. In some embodiments, the barcode can be inserted in, before or after the nucleic acid sequence encoding the first self cleaving peptide.

In any of the constructs that encode a poly A sequence, the poly A sequence is used as a terminator sequence can be substituted with another suitable nucleic acid encoding a terminator sequence that stops or terminates transcription.

In some embodiments, the nucleic acid construct encodes a synthetic antigen receptor, wherein the synthetic antigen receptor is a chimeric antigen receptor (CAR) or a SynNotch receptor. See, for example, Sadelain et al., *Cancer Discov.* 3(4): 388-398 (2013)); Srivastava *Trends Immunol.* 36(8): 494-502 (2015)); Toda et al. *Science* 361(6398): 156-162 (2018); and Cho et al. *Scientific Reports* 8: 3846 (2018) regarding CAR and SynNotch design and uses).

In some embodiments, any one of the nucleic acid constructs described herein comprises one or more barcode sequences indicating the identity of the polypeptide. In some embodiments, any one of the nucleic acid constructs described herein comprises a pair of unique barcodes, that flank the nucleotide sequence encoding the polypeptide (i.e., a different barcode at either end of the nucleotide sequence encoding the polypeptide). In some embodiments, any one of the nucleic acid constructs described herein comprise one or more barcodes located before, after or in the self-cleaving peptide sequence or a polyA sequence.

In some embodiments, the nucleic acid construct comprises one or more linker sequences separate the components of the nucleic acid construct. In some embodiments, the one or more linker sequences have the same sequence. See, FIGS. 22 and 34 for exemplary constructs.

Also provided is a library comprising two or more nucleic acid constructs described herein, wherein each construct encodes a different polypeptide. Also provided is a population of cells comprising any of the libraries described herein. Further provided is a cell comprising one or more of the nucleic constructs described herein. In some embodiments, the cell is a human T-cell.

Heterologous Polypeptides Co-Expressed Under the Control of Endogenous Loci

Provided herein is a human T cell that heterologously expresses a polypeptide, wherein the polypeptide is encoded by a nucleic acid construct inserted into the TCR locus of the cell. Any of the polypeptides described herein can be heterologously expressed in a human T cell. Exemplary polyeptides include, but are not limited to, the amino acid sequences set forth as SEQ ID Nos: 37-72. Other polypeptides that can be heterologously expressed include polypeptides comprising the amino acid sequences set forth as SEQ ID Nos: 73-116. A polypeptide comprising an amino acid sequence that is at least 80%, 85%, 90%, 99%, or 100% identical to any one of the amino acid sequences set forth as SEQ ID Nos: 37-116 can also be heterologously expressed in a human T cell.

In some embodiments, the polypeptide is a truncated human PD-1 protein comprising the human PD-1 extracellular domain and transmembrane domain and lacking 80-90 (e.g., 87) carboxyl terminal PD-1 amino acids. In some embodiments, the truncated human PD-1 protein comprises the first 1-20 (e.g., 12) amino acids of the human PD-1 intracellular domain but lacks the remaining human PD-1 protein intracellular domain. In some embodiments, the truncated human PD-1 protein comprises or consists of SEQ ID NO: 37. In some embodiments, a relevant domain comprises an amino acid sequence at least 95% or 100% identical to the sequence set forth in Table 1.

In some embodiments the polypeptide comprises a human PD-1 extracellular domain or portion thereof of at least 120 or 130 amino acids (and optionally 1-20 (e.g., 11) amino acids of the 4-1BB extracellular domain) linked to a human 4-1BB intracellular domain via a transmembrane domain. In some embodiments, the transmembrane domain is a human 4-1BB or PD-1 transmembrane domain. In some embodiments, the polypeptide comprises or consists of SEQ ID NO: 38. In some embodiments, a relevant domain comprises an amino acid sequence at least 95% or 100% identical to the sequence set forth in Table 1.

In some embodiments the polypeptide comprises a human PD-1 extracellular domain linked to a human MyD88 intracellular domain or a portion thereof of at least 90 or 100 amino acids (and optionally 1-10 amino acids of the PD-1 intracellular domain) via a transmembrane domain. In some embodiments, the transmembrane domain is a human PD-1 or MyD88 transmembrane domain. In some embodiments the polypeptide comprises or consists of SEQ ID NO: 39. In some embodiments, a relevant domain comprises an amino acid sequence at least 95% or 100% identical to the sequence set forth in Table 1.

In some embodiments the polypeptide comprises a human PD-1 extracellular domain linked to a human ICOS intracellular domain via a transmembrane domain. In some embodiments, the transmembrane domain is a human ICOS or PD-1 transmembrane domain. In some embodiments the polypeptide comprises or consists of SEQ ID NO: 40. In some embodiments, a relevant domain comprises an amino acid sequence at least 95% or 100% identical to the sequence set forth in Table 1.

In some embodiments the polypeptide is a truncated human CTLA4 protein comprising the human CTLA4 extracellular domain and transmembrane domain and lacking 30-40 (e.g., 34) carboxyl terminal CTLA4 amino acids. In some embodiments, the truncated human CTLA4 protein comprises the first 1-12 (e.g., 6) amino acids of the human CTLA4 intracellular domain but lacks the remaining human CTLA4 protein intracellular domain. In some embodiments the truncated CTLA4 protein comprises or consists of SEQ ID NO: 41. In some embodiments, a relevant domain comprises an amino acid sequence at least 95% or 100% identical to the sequence set forth in Table 1.

In some embodiments the polypeptide comprises a human CTLA4 extracellular domain linked to a human CD28 intracellular domain or a portion thereof of at least 30 or 40 amino acids (and optionally 1-10 amino acids of the CTLA4 intracellular domain) via a transmembrane domain. In some embodiments, the transmembrane domain is a human CTLA4 or CD28 transmembrane domain. In some embodiments the polypeptide comprises or consists of SEQ ID NO: 42. In some embodiments, a relevant domain comprises an amino acid sequence at least 95% or 100% identical to the sequence set forth in Table 1.

In some embodiments, the polypeptide is a truncated human CD200R protein comprising the human CD200R extracellular domain and transmembrane domain and lacking 50-60 carboxyl terminal CD200R amino acids. In some embodiments, the truncated human CD200R protein comprises the first 1-12 (e.g., 6) amino acids of the human CD200R intracellular domain but lacks the remaining human CD200R protein intracellular domain. In some embodiments the truncated human CD200R protein comprises or consists of SEQ ID NO: 43. In some embodiments, a relevant domain comprises an amino acid sequence at least 95% or 100% identical to the sequence set forth in Table 1.

In some embodiments, the polypeptide is a truncated human BTLA protein comprising the human BTLA extracellular domain and transmembrane domain and lacking 100-110 (e.g., 104) carboxyl terminal BTLA amino acids. In some embodiments, the truncated human BTLA protein comprises the first 1-12 (e.g., 6) amino acids of the human BTLA intracellular domain but lacks the remaining human BTLA protein intracellular domain. In some embodiments, the truncated human BTLA4 protein comprises or consists of SEQ ID NO: 44. In some embodiments, a relevant domain comprises an amino acid sequence at least 95% or 100% identical to the sequence set forth in Table 1.

In some embodiments, the polypeptide comprises a human BTLA extracellular domain or a portion thereof of at least 110 or 120 amino acids (and optionally 1-20 amino acids of the CD28 extracellular domain) linked to a human CD28 intracellular domain via a transmembrane domain. In some embodiments, the transmembrane domain is a human CD28 or BTLA transmembrane domain. In some embodiments the polypeptide comprises or consists of SEQ ID NO: 45. In some embodiments, a relevant domain comprises an amino acid sequence at least 95% or 100% identical to the sequence set forth in Table 1.

In some embodiments, the polypeptide is a truncated human TIM-3 protein comprising the human TIM-3 extracellular domain and transmembrane domain and lacking 65-75 (e.g., 71) carboxyl terminal TIM-3 amino acids. In some embodiments, the truncated human TIM-3 protein comprises the first 1-12 (e.g., 6) amino acids of the human TIM-3 intracellular domain but lacks the remaining human TIM-3 protein intracellular domain. In some embodiments the polypeptide comprises or consists of SEQ ID NO: 46. In some embodiments, relevant domain comprises an amino acid sequence at least 95% or 100% identical to the sequence set forth in Table 1.

In some embodiments, the polypeptide comprises a human TIM-3 extracellular domain or a portion thereof of at least 160 or 170 amino acids (and optionally 1-20 amino acids of the CD28 extracellular domain) linked to a human CD28 intracellular domain via a transmembrane domain. In some embodiments, the transmembrane domain is a human CD28 or TIM-3 transmembrane domain. In some embodiments the polypeptide comprises or consists of SEQ ID NO: 47. In some embodiments, a relevant domain comprises an amino acid sequence at least 95% or 100% identical to the sequence set forth in Table 1.

In some embodiments, the polypeptide is a truncated human TIGIT protein comprising the human TIGIT extracellular domain and transmembrane domain and lacking 70-80 (e.g., 75) carboxyl terminal TIGIT amino acids. In some embodiments, the truncated human TIGIT protein comprises the first 1-12 (e.g., 6) amino acids of the human TIGIT intracellular domain but lacks the remaining human TIGIT protein intracellular domain. In some embodiments the polypeptide comprises or consists of SEQ ID NO: 48. In some embodiments, relevant domain comprises an amino acid sequence at least 95% or 100% identical to the sequence set forth in Table 1.

In some embodiments, the polypeptide comprises a human TIGIT extracellular domain or a portion thereof of at least 100 or 110 amino acids (and optionally 1-20 amino acids of the CD28 extracellular domain) linked to a human CD28 intracellular domain via a transmembrane domain. In some embodiments, the transmembrane domain is a human CD28 or TIGIT transmembrane domain. In some embodiments the polypeptide comprises or consists of SEQ ID NO: 49. In some embodiments, relevant domain comprises an amino acid sequence at least 95% or 100% identical to the sequence set forth in Table 1.

In some embodiments, the polypeptide is a truncated human TGFβR2 protein comprising the human TGFβR2 extracellular domain and transmembrane domain and lacking 360-370 (e.g., 366) carboxyl terminal TGFβR2 amino acids. In some embodiments, the truncated human TGFβR2 protein comprises the first 1-20 (e.g., 13) amino acids of the human TGFβR2 intracellular domain but lacks the remaining human TGFβR2 protein intracellular domain. In some embodiments the polypeptide comprises or consists of SEQ ID NO: 50. In some embodiments, a relevant domain comprises an amino acid sequence at least 95% or 100% identical to the sequence set forth in Table 1.

In some embodiments, the polypeptide comprises a human TGFβR2 extracellular domain or a portion thereof of at least 130 or 140 amino acids (and optionally 1-20 amino acids of the 4-1BB extracellular domain) linked to a human 4-1BB intracellular domain via a transmembrane domain. In some embodiments, the transmembrane domain is a human 4-1BB or TGFβR2 transmembrane domain. In some embodiments the polypeptide comprises or consists of SEQ ID NO: 51. In some embodiments, a relevant domain comprises an amino acid sequence at least 95% or 100% identical to the sequence set forth in Table 1.

In some embodiments, the polypeptide comprises a human TGFβR2 extracellular domain linked to a human Myd88 intracellular domain or a portion thereof of at least 90 or 100 amino acids (and optionally 1-20 amino acids of the TGFβR2 intracellular domain) via a transmembrane domain. In some embodiments, the transmembrane domain is a human TGFβR2 or Myd88 transmembrane domain. In some embodiments the polypeptide comprises or consists of SEQ ID NO: 52. In some embodiments, a relevant domain comprises an amino acid sequence at least 95% or 100% identical to the sequence set forth in Table 1.

In some embodiments, the polypeptide comprises a truncated human IL-10RA protein comprising the human IL-10RA extracellular domain and transmembrane domain and lacking 310-320 (e.g., 315) carboxyl terminal IL-10RA amino acids. In some embodiments, the truncated human IL-10RA protein comprises the first 1-20 (e.g., 13) amino acids of the human IL-10RA intracellular domain but lacks the remaining human IL-10RA protein intracellular domain. In some embodiments the polypeptide comprises or consists of SEQ ID NO: 53. In some embodiments, a relevant domain comprises an amino acid sequence at least 95% or 100% identical to the sequence set forth in Table 1.

In some embodiments, the polypeptide comprises a human IL-10RA extracellular domain linked to a human IL-7RA intracellular domain via a transmembrane domain. In some embodiments, the transmembrane domain comprises a human IL-7RA or IL-10RA transmembrane domain or a portion thereof at least 20 amino acids long. In some embodiments the polypeptide comprises or consists of SEQ ID NO: 54. In some embodiments, a relevant domain comprises an amino acid sequence at least 95% or 100% identical to the sequence set forth in Table 1.

In some embodiments, the polypeptide comprises a human IL-4RA extracellular domain linked to a human IL-7RA intracellular domain via a transmembrane domain. In some embodiments, the transmembrane domain comprises a human IL-7RA or IL-4RA transmembrane domain or a portion thereof at least 20 amino acids long. In some embodiments the polypeptide comprises or consists of SEQ ID NO: 55. In some embodiments, a relevant domain comprises an amino acid sequence at least 95% or 100% identical to the sequence set forth in Table 1.

In some embodiments, the polypeptide is a truncated human Fas protein comprising the human Fas extracellular domain and transmembrane domain and lacking 132-142 (e.g., 138) carboxyl terminal Fas amino acids. In some embodiments, the truncated human Fas protein comprises the first 1-12 (e.g., 6) amino acids of the human Fas intracellular domain but lacks the remaining human Fas protein intracellular domain. In some embodiments the polypeptide comprises or consists of SEQ ID NO: 59. In some embodiments, a relevant domain comprises an amino acid sequence at least 95% or 100% identical to the sequence set forth in Table 1.

In some embodiments, the polypeptide comprises a human Fas extracellular domain linked to a human CD28 intracellular domain or a portion thereof of at least 30 or 40 amino acids (and optionally 1-20 amino acids of the Fas intracellular domain) via a transmembrane domain. In some embodiments, the transmembrane domain is a human Fas or CD28 transmembrane domain. In some embodiments the polypeptide comprises or consists of SEQ ID NO: 60. In some embodiments, relevant domain comprises an amino acid sequence at least 95% or 100% identical to the sequence set forth in Table 1.

In some embodiments, the polypeptide comprises a human Fas extracellular domain linked to a human 4-1BB intracellular domain or a portion thereof of at least 30 or 40 amino acids (and optionally 1-20 amino acids of the Fas intracellular domain) via a transmembrane domain. In some embodiments, the transmembrane domain is a human Fas or 4-1BB transmembrane domain. In some embodiments the polypeptide comprises or consists of SEQ ID NO: 61. In some embodiments, relevant domain comprises an amino acid sequence at least 95% or 100% identical to the sequence set forth in Table 1.

In some embodiments, the polypeptide comprises a human Fas extracellular domain linked to a human MyD88 intracellular domain or a portion thereof of at least 90 or 100 amino acids (and optionally 1-20 amino acids of the Fas intracellular domain) via a transmembrane domain. In some embodiments the polypeptide comprises or consists of SEQ ID NO: 62. In some embodiments, the transmembrane domain is a human Fas or MyD88 transmembrane domain. In some embodiments, relevant domain comprises an amino acid sequence at least 95% or 100% identical to the sequence set forth in Table 1.

In some embodiments, the polypeptide comprises a human Fas extracellular domain linked to a human ICOS intracellular domain or a portion thereof of at least 25 or 35 amino acids (and optionally 1-20 amino acid of the Fas intracellular domain) via a transmembrane domain. In some embodiments, the transmembrane domain is a human Fas or ICOS transmembrane domain. In some embodiments the polypeptide comprises or consists of SEQ ID NO: 63. In some embodiments, relevant domain comprises an amino acid sequence at least 95% or 100% identical to the sequence set forth in Table 1.

In some embodiments, the polypeptide is a truncated human TRAIL-R2 protein comprising the human TRAIL-R2 extracellular domain and transmembrane domain and lacking 196-206 (e.g., 202) carboxyl terminal TRAIL-R2 amino acids. In some embodiments, the truncated human TRAIL-R2 protein comprises the first 1-12 (e.g., 6) amino acids of the human TRAIL-R2 intracellular domain but lacks the remaining human TRAIL-R2 protein intracellular domain. In some embodiments the polypeptide comprises or consists of SEQ ID NO: 64. In some embodiments, relevant domain comprises an amino acid sequence at least 95% or 100% identical to the sequence set forth in Table 1.

In some embodiments, the polypeptide comprises a human TRAIL-R2 extracellular domain linked to a human CD28 intracellular domain or a portion thereof of at least 30 or 40 amino acids (and optionally 1-20 amino acids of the TRAIL-R2 intracellular domain) via a transmembrane domain. In some embodiments, the transmembrane domain is a human TRAIL-R2 or CD28 transmembrane domain. In some embodiments the polypeptide comprises or consists of SEQ ID NO: 65. In some embodiments, relevant domain comprises an amino acid sequence at least 95% or 100% identical to the sequence set forth in Table 1.

In some embodiments, the polypeptide comprises a full-length CCR10, MCT4, SOD1, TCF7, IL-2RA, IL-7RA or 41BB protein.

In some embodiments, the polypeptide comprises an amino acid sequence that is at least 95% identical to an amino acid sequence selected from the group consisting of SEQ ID NO: 42, SEQ ID NO: 45, SEQ ID NO: 47, SEQ ID NO: 50, SEQ ID NO: 51, SEQ ID NO: 52, SEQ ID NO: 56, SEQ ID NO: 57, SEQ ID NO: 59, SEQ ID NO: 61, SEQ ID NO: 62, SEQ ID NO: 64, SEQ ID NO: 67, and SEQ ID NO: 69.

TABLE 1

| Human protein | Domain | SEQ ID NO: |
|---|---|---|
| PD-1 | Extracellular | 73 |
| PD-1 | Transmembrane | 74 |
| PD-1 | Intracellular | 75 |
| 4-1BB | Extracellular | 76 |
| 4-1BB | Transmembrane | 77 |
| 4-1BB | Intracellular | 78 |
| ICOS | Extracellular | 79 |
| ICOS | Transmembrane | 80 |
| CTLA4 | Extracellular | 81 |
| CTLA4 | Transmembrane | 82 |
| CTLA4 | Intracellular | 83 |
| CD28 | Extracellular | 85 |
| CD28 | Transmembrane | 86 |
| CD28 | Intracellular | 87 |
| CD200R | Extracellular | 88 |
| CD200R | Transmembrane | 89 |
| CD200R | Intracellular | 90 |
| BTLA | Extracellular | 91 |
| BTLA | Transmembrane | 92 |
| BTLA | Intracellular | 93 |
| Tim-3 | Extracellular | 94 |
| Tim-3 | Transmembrane | 95 |
| Tim-3 | Intracellular | 96 |
| TIGIT | Extracellular | 97 |
| TIGIT | Transmembrane | 98 |
| TIGIT | Intracellular | 99 |
| TGFβR2 | Extracellular | 100 |
| TGFβR2 | Transmembrane | 101 |
| TGFβR2 | Intracellular | 102 |
| IL-10RA | Extracellular | 103 |
| IL-10RA | Transmembrane | 104 |
| IL-10RA | Intracellular | 105 |
| IL-4RA | Extracellular | 106 |
| IL-4RA | Transmembrane | 107 |
| IL-4RA | Intracellular | 108 |
| IL-7RA | Extracellular | 109 |
| IL-7RA | Transmembrane | 110 |
| IL-7RA | Intracellular | 111 |
| Fas | Extracellular | 111 |
| Fas | Transmembrane | 112 |
| Fas | Intracellular | 113 |
| TRAILR2 | Extracellular | 114 |
| TRAILR2 | Transmembrane | 115 |
| TRAILR2 | Intracellular | 116 |

Nucleic acid sequences described herein, for example, SEQ ID Nos: 1-36, and nucleic acid sequences encoding any of the polypeptides described herein can be inserted into the genome of a T cell at any locus, for example, a TCR locus of a T cell. In some embodiments, a nucleic acid sequence encoding any one of SEQ ID Nos: 37-116 is inserted into the TCR locus of the T cell. In some embodiments, a nucleic acid sequence that is at least 80%, 85%, 90%, 99%, or 100% identical to any one of the nucleic acid sequences set forth as SEQ ID Nos: 1-36 or a nucleic acid sequence that encodes any one of SEQ ID Nos: 37-116 is inserted into the TCR locus of the T cell.

In some embodiments, the nucleic acid sequence or construct comprises a nucleic acid sequence that is at least 95% identical to a nucleic acid sequence selected from the consisting of SEQ ID NO: 6, SEQ ID NO: 9, SEQ ID NO: 11, SEQ ID NO: 14, SEQ ID NO: 15, SEQ ID NO: 16, SEQ ID NO: 20, SEQ ID NO: 21, SEQ ID NO: 23, SEQ ID NO: 25, SEQ ID NO: 26, SEQ ID NO: 27, SEQ ID NO: 31 and SEQ ID NO: 33. The nucleic acid sequence that is at least 95% identical to a nucleic acid sequence selected from the consisting of SEQ ID NO: 6, SEQ ID NO: 9, SEQ ID NO: 11, SEQ ID NO: 14, SEQ ID NO: 15, SEQ ID NO: 16, SEQ ID NO: 20, SEQ ID NO: 21, SEQ ID NO: 23, SEQ ID NO: 25, SEQ ID NO: 26, SEQ ID NO: 27, SEQ ID NO: 31 and SEQ ID NO: 33 can be inserted at any locus in the genome of a T cell, for example a TCR locus of a T cell.

The inventors have discovered that the nucleic acid constructs described herein can be inserted into T cells to modify the function of the T cells. In some embodiments, the constructs encode a fusion protein comprising the extracellular domain of a first protein linked to an intracellular domain of a second protein via a transmembrane domain (Table 2). In some embodiments, the fusion proteins can be expressed in a T-cell by expression of a heterologous coding sequence inserted into the TCR or other T-cell locus, as described elsewhere herein. However, in view of the discovery that the intracellular domain of the second protein modified the function (e.g., signaling), of the first protein, other options are also possible. For instance, in some embodiments, a heterologous nucleic acid construct encoding the intracellular domain of the second protein can be inserted into the genome of the T cell to modify an endogenous protein (i.e., having the desired extracellular domain) in the cell. For example, the heterologous intracellular domain can be linked to the cytoplasmic domain or a fragment thereof of the endogenous protein as encoded by the endogenous locus to create a modified endogenous (fusion) protein that has the activity of the intracellular domain. The endogenous protein can be the first protein in any of the constructs tested by the inventors or a different protein. Alternatively, the endogenous protein can be the second protein in any of the constructs, in which case a coding sequence for a heterologous extracellular domain of the fusions is introduced into the endogenous locus, thereby generating a fusion under the regulation of the endogenous locus. The heterologous intracellular or extracellular domain can be inserted into the intracellular domain of the endogenous protein as shown in FIG. 2.

For example, a polypeptide comprising a human PD-1 extracellular domain or portion thereof of at least 120 or 130 amino acids (and optionally 1-20 (e.g., 11) amino acids of the 4-1BB extracellular domain) linked to a human 4-1BB intracellular domain via a transmembrane domain can be expressed from either the PD-1 or 4-BB endogenous locus, wherein the other member is introduced as shown in FIG. 2 (e.g., the 4-1BB intracellular domain is fused to the endogenous PD-1 extracellular domain in the endogenous PD-1 locus).

In another example, the polypeptide comprising a human PD-1 extracellular domain linked to a human ICOS intracellular domain via a transmembrane domain can be expressed from either the PD-1 or ICOS endogenous locus, wherein the other member is introduced as shown in FIG. 2 (e.g., the ICOS intracellular domain is fused to the endogenous PD-1 extracellular domain).

In another example, the polypeptide comprising a human CTLA4 extracellular domain linked to a human CD28 intracellular domain or a portion thereof of at least 30 or 40 amino acids (and optionally 1-10 amino acids of the CTLA4 intracellular domain) via a transmembrane domain can be expressed from either the CTLA4 or CD28 endogenous locus, wherein the other member is introduced as shown in FIG. 2 (e.g., the CD28 intracellular domain is fused to the endogenous CTLA4 extracellular domain in the endogenous CTLA4 locus).

In another example, the polypeptide comprises a human BTLA extracellular domain or a portion thereof of at least 110 or 120 amino acids (and optionally 1-20 amino acids of the CD28 extracellular domain) linked to a human CD28 intracellular domain via a transmembrane domain can be expressed from either the BTLA or CD28 endogenous locus, wherein the other member is introduced as shown in FIG. 2 (e.g., the CD28 intracellular domain is fused to the endogenous BTLA extracellular domain in the endogenous BTLA locus).

In another example, the polypeptide comprising a human TIM-3 extracellular domain or a portion thereof of at least 160 or 170 amino acids (and optionally 1-20 amino acids of the CD28 extracellular domain) linked to a human CD28 intracellular domain via a transmembrane domain can be expressed from either the TIM-3 or CD28 endogenous locus, wherein the other member is introduced as shown in FIG. 2 (e.g., the CD28 intracellular domain is fused to the endogenous TIM-3 extracellular domain in the endogenous Tim-3 locus).

In another example, the polypeptide comprising a human TIGIT extracellular domain or a portion thereof of at least 100 or 110 amino acids (and optionally 1-20 amino acids of the CD28 extracellular domain) linked to a human CD28 intracellular domain via a transmembrane domain can be expressed from either the TIGIT or CD28 endogenous locus, wherein the other member is introduced as shown in FIG. 2 (e.g., the CD28 intracellular domain is fused to the endogenous TIGIT extracellular domain in the endogenous TIGIT locus).

In another example, the polypeptide comprising a human TGFβR2 extracellular domain or a portion thereof of at least 130 or 140 amino acids (and optionally 1-20 amino acids of the 4-1BB extracellular domain) linked to a human 4-1BB intracellular domain via a transmembrane domain can be expressed from either the TGFβR2 or 41BB endogenous locus, wherein the other member is introduced as shown in FIG. 2 (e.g., the 41BB intracellular domain is fused to the endogenous TGFβR2 extracellular domain in the endogenous TGFβR2 locus).

In another example, the polypeptide comprising a human TGFβR2 extracellular domain linked to a human Myd88 intracellular domain or a portion thereof of at least 90 or 100 amino acids (and optionally 1-20 amino acids of the TGFβR2 intracellular domain) via a transmembrane domain can be expressed from either the TGFβR2 or Myd88 endogenous locus, wherein the other member is introduced as shown in FIG. 2 (e.g., the Myd88 intracellular domain is fused to the endogenous TGFβR2 extracellular domain in the endogenous TGFβR2 locus).

In another example, the polypeptide comprising a human IL-10RA extracellular domain linked to a human IL-7RA intracellular domain via a transmembrane domain can be expressed from either the IL-10RA or IL-7RA endogenous locus, wherein the other member is introduced as shown in FIG. 2 (e.g., the IL-7RA intracellular domain is fused to the endogenous IL-10RA extracellular domain in the endogenous IL-10RA locus).

In some examples, the polypeptide comprising a human IL-4RA extracellular domain linked to a human IL-7RA intracellular domain via a transmembrane domain can be expressed from either the IL-4RA or IL-7RA endogenous locus, wherein the other member is introduced as shown in FIG. 2 (e.g., the IL-7RA intracellular domain is fused to the endogenous IL-4RA extracellular domain in the endogenous IL-4RA locus).

In some examples, the polypeptide comprising a human Fas extracellular domain linked to a human CD28 intracellular domain or a portion thereof of at least 30 or 40 amino acids (and optionally 1-20 amino acids of the Fas intracellular domain) via a transmembrane domain can be expressed from either the Fas or CD28 endogenous locus, wherein the other member is introduced as shown in FIG. 2 (e.g., the CD28 intracellular domain is fused to the endogenous Fas extracellular domain in the endogenous Fas locus).

In some examples, the polypeptide comprising a human Fas extracellular domain linked to a human 41BB intracellular domain or a portion thereof of at least 30 or 40 amino acids (and optionally 1-20 amino acids of the Fas intracellular domain) via a transmembrane domain can be expressed from either the Fas or CD28 endogenous locus, wherein the other member is introduced as shown in FIG. 2 (e.g., the 41BB intracellular domain is fused to the endogenous Fas extracellular domain in the endogenous Fas locus).

In some examples, the polypeptide comprising a human Fas extracellular domain linked to a human MyD88 intracellular domain or a portion thereof of at least 90 or 100 amino acids (and optionally 1-20 amino acids of the Fas intracellular domain) via a transmembrane domain can be expressed from either the Fas or MyD88 endogenous locus, wherein the other member is introduced as shown in FIG. 2 (e.g., the MyD88 intracellular domain is fused to the endogenous Fas extracellular domain in the endogenous Fas locus).

In some examples, the polypeptide comprising a human Fas extracellular domain linked to a human ICOS intracellular domain or a portion thereof of at least 25 or 35 amino acids (and optionally 1-20 amino acid of the Fas intracellular domain) via a transmembrane domain can be expressed from either the Fas or ICOS endogenous locus, wherein the other member is introduced as shown in FIG. 2 (e.g., the ICOS intracellular domain is fused to the endogenous Fas extracellular domain in the endogenous Fas locus).

In some examples, the polypeptide comprising a human TRAIL-R2 extracellular domain linked to a human CD28 intracellular domain or a portion thereof of at least 30 or 40 amino acids (and optionally 1-20 amino acids of the TRAIL-R2 intracellular domain) via a transmembrane domain can be expressed from either the TRAIL-R2 or CD28 endogenous locus, wherein the other member is introduced as shown in FIG. 2 (e.g., the CD28 intracellular domain is fused to the endogenous TRAIL-R2 extracellular domain in the endogenous TRAIL-R2 locus).

In embodiments where a truncated polypeptide has been shown to have activity (e.g., and Fas) these truncated proteins can be expressed from a heterologous expression cassette (i.e., a promoter operably linked to a coding sequence) or the endogenous locus in a T-cell can be modified as described herein to express the truncated version. Other truncated polypeptides (e.g., PD-1, CTL4, CD200R, BTLA, TIM-3, TIGIT, IL-10RA, Fas) can also be expressed (e.g., integrated or for example expressed from a viral vector).

Finally, the following full-length gene products were shown herein to have an effect on T-cell proliferation (e.g. MCT4 and TCF7). These gene products and other full length genes (e.g. CCR10, SOD1, Il-2RA, IL-7RA, 41BB) can be expressed from a heterologous expression cassette (integrated or for example expressed from a viral vector) introduced into the T-cells, or their endogenous loci can be modified to have a heterologous promoter sequence (e.g., as shown generically in FIG. 2) resulting in greater expression of the gene product compared to the endogenous promoter.

Any polypeptide sequence, nucleic acid sequence, T cell comprising a polypeptide or nucleic acid sequence, or a method that uses a T cell, polypeptide or nucleic acid sequence described herein can be claimed.

Insertion of a heterologous coding sequence into the TCR locus means that the expression of the heterologous protein will be controlled by the endogenous TCR promoter and in some embodiments will be expressed as part of a larger fusion protein with a TCR polypeptide that is subsequently cleaved to form separate TCR and heterologous polypeptides. As noted earlier, the TCR polypeptide can be endogenous or also added to the TCR locus to provide a novel TCR affinity (for example, but not limited to, to a cancer antigen) to the T-cell. In some embodiments, the nucleic acid construct is inserted in a target insertion site in exon 1 of a TCR-alpha subunit constant gene (TRAC). In some embodiments, the nucleic acid construct is inserted in a target insertion site in exon 1 of a TCR-beta subunit constant gene (TRBC). Upon insertion of the nucleic acid construct into the TCR locus of a cell, the construct is under the control of an endogenous TCR promoter, for example a TRAC1 promoter or a TRBC promoter. As set forth below, the nucleic acid constructs provided herein encode a TCR or synthetic antigen receptor that is co-expressed with the polypeptide. Once the construct is incorporated into the genome of the T cell by HDR, and under the control of the endogenous promoter the T cells can be cultured under conditions that allow transcription of the inserted construct into a single mRNA sequence encoding a fusion polypeptide that is then processed into separate heterologous polypeptides (e.g., for example by cleavage of a peptide sequence linking the polypeptides). Insertion of any of the nucleic acid constructs described herein encoding the components of a heterologous T cell receptor and a heterologous polypeptide will produce a T cell with the specificity of the heterologous TCR receptor and the function of the heterologous polypeptide. In some embodiments, the T cell expresses an antigen-specific TCR that recognizes a target antigen. Similarly, insertion of any of the nucleic acid constructs described herein encoding a synthetic antigen receptor and a heterologous polypeptide will produce a T cell with the specificity of the heterologous TCR receptor and the function of the heterologous polypeptide. In some embodiments, the T cell expresses a synthetic antigen receptor that recognizes a target antigen.

In some embodiments, the heterologous nucleic acid inserted into the human T cell encodes, in the following order, (i) a first self-cleaving peptide sequence; (ii) a first heterologous TCR subunit chain, wherein the TCR subunit chain comprises a variable region and a constant region of the TCR subunit; (iii) a second self-cleaving peptide sequence; (iv) a heterologous polypeptide as described herein; (v) a third self-cleaving peptide sequence; (vi) a variable region of a second heterologous TCR subunit chain; and (vii) a portion of the N-terminus of the endogenous TCR subunit, wherein, if the endogenous TCR subunit of the cell is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit of the cell is a TCR-β subunit, the first heterologous TCR subunit chain is a heterologous TCR-α subunit chain and the second heterologous TCR subunit chain is a heterologous TCR-β subunit chain.

In the compositions and methods described herein, if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain. In some methods, if the endogenous TCR subunit is a TCR-β subunit, the first heterologous TCR subunit chain is a heterologous TCR-α subunit chain and the second heterologous TCR subunit chain is a heterologous TCR-β subunit chain.

As used throughout, the term "endogenous TCR subunit" is the TCR subunit, for example, TCR-α or TCR-β that is endogenously expressed by the cell that the nucleic acid construct is introduced into. As set forth above, the nucleic acid constructs described herein encode multiple amino acid sequences that are expressed as a multicistronic sequence that is processed, i.e., self-cleaved, to produce two or more amino acid sequences, for example, a TCR-α subunit, a TCR-β subunit and the polypeptide encoded by the construct, or a synthetic antigen receptor (e.g. a CAR or SynNotch receptor) and the polypeptide encoded by the construct.

In some nucleic acid constructs, the size of the nucleic acid encoding the N-terminal portion of the endogenous TCR subunit will depend on the number of nucleotides in the endogenous TRAC or TRBC nucleic acid sequence between the start of TRAC exon 1 or TRBC exon 1 and the targeted insertion site. For example, if the number of nucleotides between the start of TRAC exon 1 and the insertion site is less than or greater than 25 nucleotides, a nucleic acid of less than or greater than 25 nucleotides encoding the N-terminal portion of the endogenous TCR-α subunit can be in the construct.

In the example above, translation of the mRNA sequence transcribed from the construct results in expression of one protein that self-cleaves into four, separate polypeptide sequences, i.e., an inactive, endogenous variable region peptide lacking a transmembrane domain, (which can be, e.g., degraded in the endoplasmic reticulum or secreted following translation), a full-length heterologous antigen-specific TCR-β chain or TCR-α chain, a polypeptide sequence as described herein, and a full length heterologous antigen-specific TCR-α chain or TCR-β chain. The full-length antigen specific TCR-β chain and the full length antigen-specific TCR-α chain form a TCR with desired antigen-specificity. In some embodiments, the polypeptide enhances or imparts a desired function(s) in the T cell. mRNA transcribed from any of the other nucleic acid constructs described herein are similarly processed in a T cell. In some embodiments, the construct encodes two, three, four, five, six, seven or more polypeptide seqeuces, optionally separated by nucleic acid sequences encoding a self-cleaving sequences.

In some embodiments, the heterologous nucleic acid construct encodes, in the following order, (i) a first self-cleaving peptide sequence; (ii) a polypeptide; (iii) a second self-cleaving peptide sequence; (iv) a first heterologous TCR subunit chain, wherein the TCR subunit chain comprises the variable region and the constant region of the TCR subunit; (v) a third self-cleaving peptide sequence; (vi) a variable region of a second heterologous TCR subunit chain; and (vii) a portion of the N-terminus of an endogenous TCR subunit, wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct encodes, in the following order, (i) a first self-cleaving peptide sequence; (ii) a first heterologous TCR subunit chain, wherein the TCR subunit chain comprises the variable region and the constant region of the TCR subunit; (iii) a second self-cleaving peptide sequence; (iv) a second heterologous TCR subunit chain, wherein the TCR subunit chain comprises the variable region and the constant region of the TCR subunit; (v) a third self-cleaving peptide sequence; (vi) a polypeptide; and (vii) a fourth self-cleaving peptide sequence or a poly A sequence, wherein if the endogenous TCR subunit is a TCR-alpha (TCR-α) subunit, the first heterologous TCR subunit chain is a heterologous TCR-beta (TCR-β) subunit chain and the second heterologous TCR subunit chain is a heterologous TCR-α subunit chain, and wherein if the endogenous TCR subunit is a TCR-β subunit, the first heterologous TCR subunit chain is a heterologous TCR-α subunit chain and the second heterologous TCR subunit chain is a heterologous TCR-β subunit chain.

In some embodiments, the nucleic acid construct encodes, in the following order, (i) a first self-cleaving peptide sequence; (ii) a synthetic antigen receptor; (iii) a second self-cleaving peptide sequence; (iv) a polypeptide; and (v) a third self-cleaving peptide sequence or a polyA sequence.

In some embodiments, the nucleic acid construct encodes, in the following order, (i) a first self-cleaving peptide sequence; (ii) a polypeptide; (iii) a second self-cleaving peptide sequence; (iv) a synthetic antigen receptor; and (v) a third self-cleaving peptide sequence or a polyA sequence.

In some embodiments, the nucleic acid construct encodes a synthetic antigen receptor, wherein the synthetic antigen receptor is a chimeric antigen receptor (CAR) or a SynNotch receptor. See, for example, Sadelain et al., *Cancer Discov.* 3(4): 388-398 (2013)); Srivastava *Trends Immunol.* 36(8): 494-502 (2015)); Toda et al. *Science* 361(6398): 156-162 (2018); and Cho et al. *Scientific Reports* 8: 3846 (2018) regarding CAR and SynNotch design and uses).

In any of the constructs that encode a poly A sequence, the poly A sequence is used as a terminator sequence can be substituted with another suitable nucleic acid encoding a terminator sequence that stops or terminates transcription.

Examples of self-cleaving peptides include, but are not limited to, self-cleaving viral 2A peptides, for example, a porcine teschovirus-1 (P2A) peptide, a Thosea asigna virus (T2A) peptide, an equine rhinitis A virus (E2A) peptide, or a foot-and-mouth disease virus (F2A) peptide. Self-cleaving 2A peptides allow expression of multiple gene products from a single construct. (See, for example, Chng et al. "Cleavage efficient 2A peptides for high level monoclonal antibody expression in CHO cells," *MAbs* 7(2): 403-412 (2015)). In some embodiments, the nucleic acid construct comprises two or more self-cleaving peptides. In some embodiments, the two or more self-cleaving peptides are all the same. In other embodiments, at least one of the two or more self-cleaving peptides is different.

In some embodiments, one or more linker sequences separate the components of the nucleic acid construct. The linker sequence can be two, three, four, five, six, seven, eight, nine, ten amino acids or greater in length.

In some embodiments, the nucleic acid construct comprises flanking homology arm sequences having homology to a human TCR locus. In the compositions and methods described herein, the length of one or both homology arm sequences is at least about 50, 100, 150, 200, 250, 300, 350, 400 or 450 nucleotides. In some cases, a nucleotide sequence that is homologous to a genomic sequence is at least 80%, 90%, 95%, 99% or 100% complementary to the genomic sequence. In some embodiments, one or both homology arm sequences optionally comprises a mismatched nucleotide sequence compared to a homologous sequence in the genomic sequence in the TCR locus flanking the insertion site in the TCR locus.

In some embodiments, the nucleic acid construct optionally encodes a selectable marker that can be used to separate or isolate subpopulations of modified T cells. In some embodiments, the nucleic acid construct optionally comprises a barcode sequence that indicates the identity of the polypeptide.

Any of the polypeptides described herein can be encoded by any of the nucleic acid constructs described herein. In some embodiments, the polypeptide sequence encoded by the heterologous nucleic acid construct is at least 95% identical to an amino acid sequence selected from the group consisting of SEQ ID NO: 42, SEQ ID NO: 45, SEQ ID NO: 47, SEQ ID NO: 50, SEQ ID NO: 51, SEQ ID NO: 52, SEQ ID NO: 56, SEQ ID NO: 57, SEQ ID NO: 59, SEQ ID NO: 61, SEQ ID NO: 62, SEQ ID NO: 64, SEQ ID NO: 67, and SEQ ID NO: 69. In some embodiments, the nucleic acid construct comprises a nucleic acid sequence encoding a polypeptide comprising an amino acid sequence at least 95% identical to a protein selected from the group consisting of: SEQ ID NO: 38, SEQ ID NO: 40, SEQ ID NO: 45, SEQ ID NO: 46, SEQ ID NO: 47, SEQ ID NO: 48, SEQ ID NO: 49, SEQ ID NO: 51, SEQ ID NO: 52, SEQ ID NO: 53, SEQ ID NO: 54, SEQ ID NO: 60, SEQ ID NO: 61, SEQ ID NO: 62, SEQ ID NO: 63, SEQ ID NO: 64 and SEQ ID NO: 65.

Also provided is a human T cell comprising any of the nucleic acid sequences described herein. Populations (e.g., a plurality) of human T cells comprising any of the nucleic acid sequences described herein are also provided.

Methods of Modifying T cells

Any of the nucleic acid constructs encoding any of the polypeptides described herein can be used to make modified T cells. In some embodiments, the method comprises (a) introducing into the human T cell (i) a targeted nuclease that cleaves a target region in the TCR locus of a human T cell to create a target insertion site in the genome of the cell; and (ii) a nucleic acid construct encoding any of the polypeptides described herein, for example; a truncated human PD-1 protein comprising the human PD-1 extracellular domain and transmembrane domain and lacking 80-90 (e.g., 87) carboxyl terminal PD-1 amino acids; a polypeptide comprising a human PD-1 extracellular domain or portion thereof of at least 120 or 130 amino acids (and optionally 1-20 (e.g., 11) amino acids of the 4-1BB extracellular domain) linked to a human 4-1BB intracellular domain via a transmembrane domain; a polypeptide comprising a human PD-1 extracellular domain linked to a human MyD88 intracellular domain or a portion thereof of at least 90 or 100 amino acids (and optionally 1-10 amino acids of the PD-1 intracellular domain) via a transmembrane domain; a polypeptide comprising a human PD-1 extracellular domain linked to a human ICOS intracellular domain via a transmembrane domain; a truncated human CTLA4 protein comprising the human CTLA4 extracellular domain and transmembrane domain and lacking 30-40 (e.g., 34) carboxyl terminal CTLA4 amino acids; a polypeptide comprising a human CTLA4 extracellular domain linked to a human CD28 intracellular domain or a portion thereof of at least 30 or 40 amino acids (and optionally 1-10 amino acids of the CTLA4 intracellular domain) via a transmembrane domain; a truncated human CD200R protein comprising the human CD200R extracellular domain and transmembrane domain and lacking 50-60 carboxyl terminal CD200R amino acids; a truncated human BTLA protein comprising the human BTLA extracellular domain and transmembrane domain and lacking 100-110 (e.g., 104) carboxyl terminal BTLA amino acids. In some embodiments, the truncated human BTLA protein comprises the first 1-12 (e.g., 6) amino acids of the human BTLA intracellular domain but lacks the remaining human BTLA protein intracellular domain; a polypeptide comprising a human BTLA extracellular domain or a portion thereof of at least 110 or 120 amino acids (and optionally 1-20 amino acids of the CD28 extracellular domain) linked to a human CD28 intracellular domain via a transmembrane domain; a truncated human TIM-3 protein comprising the human TIM-3 extracellular domain and transmembrane domain and lacking 65-75 (e.g., 71) carboxyl terminal TIM-3 amino acids; a polypeptide comprising a human TIM-3 extracellular domain or a portion thereof of at least 160 or 170 amino acids (and optionally 1-20 amino acids of the CD28 extracellular domain) linked to a human CD28 intracellular domain via a transmembrane domain; a truncated human TIGIT protein comprising the human TIGIT extracellular domain and transmembrane domain and lacking 70-80 (e.g., 75) carboxyl terminal TIGIT amino acids; a polypeptide comprising a human TIGIT extracellular domain or a portion thereof of at least 100 or 110 amino acids (and optionally 1-20 amino acids of the CD28 extracellular domain) linked to a human CD28 intracellular domain via a transmembrane domain; a truncated human TGF$\beta$R2 protein comprising the human TGF$\beta$R2 extracellular domain and transmembrane domain and lacking 360-370 (e.g., 366) carboxyl terminal TGF$\beta$R2 amino acids; a polypeptide comprising a human TGF$\beta$R2 extracellular domain or a portion thereof of at least 130 or 140 amino acids (and optionally 1-20 amino acids of the 4-1BB extracellular domain) linked to a human 4-1BB intracellular domain via a transmembrane domain; a polypeptide comprising a human TGF$\beta$R2 extracellular domain linked to a human Myd88 intracellular domain or a portion thereof of at least 90 or 100 amino acids (and optionally 1-20 amino acids of the TGF$\beta$R2 intracellular domain) via a transmembrane domain; a truncated human IL-10RA protein comprising the human IL-10RA extracellular domain and transmembrane domain and lacking 310-320 (e.g., 315) carboxyl terminal IL-10RA amino acids; a polypeptide comprising a human IL-10RA extracellular domain linked to a human IL-7RA intracellular domain via a transmembrane domain; a polypeptide comprising a human IL-4RA extracellular domain linked to a human IL-7RA intracellular domain via a transmembrane domain; a truncated human Fas protein comprising the human Fas extracellular domain and transmembrane domain and lacking 132-142 (e.g., 138) carboxyl terminal Fas amino acids; a polypeptide comprising a human Fas extracellular domain linked to a human CD28 intracellular domain or a portion thereof of at least 30 or 40 amino acids (and optionally 1-20 amino acids of the Fas intracellular domain) via a transmembrane domain; a polypeptide comprising a human Fas extracellular domain linked to a human 4-1BB intracellular domain or a portion thereof of at least 30 or 40 amino acids (and optionally 1-20 amino acids of the Fas intracellular domain) via a transmembrane domain; a polypeptide comprising a human Fas extracellular domain linked to a human MyD88 intracellular domain or a portion thereof of at least 90 or 100 amino acids (and optionally 1-20 amino acids of the Fas intracellular domain) via a transmembrane domain; a polypeptide comprising a human Fas extracellular domain linked to a human ICOS intracellular domain or a portion thereof of at least 25 or 35 amino acids (and optionally 1-20 amino acid of the Fas intracellular domain) via a transmembrane domain; a truncated human TRAIL-R2 protein comprising the human TRAIL-R2 extracellular domain and transmembrane domain and lacking 196-206 (e.g., 202) carboxyl terminal TRAIL-R2 amino acids; a polypeptide comprising a human TRAIL-R2 extracellular domain linked to a human CD28 intracellular domain or a portion thereof of at least 30 or 40 amino acids (and optionally 1-20 amino acids of the TRAIL-R2 intracellular domain) via a transmembrane domain; a polypeptide comprising an IL2RA protein, an IL7RA protein, an MCT4 protein or a TCF7 protein; or a polypeptide comprising an amino acid sequence at least 95% identical to a protein selected from the group consisting of SEQ ID NO: 6, SEQ ID NO: 9, SEQ ID NO: 11, SEQ ID NO: 14, SEQ ID NO: 15, SEQ ID NO: 16, SEQ ID NO: 20, SEQ ID NO: 21, SEQ ID NO: 23, SEQ ID NO: 25, SEQ ID NO: 26, SEQ ID NO: 28, SEQ ID NO: 31, and SEQ ID NO: 33; and (b) allowing recombination to occur, thereby inserting the nucleic acid construct in the target insertion site to generate a modified human T cell.

In some embodiments, the nucleic acid is inserted into a T cell by introducing into the T cell, (a) a targeted nuclease that cleaves a target region in exon 1 of a TCR-$\alpha$ subunit constant gene (TRAC) to create an insertion site in the genome of the T cell; and (b) the nucleic acid construct, wherein the nucleic acid construct is incorporated into the insertion site by homology directed repair (HDR). In some embodiments, the nucleic acid construct is inserted into a T cell by introducing into the T cell, (a) a targeted nuclease that cleaves a target region in exon 1 of a TCR-$\beta$ subunit constant gene (TRBC) to create an insertion site in the genome of the T cell; and (b) the nuclei acid construct, wherein the nucleic acid sequence is incorporated into the insertion site by homology directed repair (HDR).

In some embodiments, the nucleic acid construct is inserted by introducing a viral vector comprising the nucleic acid construct into the cell. Examples of viral vectors include, but are not limited to, adeno-associated viral (AAV) vectors, retroviral vectors or lentiviral vectors. In some embodiments, the lentiviral vector is an integrase-deficient lentiviral vector.

In some embodiments, the the nucleic acid construct is inserted by introducing a non-viral vector comprising the the nucleic acid construct into the cell. In non-viral delivery methods, the nucleic acid can be naked DNA, or in a non-viral plasmid or vector. For non-viral delivery methods, the DNA template can be inserted using a non-viral genome targeting protocol based on a Cas9 'shuttle' system and an anionic polymer.

In some cases, the nucleic acid sequence is introduced into the cell as a linear DNA template. In some cases, the nucleic acid sequence is introduced into the cell as a double-stranded DNA template. In some cases the DNA template is introduced into the cell using a transposon delivery system. In some cases, the DNA template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA. In some cases, the DNA template is a double-stranded or single-stranded plasmid or mini-circle.

In some embodiments, the targeted nuclease is selected from the group consisting of an RNA-guided nuclease domain, a transcription activator-like effector nuclease (TALEN), a zinc finger nuclease (ZFN) and a megaTAL (See, for example, Merkert and Martin "Site-Specific Genome Engineering in Human Pluripotent Stem Cells," *Int. J. Mol. Sci.* 18(7): 1000 (2016)). In some embodiments, the RNA-guided nuclease is a Cas9 nuclease and the method further comprises introducing into the cell a guide RNA that specifically hybridizes to a target region in the genome of the cell, for example, a target region in exon 1 of the TRAC gene in a T cell. In other embodiments, the RNA-guided nuclease is a Cas9 nuclease and the method further comprises introducing into the cell a guide RNA that specifically hybridizes to a target region in exon 1 of the TRBC gene.

As used throughout, a guide RNA (gRNA) sequence is a sequence that interacts with a site-specific or targeted nuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence or protospacer sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%). In some embodiments, the Cas9 protein can be in an active endonuclease form, such that when bound to target nucleic acid as part of a complex with a guide RNA or part of a complex with a DNA template, a double strand break is introduced into the target nucleic acid. In the methods provided herein, a Cas9 polypeptide or a nucleic acid encoding a Cas9 polypeptide can be introduced into the cell. The double strand break can be repaired by HDR to insert the DNA template into the genome of the cell. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to, for example, a region in exon 1 of the TRAC or exon 1 of the TRAB that contains an NGG sequence. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to those described in Esvelt et al., Nature Methods 10: 1116-1121 (2013).

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region, for example exon 1 of a TRAC gene or exon 1 of a TRBC gene. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," *Cell* 154(6): 1380-1389 (2013)).

In some embodiments, the Cas9 nuclease, the guide RNA and the nucleic acid sequence are introduced into the cell as a ribonucleoprotein complex (RNP)-nucleic acid sequence (e.g. a DNA template) complex, wherein the RNP-nucleic acid sequence complex comprises: (i) the RNP, wherein the RNP comprises the Cas9 nuclease and the guide RNA; and (ii) the nucleic acid sequence or construct.

In some embodiments, the molar ratio of RNP to DNA template can be from about 3:1 to about 100:1. For example, the molar ratio can be from about 5:1 to 10:1, from about 5:1 to about 15:1, 5:1 to about 20:1; 5:1 to about 25:1; from about 8:1 to about 12:1; from about 8:1 to about 15:1, from about 8:1 to about 20:1, or from about 8:1 to about 25:1.

In some embodiments, the DNA template in the RNP-DNA template complex is at a concentration of about 2.5 μM to about 25 μM. In some embodiments, the amount of DNA template is about 1 μg to about 10 μg.

In some cases, the RNP-DNA template complex is formed by incubating the RNP with the DNA template for less than about one minute to about thirty minutes, at a temperature of about 20° C. to about 25° C. In some embodiments, the RNP-DNA template complex and the cell are mixed prior to introducing the RNP-DNA template complex into the cell.

In some embodiments the nucleic acid sequence or the RNP-DNA template complex is introduced into the cells by electroporation. Methods, compositions, and devices for electroporating cells to introduce a RNP-DNA template complex can include those described in the examples herein. Additional or alternative methods, compositions, and devices for electroporating cells to introduce a RNP-DNA template complex can include those described in WO/2006/001614 or Kim, J. A. et al. Biosens. Bioelectron. 23, 1353-1360 (2008). Additional or alternative methods, compositions, and devices for electroporating cells to introduce a RNP-DNA template complex can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186,559; 7,771,984; 7,991,559; 6,485,961; 7,029,916; and U.S. Patent Appl. Pub. Nos: 2014/0017213; and 2012/0088842. Additional or alternative methods, compositions, and devices for electroporating cells to introduce a RNP-DNA template complex can include those described in Geng, T. et al., J. Control Release 144, 91-100 (2010); and Wang, J., et al. Lab. Chip 10, 2057-2061 (2010).

In some embodiments, the RNP is delivered to the cells in the presence of an anionic polymer. In some embodiments, the anionic polymer is an anionic polypeptide or an anionic polysaccharide. In some embodiments, the anionic polymer is an anionic polypeptide (e.g., a polyglutamic acid (PGA), a polyaspartic acid, or polycarboxyglutamic acid). In some embodiments, the anionic polymer is an anionic polysaccharide (e.g., hyaluronic acid (HA), heparin, heparin sulfate, or glycosaminoglycan). In some embodiments, the anionic polymer is poly(acrylic acid) (PAA), poly(methacrylic acid) (PMAA), poly(styrene sulfonate), or polyphosphate. In some embodiments, the anionic polymer has a molecular weight of at least 15 kDa (e.g., between 15 kDa and 50 kDa). In some embodiments, the anionic polymer and the Cas protein are in a molar ratio of between 10:1 and 120:1, respectively (e.g., 10:1, 20:1, 30:1, 40:1, 50:1, 60:1, 70:1, 80:1, 90:1, 100:1, 110:1, or, 120:1). In some embodiments of this aspect, the molar ratio of sgRNA:Cas protein is between 0.25:1 and 4:1 (e.g., 0.25:1, 0.5:1, 1:1, 1.2:1, 1.4:1, 1.6:1, 1.8:1, 2:1, 2.2:1, 2.4:1, 2.6:1, 2.8:1, 3:1, 3.2:1, 3.4:1, 3.6:1, 3.8:1, or 4:1).

In some embodiments, the donor template comprises a homology directed repair (HDR) template and one or more DNA-binding protein target sequences. In some embodiments, the donor template has one DNA-binding protein target sequence and one or more protospacer adjacent motif (PAM). The complex containing the DNA-binding protein (e.g., a RNA-guided nuclease), the donor gRNA, and the donor template can shuttle the donor template, without cleavage of the DNA-binding protein target sequence, to the desired intracellular location (e.g., the nucleus) such that the HDR template can integrate into the cleaved target nucleic acid. In some embodiments, the DNA-binding protein target sequence and the PAM are located at the 5' terminus of the HDR template. Particularly, in some embodiments, the PAM can be located at the 5' terminus of the DNA-binding protein target sequence. In other embodiments, the PAM can be located at the 3' terminus of the DNA-binding protein target sequence. In some embodiments, the DNA-binding protein target sequence and the PAM are located at the 3' terminus of the HDR template. Particularly, in some embodiments, the PAM can be located at the 5' terminus of the DNA-binding protein target sequence. In other embodiments, the PAM is located at the 3' terminus of the DNA-binding protein target sequence. In some embodiments, the donor template has two DNA-binding protein target sequences and two PAMs. Particularly, in some embodiments, a first DNA-binding protein target sequence and a first PAM are located at the 5' terminus of the HDR template and a second DNA-binding protein target sequence and a second PAM are located at the 3' terminus of the HDR template. In some embodiments, the first PAM is located at the 5' terminus of the first DNA-binding protein target sequence and the second PAM is located at the 5' of the second DNA-binding protein target sequence. In other embodiments, the first PAM is located at the 5' terminus of the first DNA-binding protein target sequence and the second PAM is located at the 3' of the second DNA-binding protein target sequence. In yet other embodiments, the first PAM is located at the 3' terminus of the first DNA-binding protein target sequence and the second PAM is located at the 5' of the second DNA-binding protein target sequence. In yet other embodiments, the first PAM is located at the 3' terminus of the first DNA-binding protein target sequence and the second PAM is located at the 3' of the second DNA-binding protein target sequence.

In some embodiments, the nucleic acid sequence or RNP-DNA template complex are introduced into about $1\times10^5$ to about $100\times10^6$ cells T cells. For example, the nucleic acid sequence or RNP-DNA template complex can be introduced into about $1\times10^5$ cells to about $5\times10^5$ cells, about $1\times10^5$ cells to about $1\times10^6$ cells, $1\times10^5$ cells to about $1.5\times10^6$ cells, $1\times10^5$ cells to about $2\times10^6$ cells, about $1\times10^6$ cells to about $1.5\times10^6$ cells or about $1\times10^6$ cells to about $2\times10^6$ cells.

In the methods and compositions provided herein, the human T cells can be primary T cells. In some embodiments, the T cell is a regulatory T cell, an effector T cell, or a naïve T cell. In some embodiments, the effector T cell is a $CD8^+$ T cell. In some embodiments, the T cell is an CD4+ cell. In some embodiments, the T cell is a $CD4^+CD8^+$ T cell. In some embodiments, the T cell is a $CD4^-CD8^-$T cell. In some embodiments, the T cell is a T cell that expresses a TCR receptor or differentiates into a T cell that expresses a TCR receptor.

Methods of Treatment

Any of the methods and compositions described herein can be used to modify T cells obtained from a human subject. Any of the methods and compositions described herein can be used to modify T cells obtained from a human subject to enhance an immune response in the subject. Any of the methods and compositions described herein can be used to modify T cells obtained from a human subject to treat or prevent a disease (e.g., cancer, an infectious disease, an autoimmune disease, transplantation rejection, graft vs. host disease or other inflammatory disorder in a subject).

Provided herein is a method of enhancing an immune response in a human subject comprising administering any of the modified T cells described herein, i.e., T cells that heterologously express a polypeptide described herein, for example; a truncated human PD-1 protein comprising the human PD-1 extracellular domain and transmembrane domain and lacking 80-90 (e.g., 87) carboxyl terminal PD-1 amino acids; a polypeptide comprising a human PD-1 extracellular domain or portion thereof of at least 120 or 130 amino acids (and optionally 1-20 (e.g., 11) amino acids of the 4-1BB extracellular domain) linked to a human 4-1BB intracellular domain via a transmembrane domain; a polypeptide comprising a human PD-1 extracellular domain linked to a human MyD88 intracellular domain or a portion thereof of at least 90 or 100 amino acids (and optionally 1-10 amino acids of the PD-1 intracellular domain) via a transmembrane domain; a polypeptide comprising a human PD-1 extracellular domain linked to a human ICOS intracellular domain via a transmembrane domain; a truncated human CTLA4 protein comprising the human CTLA4 extracellular domain and transmembrane domain and lacking 30-40 (e.g., 34) carboxyl terminal CTLA4 amino acids; a polypeptide comprising a human CTLA4 extracellular domain linked to a human CD28 intracellular domain or a portion thereof of at least 30 or 40 amino acids (and optionally 1-10 amino acids of the CTLA4 intracellular domain) via a transmembrane domain; a truncated human CD200R protein comprising the human CD200R extracellular domain and transmembrane domain and lacking 50-60 carboxyl terminal CD200R amino acids; a truncated human BTLA protein comprising the human BTLA extracellular domain and transmembrane domain and lacking 100-110 (e.g., 104) carboxyl terminal BTLA amino acids. In some embodiments, the truncated human BTLA protein comprises the first 1-12(e.g., 6) amino acids of the human BTLA intracellular domain but lacks the remaining human BTLA protein intracellular domain; a polypeptide comprising a human BTLA extracellular domain or a portion thereof of at least 110 or 120 amino acids (and optionally 1-20 amino acids of the CD28 extracellular domain) linked to a human CD28 intracellular domain via a transmembrane domain; a truncated human TIM-3 protein comprising the human TIM-3 extracellular domain and transmembrane domain and lacking 65-75 (e.g., 71) carboxyl terminal TIM-3 amino acids; a polypeptide comprising a human TIM-3 extracellular domain or a portion thereof of at least 160 or 170 amino acids (and optionally 1-20 amino acids of the CD28 extracellular domain) linked to a human CD28 intracellular domain via a transmembrane domain; a truncated human TIGIT protein comprising the human TIGIT extracellular domain and transmembrane domain and lacking 70-80 (e.g., 75) carboxyl terminal TIGIT amino acids; a polypeptide comprising a human TIGIT extracellular domain or a portion thereof of at least 100 or 110 amino acids (and optionally 1-20 amino acids of the CD28 extracellular domain) linked to a human CD28 intracellular domain via a transmembrane domain; a truncated human TGFβR2 protein comprising the human TGFβR2 extracellular domain and transmembrane domain and lacking 360-370 (e.g., 366) carboxyl terminal TGFβR2 amino acids; a polypeptide comprising a human TGFβR2 extracellular domain or a portion thereof of at least 130 or 140 amino acids (and optionally 1-20 amino acids of the 4-1BB extracellular domain) linked to a human 4-1BB intracellular domain via a transmembrane domain; a polypeptide comprising a human TGFβR2 extracellular domain linked to a human Myd88 intracellular domain or a portion thereof of at least 90 or 100 amino acids (and optionally 1-20 amino acids of the TGFβR2 intracellular domain) via a transmembrane domain; a truncated human IL-10RA protein comprising the human IL-10RA extracellular domain and transmembrane domain and lacking 310-320 (e.g., 315) carboxyl terminal IL-10RA amino acids; a polypeptide comprising a human IL-10RA extracellular domain linked to a human IL-7RA intracellular domain via a transmembrane domain; a polypeptide comprising a human IL-4RA extracellular domain linked to a human IL-7RA intracellular domain via a transmembrane domain; a truncated human Fas protein comprising the human Fas extracellular domain and transmembrane domain and lacking 132-142 (e.g., 138) carboxyl terminal Fas amino acids; a polypeptide comprising a human Fas extracellular domain linked to a human CD28 intracellular domain or a portion thereof of at least 30 or 40 amino acids (and optionally 1-20 amino acids of the Fas intracellular domain) via a transmembrane domain; a polypeptide comprising a human Fas extracellular domain linked to a human 4-1BB intracellular domain or a portion thereof of at least 30 or 40 amino acids (and optionally 1-20 amino acids of the Fas intracellular domain) via a transmembrane domain; a polypeptide comprising a human Fas extracellular domain linked to a human MyD88 intracellular domain or a portion thereof of at least 90 or 100 amino acids (and optionally 1-20 amino acids of the Fas intracellular domain) via a transmembrane domain; a polypeptide comprising a human Fas extracellular domain linked to a human ICOS intracellular domain or a portion thereof of at least 25 or 35 amino acids (and optionally 1-20 amino acid of the Fas intracellular domain) via a transmembrane domain; a truncated human TRAIL-R2 protein comprising the human TRAIL-R2 extracellular domain and transmembrane domain and lacking 196-206 (e.g., 202) carboxyl terminal TRAIL-R2 amino acids; a polypeptide comprising a human TRAIL-R2 extracellular domain linked to a human CD28 intracellular domain or a portion thereof of at least 30 or 40 amino acids (and optionally 1-20 amino acids of the TRAIL-R2 intracellular domain) via a transmembrane domain; a polypeptide comprising an IL2RA protein, an IL7RA protein, an MCT4 protein or a TCF7 protein; or a polypeptide comprising one or more amino acid sequences selected from the group consisting of SEQ ID NO: 37-SEQ ID NO: 116.

In some embodiments, T cells are obtained from the subject and modified using any of the methods provided herein to express an antigen-specific TCR or synthetic antigen receptor, prior to administering the modified T cells to the subject. In some embodiments, the subject has cancer and the target antigen is a cancer-specific antigen. In some embodiments, the subject has an autoimmune disorder and the antigen is an antigen associatd with the autoimmune disorder. In some embodiments, the subject has an infection and target antigen is an antigen associated with the infection.

Also provided is a method for treating cancer in a human subject comprising: a) obtaining T cells from the subject; b) modifying the T cells using any of the methods provided herein to express an antigen-specific TCR or a synthetic antigen receptor that recognizes a target antigen in the subject; and c) administering the modified T cells to the subject, wherein the human subject has cancer and the target antigen is a cancer-specific antigen. As used throughout, the phrase "cancer-specific antigen" means an antigen that is unique to cancer cells or is expressed more abundantly in cancer cells than in in non-cancerous cells. In some embodiments, the cancer-specific antigen is a tumor-specific antigen.

In some embodiments, tumor infiltrating lymphocytes, a heterogeneous and cancer-specific T-cell population, are obtained from a cancer subject and expanded ex vivo. The characteristics of the patient's cancer determine a set of tailored cellular modifications, and these modifications are applied to the tumor infiltrating lymphocytes using any of the methods described herein.

Also provided herein is a method of treating an autoimmune disease in a human subject comprising: a) obtaining T cells from the subject; b) modifying the T cells using any of the methods provided herein to express an antigen-specific TCR or synthetic antigen receptor that recognizes a target antigen in the subject; and c) administering the modified T cells to the subject, wherein the human subject has an autoimmune disorder and the target antigen is antigen associated with the autoimmune disorder. In some embodiments, the T cells are regulatory T cells.

Also provided herein is a method of treating an infection in a human subject comprising: a) obtaining T cells from the subject; b) modifying the T cells using any of the methods provided herein to express an antigen-specific TCR or a synthetic antigen receptor that recognizes a target antigen in the subject; and c) administering the modified T cells to the subject, wherein the subject has an infection and the target antigen is an antigen associated with the infection in the subject.

Any of the methods of treatment provided herein can further comprise expanding the population of T cells before the T cells are modified. Any of the methods of treatment provided herein can further comprise expanding the population of T cells after the T cells are modified and prior to administration to the subject.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Described herein is non-viral genome targeting as a discovery platform for large therapeutic endogenous genetic modifications. An arrayed knockin screen of large DNA payloads at 91 unique genomic sites in primary human T cells was performed and a rule set for predicting genomic loci that can be efficiently targeted was determined. These productive tools to efficiently create Genetically Engineered Endogenous Proteins (GEEPs), which alter cellular input, output, and regulatory control by combining synthetic modifications seamlessly with endogenous genetic elements. Finally, a generalized technique for large pooled knockins was developed based on unique features of homology directed repair. High-throughput pooled screening of targeted endogenous knockins to the T cell receptor locus revealed novel functional protein chimeras that combined with a new TCR specificity to enhance T cell function in the presence of tumor suppressive signals, including in in vivo solid tumor models. Overall, a robust discovery platform for next-generation cell therapies enabled by non-viral genome targeting is provided herein.

The FDA approval in 2017 of two T-cell based therapies for B cell leukemias and lymphomas capped 30 years of development of engineered T cell therapies. While the foundational technology for this engineering has advanced since the earliest engineered T cell clinical trials, two core aspects remain unchanged—the need for a viral infection, and random integration of that viral genome into the cell's DNA. An efficient non-viral genome targeting method that removes the need for a viral vector when delivering large new DNA sequences was recently developed (Roth et al. *Nature* 559: 405-409 (2018)). Further, with the application of targetable nucleases such as CRISPR/Cas9, these DNA sequences can be targeted for integration to specific genomic sites with single base pair resolution through homology directed repair. Advantages of targeting therapeutic genes to specific genomic sites have been shown through replacement of the endogenous T cell receptor with a CAR or new TCR specificity, placing the new antigen receptor under endogenous regulatory control.

Figure 1C:
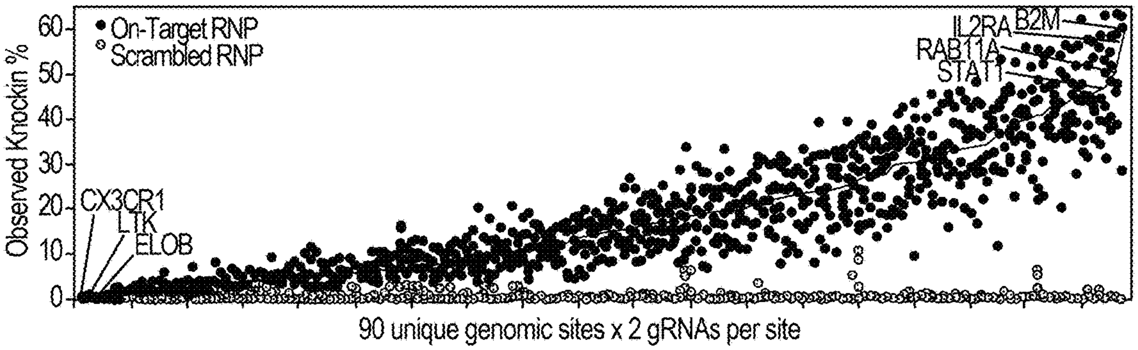
Figure 1E:
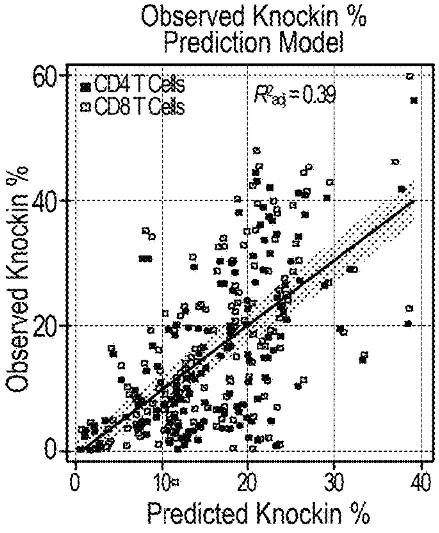
Figure 1D:
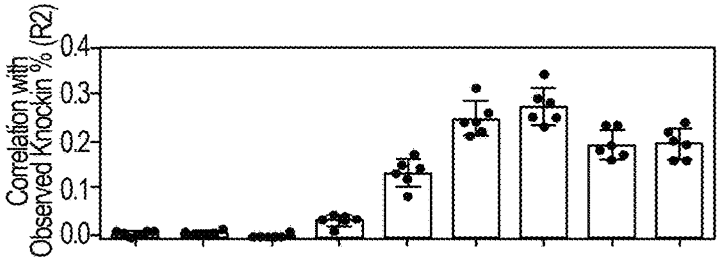
Figure 1F:
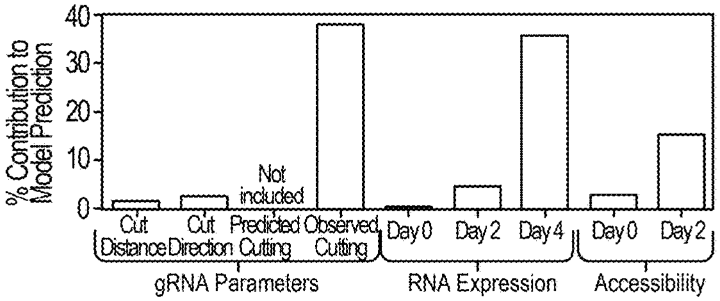

The ability to target large new DNA sequences to specific sites opens a variety of questions specific to the engineering of endogenous genomic loci. Unlike random viral vector integration, each target locus is unique, requiring a new combination of gRNA to instigate a dsDNA break, and homology arms to target the new DNA sequence to that site during homology directed repair. In practice, gene targeting at different genomic loci yields drastically different efficiencies. To determine the spectrum of endogenous genomic loci amenable to non-viral genome targeting, a large arrayed knockin screen, integrating a GFP or tNGFR template (~800 bp) into 91 unique genomic loci in six healthy human donors (FIG. 1*a, b*) was performed. Targeting of diverse genes, including TCR complex members, immune surface receptors, checkpoint receptors, transcription factors, and many cytoskeletal and housekeeping genes, showed a wide range of observed knockin efficiencies (FIG. 1*c* and FIG. 5). The screen was performed in both CD4 and CD8 T cells with GFP or tNGFR knockin percentages recorded in both resting and restimulated cells (FIG. 6). RNA expression of the target gene and DNA accessibility at the gRNA cut site were both correlated with observed knockin efficiency (FIG. 1*d*). A multivariate linear regression showed greater predictive value than any gRNA, RNA expression, or DNA accessibility parameter individually (FIG. 1*d* and FIGS. 7, 8), and demonstrated that gRNA cutting efficiency, target gene RNA expression, and target site DNA accessibility independently contributed to observed knockin efficiency (FIG. 1*e*).

Figure 2A:
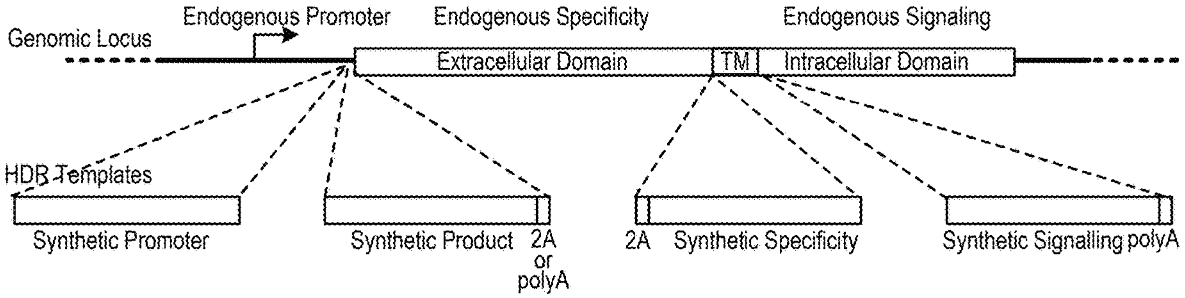
FIGS. 2*a*-2*g* show Genetically Engineered Endogenous Proteins (GEEPs) and their properties. (a) Schematic description of all the different ways we validated for engineering cell-surface proteins at the endogenous gene locus. Within any given cell-surface protein's gene locus, we can modify (from left to right) the 5' non-coding region to override endogenous gene regulation with a synthetic/exogenous promoter, add or replace the protein expressed under a particular endogenous promoter, replace receptor specificity by targeting a sequence encoding a novel extracellular domain to the exon encoding the transmembrane domain, and alter the signaling of a receptor by knocking-in new signaling domain(s). (b) To test whether we could tune gene expression by knocking-in a synthetic promoter, we targeted a SFFV promoter to the 5' non-coding region of IL2RA and PDCD1. When we analyzed edited T cells cultured without restimulation by flow cytometry 7 days after electroporation, we saw that successful knock-in led to sustained expression of either protein. (Top) We show that T cells edited with on-target conditions for IL2RA (IL2RA RNP+SFFV HDR DNA Template) maintain high expression of CD25 whereas T cells edited with control conditions (Scrambled RNP+ SFFV HDR DNA Template) see CD25 expression levels return to baseline. (Bottom) Similarly, T cells edited with on-target conditions for PDCD1 (PDCD1 RNP+SFFV HDR DNA Template) maintain high levels of PD1 whereas T cells edited with control conditions see PD1 expression levels return to baseline. (c) To test whether we could put a synthetic product under the regulation of an endogenous promoter, we targeted an insert encoding tNGFR and either a 2A sequence or a PolyA tail to the N-terminal coding region of PD1 such that tNGFR would be expressed with or without PD1, respectively, under the regulation of the PD1 promoter. When we restimulated edited T cells and analyzed them by flow cytometry 48 hours later, we saw high co-expression of PD1 and tNGFR with the tNGFR-2A insert (Top) and high expression of tNGFR along with PD1 KO with the tNGFR-PolyA insert (Bottom). (d) To test whether we could alter the extracellular specificity of a receptor, we tested to see whether we could alter TCR specificity. Using a previously described targeting strategy, we were able to knock-in the 1G4 TCR receptor into the endogenous TRAC locus with a very high knock-in efficiency. (e) To test whether we could knock-in additional or replacement signaling domains to create synthetic signaling cascades, we designed constructs that would incorporate either the CD28 or 41BB intracellular domain on the C-terminus of one of the CD3 subunits. To make readout of an intracellular domain knock-in easier, we also included a fluorescent protein preceded by a 2A sequence in the construct as a marker for successful knock-in. Successful integration would yield a multicistronic sequence expressing a CD3 chain containing a new signaling domain fused to the C-terminus and a fluorescent protein simultaneously. (Top) We show successful integration of the CD28 intracellular domain at the C-terminus of CD3 epsilon, as measured by the percentage of GFP+ cells. (Bottom) Additionally, we show successful integration of the 41BB intracellular domain at the C-terminus of CD3 epsilon, as measured by the percentage of mCherry+ cells. (f) To test whether putting a synthetic product under an endogenous promoter truly mimicked the corresponding endogenous protein's expression dynamics, we profiled T cells with tNGFR-2A knocked in to the IL2RA N terminus by flow cytometry over the course of 5 days and compared tNGFR expression dynamics to that of IL2RA. In both CD8 and CD4 subsets, IL2RA and tNGFR expression both decreased over time in the absence of restimulation. Similarly, in restimulated cells, both CD8 and CD4 cells saw a simultaneous upregulation of IL2RA and tNGFR. (g) Results of a competitive mixed proliferation assay testing the advantage of synthetic CD3 signaling. We pooled unsorted edited T cells with CD28IC-2A-GFP, 41BBIC-2A-mCherry, or 2A-BFP knocked-in to the same CD3 complex member's gene locus. We then cultured the mixed cell population without stimulation, with CD3 stimulation only, with CD28 stimulation only, or with CD3/CD28 stimulation. After 4 days in culture, samples were analyzed by flow cytometry for relative outgrowth of GFP+ and mCherry+ subpopulations relative to the BFP+ subpopulation. We then normalized the proportions to those found in the corresponding unstimulated condition.

The ability to determine genomic loci that can potentially be efficiently modified, coupled with the ability to add large new DNA sequences to specific sites, opens the question of how new synthetic genetic instructions specifically added to endogenous loci could uniquely modify cellular function (FIG. 2*a*). Randomly integrated new genetic material imparts an orthogonal functionality, but targeted knockins can integrate synthetic elements with endogenous sequences to create Genetically Engineered Endogenous Proteins (GEEPs). Using an improved non-viral genome targeting protocol based on a Cas9 'shuttle' system and an anionic polymer. GEEPs were efficiently created across multiple locations within a target genomic locus (FIG. 2*a*).

Figure 2B:
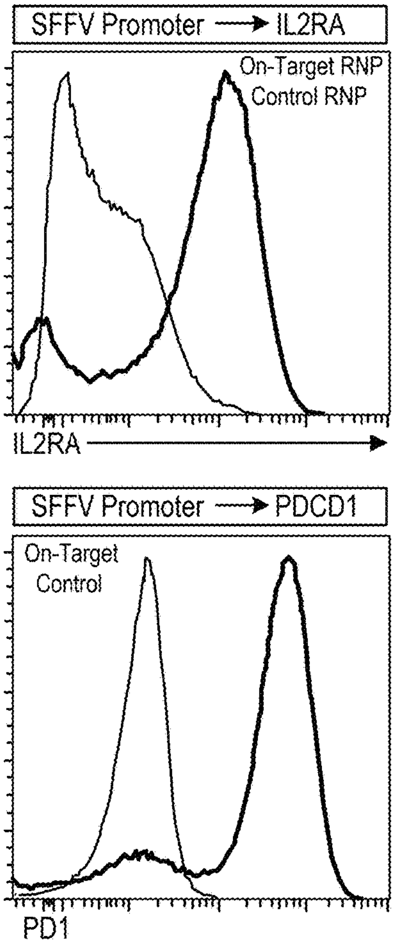
Figure 2C:
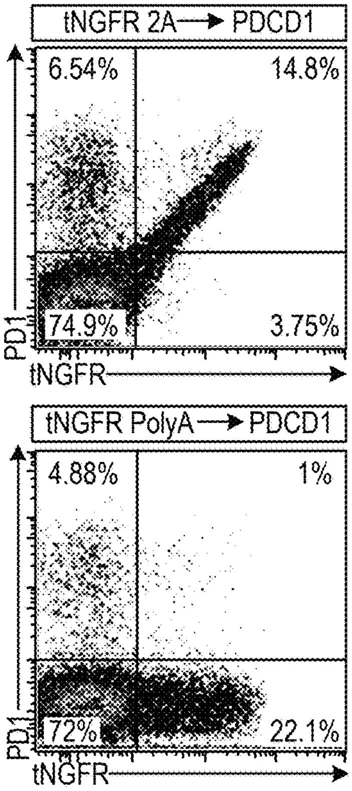
Figure 2D:
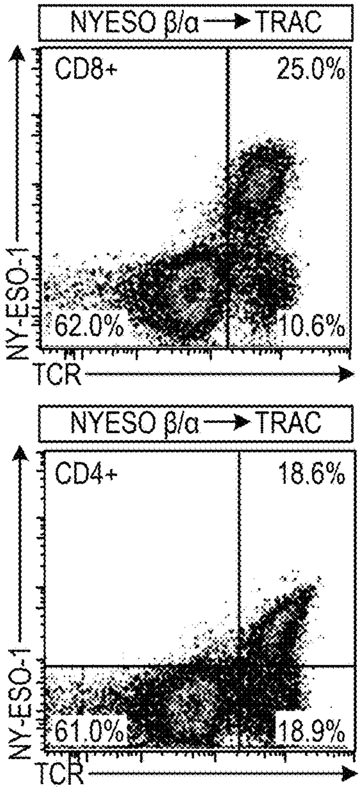
Figure 2E:
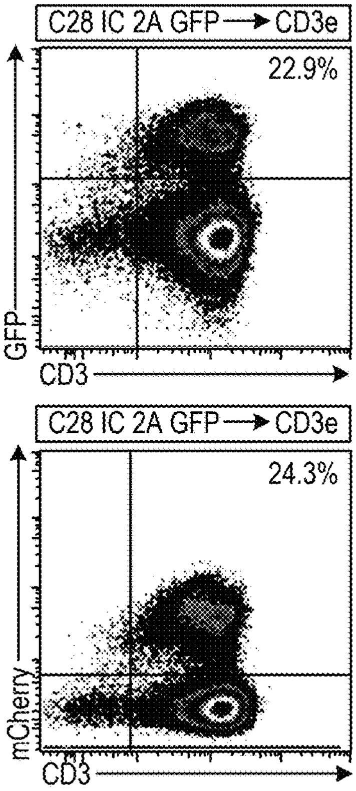
Figure 2F:
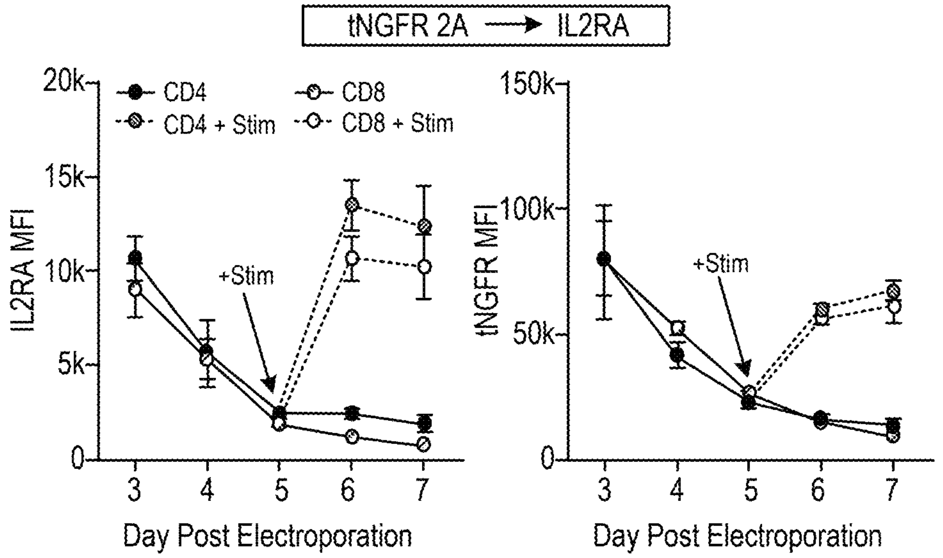
Figure 2G:
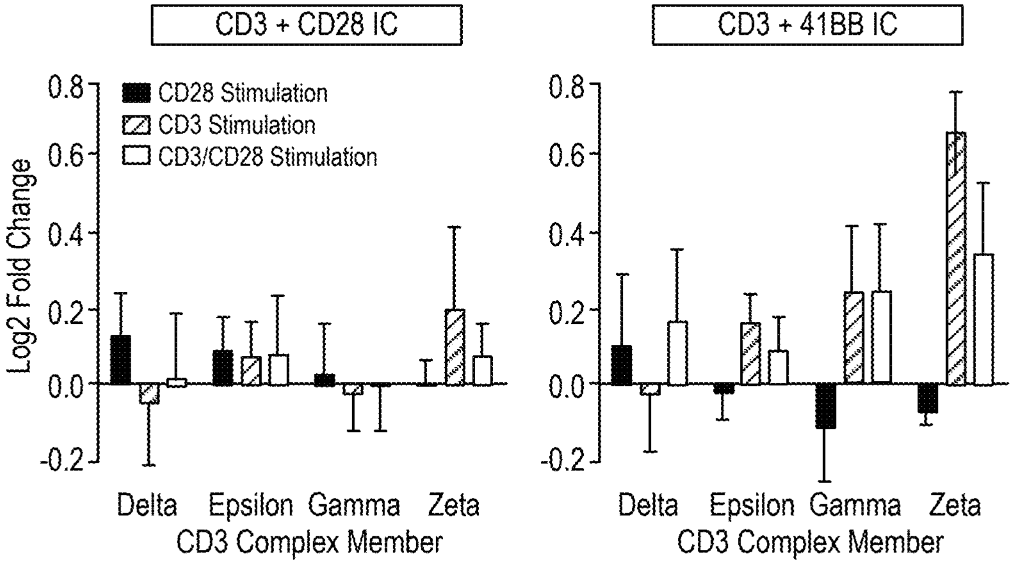

Integration of a new viral promoter to the transcriptional start site of an endogenous gene creates a 'promoter GEEP' with a synthetic promoter driving expression of an endogenous gene product (FIG. 2*b*). Promoter GEEPs at IL2RA and PDCD1 showed continuing high expression of IL2RA and PD1 in resting cells 9 days after TCR stimulation, whereas the endogenous regulatory circuit for these activation-dependent genes showed low expression levels (FIG. 2*b* and FIG. 9). In contrast, integration of a new gene product at the same site creates a 'product GEEP' with an endogenous regulatory circuit driving expression of a new synthetic gene product (FIG. 2*c*). Product GEEPs were createdat the PDCD1 locus containing either a 2A peptide to maintain expression of the endogenous PD1 gene or a polyA sequence to remove endogenous PD1 gene expression (FIG. 2*c* and FIG. 10). Product GEEPs created at the IL2RA, CD28, and LAG3 loci all mirrored the expression dynamics of their respective endogenous genes (FIG. 2*d* and FIG. 11). Integration of a new extracellular domain specifically in front of a target surface receptors transmembrane domain creates a 'specificity GEEP' with a synthetic specificity driving endogenous signaling (FIG. 2*e*), such as at the endogenous TCRα locus where the ability to replace the extracellular TCR specificity while maintaining the endogenous constant signaling domains. Finally, integration of a new signaling domain to a surface receptor after the transmembrane domain creates a 'signaling GEEP' where an endogenous specificity drives synthetic signaling (FIG. 2*f*). Signaling GEEPs were created at all four CD3 gene loci (CD3D, CD3E, CD3G. CD3Z) with either a CD28 intraceullar domain or a 41BB intracellular domain appended (FIG. 12). While none of the CD28 intracellular domain fusions showed increased proliferation in the presence of CD3 stimulation in comparison to control knockin cells (FIG. 12), a CD3ζ-41BB signaling GEEP specifically showed increased proliferation in response to CD3 stimulation in the absence of CD28 costimulation (FIG. 2*g*).

Having developed guidelines for determining targetable genomic loci and the design of Genetically Engineered Endogenous Proteins to combine synthetic elements with endogenous sequences, whether combining multiple large DNA sequences into a single therapeutic endogenous knockin gene cassette could enhance T cell functionality in immunotherapy settings was determined. T cells' efficacy is a product of both their antigenic specificity and functionality. First, it was demonstrated that a three gene cassette could be integrated at the endogenous TCR-α locus to both replace the endogenous TCR with a new specificity, as well as drive expression of a new gene off of the high-expression endogenous TCR promoter (FIG. 3*a*). Knockin of a TCRβ-tNGFR-TCRα cassette to TRAC exon 1 showed that almost all cells with successful knockin of the new TCR (NY-ESO-1 melanoma cancer antigen specific 1G4 clone) also showed expression of the additional tNGFR gene (FIG. 3*b*). Knockin of a four gene cassette to the TCR-α locus was similarly successful (FIG. 13).

To determine if this new gene product could modify T cell function, the tNGFR was replaced with a previously described dominant negative TGFβR2 receptor that minimizes the inhibitory effects of TGFβsignaling on T cells (Ishigame et al. *J. Immunol.* 190(12): 6340-6350 (2013)). A head-to-head proliferation assay showed increased relative proliferation after delivery of the new NY-ESO-1 TCR specificity with dnTGFβR2 in the selectively in the presence of exogenous TGFβ in comparison to addition of the new TCR and tNGFR control (FIG. 3*c* and FIG. 14). Antigen specific killing of a target melanoma cell line (A375 cells) that expresses the NY-ESO-1 antigen on the 1G4 TCR's specific MHC-A2 allele similarly showed improved killing with delivery of the new NY-ESO-1 TCR+dnTGFβR2 in comparison to the new NY-ESO-1 TCR+tNGFR (FIG. 3*d* and FIG. 14). Non-viral knockin to the endogenous TCR-α locus can thus efficiently modify both T cell specificity as well as T cell functionality with a single gene cassette.

The development of small molecule and biologic drugs depended significantly on the application of high-throughput screening methodologies to enable many potential therapeutic candidates to be assayed simultaneously. However, a comparable screening methodology, pooled knockins of large DNA sequences, has not yet been applied to accelerate the development of cell-based therapies. To overcome this limitation, as described herein, a generalized non-viral pooled knockin screening method to rapidly assay many targeted knockins in a pooled cell population (FIG. 4*a*) was developed. Building on a single knockin of a new TCR specificity and a new function-altering gene (FIG. 3), it was hypothesized that pooled knockin of a HDR template library, where each member contains a constant new TCR specificity along with a unique third gene product, could rapidly identify new DNA sequences that modify T cell function in specific therapeutically relevant contexts (FIG. 4*a*).

First, a DNA sequencing strategy to selectively amplify on-target knockins in contrast to the NHEJ-edited or wild-type target genomic locus, episomal non-integrated HDR template, or off-target integrations was developed (FIG. 15). Because the homology arms of an HDR template are used for complementary base pairing with the target locus but are not themselves copied into the target site, a short region of DNA base pair mismatches with the target genomic locus introduced to the 3' homology arm created a PCR amplicon unique to on-target knockins (FIG. 15*a*), without a large reduction in knockin efficiency (FIG. 15*b,c*). Addition of a barcode unique for each insert within degenerate bases of the TCR-α VJ region of the TCR+functional gene cassette thus enabled a DNA readout of the abundance of each individual insert in the pooled population. Detailed experimentation with a two-member library (new NY-ESO-1 TCR+either GFP or RFP) including testing library pooling prior to DNA assembly, HDRT production by PCR, electroporation of the HDRT, or culture/expansion of the cells followed by sequencing of sorted GFP+ or RFP+ cells revealed a minimal amount of template switching when pooling prior to electroporation, which increased when pooling at earlier stages (FIG. 16). Barcode sequencing that reproduced the observed proportions of GFP+ and RFP+ could be accomplished off of both isolated genomic DNA and mRNA converted to cDNA (FIG. 16). Therefore, a simple pooled knockin methodology that can target many new large DNA sequences to a specific target genomic locus and easily determine their relative abundance in a cell population by DNA sequencing was demonstrated.

Figure 35C:
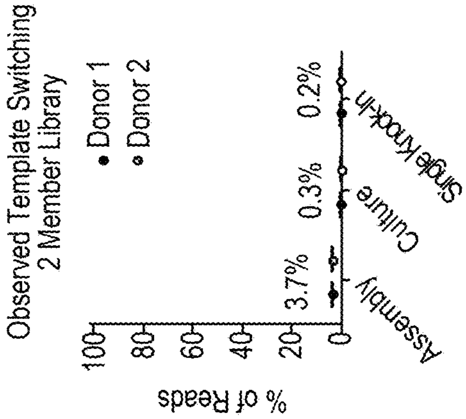
Figure 35D:
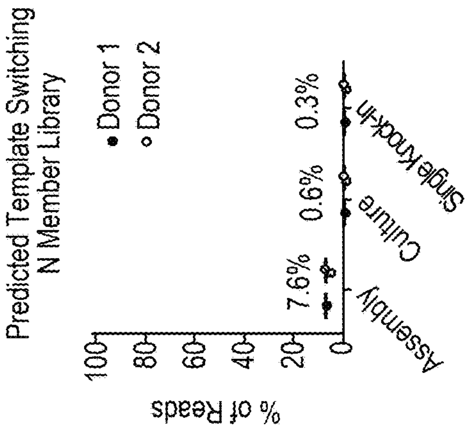

Template switching was evaluated using two example constructs (mCherry vs GFP in the polycistronic cassette shown in FIG. 34). A plasmid pool (n=2) was built by pooled assembly. HDR template was generated from the plasmid pool and electroporated into primary T cells of two individual healthy donors. Cells were sorted based on NY-ESO-1 TCR and GFP or mCherry expression. The number of correct barcode reads was analyzed by amplicon sequencing of cDNA. The percentage of correctly assigned reads was compared to T cells which were electroporated separately with mCherry/GFP templates and pooled during culture and T cells electroporated with only one of the constructs (FIGS. 35*a* and *b*). Template switching was calculated for the 2-member library (FIG. 35*c*) and predicted for an N-member library (FIG. 2*d*). Using the barcoding strategy of FIG. 34, the predicted template switching for an N-member library was decreased from 50% in the previous design to a mean of 7.6% in the improved pooled knock-in library design. Observed and predicted template switching for improved pooled knock-in library design: (FIG. 35*a*) The percentage of sequenced reads that contained the GFP or (FIG. 35*b*) mCherry HDR template's barcode corresponded with the observed percentage of cells expressing GFP or mCherry protein by flow cytometry across pooling conditions. FIG. 35*c* shows the am=mount of observed template switching for the 2-member library and FIG. 35*d* shows predicted template switching for an N-member library. Predicted template switching of the library design at the pooled assembly stage was 7.6%. All experiments performed in n=2 unique healthy donors. Using the exemplary construct shown in FIG. 34 decreases the amount of template switching which can occur during pooling at early steps of library assembly. Since pooling can be made feasible at early protocol steps (e.g. during library assembly), scaling up the approach from dozens to hundreds of tested constructs is possible.

The pooled knockin screening was next applied to the discovery of potential therapeutically relevant modifications of endogenous genetic loci in primary human T cells. A 36 member library of previously published as well as novel protein chimeras that could rewire inhibitory or suppressive signals to provide activating or stimulatory signals to T cells in concert with introduction of a new TCR specificity was designed (FIG. 17). Technical validations of pooled knockin screening with this larger library showed efficient knockin of each library member and that sequencing the unique barcodes was still accurately reflecting their proportions in the cell population (FIG. 18*a-e*). For an initial application, the pooled modified T cell library was stimulated and population abundance was compared to input. Remarkably, chimeric receptors based on the FAS apoptotic gene with a variety of immunomodulatory intracellular domain showed drastic relative increases in proliferation compared to the majority of library members (FIG. 4*b* and FIG. 18*f*). These large pooled knockin screen results were highly reproducible, could be performed with earlier pooling stages and in bulk edited or sorted cells, and did not prevent robust cell expansion after electroporation (FIG. 18*g-k*).

Figure 19A:
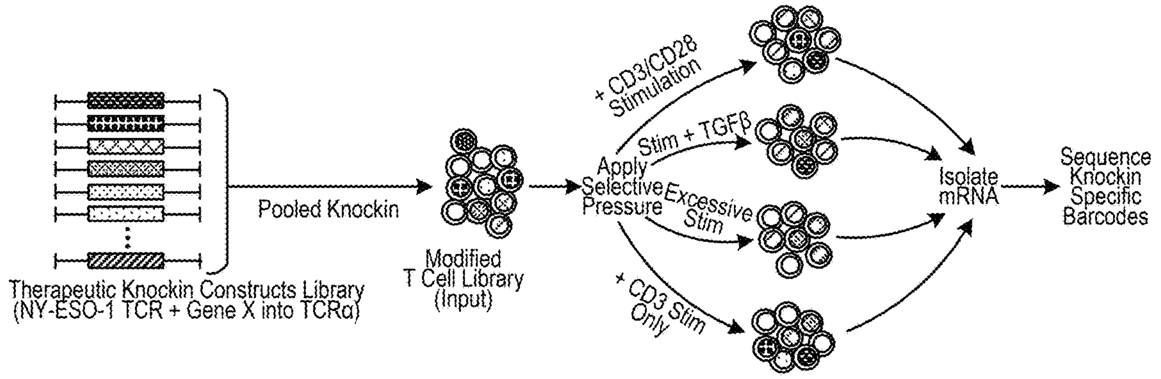
Figure 19B:
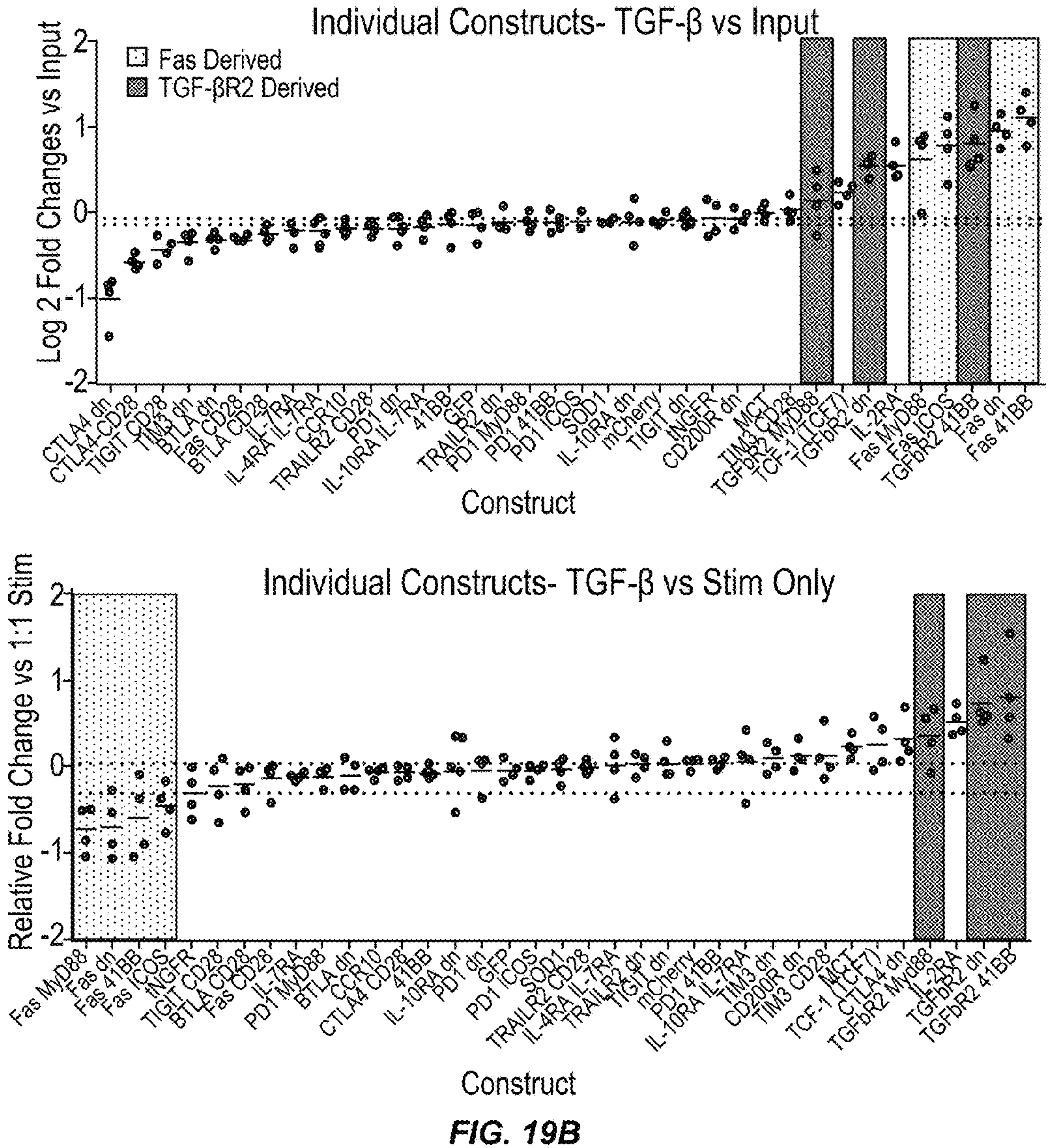
Figure 19C:
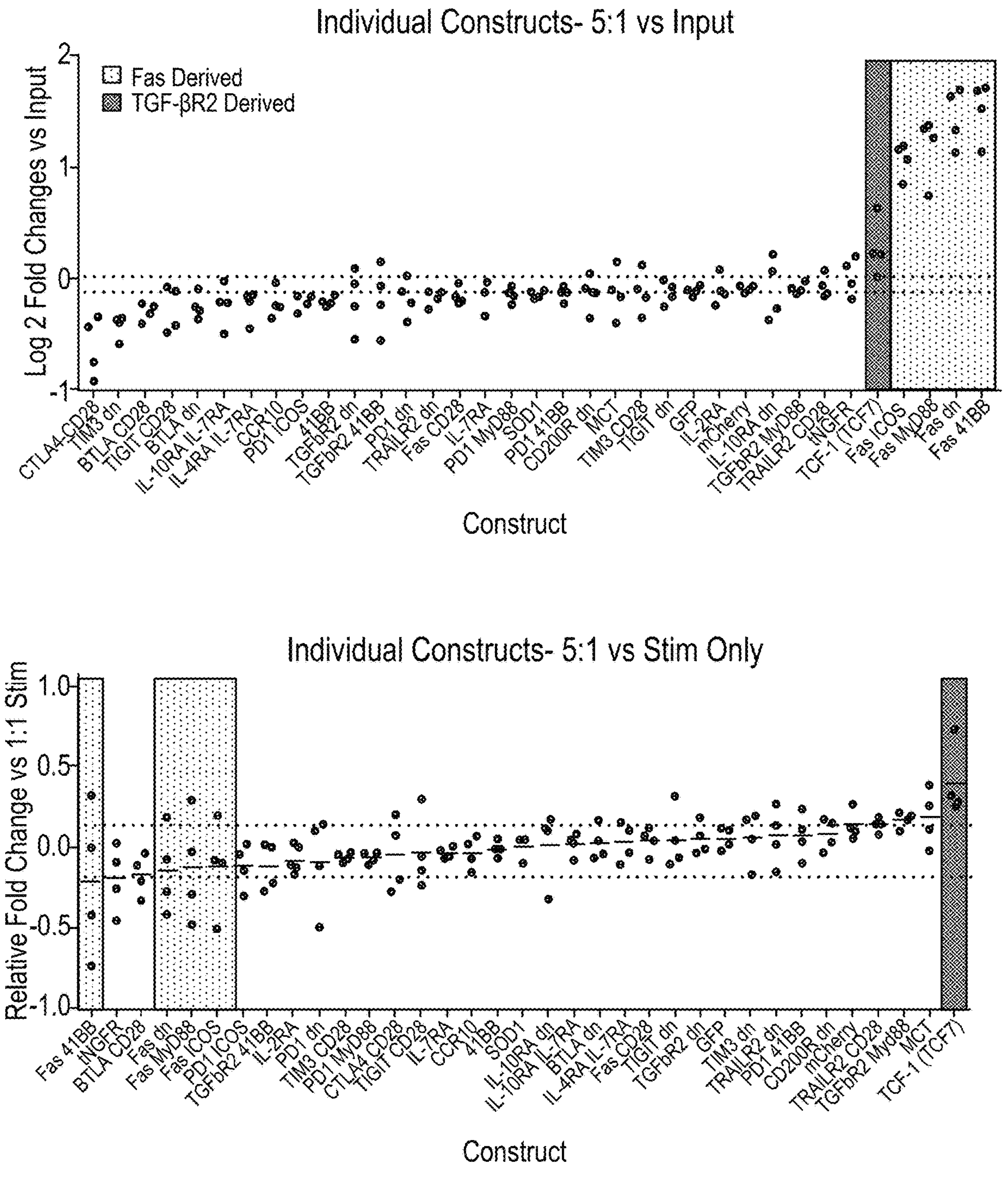
Figure 19D:
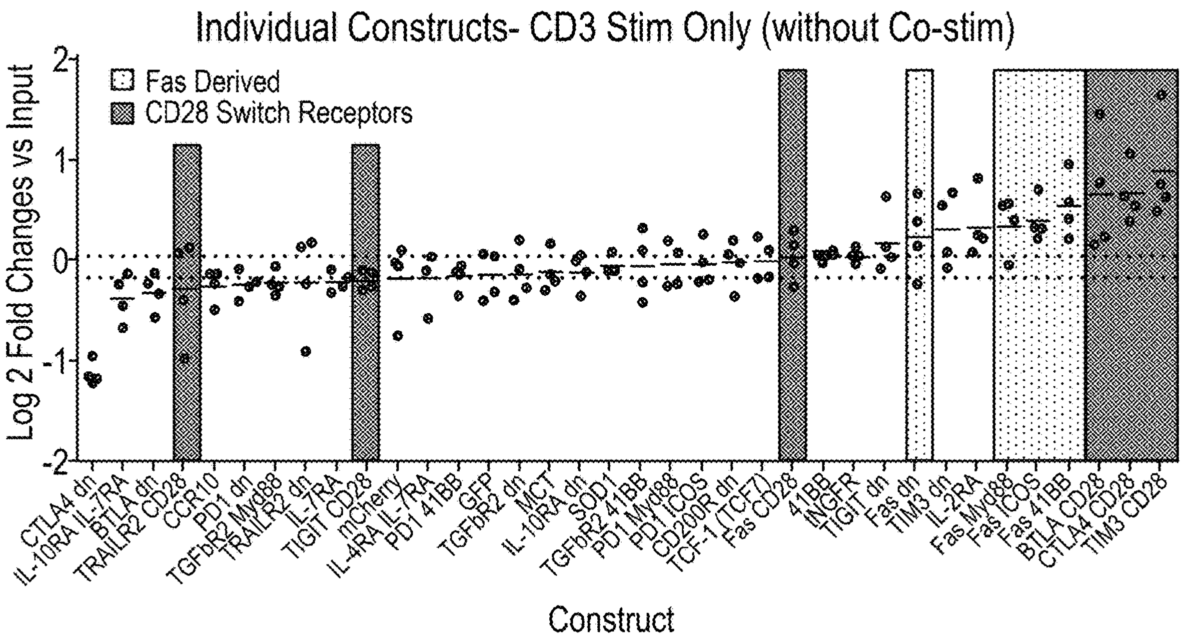
Figure 19D:
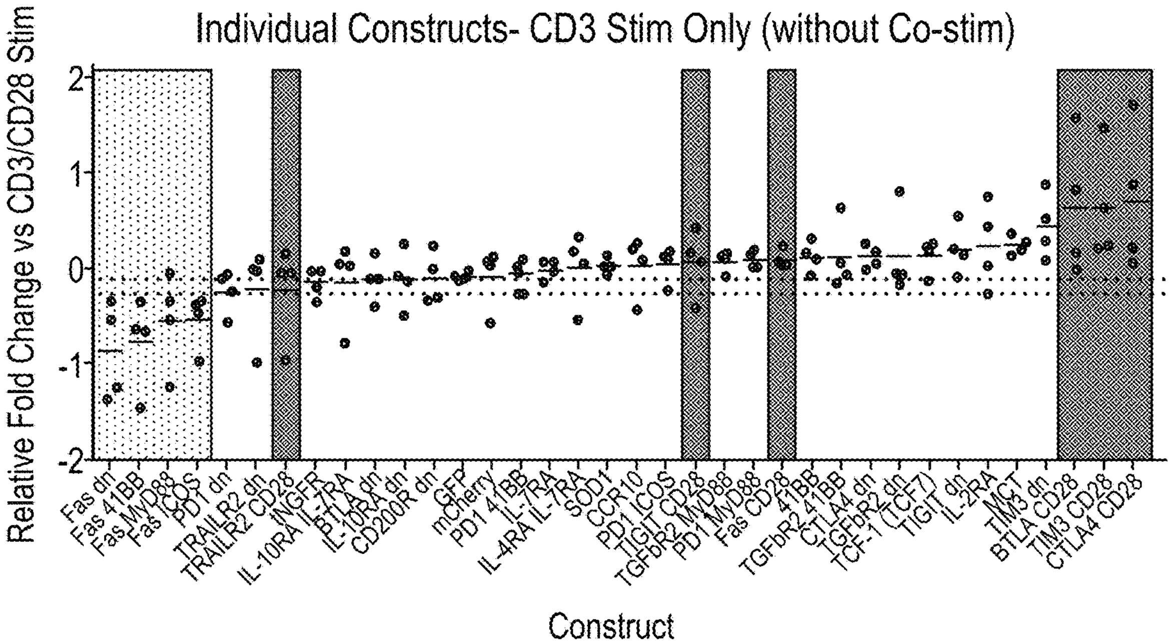
Figure 20A:
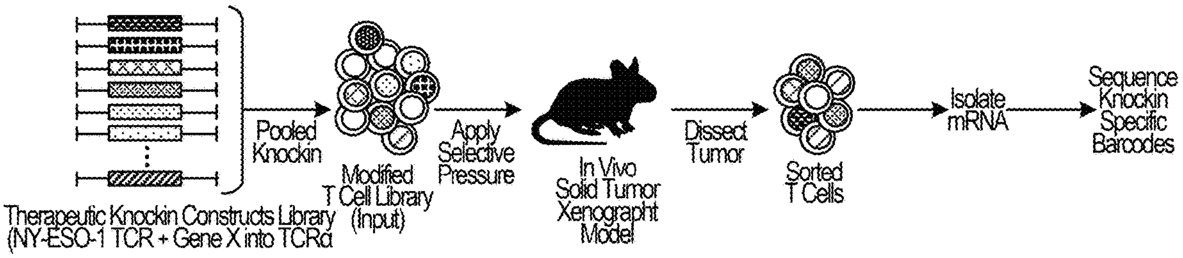
Figure 20B:
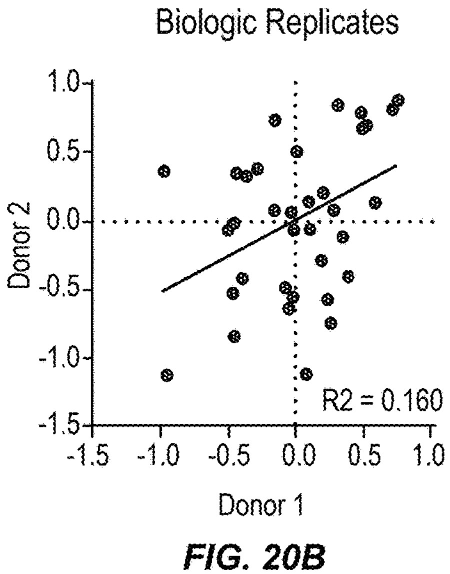
Figure 20C:
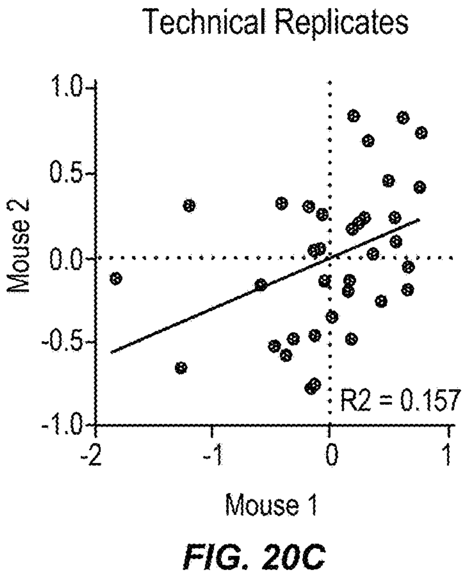
Figure 20D:
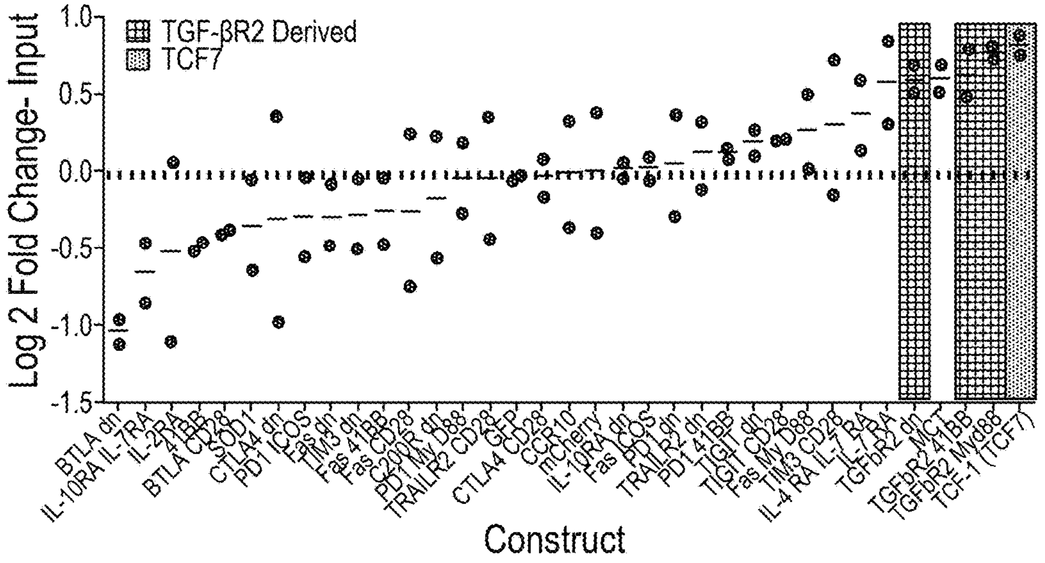
Figure 21A:
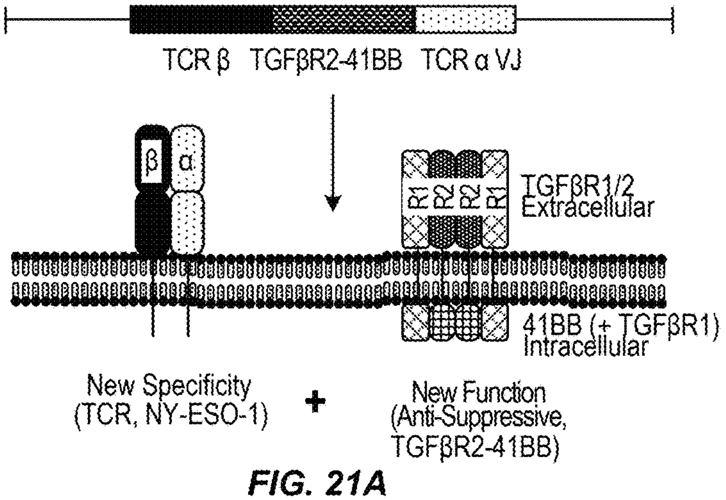
Figure 21B:
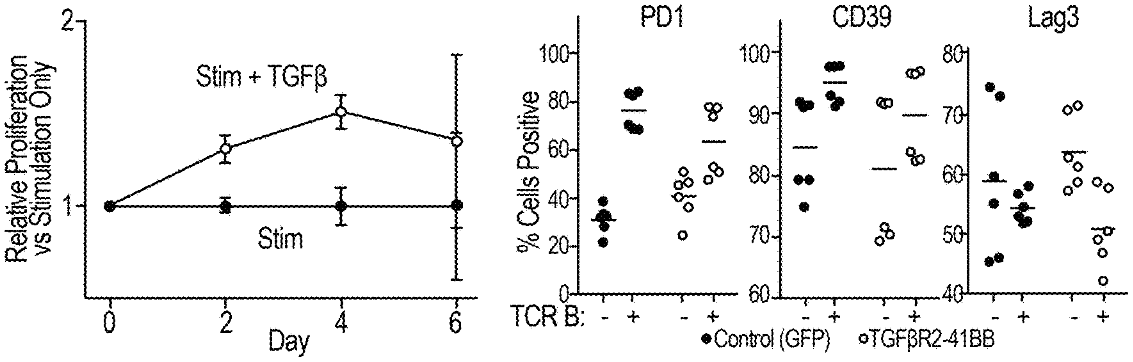
Figure 21C:
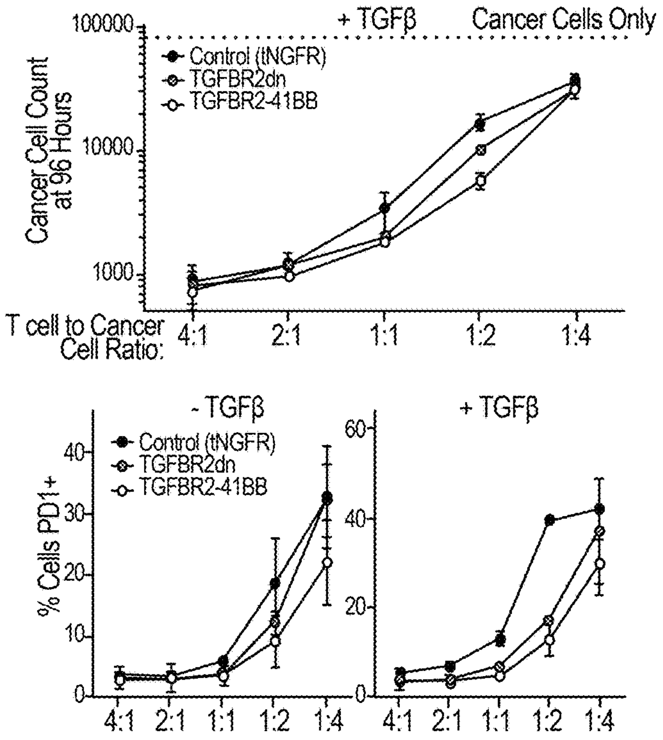
Figure 21D:
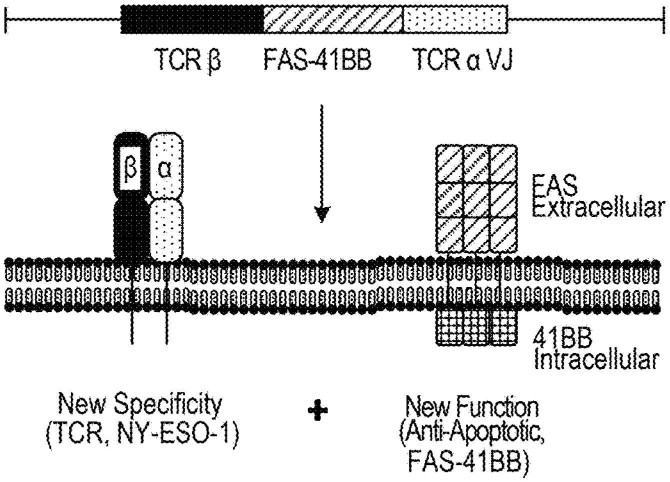
Figure 21E:
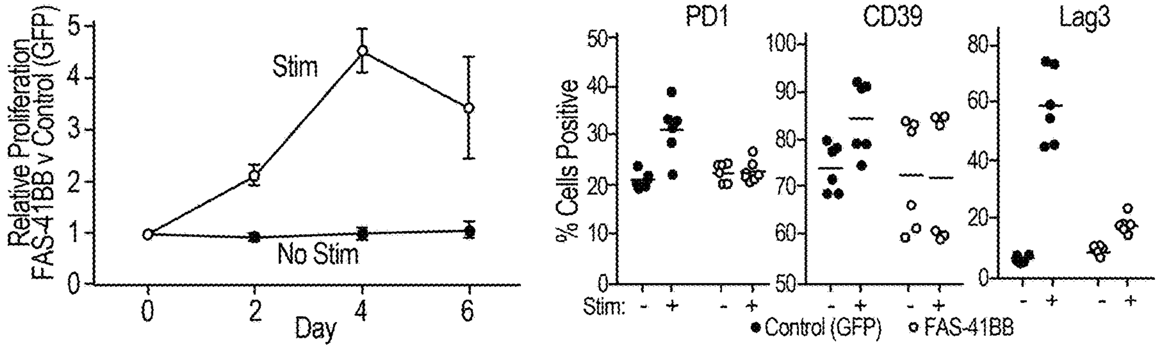
Figure 21F:
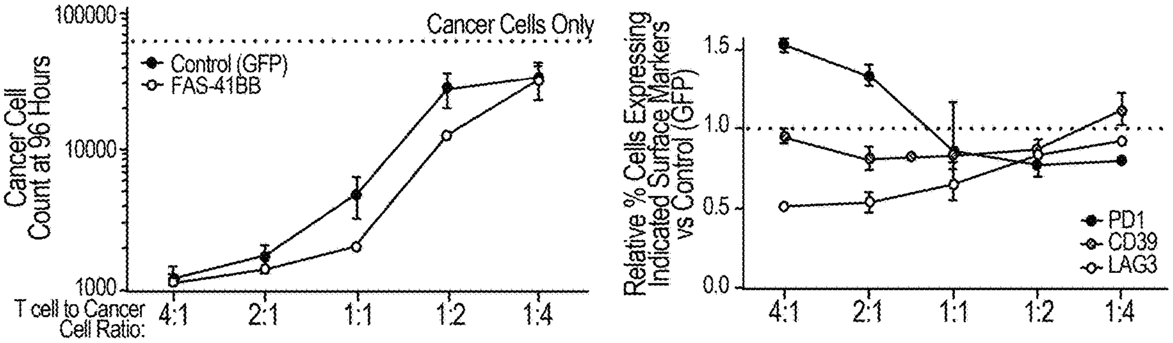
Figure 21G:
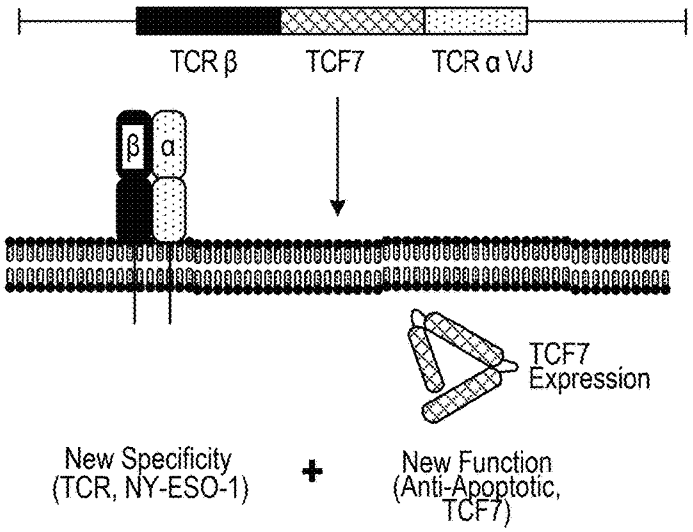
Figure 21H:
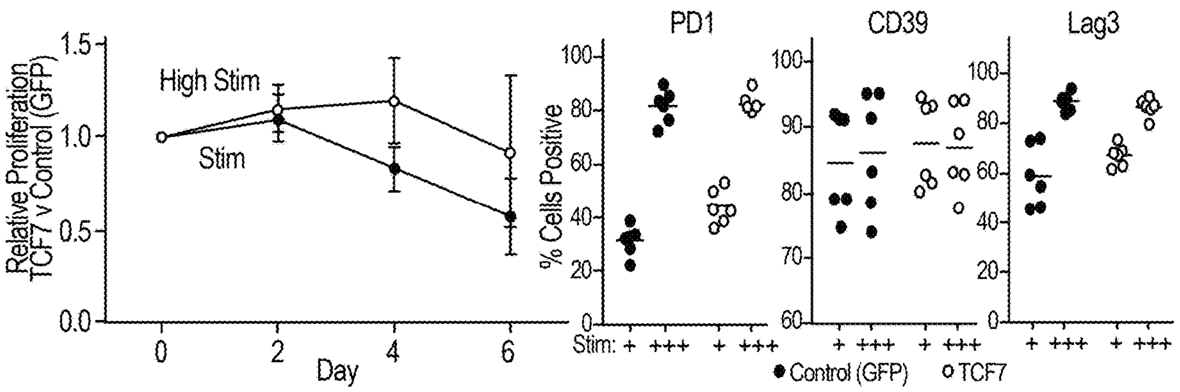
Figure 21I:
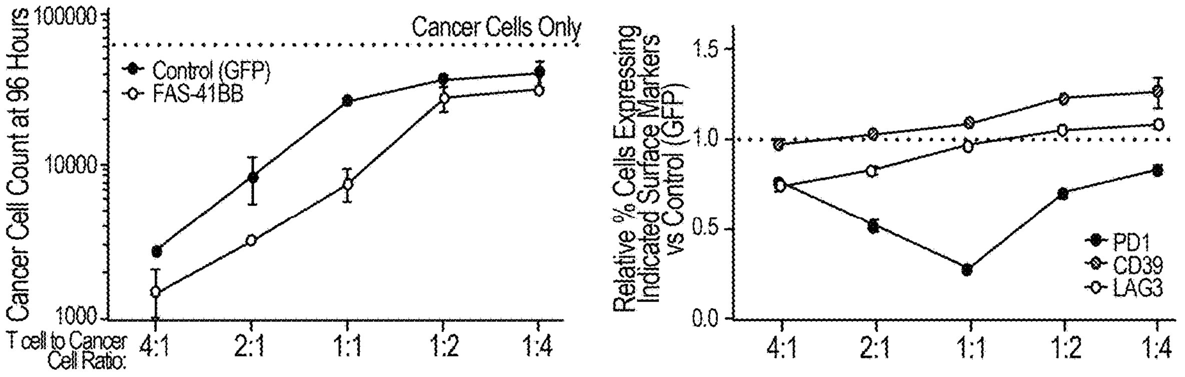

Taking advantage of the pooled knockin screen's ability to rapidly determine functional effects in a given assay for many gene products, a series of diverse in vitro selective pressures were applied to primary human T cells modified with the 36 member TCR+Function-modifying gene library (FIG. 4*c* and FIG. 18*a*). In the absence of restimulation, IL2RA expressing T cells expanded relatively (FIG. 18*k*), whereas with stimulation, Fas derived chimeras showed much greater relative expansion (FIG. 14*f*). Addition of the immunosuppressive cytokine TGFβ in contrast gave the dnTGFβR2 construct a selective proliferative advantage, and a novel chimeric TGFβR2-41BB showed even greater proliferation (FIG. 19*b*). Excessive stimulation mirroring the antigenic abundance seen in tumour environments revealed a selective proliferative advantage for the transcription factor TCF7 (FIG. 19*c*). And stimulation through the TCR without CD28 co-stimulation showed a proliferative advantage for a variety of CD28 chimeric receptors such as a TIM3-CD28 chimera and a CTLA4-CD28 chimera (FIG. 19*d*).

Figure 4D:
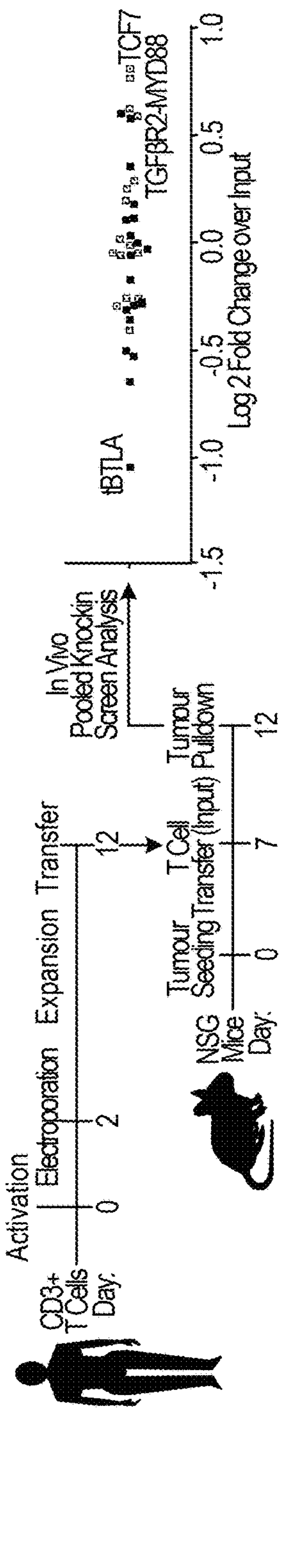

Next, an in vivo pooled knockin screen using an antigen specific human melanoma xenograft model was performed (Roth et al. *Nature* 559: 405-409 (2018)). A pooled modified T cell library was transferred into immunodeficient NSG mice bearing a human melanoma expressing the NY-ESO-1 antigen, and T cells were extracted from the tumour five days later (FIG. 4*d*). A variety of hits from the in vitro screens also showed selective proliferative enrichment in the in vivo tumour environment, including TCF7 and the TGFβR2-41BB chimera (FIG. 4*d* and FIG. 20). Some hits from the in vivo screen, such as the metabolic protein MCT4, had not shown enrichment in any of the in vitro screens performed.

Figure 4E:
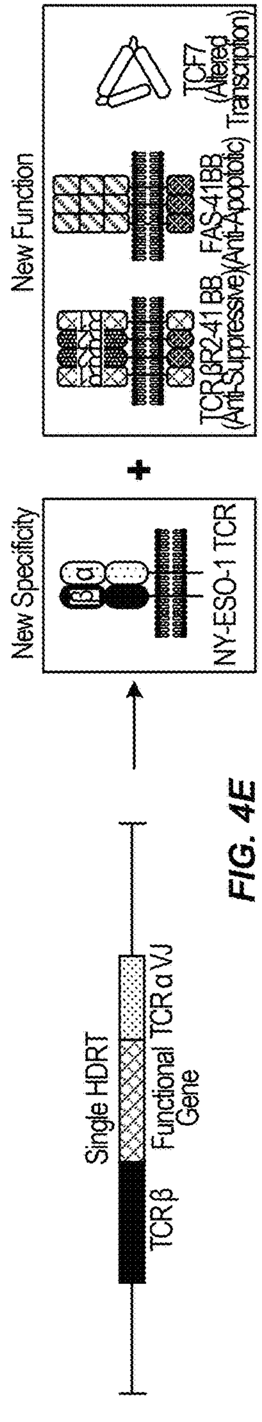
Figure 4F:
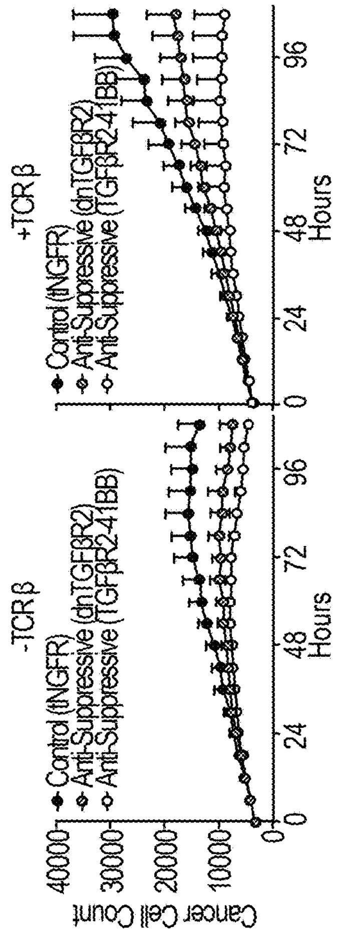
Figure 4G:
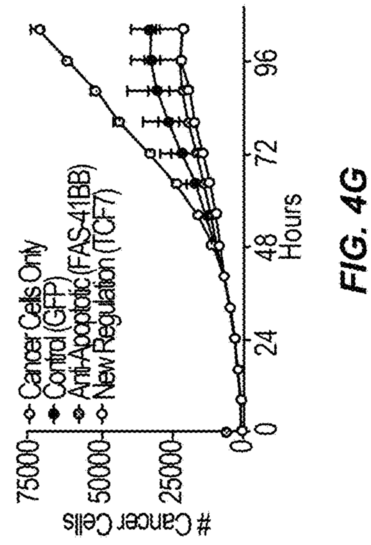
Figure 5A:
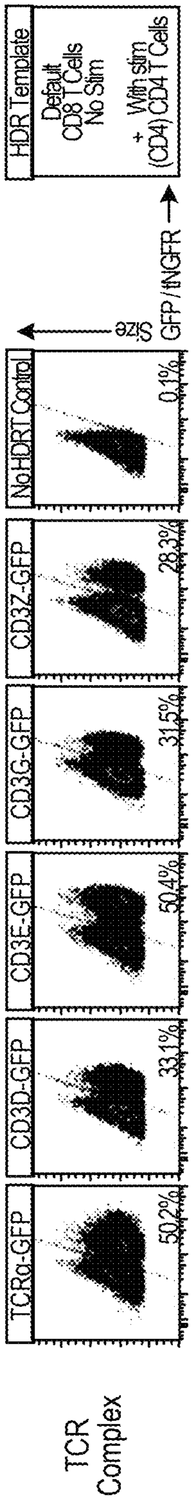
Figure 5B:
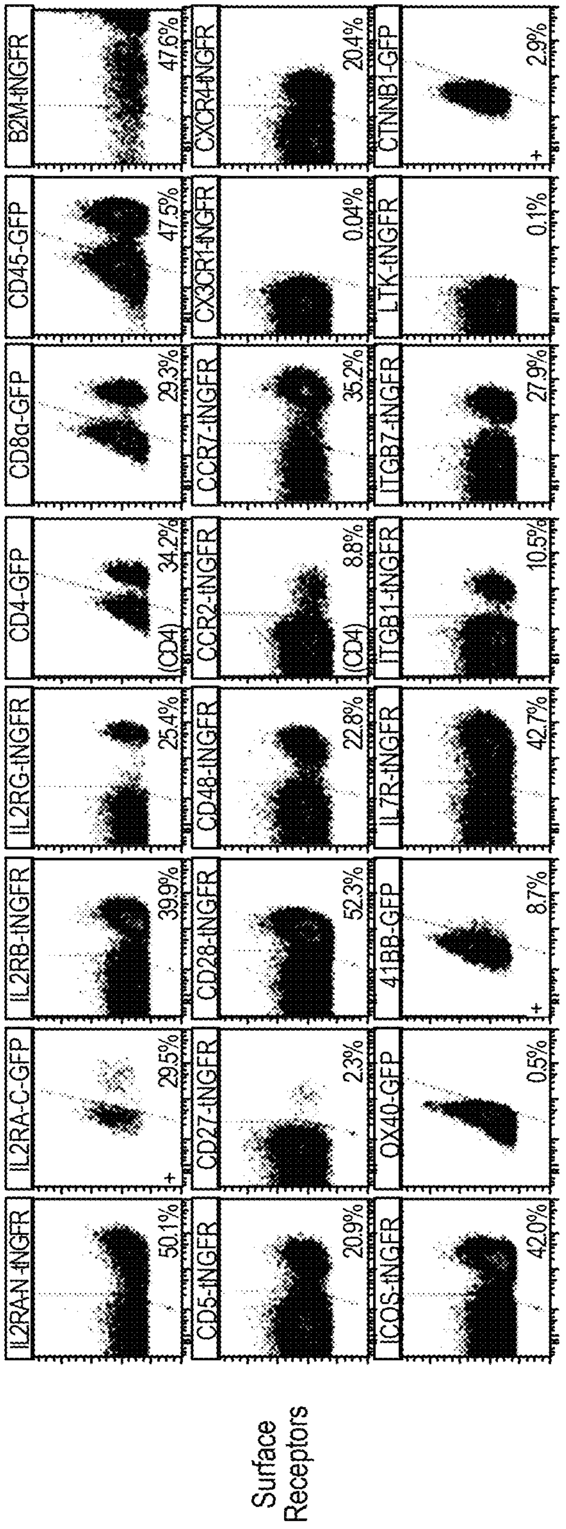
Figure 5C:
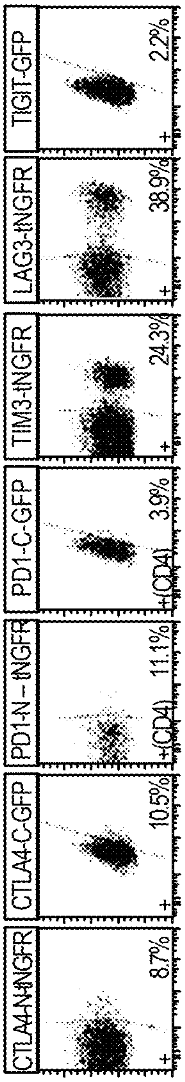
Figure 5D:
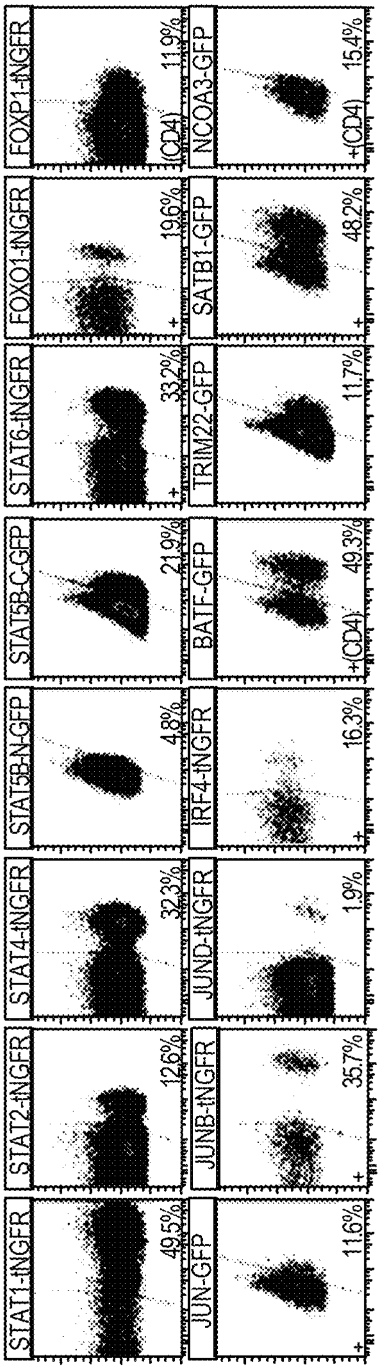
Figure 5E:
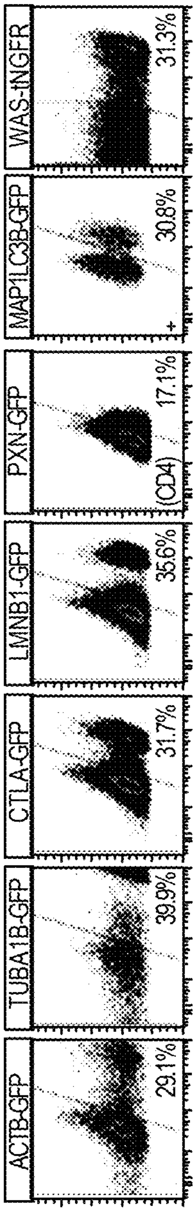
Figure 5F:
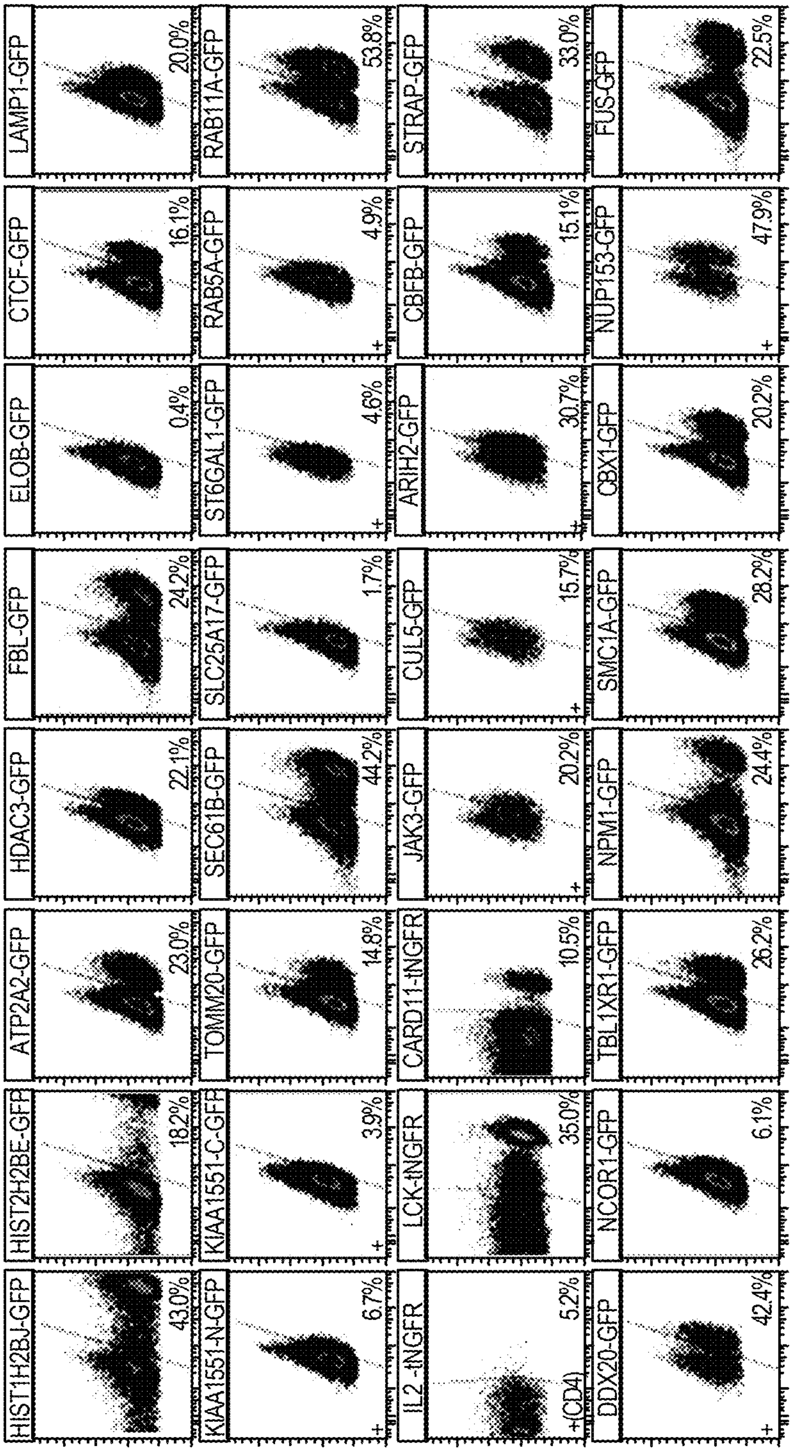
Figure 6A:
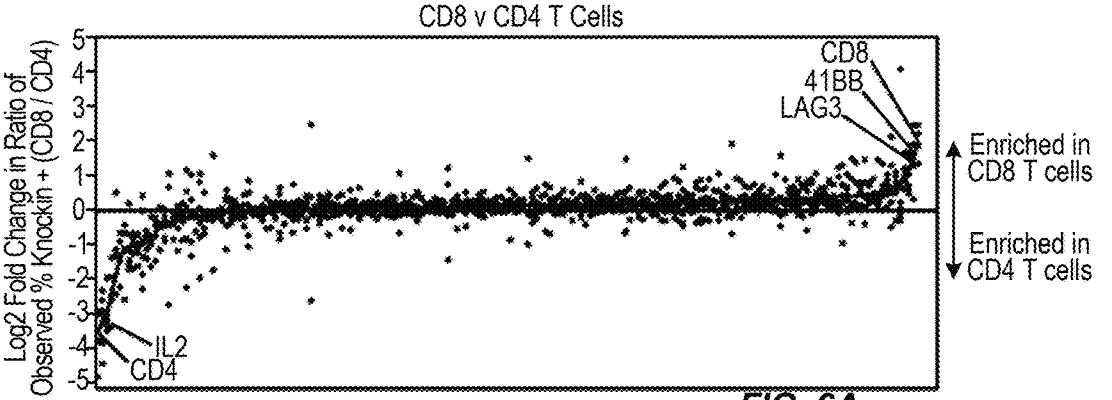
Figure 6B:
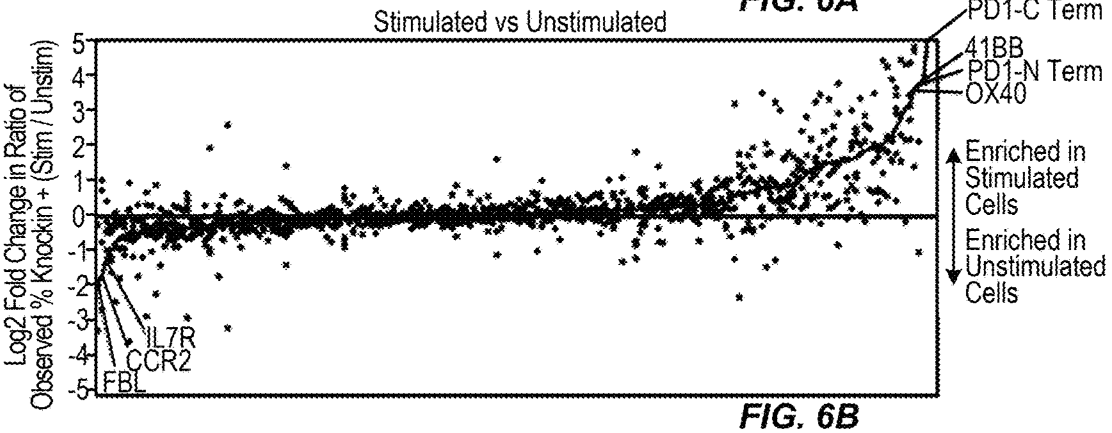
Figure 6C:
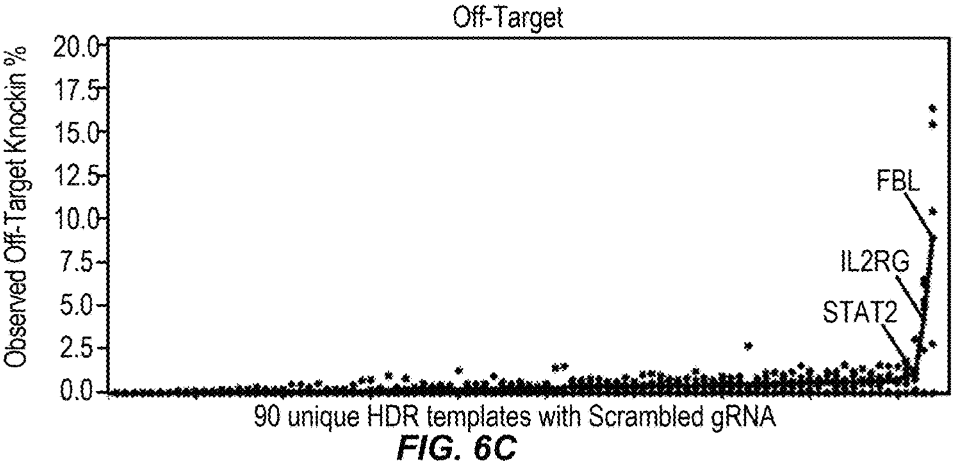
Figure 6D:
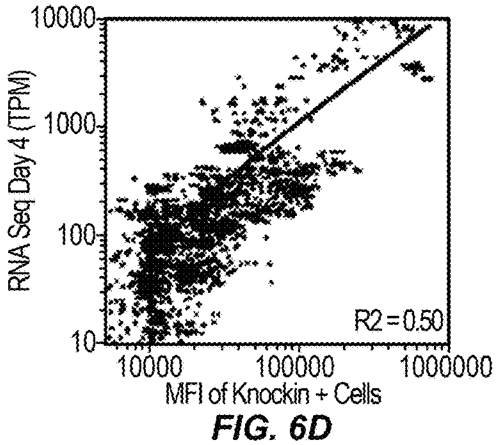
Figure 6E:
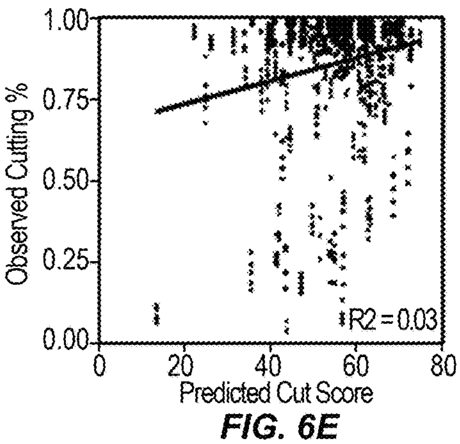
Figures 7A, 7B, 7C, 7D, 7E:
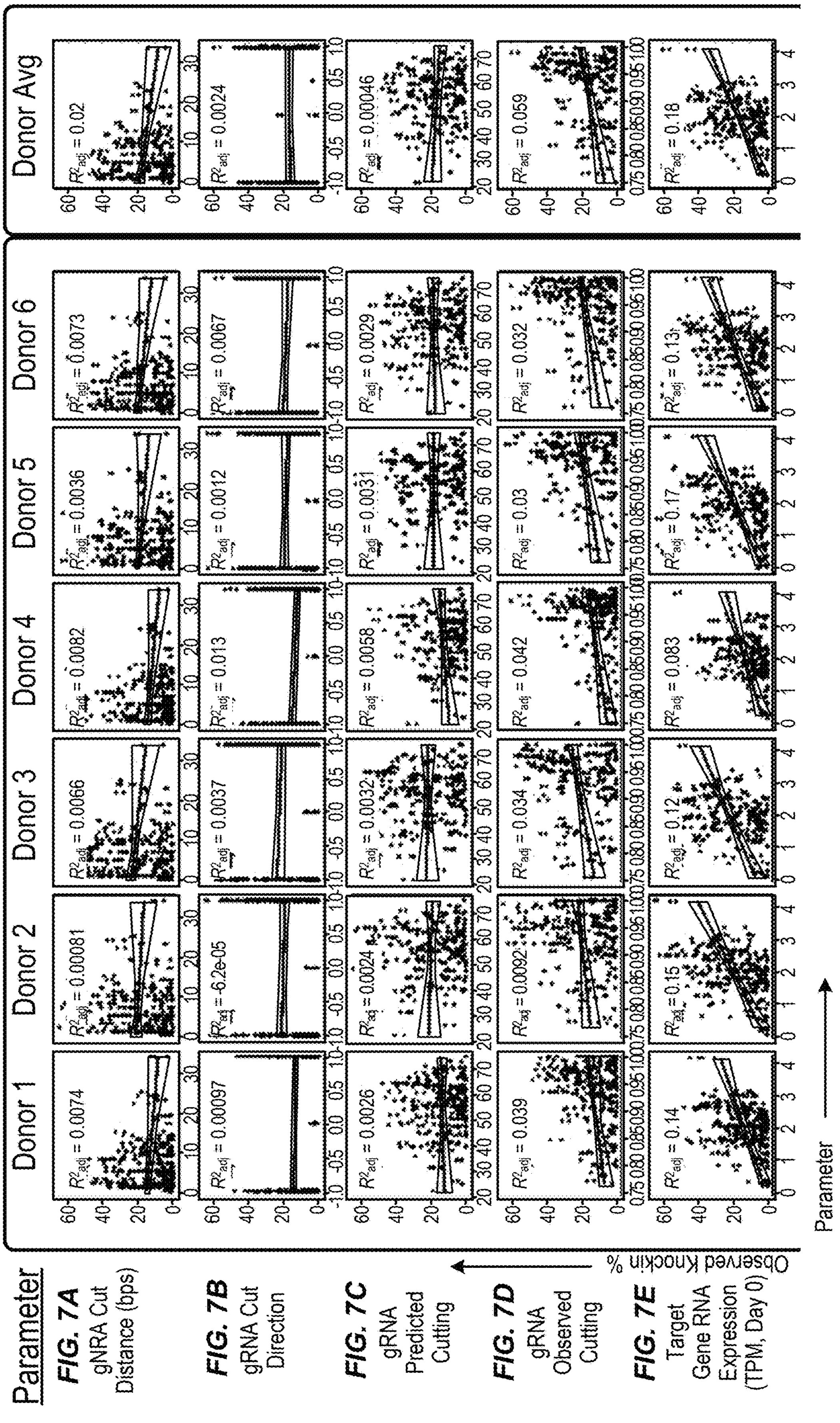
Figure 8A:
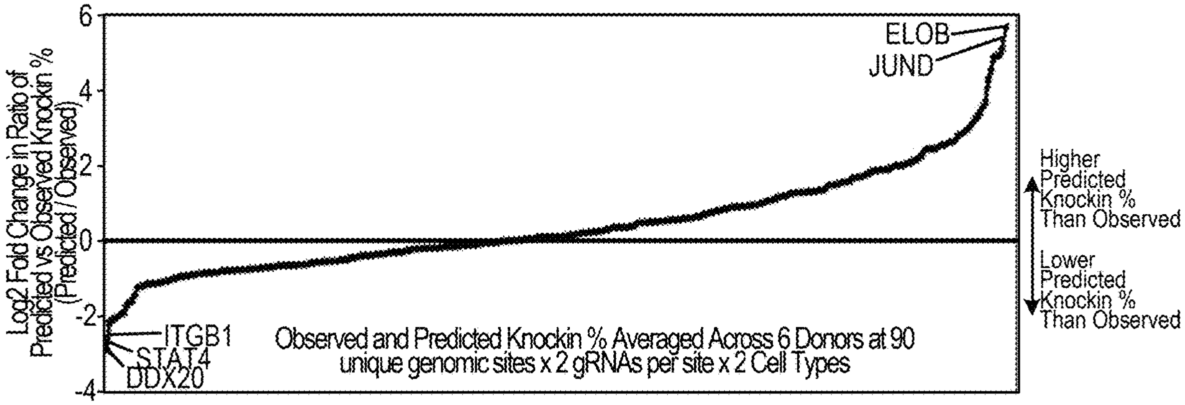
Figure 8B:
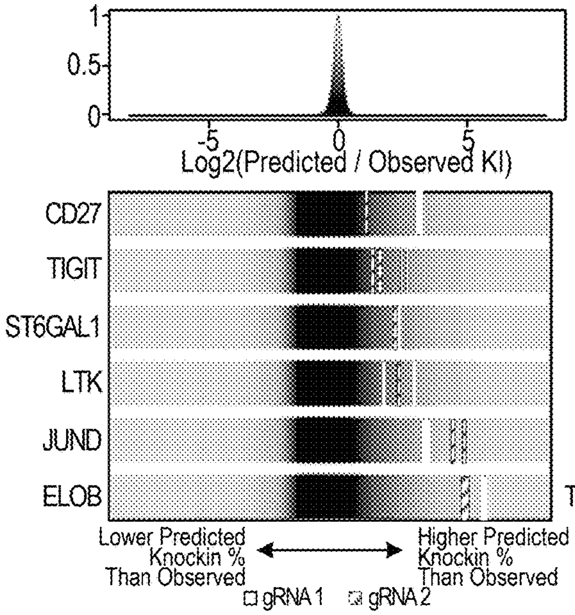
Figure 8C:
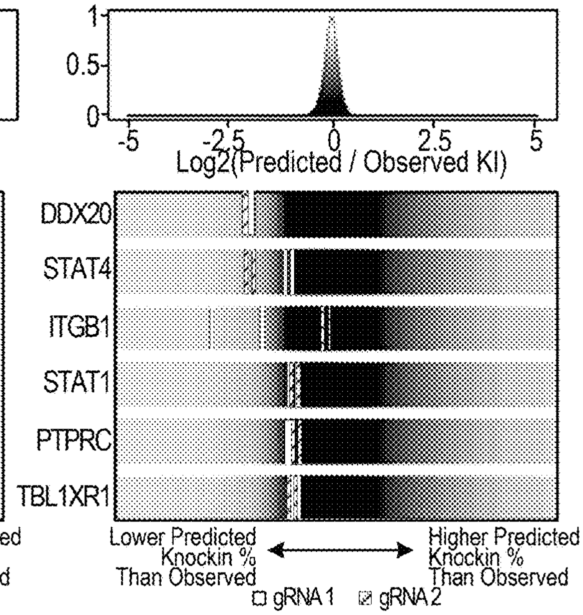
Figure 8D:
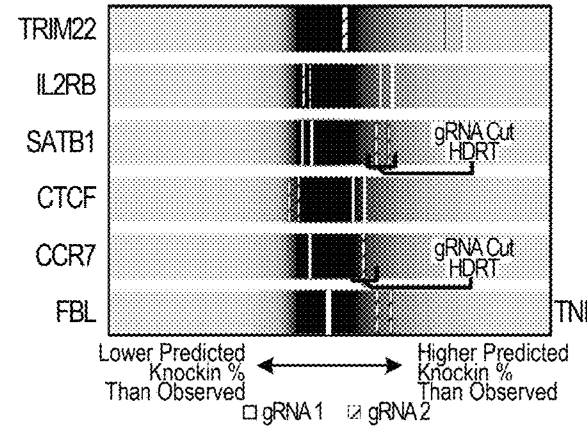
Figure 8E:
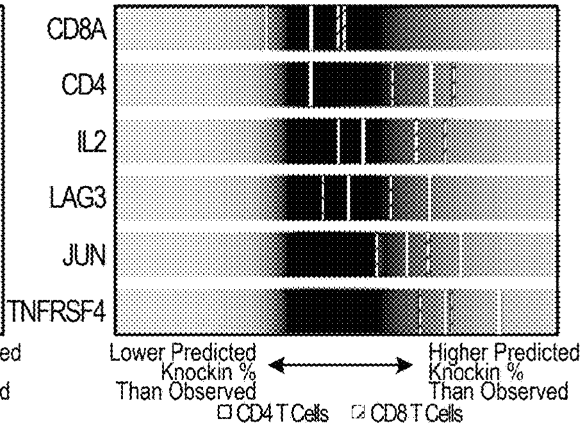
Figure 9A:
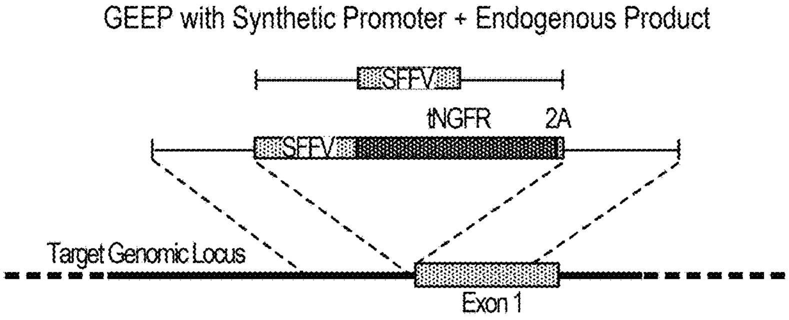
Figure 9B:
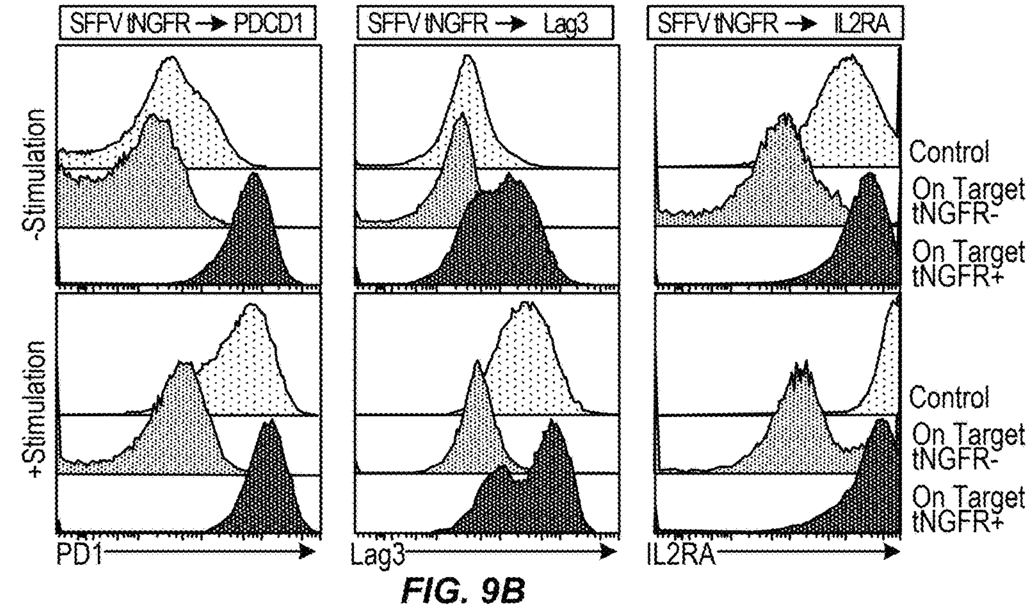
Figure 9C:
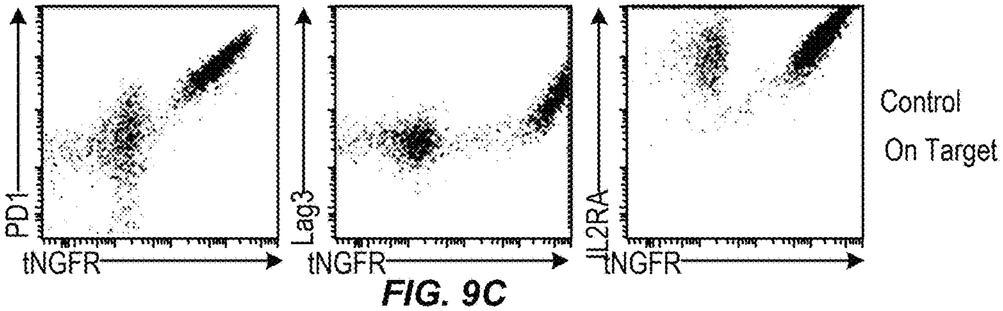
Figure 9D:
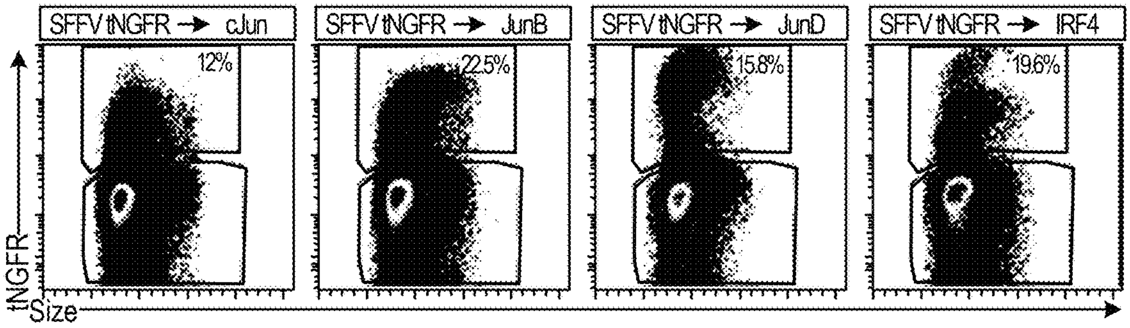
Figure 11A:
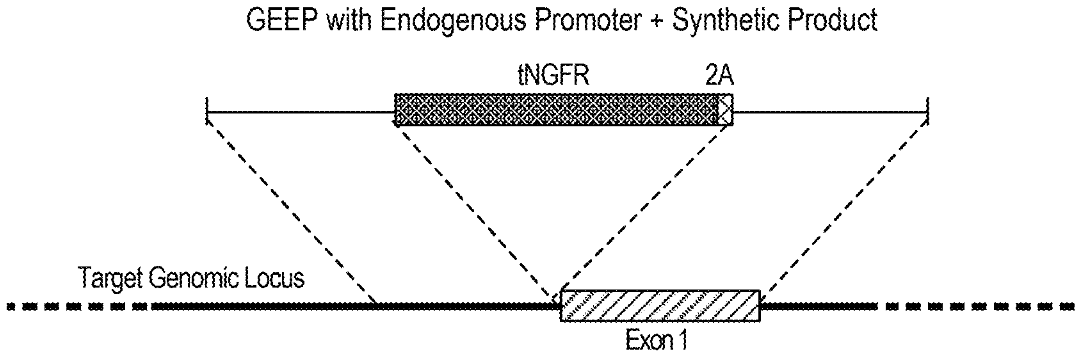
Figures 11B, 11C, 11D:
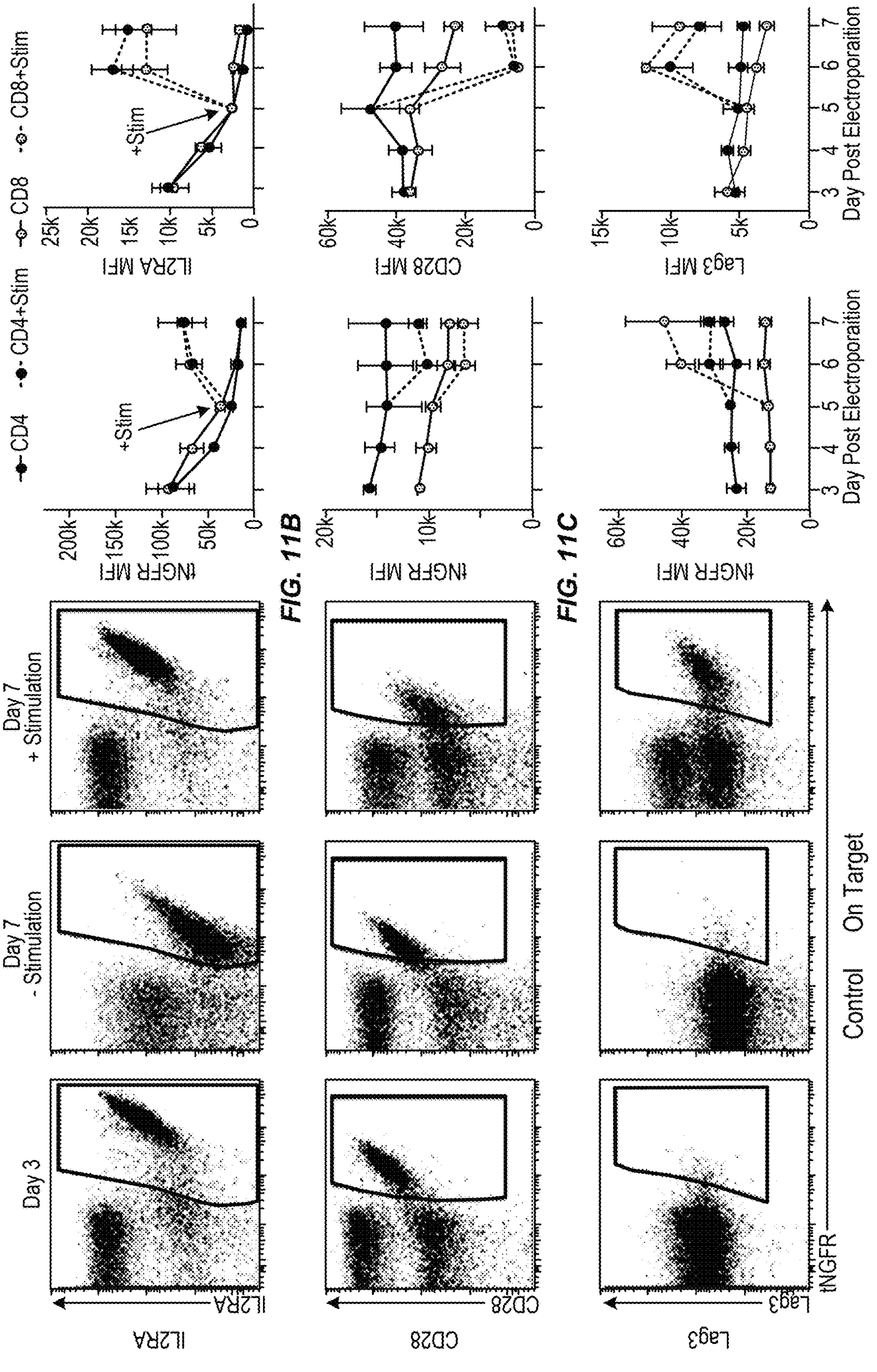

Pooled knockin screening rapidly revealed many new DNA sequences that could enhance T cell function when integrated to the endogenous TCR-α locus along with a new TCR specificity within a single cassette (FIG. 4*e*). Individual validations were performed for three of these sequences—an anti-suppressive TGFβR2-41BB chimera, an anti-apoptotic FAS-41BB chimera, and the transcriptional program altering TCF7. The TGFβR2-41BB chimera improved antigen specific cancer cell killing with and without exogenous TGFβ (FIG. 4*f* and FIG. 21*a-c*). The Fas-41BB chimera showed dramatically increased proliferation after TCR stimulation, and greater antigen specific target cell killing (FIG. 4*g* and FIG. 21*d-f*). Indeed, a recent independent study found similar effects with a dominant negative FAS protein. Finally, knockin of a new TCR specificity along with the transcription factor TCF7 recapitulated the mild increase in proliferation with excessive amounts of stimulation seen in the pooled screens as well as similarly increasing antigen specific target cell killing (FIG. 4*g* and FIG. 21*g-i*).

Figure 25A:
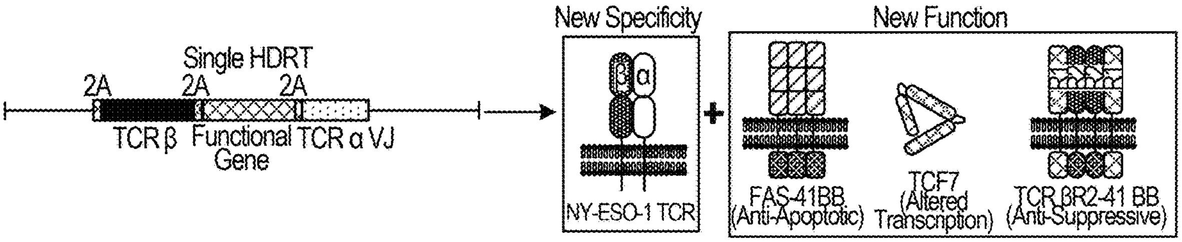
Figure 25B:
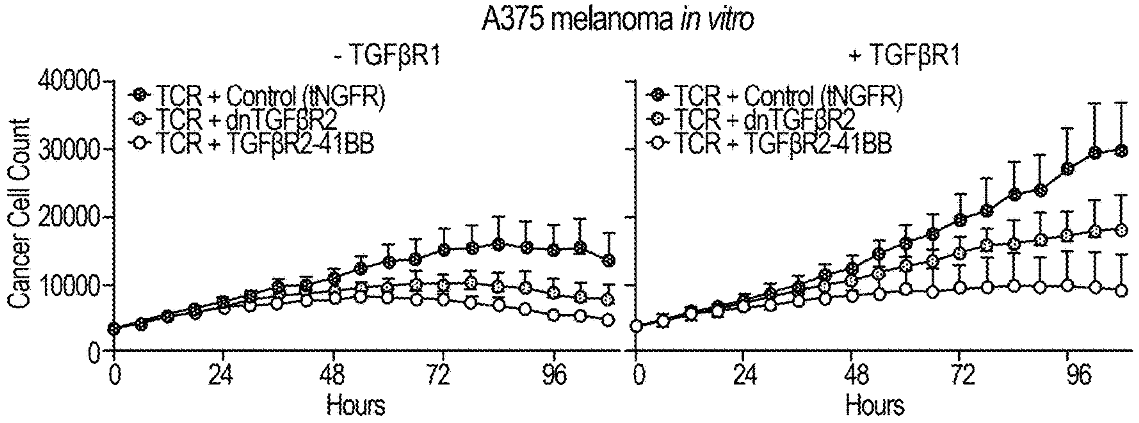
Figure 25C:
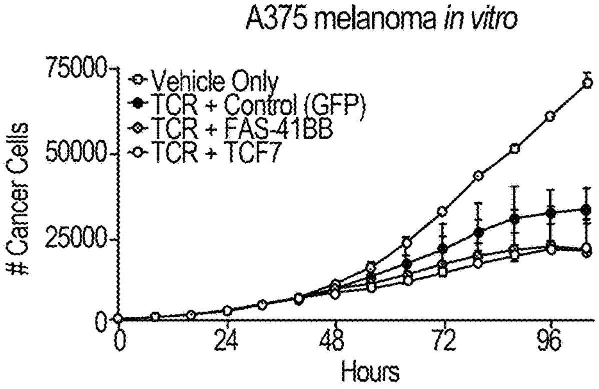

As noted above, to validate the hits from our pooled knock-in screens, we first performed individual validations of the original proliferative phenotypes as well as in vitro cancer killing assays (using A375 melanoma cells) for TCF7, TGFβR2-41BB, and the strong in vitro hit, FAS-41BB (FIG. 25*a*). The anti-apoptotic FAS-41BB chimera (FIG. 26) and the transcriptional program altering TCF7 (FIG. 27) each improved context-dependent expansion as well as in vitro killing of NY-ESO-1+ cancer cells (FIG. 25*b*). An anti-suppressive TGFβR2-41BB chimera similarly showed improved in vitro killing of NY-ESO-1+ cancer cells especially in the presence of exogenous TGFβ(FIG. 25*c*).

Figure 25D:
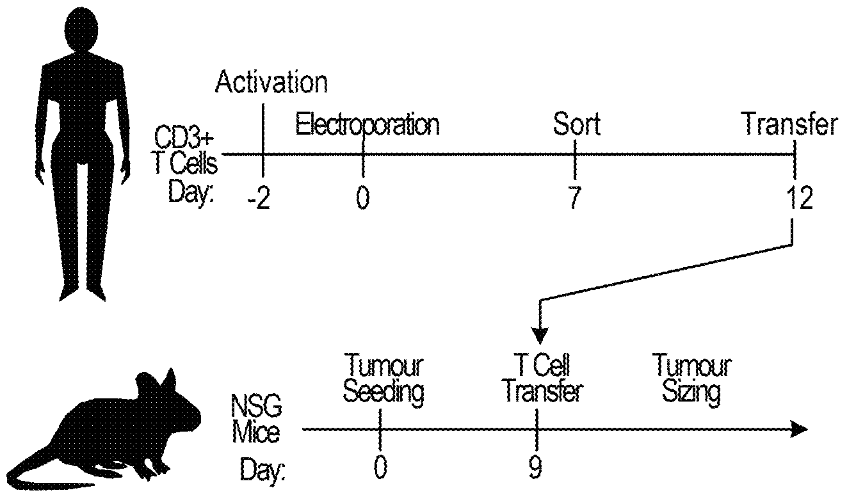
Figure 25E:
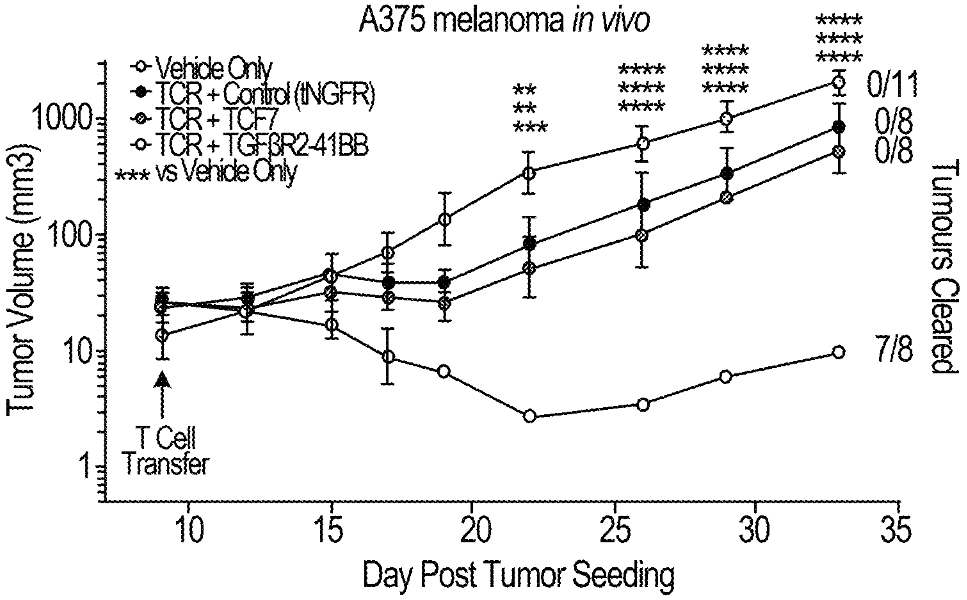
Figure 26A:
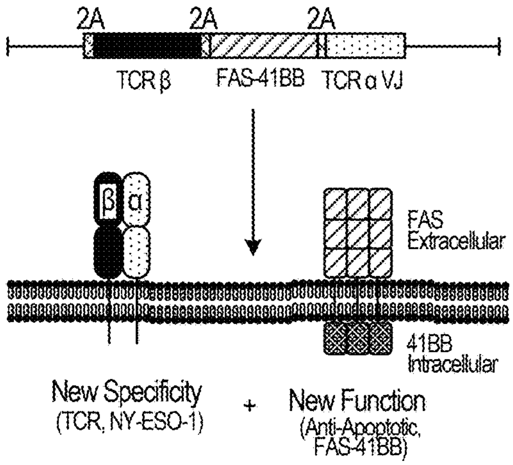
Figure 26B:
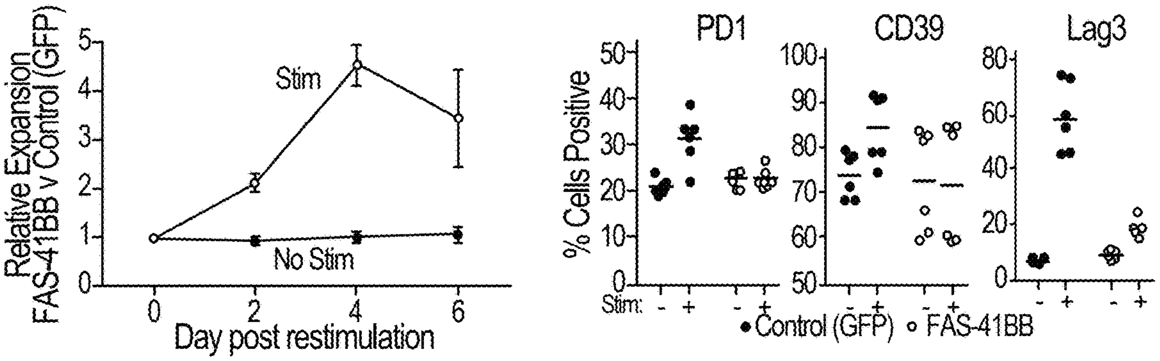
Figure 26C:
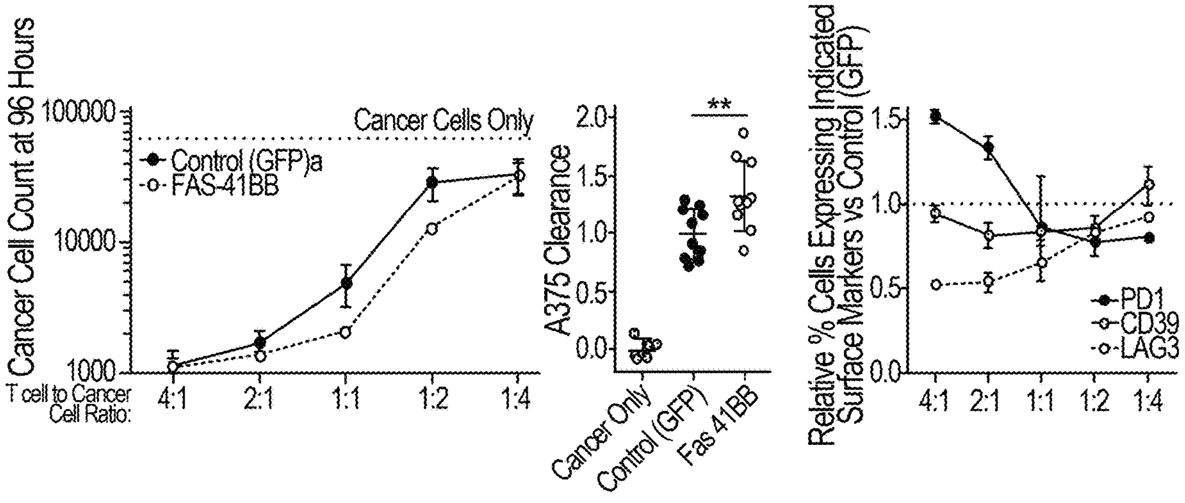
Figure 26E:
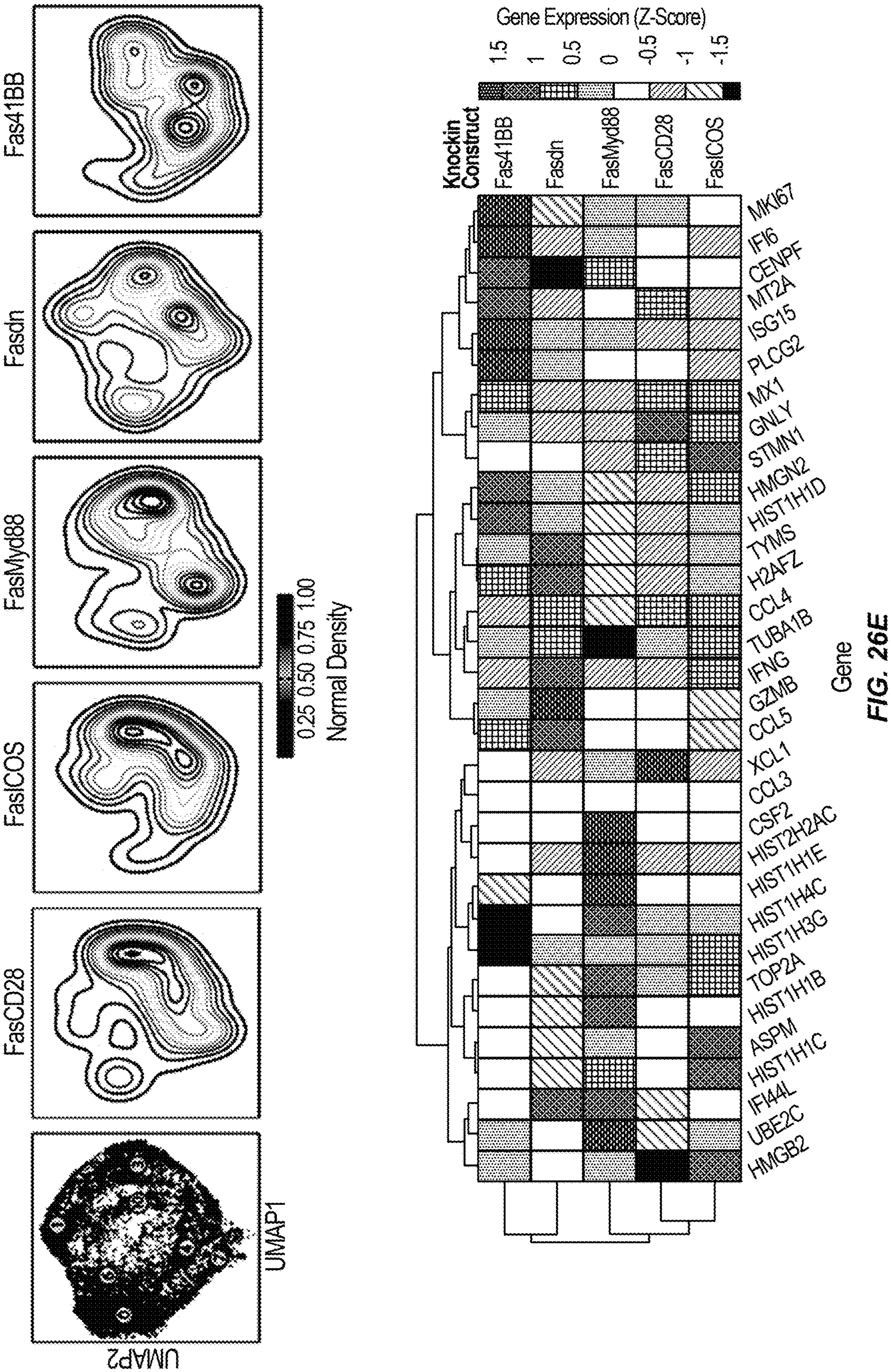
Figure 27A:
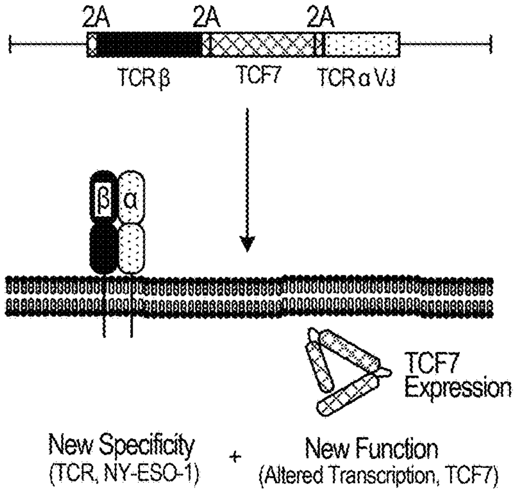
Figure 27B:
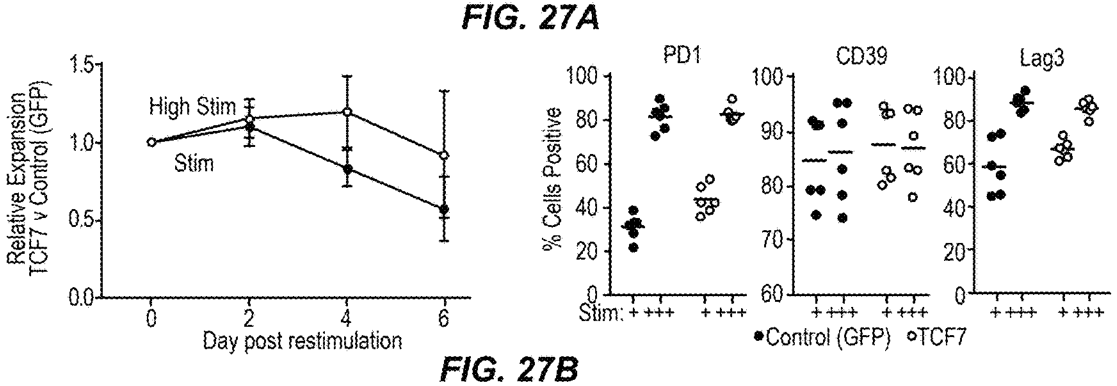
Figure 27C:
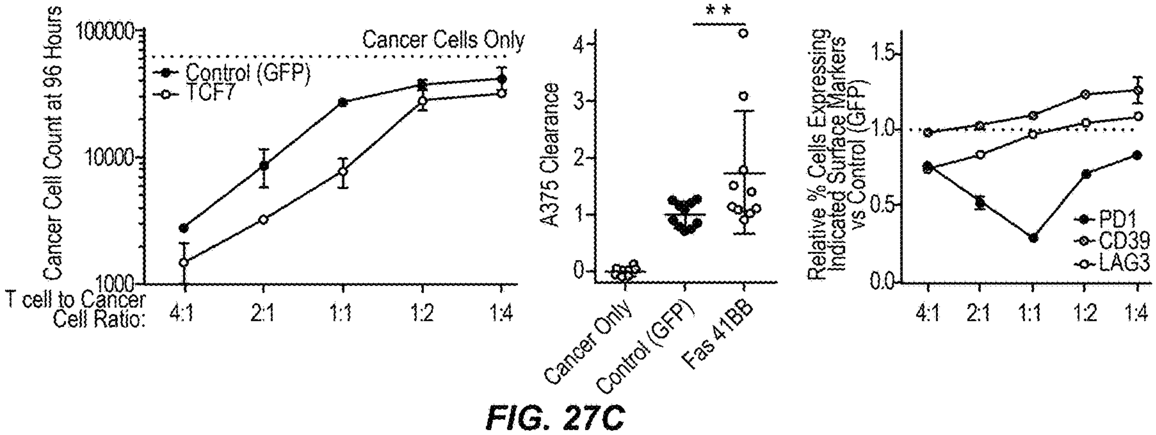
Figure 27D:
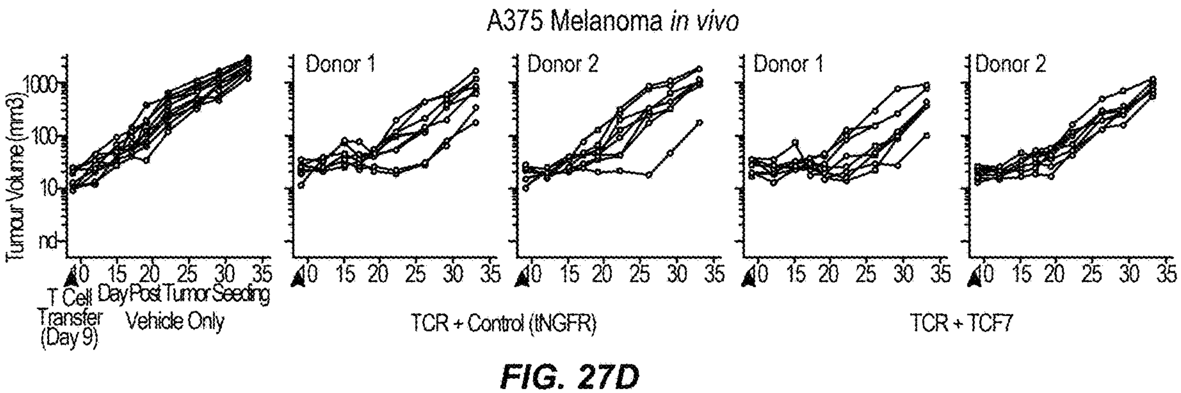
Figure 28A:
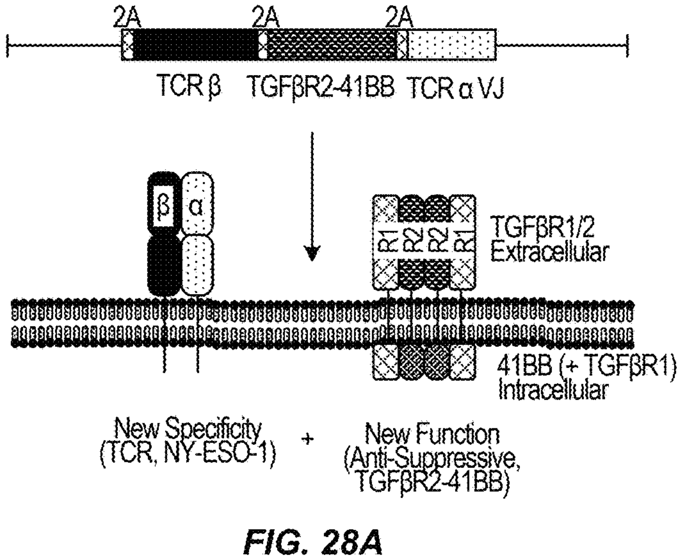
Figure 28B:
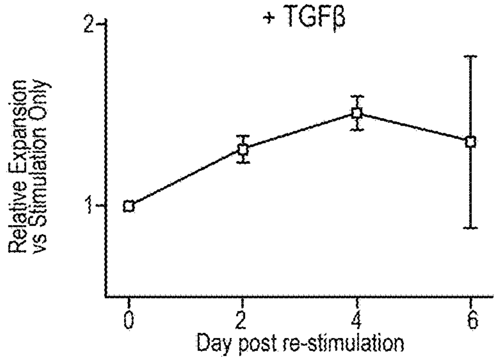
Figure 28C:
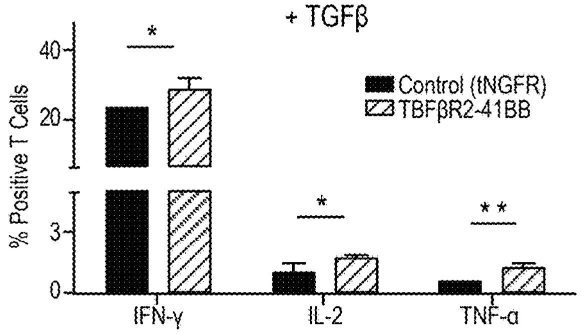
Figure 28D:
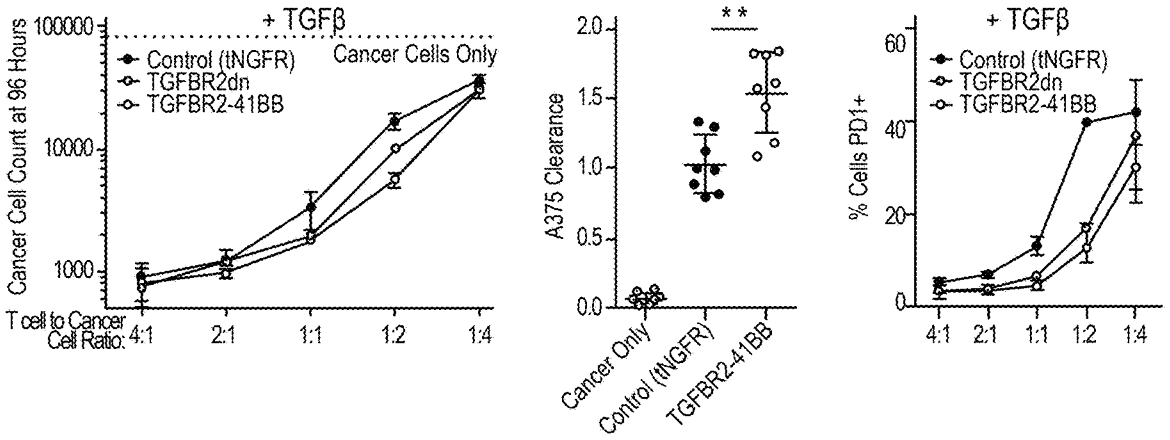
Figure 28E:
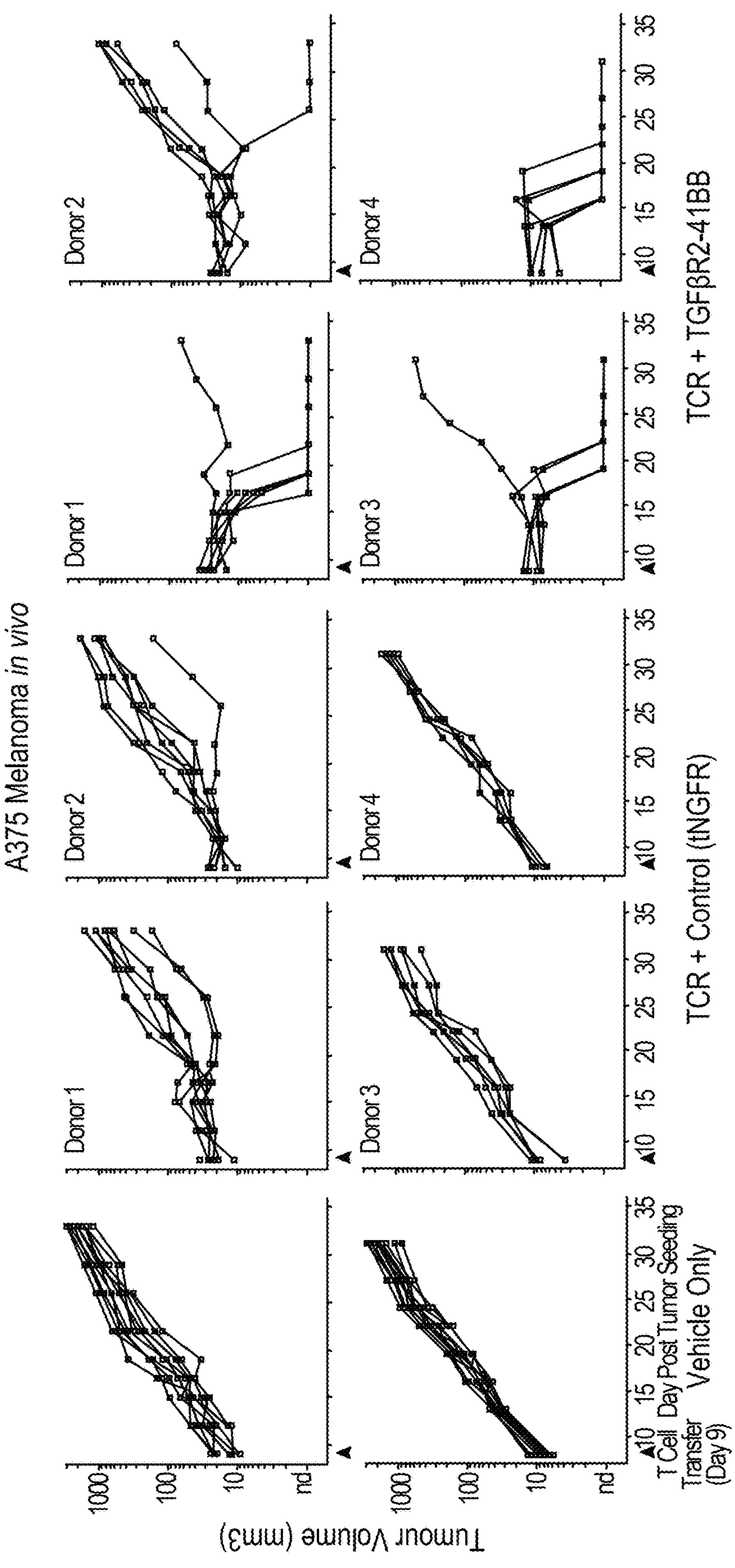

We further examined in vivo the functional capacity of TCF7 or TGFβR2-41BB in a solid tumour xenograft model (FIG. 25*d*). T cells engineered with a polycistronic cassette expressing a NY-ESO-1 specific TCR (1G4 clone) with either a control construct (tNGFR), the transcription factor TCF7, or the chimeric TGFβR2-41BB receptor all showed statistically significant reductions in tumour size relative to vehicle only (FIG. 25*e*). While both TCF7 and TGFβR2-41BB showed increased abundance in the in vivo screens, their transcriptional signatures measured by single cell RNA sequencing showed drastic differences, with TGFβR2-41BB showing much greater expression of effector cytokines such as IFN-γ than TCF7. In agreement with these data, TCF7 did not show increased tumour control relative to tNGFR controls (FIG. 25*e* and FIG. 27), while the TGFβR2-41BB receptor showed dramatic reductions in tumour size and resulted in tumour clearance in many of the mice tested across four human T cell donors (FIG. 25*e* and FIG. 28). Thus, a TGFβR2-41BB chimera improved anti-tumour efficacy in an in vivo solid tumour model.

Overall, the non-viral genome targeting platform described herein is an adaptable discovery platform for the modification of T cell specificity and function. Through a large arrayed knockin screen features of endogenous genetic loci that enable efficient gene targeting, a crucial metric when transitioning from randomly integrating viral gene delivery to targeted non-viral methods, were determined. A framework for the integration of synthetic DNA elements at endogenous loci to create Genetically Engineered Endogenous Proteins (GEEPs) was developed. Further, the integration of multiple gene products to a specific endogenous site, the TCRα locus, allowed for simultaneous manipulation of T cell specificity as well as functionality with a single gene cassette.

CRISPR technology has drastically increased the ability to manipulate the human genome in therapeutically relevant cell types. But high throughput screening methods are used to explore the effectively infinite number of potential manipulations possible for therapeutic relevance. A pooled knockin screening method that allows for generalized knockin of pools of large DNA sequences at a defined genomic target site was developed. Application of pooled knockin screening in vitro and in vivo revealed novel gene chimeras that enhanced T cell function in the challenging tumour environment when introduced along with a new TCR specificity. Cell therapy promises that cells themselves can be a new pillar of therapeutic medicine alongside small molecules and biologics. Pooled knockin screening will enable the same drug discovery process based on high-throughput screening that produced the vast majority of small molecule and biologic therapeutics to be applied to cell based therapies. Pooled knockin screening using non-viral genome targeting is an ideal platform for modifying T cell specificity and function for the next generation of cell therapies.

Methods

Isolation of Human Primary T Cells for Gene Targeting

Primary human T cells were isolated from either fresh whole blood or residuals from leukoreduction chambers after Trima Apheresis (Blood Centers of the Pacific) from healthy donors. Peripheral blood mononuclear cells (PBMCs) were isolated from whole blood samples by Ficoll centrifugation using SepMate tubes (STEMCELL (Vancouver, CA), per manufacturer's instructions). T cells were isolated from PBMCs from all cell sources by magnetic negative selection using an EasySep Human T Cell Isolation Kit (STEMCELL, per manufacturer's instructions). Isolated T cells were either used immediately following isolation for electroporation experiments or frozen down in Bambanker freezing medium (Bulldog Bio) per manufacturer's instructions for later use. Freshly isolated T cells were stimulated as described below. Previously frozen T cells were thawed, cultured in media without stimulation for 1 day, and then stimulated and handled as described for freshly isolated samples. Fresh blood was taken from healthy human donors under a protocol approved by the UCSF Committee on Human Research (CHR #13-11950).

Primary Human T Cell Culture

XVivo15 medium (STEMCELL) supplemented with 5% fetal bovine serum, 50 μM 2-mercaptoethanol, and 10 μM N-acetyl L-cystine was used to culture primary human T cells. In preparation for electroporation, T cells were stimulated for 2 days at a starting density of approximately 1 million cells per mL of media with anti-human CD3/CD28 magnetic Dynabeads (ThermoFisher), at a bead to cell ratio of 1:1, and cultured in XVivo15 media containing IL-2 (500 U ml-1; UCSF Pharmacy), IL-7 (5 ng $ml^{-1}$; ThermoFisher (Waltham, MA)), and IL-15 (5 ng ml-1; Life Tech). Following electroporation, T cells were cultured in XVivo15 media containing IL-2 (500 U $ml^{-1}$) and maintained at approximately 1 million cells per mL of media. Every 2-3 days, electroporated T cells were topped up, with or without splitting, with additional media along with additional fresh IL-2 (final concentration of 500 U $ml^{-1}$). When necessary, T cells were transferred to larger culture vessels.

RNP Production

RNPs were produced by complexing a two-component gRNA to Cas9. The two-component gRNA consisted of a crRNA and a tracrRNA, both chemically synthesized (Dharmacon (Lafayette, COO, IDT (Coralville, IA)) and lyophilized. Upon arrival, lyophilized RNA was resuspended in 10 mM Tris-HCL (7.4 pH) with 150 mM KCl at a concentration of 160 μM and stored in aliquots at −80° C. Cas9-NLS (QB3 Macrolab) was recombinantly produced, purified, and stored at 40 μM in 20 mM HEPES-KOH, pH 7.5, 150 mM KCl, 10% glycerol, 1 mM DTT. To produce RNPs, the crRNA and tracrRNA aliquots were thawed, mixed 1:1 by volume, and annealed by incubation at 37° C. for 30 min to form an 80 μM gRNA solution. Next, the gRNA solution was mixed 1:1 by volume with Cas9-NLS (2:1 gRNA to Cas9 molar ratio) and incubated at 37° C. for 15 min to form a 20 μM RNP solution. RNPs were electroporated immediately after complexing.

Double-Stranded HDR DNA Template Production

Each double-stranded homology directed repair DNA template (HDRT) contained a novel/synthetic DNA insert flanked by homology arms. We used Gibson Assemblies to construct plasmids containing the HDRT and then used these plasmids as templates for high-output PCR amplification (Kapa Hot Start polymerase (Kapa Biosystems, Basel, Switzerland). The resulting PCR amplicons/HDRTs were SPRI purified (1.0×) and eluted into H2O. The concentrations of eluted HDRTs were determined, using a 1:20 dilution, by NanoDrop and then normalized to 1 μg/μL. The size of the amplified HDRT was confirmed by gel electrophoresis in a 1.0% agarose gel.

Primary T Cell Electroporation

For all electroporation experiments, primary T cells were prepared and cultured as described above. After stimulation for 48-56 hours, T cells were collected from their culture vessels and the anti-CD3/anti-CD28 Dynabeads were magnetically separated from the T cells. Immediately before electroporation, de-beaded cells were centrifuged for 10 min at 90 g, aspirated, and resuspended in the Lonza electroporation buffer P3. Each experimental condition received a range of 750,000-1 million activated T cells resuspended in 20 μL of P3 buffer, and all electroporation experiments were carried out in 96 well format.

For arrayed knockin screens (FIG. 1), HDRTs were first aliquoted into wells of a 96-well polypropylene V-bottom plate. Poly Glutamic Acid was added between the gRNA and Cas9 complexing step during RNP assembly as described. Complexed RNPs were then added to the HDRTs and allowed to incubate together at room temperature for at least 30 s. For GEEPs knockins and pooled knockin screens (FIG. 2-4), truncated Cas9 Target Sequences (tCTS) were additionally added to the 5' and 3' ends of the HDR template enabling a Cas9 'shuttle'. For all variations, T cells resuspended in the electroporation buffer were added to the RNP and HDRT mixture, briefly mixed, and then transferred into a 96-well electroporation cuvette plate All electroporations were done using a Lonza 4D 96-well electroporation system with pulse code EH 115. Unless otherwise indicated, 3.5 μl RNPs (comprising 50 pmol of total RNP) were electroporated, along with 1-3 μl HDR Template at 1 μg μl-1 (1-3 μg HDR template total). Immediately after all electroporations, 80 μl of pre-warmed media (without cytokines) was added to each well, and cells were allowed to rest for 15 min at 37° C. in a cell culture incubator while remaining in the electroporation cuvettes. After 15 min, cells were moved to final culture vessels.

Arrayed Knockin Screening

For each of 6 unique healthy donors, 5×96 well plates of primary human T cells were electroporated. In three plates, HDR templates targeting each of 91 unique genomic loci were electroporated along with one of two on-target gRNAs or a scrambled gRNA. The final two plates were electroporated just with the on-target gRNA (complexed with Cas9 to form an RNP) but without an HDR template for amplicon sequencing. On-target and scrambled RNP plates with the HDR template were analyzed in technical duplicate for observed knockin efficiency by flow cytometry four days following electroporation, and additionally after 24 hours of restimulation with a 1:1 CD3/CD28 dynabeads:cells ratio at five days post electroporation. Genomic DNA was isolated four days following electroporation from the on-target gRNA only plates four days after electroporation.

After initial isolation (Day 0), immediately prior to electroporation (Day 2), and during post-electroporation expansion (Day 4), ~1e6 CD4 and CD8 T cells from each donor were sorted by FACS for RNA-Seq and ATAC-Seq analysis (FIG. 1*b*). Half of the sorted cells were frozen in Bambanker freezing medium (Bulldog Bio) for ATAC Sequencing, and half were frozen in RNAlater (QIAGEN) for bulk RNA sequencing.

To construct a prediction model for knockin rates, we took a multiple linear regression approach. Briefly, this model fits the observed measured parameters with the observed knockin rate and is described as:

$$Y_i = \beta_0 + \beta_1 X_{1i} + \beta_2 X_{2i} + \ldots + \beta_k X_{ki} + \in_i$$

Where for the gRNA site, Yi is the observed knockin rate, β0 is a common intercept and €i is the error in estimates. β1 to βk are regression weights (or coefficients) which measure the estimate of association between the measure parameter (Xki) and the knockin rate. To build the model, we averaged the measured values for across donors for each gRNA and cell type. For gene expression and chromatin accessibility, values were log transformed. The parameters used to generate the model are described in FIG. 1*f*. The resulting model was used to predict the observed knockin rate for all sites, across individual donors and cell types. The absolute values of all regression weights were summed and the percent of the total was determined for each parameter's regression weight.

Amplicon Sequencing

Genomic DNA was isolated from primary human T cells individually edited with each gRNA used in the arrayed knockin screen in the absence of its cognate HDR template. After aspirating the supernatant, ~100,000 cells per condition were resuspended in 20 µl of Quickextract DNA Extraction Solution (Epicenter) to a concentration of 5,000 cells per µl. Genomic DNA in Quickextract was heated to 65° C. for 6 min and then 98° C. for 2 min, according to the manufacturer's protocol. 1 µl of the mixture, containing genomic DNA from 5,000 cells, was used as template in a two-step PCR amplicon sequencing approach using NEB Q5 2× Master Mix Hot Start Polymerase with the manufacturer's recommended thermocycler conditions. After an initial 18 cycle PCR reaction with primers amplifying an approximately 200 bp region centered on the predicted gRNA cut site, a 1.0×SPRI purification was performed and half of the samples for each biologic donor were pooled for indexing (each donor had two gRNAs that cut at each insertion site-samples for one gRNA per site were pooled, yielding two unique pools per donor). A 10-cycle PCR to append P5 and P7 Illumina® sequencing adaptors and donor-specific barcodes was performed, followed again by a 1.0×SPRI purification. Concentrations were normalized across donor/gRNA indexes, samples pooled, and the library sequenced on an NovaSeq ® Mini-Seq with a 2×150 bp reads run mode Amplicons were processed with CRISPResso, using the CRISPRessoPooled command in genome mode with default parameters. We used the hg19 human reference genome assembly. Resulting amplicon regions were matched with gRNA sites for each sample. Reads with potential sequencing errors detected as single mutated bases with no indels by CRISPResso alignment were eliminated. The remaining reads were used to calculated the NHEJ percentage, or "observed cutting percentage".

Bulk RNA Sequencing

Total RNA from frozen samples was extracted using an RNeasy Mini Kit (Qiagen) according to the manufacturer's protocol. RNA quantification was performed using Qubit® and Nanodrop 2000 and quality of the RNA was determined by the Bioanalyzer RNA 6000 Nano Kit (Agilent Technologies) for 10 random samples. We confirmed that the sample had an average RNA integrity number (RIN) that was >9 and the traces revealed characteristic size distribution of intact, non-degraded total RNA. The RNA libraries were constructed with Illumina® TruSeq RNA Sample Prep Kit v2 (cat. no. RS-122-2001) according to the manufacturer's protocol. Total RNA (500 ng) from each sample was used to establish cDNA libraries. A random set of 10 out of 36 final libraries were quality checked on the High Sensitivity DNA kit (Agilent) that revealed an average fragment size of 400 bp. A total of 36 enriched libraries (3 pools of 12 uniquely indexed libraries) were constructed and sequenced using the Illumina® HiSeq™ 4000 on three separate lanes at 100 bp paired end reads per sample.

RNA-Seq reads were processed with kallisto using the *Homo sapiens* ENSEMBL GRCh37 (hg19) cDNA reference genome annotation. Transcript counts were aggregated at the gene level. Genes of interest were subsetted from the normalized gene-level counts table and analyzed as transcripts per million (TPM).

ATAC-Sequencing

ATAC-seq library were prepared following the Omni-ATAC protocol [REF—Methods 1]. Briefly, frozen cells were thawed and stained for live cells using Ghost-Dye 710 (Tonbo Biosciences, CA, USA). 50,000 lived cells were FACS sorted and washed once with cold PBS. Technical replicates were done for most of the samples. Cell pellets were resuspended in 50 µl cold ATAC-Resuspension buffer (10 mM Tris-HCl (Sigmal Aldrich, MO, USA) pH 7.4, 10 mM NaCl, 3 mM MgCl2 (Sigma Aldrich) containing 0.1% NP40 (Life Technologies, Carlsbad, CA), 0.1% Tween-20 (Sigma Aldrich) and 0.01% Digitonin (Promega, WI, USA) for 3 mins. Samples were washed once in cold resuspension buffer with 0.1% Tween 20, and centrifuged for 4 C for 10 min. Extracted nuclei were resuspended in 50 µl of Tn5 reaction buffer (1×TD buffer (Illumina®, CA, USA), 100 nM Tn5 Transposase (Ilumina), 0.01% Digitonin, 0.1% Tween-20, PBS and H20), and incubated at 37 C for 30 min at 300 rpm. Transposed samples were purified using MinElute PCR purification columns (Qiagen, Germany) as per manufacturer's protocol. Purified samples were amplified and indexed using custom Nextera barcoded PCR primers as described in [REF—Methods 2]. DNA libraries were purified using MinElute columns and pooled at equal molarity. To remove primer dimers, pooled libraries were further cleaned up using AmPure beads (Beckman Coulter, CA, USA). ATAC libraries were sequenced on a NovaSeq® in paired-end X cycle mode.

ATAC-seq reads trimmed using cutadapt v1.18 to remove Nextera transposase sequences, then aligned to hg19 using Bowtie2 v2.3.4.3. Low-quality reads were removed using samtools v1.9 view function (samtools view-F 1804-f 2-q 30-h-b). Duplicates were removed using picard v2.18.26, then reads were converted to BED format using bedtools bamtobed function and normalized to reads per million. ATAC-seq reads mapping within a 1 kb window surrounding CRISPR cut sites were counted using the bedtools intersect function.

Flow Cytometry and Cell Sorting

All flow cytometric analyses were performed on an Attune NxT Acoustic Focusing Cytometer (ThermoFisher). FACS was performed on the FACSAria platform (BD). Cell surface staining for flow cytometry and cell sorting was performed by pelleting and resuspending in 25 uL of FACS buffer (2% FBS in PBS) with antibodies diluted accordingly for 20 min at RT in the dark. Cells were washed once in FACS buffer before resuspension and analysis.

Synthetic Product+Endogenous Product Kinetics Flow Cytometry Analysis

Non-virally edited T-cells were split into multiple replicates and analyzed by flow cytometry every day for a 5-day period starting on Day 3 after electroporation. During that 5-day period, T-cells were topped up every 2 days with additional media and IL-2, to a final concentration of 500 U/mL, with or without a 1:1 split. At Day 5 post electroporation, one set of cells was stimulated with CD3/CD28 Dynabeads and the other was left unstimulated.

In Vitro Proliferation Assay

Non-virally edited T-cells were expanded in independent cultures prior to the assay. The unsorted, edited populations were pooled after approximately two weeks of expansion (with 500 U/mL of IL-2 supplemented every 2-3 days) for a competitive mixed proliferation assay.

For the CD3 competitive mixed proliferation assay, we pooled unsorted samples with CD28IC-2A-GFP, 41BBIC-2A-mCherry, or 2A-BFP knocked-in to the same CD3 complex member's gene locus. To determine the input numbers for pooling, we took into account the number of viable GFP+, mCherry+, or BFP+ in the respective populations (knock-in %*total viable cell count), as determined by flow cytometry analysis. The pooled sample was then distributed into round bottom 96 well plates at a starting total cell count of 50,000. The distributed samples were then cultured without stimulation, with CD3 stimulation only, with CD28 stimulation only, or with CD3/CD28 stimulation. CD3 and/or CD28 stimulation was done with plate bound antibodies. All samples were cultured in XVivo15 media supplemented with IL-2 (50 U/mL). After 4 days in culture, samples were analyzed by flow cytometry for relative outgrowth of GFP+ and mCherry+ subpopulations relative to the BFP+ subpopulation.

For the NY-ESO-1 competitive mixed proliferation assay, we pooled unsorted samples with either 1G4+ dnTGFβR2+ or 1G4+ tNGFR+ T cells. To determine the input number of each population, the number of viable 1G4+ TCR+ in either populations (knock-in %*total viable cell count), as determined by flow cytometry analysis, were taken into account. The pooled sample was then distributed into round bottom % well plates at a total starting cell count of 50,000. The distributed samples were then cultured without stimulation or with Immunocult (CD3/CD28/CD2). All samples were cultured XVivo15 media supplemented with IL-2 (500 U/mL) with or without the addition of TGFβ1. After 5 days in culture, samples were analyzed on flow cytometry and the relative outgrowth 1G4+ dnTGFβR2+ and 1G4+tNGFR+ subpopulations was quantified.

In Vitro Antigen Specific Killing Assay

A375-nRFP (NY-ESO-1+HLA-A*0201+) melanoma cell lines stably transduced to express nuclear RFP (Zaretsky 2016 NEJM) were seeded approximately 24 h before starting the co-culture (~1,500 cells seeded per well). Modified T cells were added at the indicated E:T ratios. The killing assay was performed in cRPMI with IL-2 and glucose. Samples were additionally topped up with TGFβ1 or an equal volume of control media. Cancer cell clearance was measured by nRFP real time imaging using an IncuCyte ZOOM (Essen, Ann Arbor, MI) for 4-5 days and determined by the following equation: (% Confluence in A375 only wells−% Confluence in Co-culture well)/(% Confluence in A375 only wells). At the end of the assay, cells were recovered, and the percentage of T-cells expressing various exhaustion markers was profiled by flow cytometry.

Pooled Knockin Screening

Targeted pooled knockin screening was performed using the non-viral genome targeting method as described, except with ~10 bps of DNA mismatches introduced into the 3' homology arm of the TRAC exon 1 targeting HDR template used to replace the endogenous TCR. A barcode unique for each member of the knockin library was also introduced into—6 degenerate bases at the 3' end of the TCRαVJ region of the HDR template (FIG. 4*a*). The 36 constructs included in the pooled knockin library were designed using the Benchling DNA sequence editor, commercially synthesized as a dsDNA geneblock (IDT), and individually cloned using Gibson Assemblies into a pUC19 plasmid containing the NY-ESO-1 TCR replacement HDR sequence (except for pooled assembly conditions, whereas all geneblocks in the library were pooled prior to assembly). The design for the 36 polypeptides included in the constructs is shown in Table 2. The sizes (protein sizes) of the extracellular domain, the transmembrane domain and the intracellular domain of each construct are described in columns six, seven and eight (under protein size [aa]), respectively, of Table 2. The library was pooled at various stages as described in figure legends (FIG. 16), but unless otherwise noted HDR templates were pooled prior to electroporation.

TABLE 2

| Group | Plasmid name | Gene X design domain | domain | Detailed deisgn | protein size [aa] extracellular domain | domain | domain |
|---|---|---|---|---|---|---|---|
| Checkpoint Inhibition | pTR-402 | PD1 | truncated | PD-1 missing IC domain with 10 aa IC overhang | 21-170 | 171-191 | 192-201 |
| | pTR-404 | PD1 | 41BB | Partial EC PD-1 domain + 4-188 TM & IC domains with 12 aa EC overhang | 21-155 (PD-1) + | 168-194 (4-188) | 195-236 (4-1BB) |
| | pTR-405 | PD1 | MyD88 | PD1 EC & TM + 7aa IC overhang + My D88 death and intermediate domains | 156-187 (4-188 21-170 (PD1) | 171-191 (PD1) | 192-198 (PD1 overhang) + 199-300 (My D88) |
| | pTR-406 | PD1 | ICOS | Partial EC PD-1 domain + ICOS TM & IC domains with 12 aa EC overhang | 36-161 | 168-188 (ICOS) | 189-226 (ICOS) |
| | pTR-407 | CTLA4 | truncated | CTLA-4 missing IC domain with 7 aa IC overhang | | 162-182 | 183-189 |
| | pTR-408 | CTLA4 | CD28 | full CTLA4 EC & TM domains with 7 aa IC overhang + full IC CD28 domain | 36-161 (CTLA4) | 162-182 (CTLA4) | 183-189 (CTLA4) + 190-231 (CD28) |

TABLE 2-continued

| | | Gene X | | | protein size [aa] | | |
|---|---|---|---|---|---|---|---|
| Group | Plasmid name | design domain | domain | Detailed deisgn | extracellular domain | domain | domain |
| | pTR-409 | CD200R | truncated | CD200R missing IC domain with 7aa IC overhang | 29-243 | 244-264 | 265-271 |
| | pTR-412 | BTLA | truncated | BTLA missing IC domain with 7 aa IC overhang | 31-157 | 158-178 | 179-185 |
| | pTR-413 | BTLA | CD28 | BILA truncated by the TM-proximal 9 aa + CD28 TM & IC domains with 12aa EC overhang until TM-proximal cysteine | 31-148 (BTLA) + 149-160 (CD28) | 161-187 (CD28) | 188-228 (CD28) |
| | pTR-414 | TIM3 | truncated | TIM3 missing IC domain with 7aa IC overhang | 22-202 | 203-223 | 224-230 |
| | pTR-415 | TIM3 | CD28 | TIM3 truncated by the TM-proximal 9 aa + CD28 TM & IC domains with 12aa EC overhang until TM-proximal cysteine | 22-193 (TIM3) + 194-205 (CD28) | 208-232 (CD28) | 233-273 (CD28) |
| | PTR-416 | TIGIT | truncated | TIGIT missing IC domain with 7aa IC overhang | 22-141 | 142-162 | 163-169 |
| | pTR-417 | TIGIT | CD28 | TIGIT truncated by the TM-proximal 9 aa + CD28 TM & IC domains with 12aa EC cverhang until TM-proximal cysteine | 22-132 (TIGIT) + 133-144 (CD28) | 145-171 (CD28) | 172-212 (CD28) |
| Suppressive Cytokines | pTR-418 | TGFbR2 | truncated | | | | |
| | pTR-420 | TGFbR2 | 41BB | Partial EC TGFbR2 domain + 4-1BB TM & IC domains with 12 aa EC overhang | 23-166 (TGFbR2) + 167-178 (4-188) | 179-205 (4-188) | 206-247 (4-1BB) |
| | pTR-421 | TGFbRZ | Myd88 | TGFbR2 EC & TM + 7aa IC overhang + My DB8 death and intermediate domains | 23-166 (TGFbR2) | 167-187 (TGFUR2) | 188-194 (TGFbR2) + 195-296 (MyD88) |
| | pTR-423 | IL-10RA | truncated | IL-10RA missing IC domain with 7aa IC overhang | 22-235 | 236-256 | 257-263 |
| | pTR-424 | IL-10RA | IL-7RA | IL-10RA EC with 1aa TM overhang + IL-7RA TM & IC | 22-235 (IL-10RA) | 236 (IL-10RA) + 237-261 (IL-7RA) | 262-456 (IL-7RA) |
| | pTR-426 | IL-4RA | IL-7RA | IL-4RA EC with 1aa TM overhang + IL-7RA TM & IC | 26-232 (IL-4RA) | 233 (IL-4RA) + 234-258 (IL-7RA) | 259-453 (IL-7RA) |
| Proliferation/ | pTR-427 | IL-2RA | | full protein | 22-240 | 241-259 | 260-272 |
| Stimulatory | pTR-428 | IL-7RA | | full protein | 21-239 | 240-264 | 265-459 |
| cytokines | pTR-430 | 4188 | | full protein | 24-186 | 187-213 | 214-255 |
| Apoptosis | PTR-431 | Fas | truncated | Fas missing IC domain with 7aa IC overhang | 26-173 | 174-190 | 191-197 |
| | pTR-432 | Fas | CD28 | Fas EC & TM domain with 7aa IC overhang + full CD28 IC domain | 26-173 | 174-190 | 191-197 (Fas) + 198-238 (CD28) |
| | pTR-433 | Fas | 41BB | Fas EC & TM domain with 7aa IC overhang + full 4-1BB IC domain | 26-173 | 174-190 | 191-197 (Fas) + 198-239 (4-1BB) |
| | pTR-434 | Fas | Myd88 | Fas EC & TM domain with 7aa IC overhang + MyD88 death and intermediate domains | 26-173 | 174-190 | 191-197 (Fas) + 198-299 (My D88) |
| | pTR-435 | Fas | ICOS | Fas EC & TM domain with 7aa IC overhang + full ICOS IC domain | 26-173 | 174-190 | 191-197 (Fas) + 198-235 (ICOS) |
| | pTR-438 | TRAILR2 | truncated | TRAIL-R2 missing IC domain with 7aa IC overhang | 56-210 | 211-231 | 232-238 |
| | pTR-439 | TRAILR2 | CD28 | TRAIL-R2 EC & TM domain with 7aa IC overhang + full CD28 IC domain | 56-210 (TRAILR2) | 211-231 (TRAILR2) | 232-238 (TRAILR2) + 239-279 (CD28) |
| Chemokines | pTR-441 | CCR10 | | full protein | | 1-362 | |
| Metabolic | pTR-443 | MCT4 | | full protein | | 2-465 | |
| Pathways | pTR-444 | SOD1 | | fullp rotein | | 1-154 | |
| Transcription factors | PTR-445 | TCF7 | | full protein | | 1-384 | |
| Controls | pTR-401 | tNGFR | | tNGFR missing IC domain with 5aa IC overhang | 29-250 | 251-272 | 273-277 |
| | pTR-446 | GFP | | sfGFP with flanking 7aa linkers | 1-7 (8nker 1)/8-236 (sfGFP)/237-243 (linker 2) | | |
| | pTR-447 | mCherry | | mCherry with flanking 7aa linkers | 1-7 (linker 1)/8-242 (n)Cherry)/243-249 (linker 2) | | |

The modified T cell libraries generated by pooled knock-ins were electroporated, cultured, and expanded as described, before being subjected to a variety of in vitro assays beginning at day 7 post electroporation and ending at day 12 post electroporation. In stimulation assays, the modified T cell library was stimulated with CD3/CD28 dynabeads at a 1:1 bead to cell ratio, and at a 5:1 bead to cell ratio for the excessive stimulation condition. In the TGFβ assay, 25 ng/mL of human TGFβ was added to the culture media. For the CD3 stimulation only condition, a 1G4 TCR (NY-ESO-1 specific) binding dextramer (Immudex) was bound to cells at 1:50 dilution in 50 uL (500,000 cells total) for 12 minutes at room temperature, prior to return to culture media. All in vitro assays began with 500,000 sorted NY-ESO-1+ T cells unless otherwise described.

At the conclusion of the in vitro or in vivo assays, T cells were pelleted and either genomic DNA was extracted (QuickExtract) or mRNA was stabilized in TRIzol™. mRNA was purified using a Zymo Direct-zol spin column according to manufacturer's instructions, and converted to cDNA using a Maxima H RT First Strand cDNA Synthesis (Thermo) according to manufacturer's instructions. Unless otherwise stated, libraries were made from isolated mRNA/cDNA. A two step PCR was performed on the isolated genomic DNA or cDNA. The first PCR (PCR1) included a forward primer binding in the TCRαVJ region of the insert and a reverse primer binding in the genomic region overlapping the site of the mismatches in the 3' homology arm (FIG. 15), and used Kapa Hifi Hotstart polymerase for 12 cycles, followed by a 1.0×SPRI purification. The second PCR used NEB Next Ultra II Q5 polymerase for 10 cycles to append β5 and β7 Illumina® sequencing adaptors and sample-specific barcodes, followed again by a 1.0×SPRI purification. Normalized libraries were pooled across samples and sequenced on an Illumina® Mini-Seq with a 2×150 bp reads run mode. Barcode counts from quality filtered reads were determined in R using PDict.

In Vivo Xenograft Model

An NY-ESO-1 melanoma tumor xenograft model was used as previously described (Roth et al. *Nature* 559: 405-409 (2018)) All mouse experiments were completed under a UCSF Institutional Animal Care and Use Committee protocol. We used 8 to 12 week old NOD/SCID/IL-2Rγ-null (NSG) male mice (Jackson Laboratory) for all experiments. Mice were seeded with tumours by subcutaneous injection into a shaved right flank of 1×106 A375 human melanoma cells (ATCC CRL-1619). At seven days post tumour seeding, tumour size was assessed and mice with tumour volumes between 20-40 mm3 were used for subsequent experiments. The length and width of the tumour was measured using electronic calipers and volume was calculated as v=1/6*π*length*width*(length+width)/2. Indicated numbers of T cells with the pooled knockin library were resuspended in 100 μl of serum-free RPMI and injected retro-orbitally. A bulk edited T cell population (10×106) containing at least 10% NY-ESO-1 knockin positive cells as transferred. Five days after T cell transfer, single-cell suspensions from tumours and spleens were produced by mechanical dissociation of the tissue through a 70 μm filter, and T cells (CD45+ TCR+) were sorted from bulkt tumorcytes by FACS. All animal experiments were performed in compliance with relevant ethical regulations per an approved IACUC protocol (UCSF), including a tumor size limit of 2.0 cm in any dimension.

Example 2

We knocked in barcoded pools of large DNA sequences encoding polycistronic gene programs, and combined pooled knock-in screening with single-cell RNA sequencing to rapidly determine high-dimensional phenotypic information for each construct.

A major limitation of traditional pooled screening approaches is that only the abundance of a given library member within a population is measured, limiting more detailed analysis of cell state and functionality. The combination of pooled perturbation with high-dimensional phenotypic readouts offers a rapid way to increase the information obtained about each individual perturbation. Single cell RNA sequencing generates such phenotypes, which we recently combined with pooled knock-out screening in primary T cells (Utzschneider, D. T. et al. T Cell Factor 1-Expressing Memory-like CD8+ T Cells Sustain the Immune Response to Chronic Viral Infections. Immunity (2016)). We next tested whether pooled knock-in screening could similarly be combined with single cell RNA sequencing to dramatically expand the amount of phenotypic information generated within a single pooled experiment.

Figure 23A:
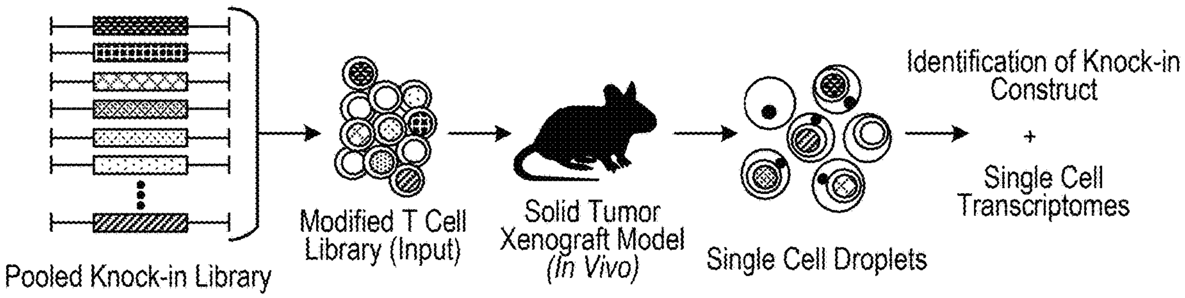
Figure 23B:
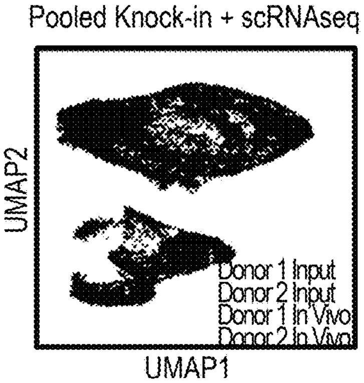
Figure 23C:
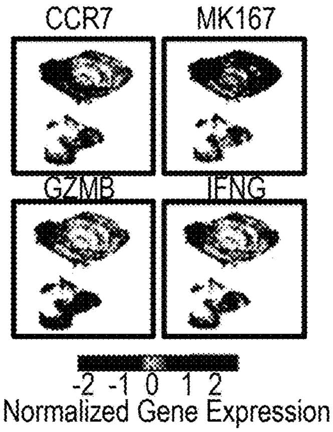
Figure 23D:
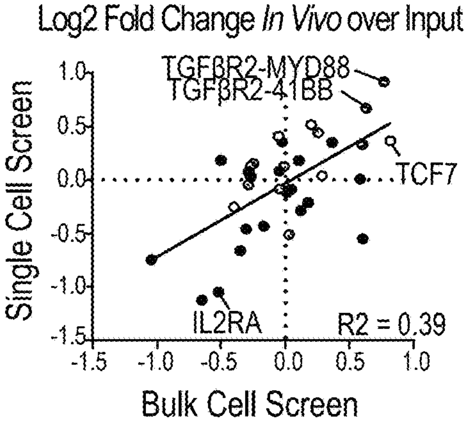
Figure 23E:
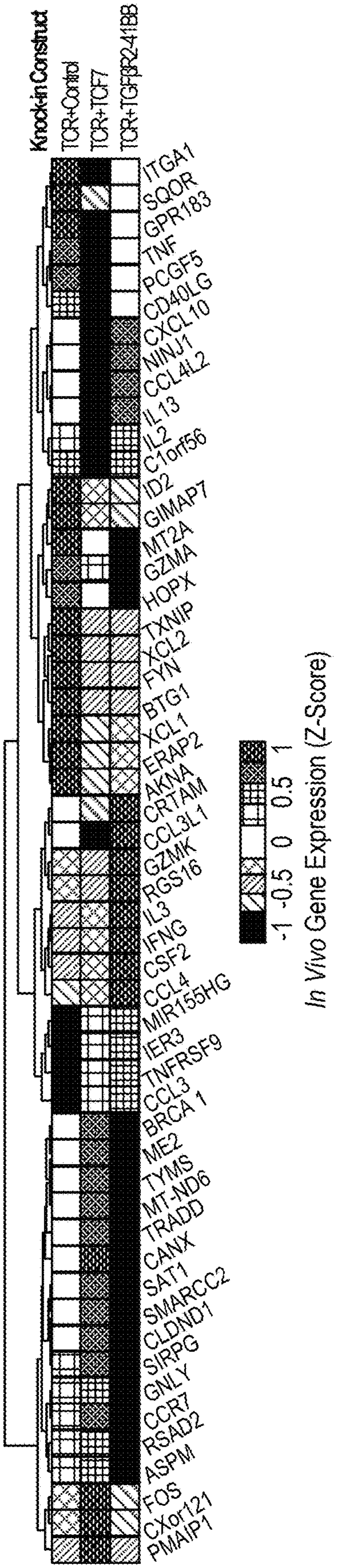
Figure 24A:
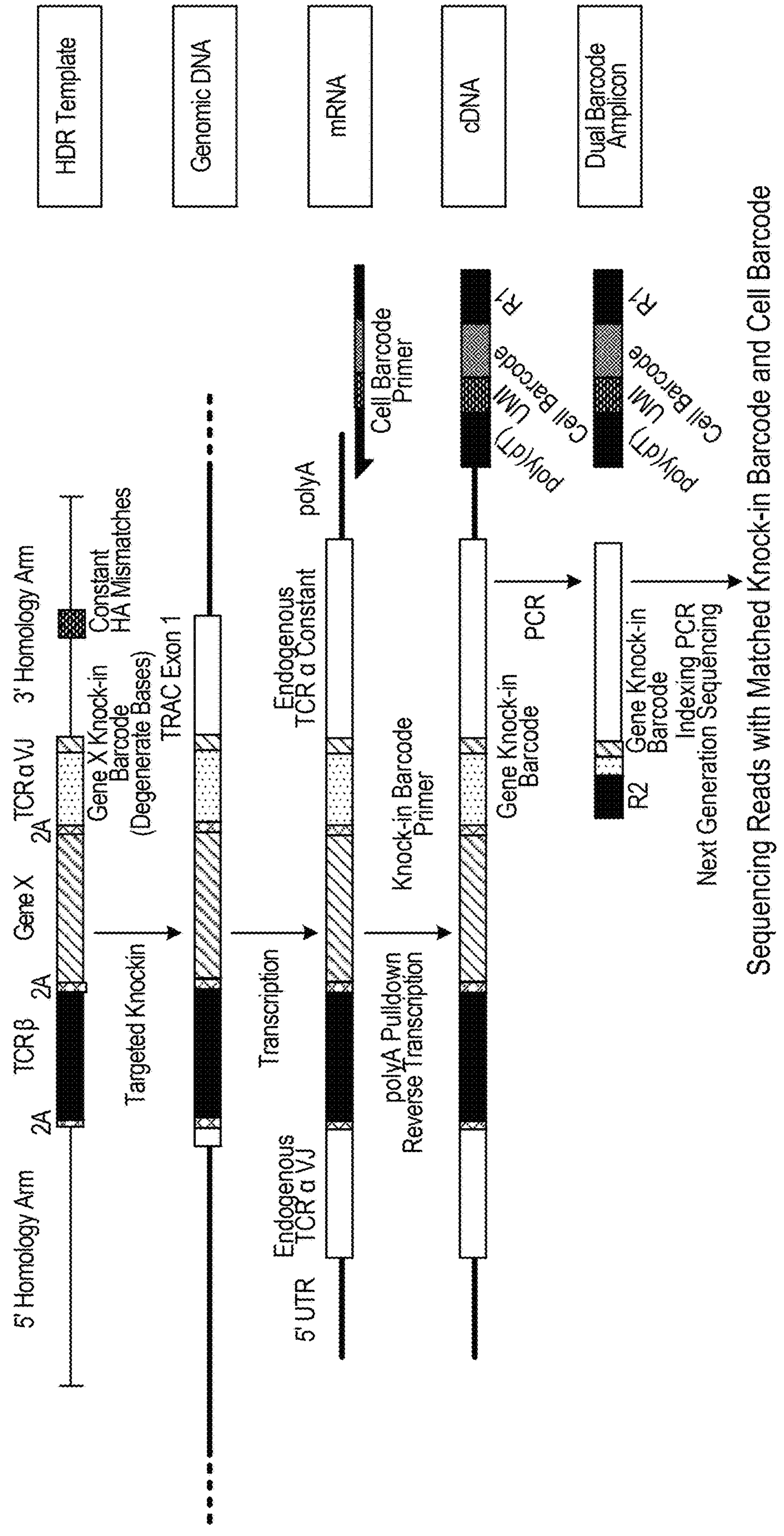
Figure 24B:
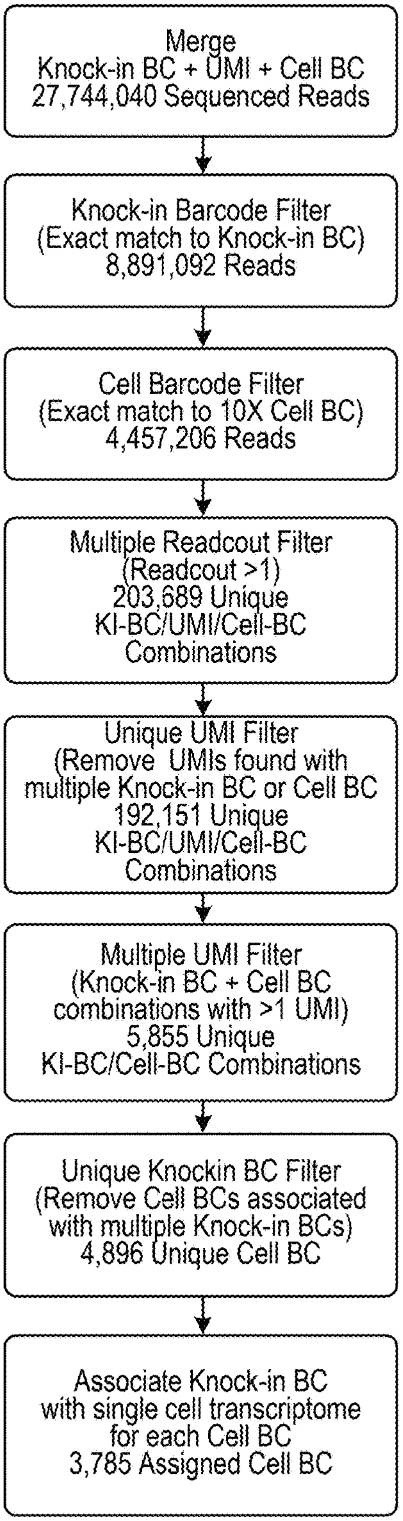
Figure 24C:
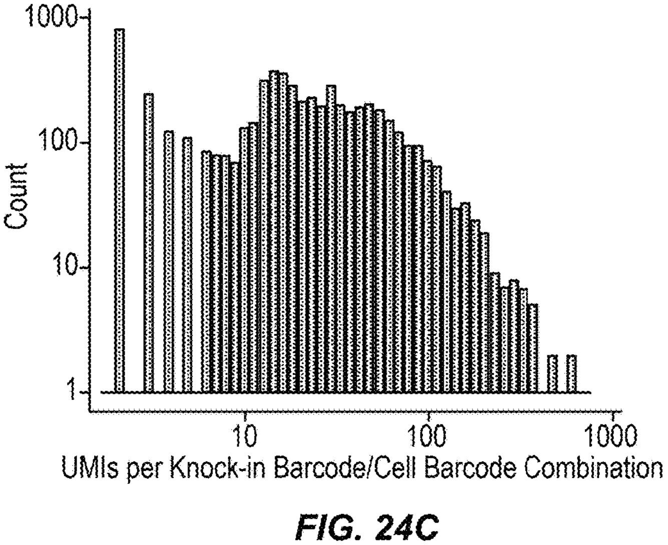
Figure 24D:
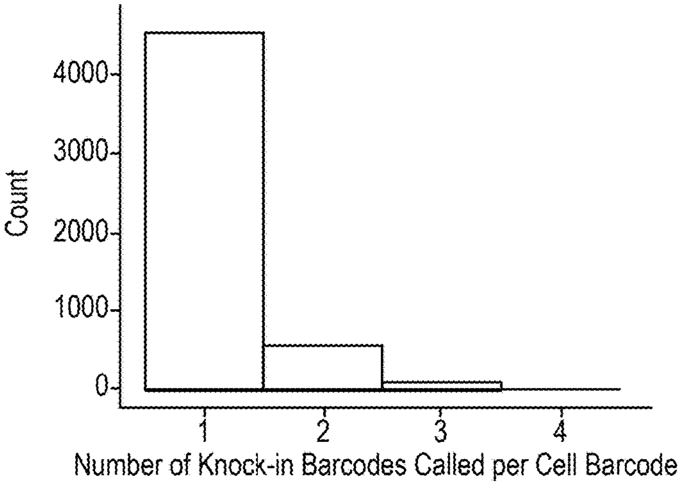
Figure 24E:
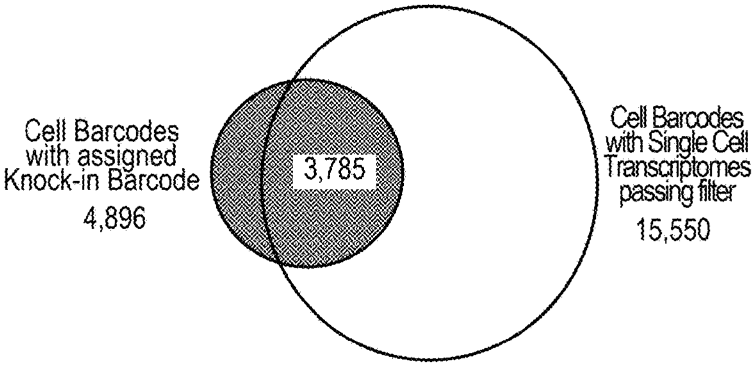

We performed a pooled knock-in screen in the A375 in vivo solid tumour model (FIG. 4*d*), comparing an input population with an in vivo population five days after T cell transfer (FIG. 23*a*). In contrast to the abundance screen, after sorting live TCR+ T cells from the tumours or input population, we performed single cell droplet isolations (10×) followed by sequencing of single cell transcriptomes in concert with targeted amplicon sequencing to determine the knock-in construct associated with each cell (FIG. 3*a* and FIG. 24*a*). A UMAP representation of the single cell transcriptomes from two unique donors showed a high degree of overlap between donors and large differences between the input cell population and the T cells that were isolated from the solid tumour after 5 days in vivo (FIG. 23*b*). The input and in vivo clusters overlapped with known proliferation and effector gene signatures (FIG. 23*c*). Computational filtering of targeted amplicon sequencing of the knock-in constructs barcodes was able to associate single-cell transcriptomes with individual knock-ins (FIG. 24*b*). The proportions of cells called with the individual knock-in barcodes from the single cell in vivo pooled knock-in screens correlated ($R^2$=0.39) with the bulk cell in vivo pooled knock-in screens (FIG. 23*d*).

However, increased abundance in a population may not always correspond to functional efficacy. Pooled knock-in screening in concert single cell RNA seq revealed library member's abundance as well as their individual transcriptional signatures. We compared against controls the in vivo single cell transcriptomes from two hits from the pooled knock-in screens: the transcription factor TCF7, which enriched in vitro following excessive stimulation (FIG. 19) and in vivo; and the switch receptor TGFβR2-41BB, which was an in vivo hit as well as the strongest in vitro hit following TGFβ suppression (FIG. 19). While both TCF7 and TGFβR2-41BB showed increased expression of genes such as TNFSFR9 (41BB) relative to controls, the TGFβR2-41BB construct showed increased expression of effector cytokines such as IFN-γ that may drive tumour clearance in the tested melanoma xenograft model.

Pooled Knock-In Screening Plus Single-Cell RNA Sequencing

Single-cell RNA sequencing was performed on 8 separate samples (2 donors, 2 recipients per donor, matched pre- and post-implantation cells) with the Chromium Single Cell 3' Reagent Kit, v3 chemistry (10× Genomics, PN-1000092) following the manufacturer's protocol. Briefly, TCR-positive cells were sorted by FACS (BD FACS Aria) and resuspended at 1000 cells/ul in PBS+1% FBS for a targeted recovery of 6000 cells per condition. We performed 11 cycles of PCR for cDNA amplification after GEM recovery, and 25% of each cDNA sample was carried into transcriptome library preparation. We performed 13 cycles of PCR to introduce Chromium i7 multiplex indices (10× Genomics, PN-120262). cDNA was diluted 1:5 in Buffer EB and quantified by Bioanalyzer DNA High Sensitivity (Agilent, 5067-4626) and/or Qubit® dsDNA High Sensitivity (Thermo Fisher, Q32854) reagents. Samples were pooled equally and sequenced on a NovaSeq® S4 flow cell (Illumina®) using read parameters 28×8×91. Raw fastq files were mapped to the human transcriptome (GRCh38)using Cell Ranger (10× Genomics, version 3.0.2) and further analyzed using Seurat (version 3.0.1).

After the initial 11 cycle cDNA amplification step described above, 50% (20 ul) of each cDNA sample was loaded into a KAPA HIFI 2×PCR reaction using 1 uM p5 forward primer (AATGATACGGCGACCACCGAGATCTACACTCTTTCCCTACACGACGCTC) (SEQ. ID NO. 117) and 1 uM of a custom TCRa-read2 reverse primer (GTGACTGGAGTTCAGACGTGTGCTCTTCCGATCTGAGGAACCAGCCTTATTGTTC ATCCGTA) (SEQ ID NO: 118) and run with the following parameters: 98° C. for 45", [98° C. for 20", 67° C. for 30", 72° C. for 30']×10, 72° C. for 60", hold at 4° C. The PCR products were purified with 0.8× AMPure XP (Beckman Coulter, A63882) and eluted in 45 ul Buffer EB (Qiagen, 1014608). We performed 9 cycles of PCR to introduce Chromium i7 multiplex indices (10× Genomics, PN-120262). cDNA was diluted 1:5 in Buffer EB and quantified by Tapestation DNA High Sensitivity (Agilent, 5067-5593)) and/or Qubit® dsDNA High Sensitivity (Thermo Fisher, Q32854) reagents. Samples were pooled equally and sequenced on a NovaSeq® SP flow cell (Illumina®) with 25% PhiX using read parameters 28×8×98. Sequencing data was analyzed and barcodes assigned as described in FIG. 24*b*.

Example 3

Pooled Knock-In of a Multiplexed Library of Large DNA Constructs

Figure 29A:
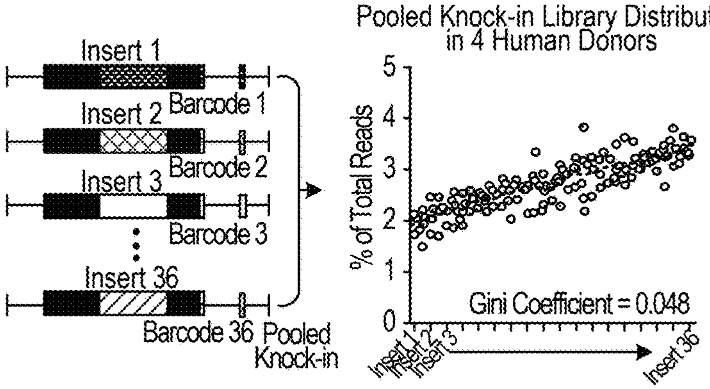
Figure 29B:
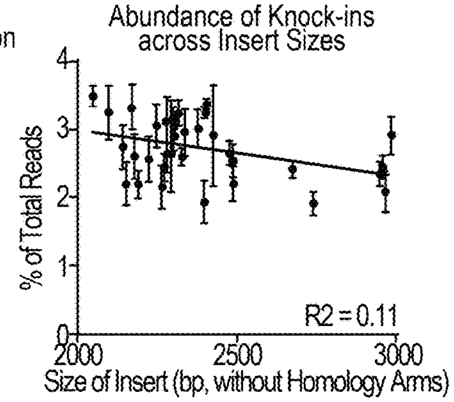
Figure 29C:
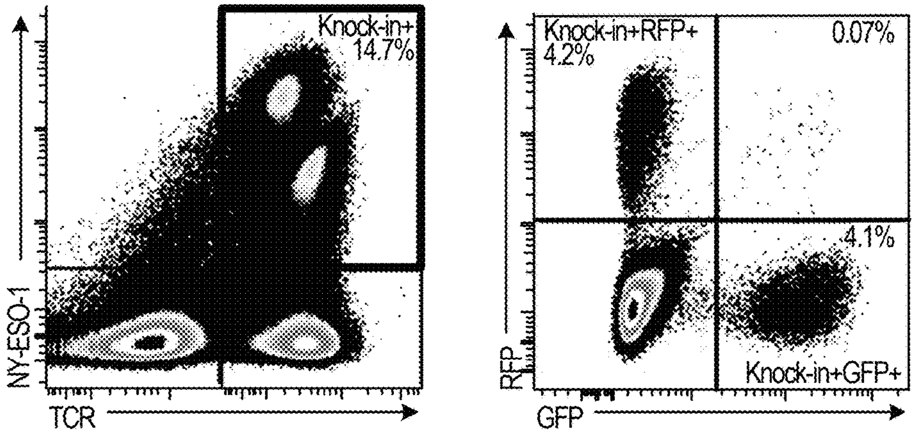
Figure 29D:
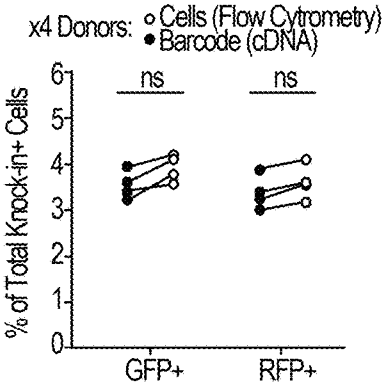

We next examined whether a larger library of 36 pooled templates could also be introduced and tracked by their DNA barcodes. Quantitative barcode sequencing demonstrated that even with the larger library all knock-in constructs were well-represented across multiple pooled knock-in experiments performed in four independent human donors (FIG. 29A). The library contained large knock-in constructs ranging from 2 kb to 3 kb and even the largest constructs were well-represented across these biological replicates (FIG. 29B). The 36-member library contained the GFP and RFP templates previously tested in the 2-member library, and when gating on knock-in positive cells (by dextramer staining for the introduced NY-ESO-1 TCR), GFP+ and RFP+ cells could be identified (FIG. 29C). As expected, the percentage of reads with the GFP or RFP sequencing barcodes closely corresponded to the percentage of GFP or RFP positive cells observed at the protein level across four human donors (FIG. 29D).

Figure 29E:
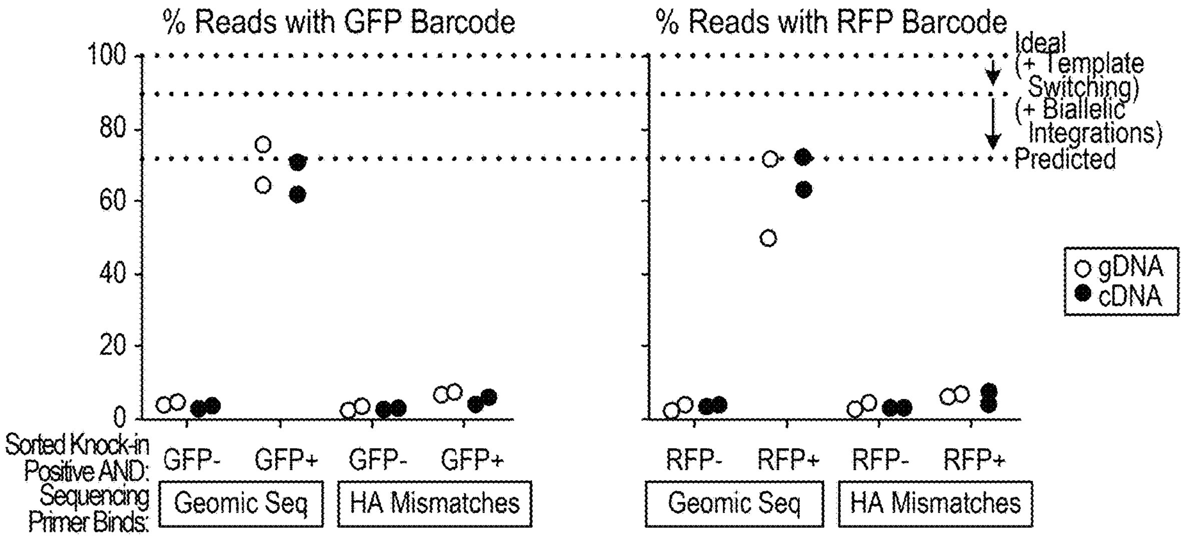
Figure 29F:
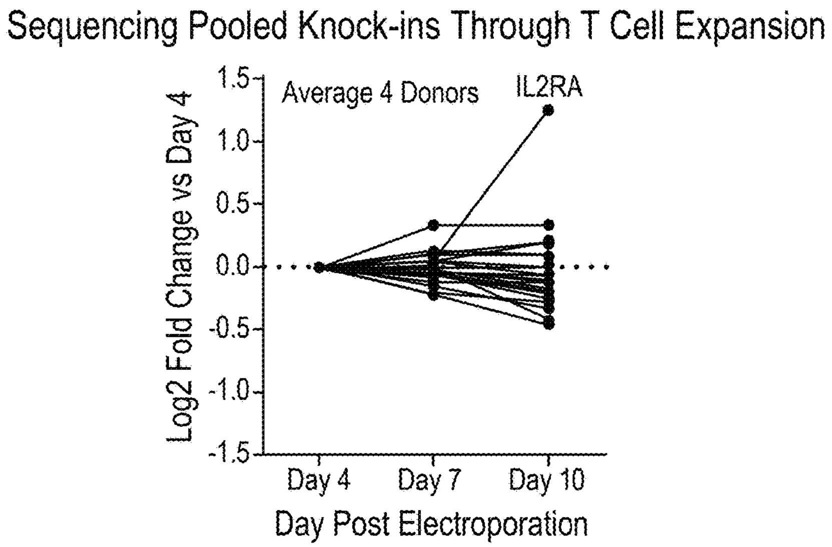
Figure 29G:
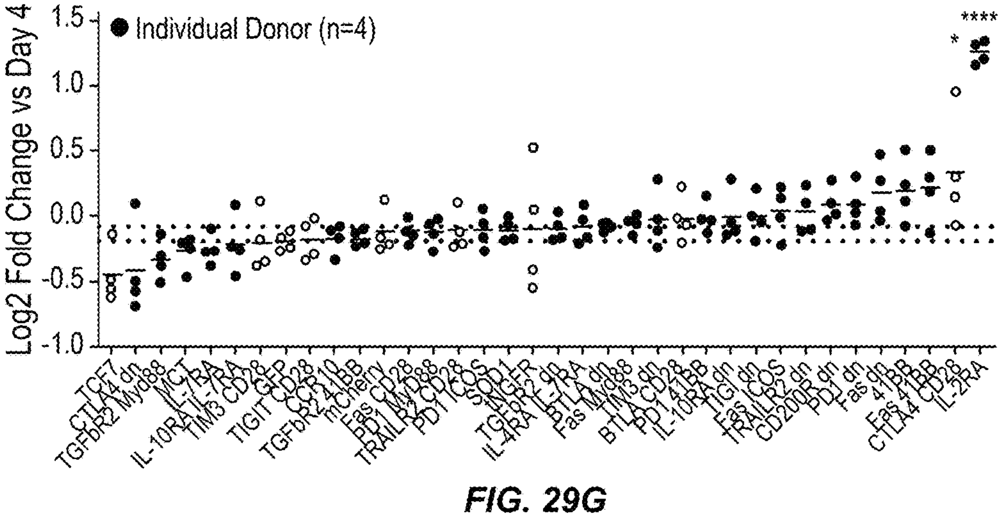

We next directly validated the homology arm mismatch sequencing strategy to selectively amplify on-target barcodes using the larger 36-member pooled knock-in library. For both gDNA and cDNA sequencing conditions, when GFP+ or RFP+ cells were sorted from the cells with successful on-target knock-in (NY-ESO-1 TCR+), the correct barcodes were selectively sequenced when using primers that bound the genomic sequence at the rate predicted when taking biallelic integrations and template switching into account (FIG. 29E). However, as expected, primers complementary to the template homology arm mismatches—which should preferentially amplify non-HDR integrated templates—did not show the same enrichment for correct barcodes in the sorted populations (FIG. 29E). Finally, we were able to readily track the relative abundances of knock-in construct barcodes over time in an expanding population of T cells cultured in interleukin 2 (IL-2). Barcode abundance was maintained throughout expansion for all constructs, with a notable exception of the knock-in construct encoding IL2RA, the high affinity receptor for the interleukin (IL-2), which enriched over time in culture consistent with its known roles promoting T cell fitness (FIGS. 29F-G). These results showed large pooled knock-in libraries can be generated and their barcodes can be quantitatively sequenced in a therapeutically relevant primary human T cell population.

Pooled Knock-In Hits Individually Validated and Improved in Vitro Cancer Cell Killing Pooled knock-in screens identified gene constructs that conferred competitive advantages to knock-in cells in the targeted population. We wanted to validate the pooled knock-in screening platform and confirm that the knock-in construct "hits" would similarly improve T cell fitness in individual knock-in experiments (FIG. 30A). First, we tested to ensure that the DNA knock-in constructs resulted in expression of the expected protein products. Surface and intracellular staining of cells with eight individual knock-in constructs revealed robust expression for each expected protein, including increased expression of Fas and CD25 (IL2RA) above endogenous expression levels in stimulated T cells (FIG. 30B and FIG. 32A). We next directly validated for eight individual knock-in constructs the fitness benefits identified in the context dependent in vitro pooled screens. Indeed, the anti-apoptotic FAS-41BB chimera and anti-suppressive TGFβR2-41BB chimera both promoted context-dependent increased expansion relative to controls (FIG. 30C and FIG. 32B). Increased cell expansion induced by the TGFβR2-41BB construct correlated with evidence of increased cell proliferation in the presence of TGFβ (measured by CFSE dilution relative to control cells) (FIG. 30C and FIG. 32B). These findings validated the pooled library-based approach to identify individual knock-in sequences to engineer T cell function.

We next tested to see if the identified knock-in constructs that promoted context-dependent T cell ex vivo expansion could also enhance in vitro cancer cell killing. Although this was not the phenotype initially tested in the pooled screens, the TGFβR2-41BB increased target in vitro cancer cell killing in T cells from four human blood donors across a range of effector to target cell ratios (FIG. 30D-E). In contrast, a truncated CTLA4 construct showed reduced cell killing (FIGS. 30D-E), consistent with its impaired fitness in the pooled knock-in screens (although diminished proliferation assessed by CFSE was not observed with this individual construct, FIG. 32B). Finally, we examined if the TGFβR2-41BB chimeric receptor also showed further context-dependent improvements in in vitro cancer killing. In the presence of exogenous TGFβ, the TGFβR2-41BB construct successfully rescued the impaired cancer cell killing across experiments performed from four healthy human donors (FIG. 30F). Although the pooled screens focused on cell-intrinsic effects on T cell fitness, they also successfully identified novel gene constructs that can enhance in vitro anti-cancer cell efficacy.

Figure 31A:
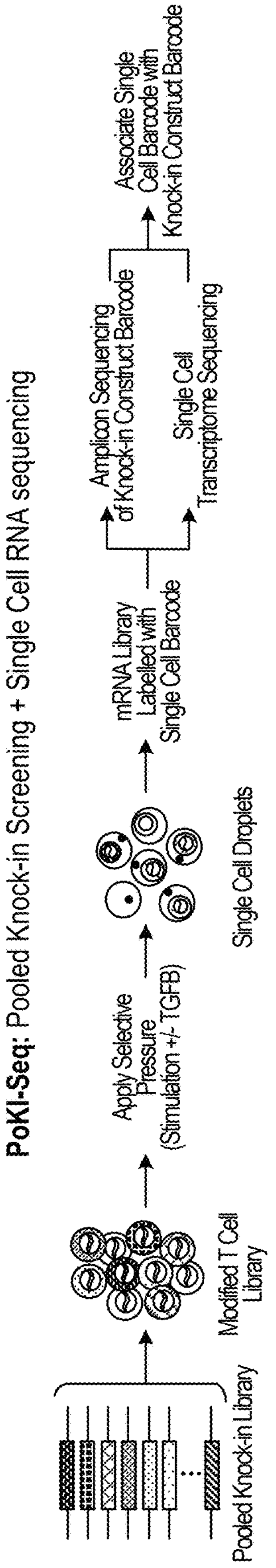

PoKI-Seq: Pooled Knock-Ins with Single-Cell Transcriptome Analysis to Assess Abundance and Cell State Pooled screening approaches reveal modifications that affect cellular abundance in a population. However, cell abundance measures only one aspect of cellular function, and an ideal screening methodology would allow systematic assessment of modified cell states as well. Recently, novel barcoding strategies have overcome this and allowed pooled populations of CRISPR knock-out cells to be assessed by scRNA-seq (Adamson et al., 2016; Datlinger et al., 2017; Dixit et al., 2016; Jaitin et al., 2016), including primary human T cells (Shifrut et al. 2018). We next tested whether pooled knock-in screening could similarly be coupled with scRNA-seq to generate high-dimensional phenotypic information on modified cell states while also recording each cell's specific knock-in construct barcodes, a method we term PoKI-Seq (Pooled Knock-In Sequencing) (FIG. 31A). Briefly, the mRNA library converted to cDNA following single cell droplet isolation (10×) was split, with part used for scRNA-seq and the other for targeted amplicon sequencing of the knock-in barcode (FIG. 33A).

Figure 31B:
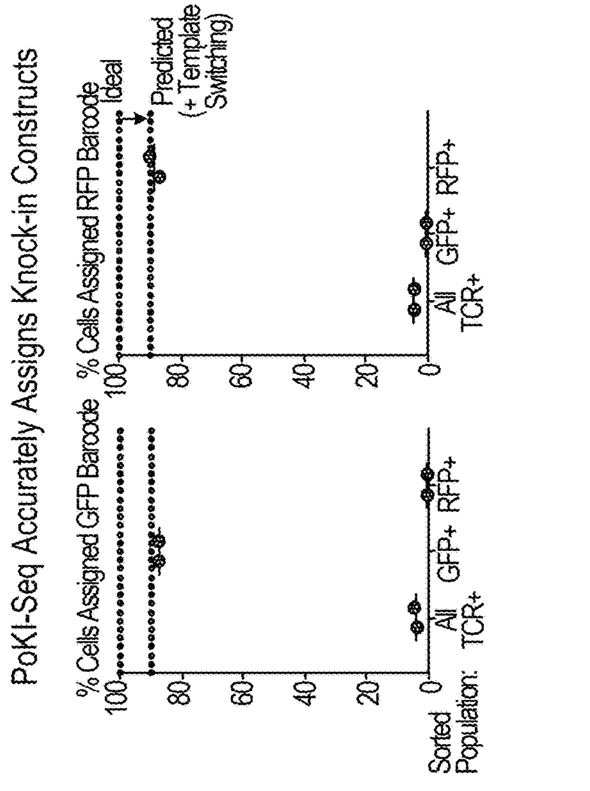
Figure 31C:
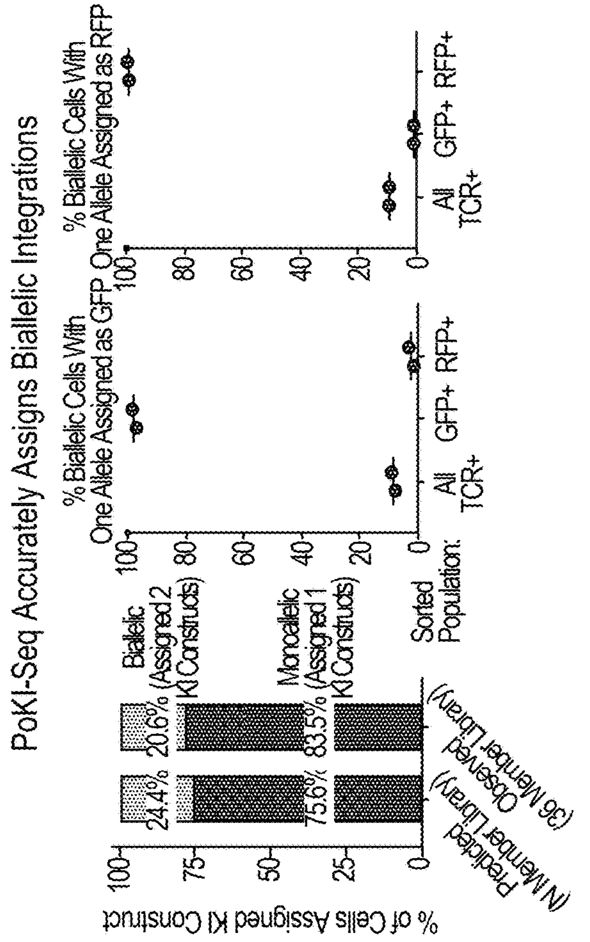

First, to validate that the fidelity of PoKI-Seq template barcodes is maintained throughout the experimental pipeline, we repeated GFP and RFP sorting experiments with the single cell platform. Sorting GFP+ or RFP+ cells from the pooled knock-in positive population (NY-ESO-1 TCR+) strongly enriched for the expected template barcodes, confirming the ability of PoKI-Seq to accurately assign specific knock-in constructs to cells (FIG. 31B). One advantage of PoKI-Seq over bulk amplicon sequencing of pooled knock-ins is the ability to discriminate cells with a single knock-in construct from those that have received more than one (most likely from biallelic integrations). The overall proportion of cells assigned two knock-in constructs (FIG. 31C) closely corresponded with predicted frequencies based on GFP/RFP 2-member library experiments. As expected, when sorted GFP and RFP positive cells were assigned two knock-in constructs, at least one of the knock-in constructs assigned was almost always either GFP or RFP respectively (FIG. 31C). These experiments confirmed the molecular biology of PoKI-seq and also demonstrated its ability to phenotype individual cells with either single or multiple knock-in constructs.

Figures 31D, 31E, 31F, 31G, 31H:
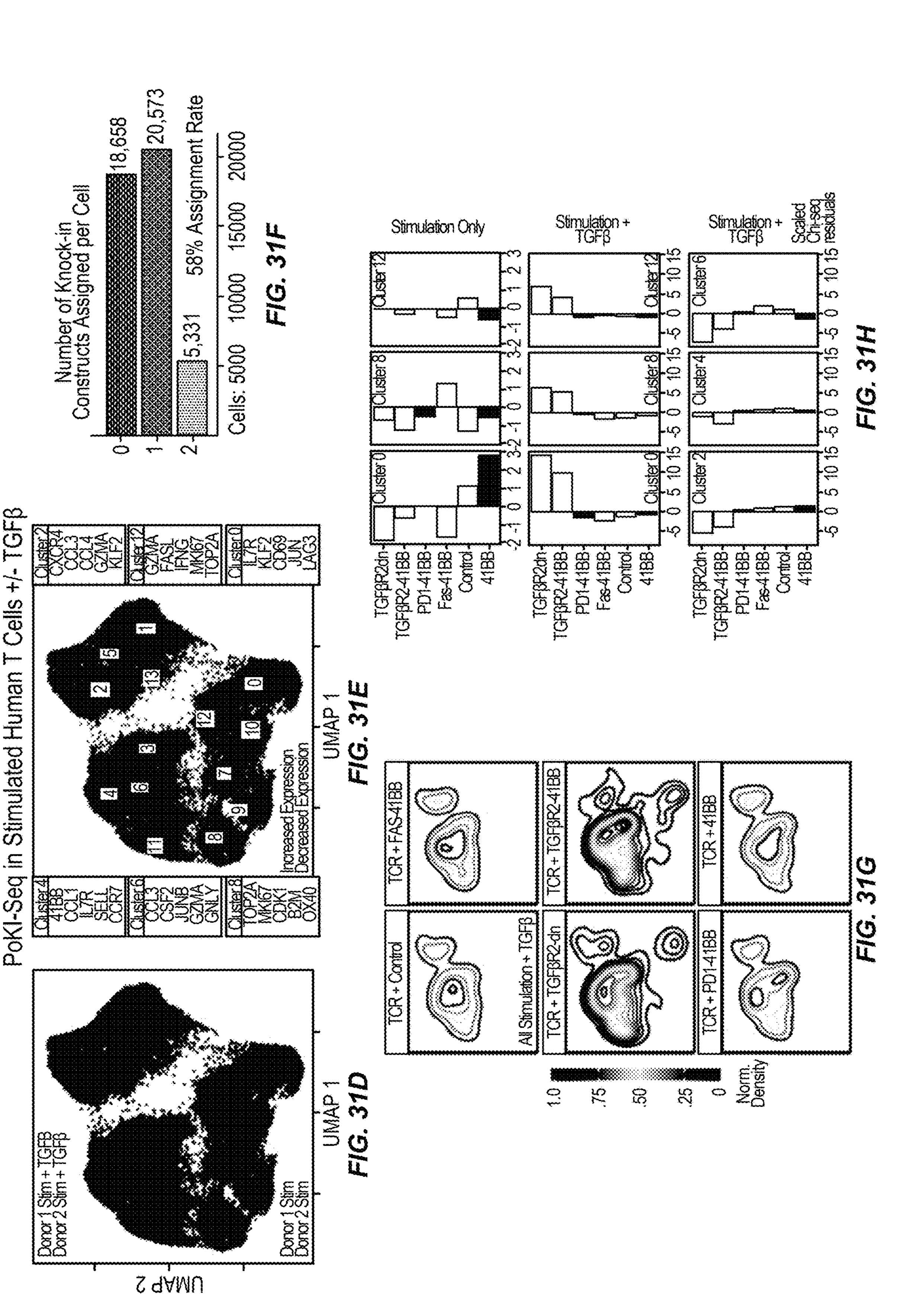
Figure 31I:
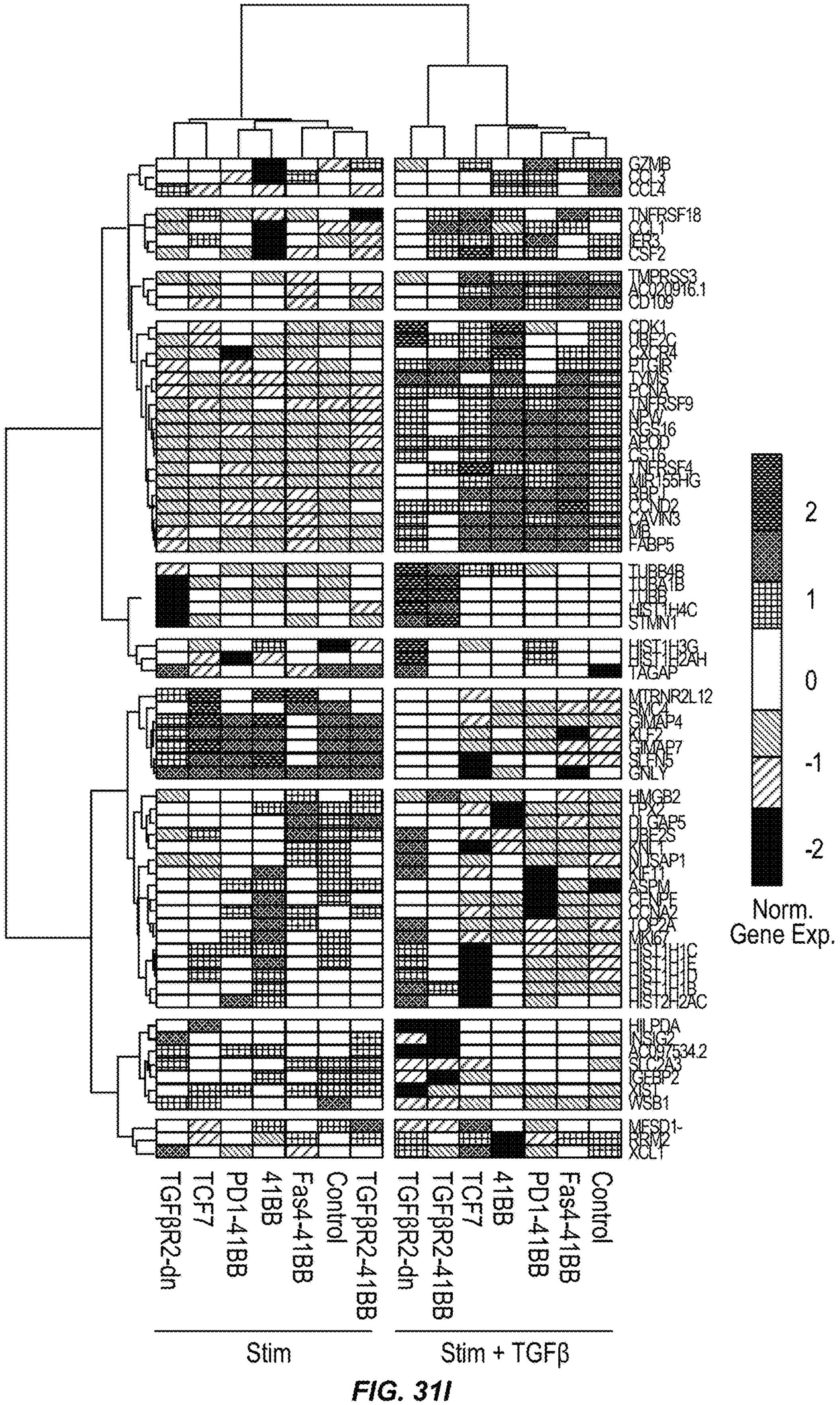
Figure 33C:
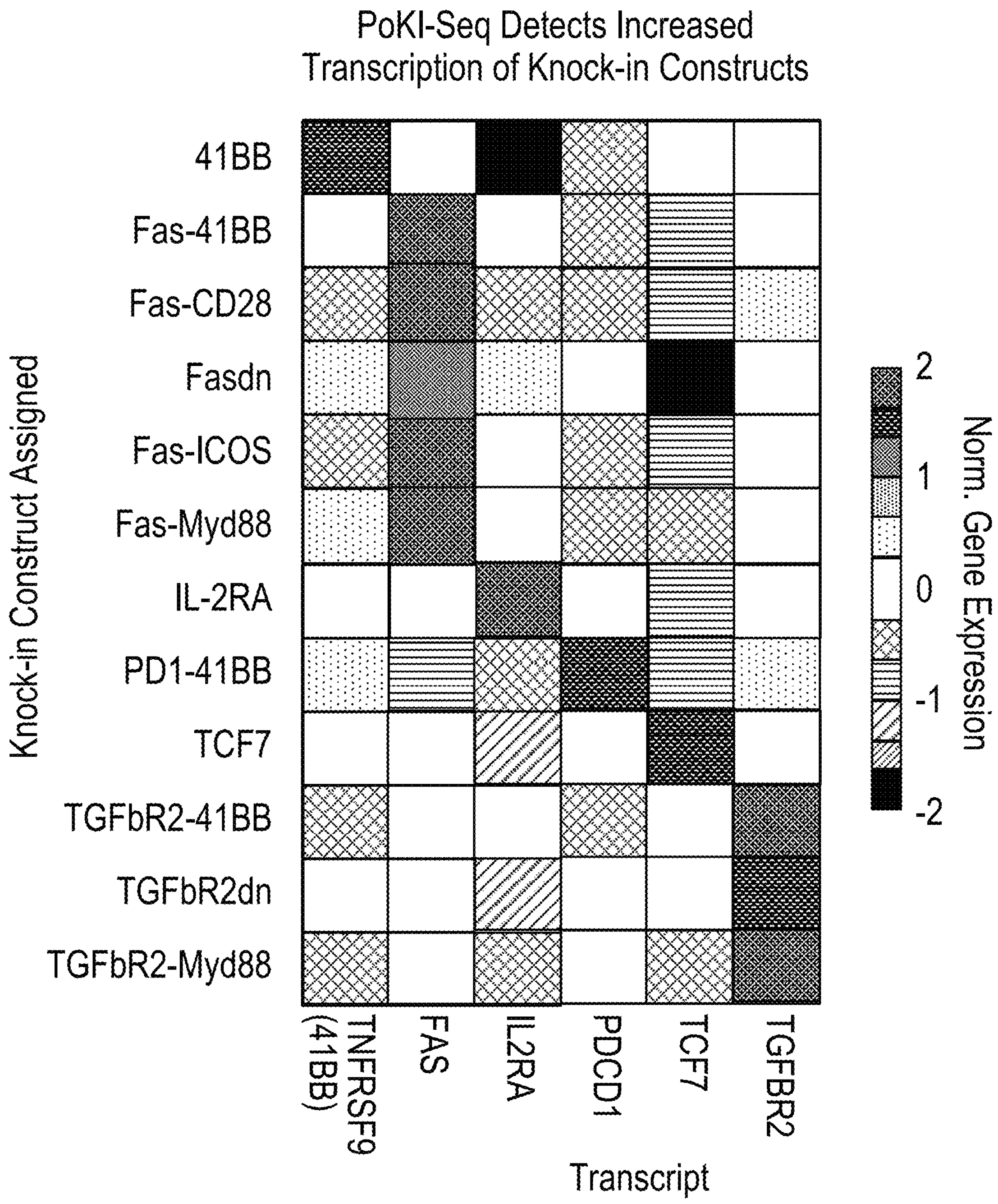

We next tested if PoKI-Seq could assign template barcodes to single cell transcriptomes in a large population of cells with the full 36-member pooled knock-in library. We performed PoKI-Seq on cells from two human blood donors following ex vivo stimulation in the presence or absence of exogenous TGFβ. Distinct clusters of cell states emerged, especially with addition of exogenous TGFβ (FIG. 31D-E). Over 40,000 individual cells were sequenced, of which ~58% were successfully assigned one (monoallelic) or two (biallelic) barcodes (FIG. 31F). Quality control metrics following PoKI-Seq confirmed robust rates of gene and UMI identification per cell and an average >130× coverage of cells assigned to each knock-in construct (per blood donor and per ex vivo condition tested) (FIG. 33B). Single cell template barcode assignments were confirmed further as transcripts encoded by corresponding knock-in constructs tended to be expressed at increased levels, similar to what had been observed at the protein level with delivery of individual knock-in constructs (FIG. 30B and FIG. 33C). These metrics together established the fidelity of barcode assignment to single cell transcriptomes for the PoKI-Seq platform.

Figure 33D:
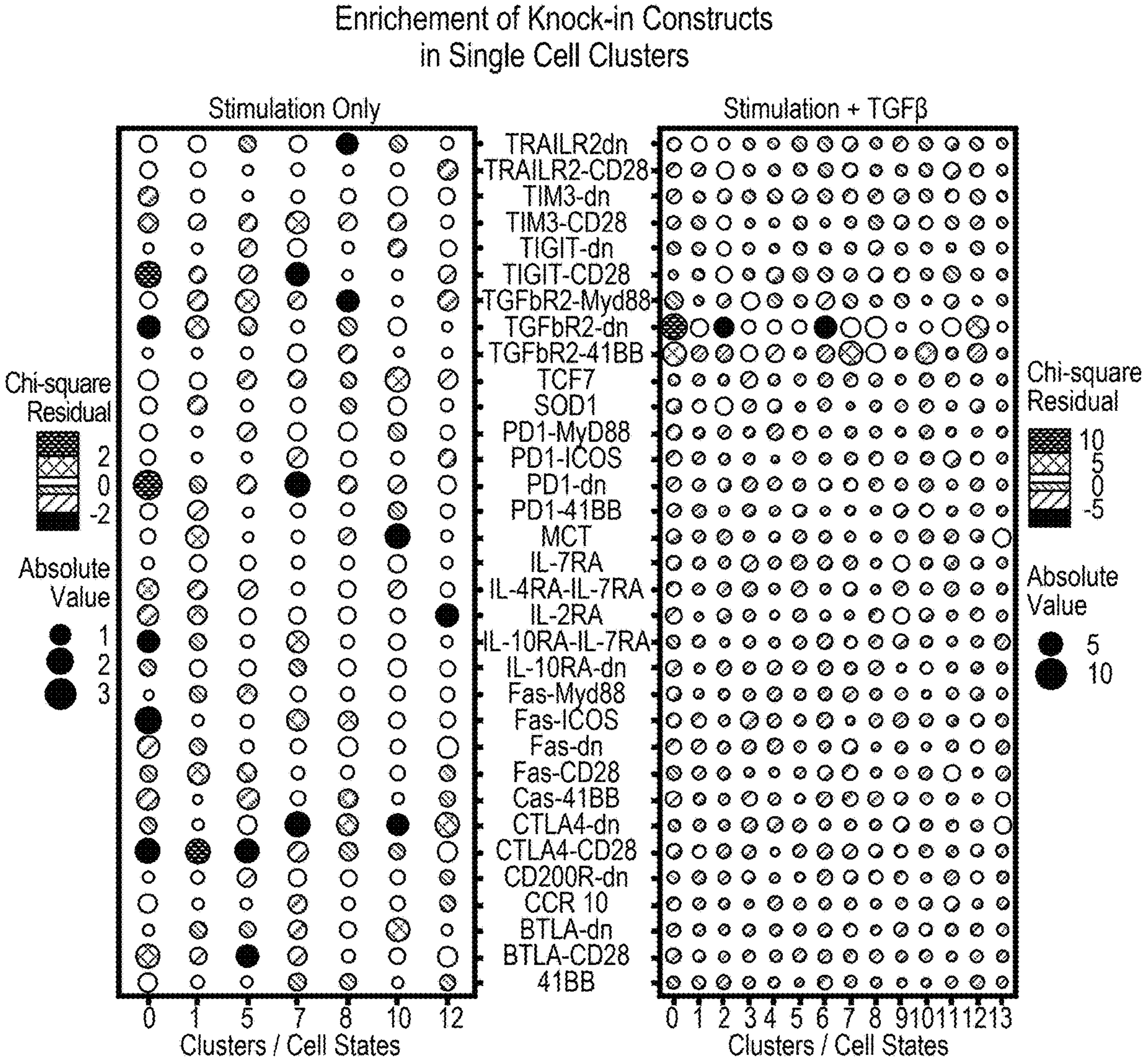
Figure 33E:
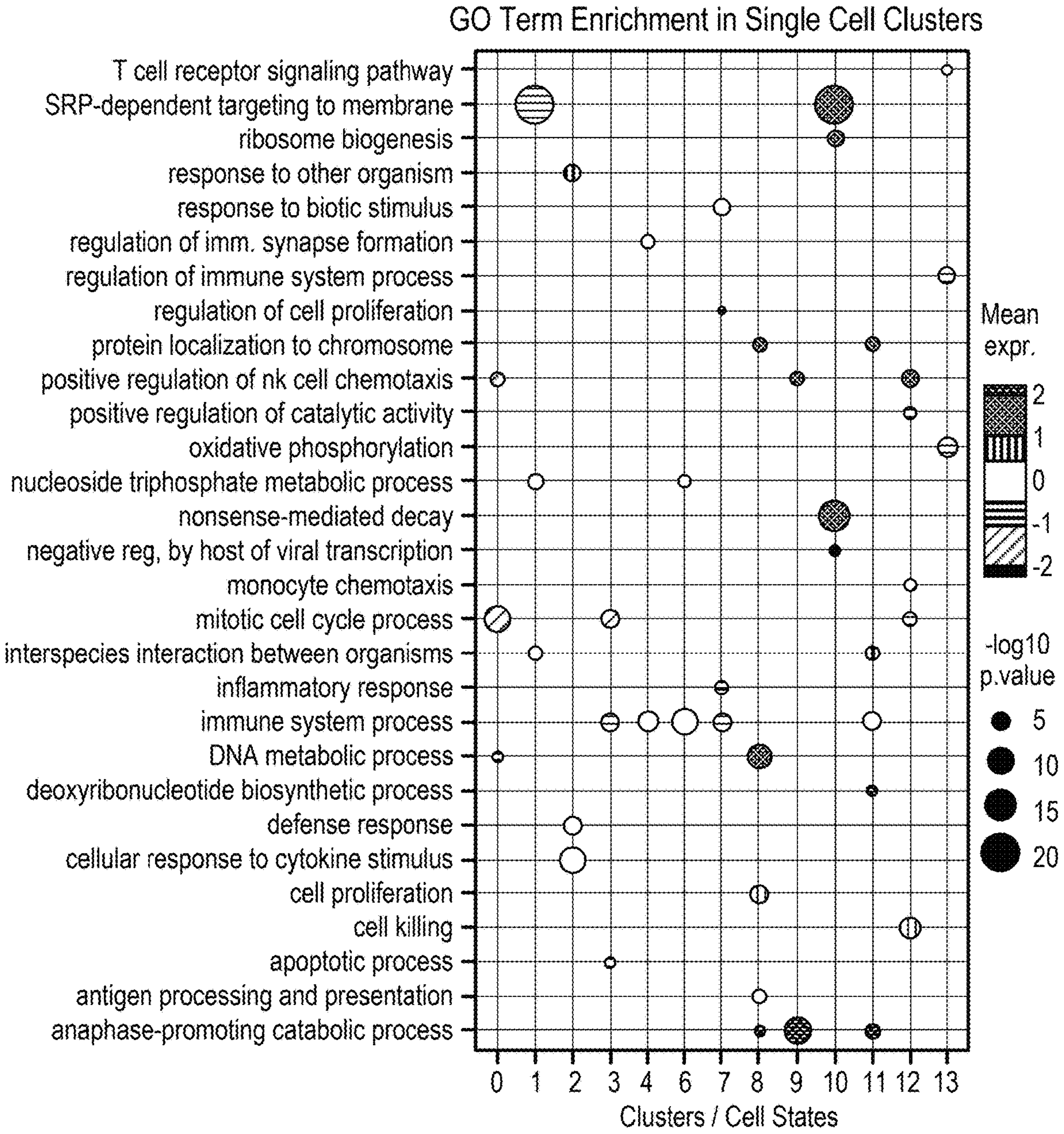
Figure 33F:
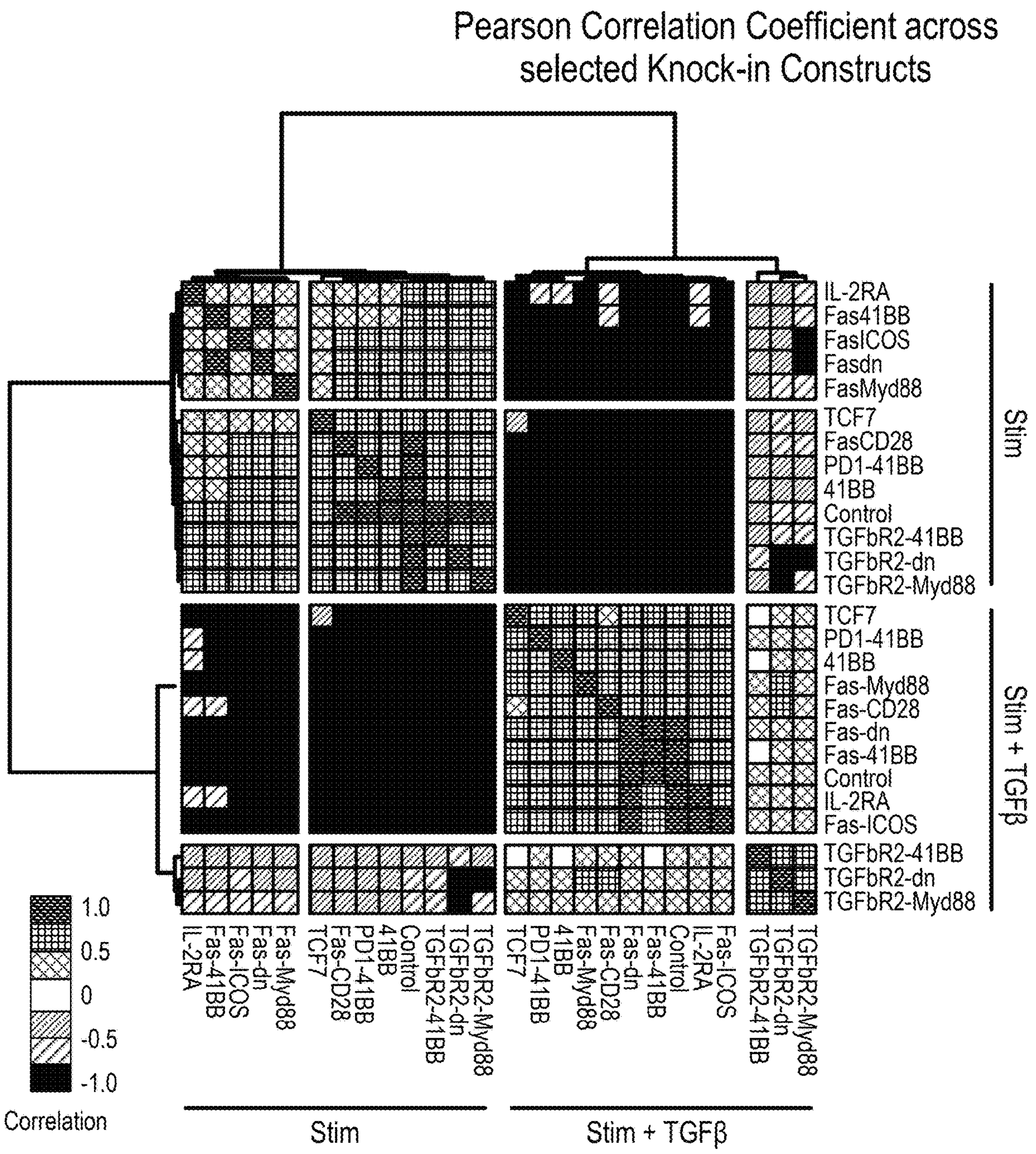

Next, we examined whether PoKI-Seq could measure cell state changes in ex vivo human T cells caused by specific knock-in constructs. Each knock-in construct caused distinct enrichment patterns in individual cell clusters in both TCR stimulation and stimulation plus TGFβ conditions that broadly corresponded to results from the in vitro pooled knock-in screens (FIG. 33D). Density plots for individual knock-in constructs revealed significant cell state differences in T cells modified with TGFβR2-derived constructs compared to control and non-TGFBR2-derived constructs in the stimulation plus TGFβ culture condition (FIG. 31G). Specifically, the TGFβR2-derived constructs showed significant enrichment in clusters otherwise associated with cells in the stimulation-only condition including cluster 8 characterized by genes associated with cell proliferation and cluster 12 characterized by genes associated with cell killing (FIGS. 31E, H and 33D,E). Similarly, the TGFβR2-derived knock-in constructs were depleted from cells in the clusters otherwise promoted by TGFβ treatment (Clusters 2, 4 and 6)(FIG. 31H). Clustering of knock-in constructs across all genes differentially expressed in the identified single cell clusters showed strong similarity between the TGFβR2-derived constructs in the presence of TGFβ and revealed downstream target genes that are modulated by the receptors. For cells stimulated without TGFβ the most prominent similarity in gene expression was among FAS derived receptors and IL2RA (FIG. 33F). Hierarchical clustering revealed that exposure to TGFβ drove the greatest transcriptional changes. For example, in the presence of exogenous TGFβ, TGFβR2-derived chimeric receptors promoted continued expression of various hallmark proliferative genes such as MKI67 and TOP2A, while these genes were inhibited by TGFβ in cells expressing other KI constructs. PoKI-Seq confirmed the shared biological effects of multiple TGFβR2-derived receptors, which convert a suppressive signal into a signal that promotes cell proliferation and an effector cell state. More generally PoKI-Seq was able to reveal target gene pathways and context-dependent changes in cell state modulated by individual knock-in constructs.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for the contents for which they are cited.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

TABLE 3

| doMAIN | Domain | nucleic acid sequence encoding polypeptide | amino acid sequence of polypeptide |
|---|---|---|---|
| PD1 | truncated | ATGCAGATCCCACAGGCGCCCTGGCCAGTCGTCTGGGCG GTGCTACAACTGGGCTGGCGGCCAGGATGGTTCTTAGAC TCCCCAGACAGGCCCTGGAACCCCCCAACCTTCTCCCCAG | MQIPQAPWPVVWAVLQLGWRPGWFLDSPDRPW NPPTFSPALLVVTEGDNATFTCSFSNTSESFVLN WYRMSPSNQTDKLAAFPEDRSQPGQDCRFRVTQ |

TABLE 3-continued

| doMAIN | Domain | nucleic acid sequence encoding polypeptide | amino acid sequence of polypeptide |
|---|---|---|---|
| | | CCCTGCTCGTGGTGACCGAAGGGGACAACGCCACCTTCA<br>CCTGCAGCTTCTCCAACACATCGGAGAGCTTCGTGCTAAA<br>CTGGTACCGCATGAGCCCCAGCAACCAGACGGACAAGCT<br>GGCAGCATTCCCTGAGGACCGTAGCCAGCCTGGCCAGGA<br>CTGCCGTTTCCGTGTCACACAACTGCCCAACGGGCGTGAC<br>TTCCACATGAGCGTGGTCAGGGCCCGGCGCAATGACAGC<br>GGCACATACCTTTGTGGGGCCATCTCCCTGGCCCCCAAGG<br>CGCAGATCAAAGAGAGCCTGCGGGCAGAGCTCAGGGTGA<br>CAGAGAGAAGGGCAGAAGTGCCCACAGCCCACCCTAGCC<br>CCTCACCTAGACCAGCCGGCCAGTTCCAAACACTGGTGG<br>TTGGTGTCGTGGGCGGCCTGCTGGGCAGCCTGGTGCTGCT<br>AGTCTGGGTCCTGGCCGTCATCTGCTCCCGGGCCGCACGT<br>GGGACAATAGGA (SEQ ID NO: 1) | LPNGRDFHMSVVRARRNDSGTYLCGAISLAPKA<br>QIKESLRAELRVTERRAEVPTAHPSPSPRPAGQFQ<br>TLVVGVVGGLLGSLVLLVWVLAVICSRAARGTI<br>G (SEQ ID NO: 37) |
| PD1 | 41BB | ATGCAGATCCCACAGGCGCCCTGGCCAGTCGTCTGGGCG<br>GTGCTACAACTGGGCTGGCGGCCAGGATGGTTCTTAGAC<br>TCCCCAGACAGGCCCTGGAACCCCCCAACCTTCTCCCCAG<br>CCCTGCTCGTGGTGACCGAAGGGGACAACGCCACCTTCA<br>CCTGCAGCTTCTCCAACACATCGGAGAGCTTCGTGCTAAA<br>CTGGTACCGCATGAGCCCCAGCAACCAGACGGACAAGCT<br>GGCAGCATTCCCTGAGGACCGTAGCCAGCCTGGCCAGGA<br>CTGCCGTTTCCGTGTCACACAACTGCCCAACGGGCGTGAC<br>TTCCACATGAGCGTGGTCAGGGCCCGGCGCAATGACAGC<br>GGCACATACCTTTGTGGGGCCATCTCCCTGGCCCCCAAGG<br>CGCAGATCAAAGAGAGCCTGCGGGCAGAGCTCAGGGTGA<br>CAGAGAGAAGGGCAGAAGTGCCCACAGCCCACCCTGCCC<br>CTGCGAGAGAGCCAGGACACTCTCCGCAGATCATCTCCTT<br>CTTTCTTGCGCTGACGTCGACTGCGTTGCTCTTCCTGCTGT<br>TCTTCCTCACGCTCCGTTTCTCTGTTGTTAAACGGGGCAG<br>AAAGAAACTCCTGTATATATTCAAACAACCATTTATGAG<br>ACCAGTACAAACTACTCAAGAGGAAGATGGCTGTAGCTG<br>CCGATTTCCAGAAGAAGAAGAAGGAGGATGTGAACTG<br>(SEQ ID NO: 2) | MQIPQAPWPVVWAVLQLGWRPGWFLDSPDRPW<br>NPPTFSPALLVVTEGDNATFTCSFSNTSESFVLN<br>WYRMSPSNQTDKLAAFPEDRSQPGQDCRFRVTQ<br>LPNGRDFHMSVVRARRNDSGTYLCGAISLAPKA<br>QIKESLRAELRVTERRAEVPTAHPAPAREPGHSP<br>QIISFFLALTSTALLFLLFFLTLRFSVVKRGRKKLL<br>YIFKQPFMRPVQTTQEEDGCSCRFPEEEEGGCEL<br>(SEQ ID NO: 38) |
| PD1 | MyD88 | ATGCAGATCCCACAGGCGCCCTGGCCAGTCGTCTGGGCG<br>GTGCTACAACTGGGCTGGCGGCCAGGATGGTTCTTAGAC<br>TCCCCAGACAGACCCTGGAACCCTCCTACCTTCTCCCCAG<br>CCCTGCTTGTGGTGACCGAAGGGGACAACGCCACCTTCA<br>CCTGCAGCTTCTCCAACACATCGGAGAGCTTCGTGCTAAA<br>CTGGTACCGCATGAGCCCTAGCAACCAGACGGACAAGCT<br>GGCAGCATTCCCTGAGGACCGTAGCCAGCCTGGCCAGGA<br>CTGCCGTTTCCGTGTCACACAACTGCCTAACGGGCGTGAC<br>TTCCACATGAGCGTGGTCAGAGCCCGGCGCAATGACAGC<br>GGCACATACCTTTGTGGGGCCATCTCCCTGGCCCCTAAGG<br>CGCAGATCAAAGAGAGCCTGCGGGCAGAGCTTAGGGTGA<br>CAGAGAGAAGAGCAGAAGTGCCTACAGCCCACCCTAGCC<br>CTTCACCTAGACCAGCCGGCCAGTTCCAAACACTGGTGGT<br>TGGTGTCGTGGGCGGCCTGCTGGGCAGCCTGGTGCTGCTA<br>GTCTGGGTCCTGGCCGTCATCTGCTCTCGGGCCGCACGAG<br>GAACACAGGTGGCGGCTGACTGGACCGCGCTGGCGGAGG<br>AGATGGATTTTGAGTACTTGGAGATCCGGCAACTGGAGA<br>CACAAGCGGACCCCACTGGCAGACTGCTGGACGCCTGGC<br>AGGGACGCCCTGGCGCCTCTGTAGGCCGACTGCTTGAGC<br>TGCTTACCAAGCTGGGCCGCGACGACGTGCTGCTGGAGC<br>TGGGACCCAGCATTGAGGAGGATTGCCAAAAGTATATCT<br>TGAAGCAGCAGCAGGAGGAGGCTGAGAAGCCTTTACAGG<br>TGGCCGCTGTAGACAGTAGTGTCCCACGGACAGCA (SEQ<br>ID NO: 3) | MQIPQAPWPVVWAVLQLGWRPGWFLDSPDRPW<br>NPPTFSPALLVVTEGDNATFTCSFSNTSESFVLN<br>WYRMSPSNQTDKLAAFPEDRSQPGQDCRFRVTQ<br>LPNGRDFHMSVVRARRNDSGTYLCGAISLAPKA<br>QIKESLRAELRVTERRAEVPTAHPSPSPRPAGQFQ<br>TLVVGVVGGLLGSLVLLVWVLAVICSRAARGTQ<br>VAADWTALAEEMDFEYLEIRQLETQADPTGRLL<br>DAWQGRPGASVGRLLELLTKLGRDDVLLELGPS<br>IEEDCQKYILKQQQEEAEKPLQVAAVDSSVPRTA<br>(SEQ ID NO: 39) |
| PD1 | ICOS | ATGCAGATCCCACAGGCGCCCTGGCCAGTCGTCTGGGCG<br>GTGCTACAACTGGGCTGGCGGCCAGGATGGTTCTTAGAC<br>TCCCCAGACAGGCCCTGGAACCCCCCAACCTTCTCCCCAG<br>CCCTGCTCGTGGTGACCGAAGGGGACAACGCCACCTTCA<br>CCTGCAGCTTCTCCAACACATCGGAGAGCTTCGTGCTAAA<br>CTGGTACCGCATGAGCCCCAGCAACCAGACGGACAAGCT<br>GGCAGCATTCCCTGAGGACCGTAGCCAGCCTGGCCAGGA<br>CTGCCGTTTCCGTGTCACACAACTGCCCAACGGGCGTGAC<br>TTCCACATGAGCGTGGTCAGGGCCCGGCGCAATGACAGC<br>GGCACATACCTTTGTGGGGCCATCTCCCTGGCCCCCAAGG<br>CGCAGATCAAAGAGAGCCTGCGGGCAGAGCTCAGGGTGA<br>CAGAGAGAAGGGCAGAAGTGCCCACAGCCCACCATATTT<br>ATGAATCACAACTTTGTTGCCAGCTGAAGTTCTGGTTACC<br>CATAGGATGTGCAGCCTTTGTTGTAGTCTGCATTTTGGGA<br>TGCATACTTATTTGTTGGCTTACAAAAAAGAAGTATTCAT<br>CCAGTGTGCACGACCCTAACGGTGAATACATGTTCATGA<br>GAGCAGTGAACACAGCCAAAAAATCTAGACTCACAGATG<br>TGACCCTA (SEQ ID NO: 4) | MQIPQAPWPVVWAVLQLGWRPGWFLDSPDRPW<br>NPPTFSPALLVVTEGDNATFTCSFSNTSESFVLN<br>WYRMSPSNQTDKLAAFPEDRSQPGQDCRFRVTQ<br>LPNGRDFHMSVVRARRNDSGTYLCGAISLAPKA<br>QIKESLRAELRVTERRAEVPTAHHIYESQLCCQL<br>KFWLPIGCAAFVVVCILGCILICWLTKKKYSSSV<br>HDPNGEYMFMRAVNTAKKSRLTDVTL (SEQ ID<br>NO: 40) |

TABLE 3-continued

| doMAIN | Domain | nucleic acid sequence encoding polypeptide | amino acid sequence of polypeptide |
|---|---|---|---|
| CTLA4 | truncated | ATGGCTTGCCTTGGATTTCAGCGGCACAAGGCTCAGCTGAACCTGGCTACCAGGACCTGGCCCTGCACTCTCCTGTTTTTTCTTCTCTTCATCCCTGTCTTCTGCAAAGCAATGCACGTGGCCCAGCCTGCTGTGGTACTGGCCAGCAGCCGAGGCATCGCCAGCTTTGTGTGTGAGTATGCATCTCCAGGCAAAGCCACTGAGGTCCGGGTGACAGTGCTTCGGCAGGCTGACAGCCAGGTGACTGAAGTCTGTGCGGCAACCTACATGATGGGGAATGAGTTGACCTTCCTAGATGATTCCATCTGCACGGGCACCTCCAGTGGAAATCAAGTGAACCTCACTATCCAAGGACTGAGGGCCATGGACACGGGACTCTACATCTGCAAGGTGGAGCTCATGTACCCACCGCCATACTACCTGGGCATAGGCAACGGAACCCAGATTTATGTAATTGATCCAGAACCGTGCCCAGATTCTGACTTCCTCCTCTGGATCCTTGCAGCAGTTAGTTCGGGGTTGTTTTTTTATAGCTTTCTCCTCACAGCTGTTTCTTTGAGCAAAATG (SEQ ID NO: 5) | MACLGFQRHKAQLNLATRTWPCTLLFFLLFIPVFCKAMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCPDSDFLLWILAAVSSGLFFYSFLLTAVSLSKM (SEQ ID NO: 41) |
| CTLA4 | CD28 | ATGGCTTGCCTTGGATTTCAGCGGCACAAGGCTCAGCTGAACCTGGCTACCAGGACCTGGCCCTGCACTCTCCTGTTTTTTCTTCTCTTCATCCCTGTCTTCTGCAAAGCAATGCACGTGGCCCAGCCTGCTGTGGTACTGGCCAGCAGCCGAGGCATCGCCAGCTTTGTGTGTGAGTATGCATCTCCAGGCAAAGCCACTGAGGTCCGGGTGACAGTGCTTCGGCAGGCTGACAGCCAGGTGACTGAAGTCTGTGCGGCAACCTACATGATGGGGAATGAGTTGACCTTCCTAGATGATTCCATCTGCACGGGCACCTCCAGTGGAAATCAAGTGAACCTCACTATCCAAGGACTGAGGGCCATGGACACGGGACTCTACATCTGCAAGGTGGAGCTCATGTACCCACCGCCATACTACCTGGGCATAGGCAACGGAACCCAGATTTATGTAATTGATCCAGAACCGTGCCCAGATTCTGACTTCCTCCTCTGGATCCTTGCAGCAGTTAGTTCGGGGTTGTTTTTTTATAGCTTTCTCCTCACAGCTGTTTCTTTGAGCAAAATGAGGAGTAAGAGGAGCAGGCTCCTGCACAGTGACTACATGAACATGACTCCCCGCCGCCCCGGGCCCACCCGCAAGCATTACCAGCCCTATGCCCCACCACGCGACTTCGCAGCCTATCGCTCC (SEQ ID NO: 6) | MACLGFQRHKAQLNLATRTWPCTLLFFLLFIPVFCKAMHVAQPAVVLASSRGIASFVCEYASPGKATEVRVTVLRQADSQVTEVCAATYMMGNELTFLDDSICTGTSSGNQVNLTIQGLRAMDTGLYICKVELMYPPPYYLGIGNGTQIYVIDPEPCPDSDFLLWILAAVSSGLFFYSFLLTAVSLSKMRSKRSRLLHSDYMNMTPRRPGPTRKHYQPYAPPRDFAAYRS (SEQ ID NO: 42) |
| CD200R | truncated | ATGCTCTGCCCTTGGAGAACTGCTAACCTAGGGCTACTGTTGATTTTGACTATCTTCTTAGTGGCCGAAGCGGAGGGTGCTGCTCAACCAAACAACTCATTAATGCTGCAAACTAGCAAGGAGAATCATGCTTTAGCTTCAAGCAGTTTATGTATGGATGAAAAACAGATTACACAGAACTACTCGAAAGTACTCGCAGAAGTTAACACTTCATGGCCTGTAAAGATGGCTACAAATGCTGTGCTTTGTTGCCCTCCTATCGCATTAAGAAATTTGATCATAATAACATGGGAAATAATCCTGAGAGGCCAGCCTTCCTGCACAAAAGCCTACAAGAAAGAAACAAATGAGACCAAGGAAACCAACTGTACTGATGAGAGAATAACCTGGGTCTCCAGACCTGATCAGAATTCGGACCTTCAGATTCGTACCGTGGCCATCACTCATGACGGGTATTACAGATGCATAATGGTAACACCTGATGGGAATTTCCATCGTGGATATCACCTCCAAGTGTTAGTTACACCTGAAGTGACCCTGTTTCAAAACAGGAATAGAACTGCAGTATGCAAGGCAGTTGCAGGGAAGCCAGCTGCGCATATCTCCTGGATCCCAGAGGGCGATTGTGCCACTAAGCAAGAATACTGGAGCAATGGCACAGTGACTGTTAAGAGTACATGCCACTGGGAGGTCCACAATGTGTCTACCGTGACCTGCCACGTCTCCCATTTGACTGGCAACAAGAGTCTGTACATAGAGCTACTTCCTGTTCCAGGTGCCAAAAAATCAGCAAAATTATATATTCCATATATC (SEQ ID NO: 7) | MLCPWRTANLGLLLILTIFLVAEAEGAAQPNNSLMLQTSKENHALASSSLCMDEKQITQNYSKVLAEVNTSWPVKMATNAVLCCPPIALRNLIIITWEIILRGQPSCTKAYKKETNETKETNCTDERITWVSRPDQNSDLQIRTVAITHDGYYRCIMVTPDGNFHRGYHLQVLVTPEVTLFQNRNRTAVCKAVAGKPAAHISWIPEGDCATKQEYWSNGTVTVKSTCHWEVHNVSTVTCHVSHLTGNKSLYIELLPVPGAKKSAKLYIPYI (SEQ ID NO: 43) |
| BTLA | truncated | ATGAAGACATTGCCTGCCATGCTTGGAACTGGGAAATTATTTTGGGTCTTCTTCTTAATCCCATATCTGGACATCTGGAACATCCATGGGAAAGAATCATGTGATGTACAGCTTTATATAAAGAGACAATCTGAACACTCCATCTTAGCAGGAGATCCCTTTGAACTAGAATGCCCTGTGAAATACTGTGCTAACAGGCCTCATGTGACTTGGTGCAAGCTCAATGGAACAACATGTGTAAAACTTGAAGATAGACAAACAAGTTGGAAGGAAGAGAAGAACATTTCATTTTTCATTCTACATTTTGAACCAGTGCTTCCTAATGACAATGGGTCATACCGCTGTTCTGCAAATTTTCAGTCTAATCTCATTGAAAGCCACTCAACAACTCTTTATGTGACAGATGTAAAAAGTGCCTCAGAACGACCCTCCAAGGACGAAATGGCAAGCAGACCCTGGCTCCTGTATCGTTTACTTCCTTTGGGGGGATTGCCTCTACTCATCACTACCTGTTTCTGCCTGTTCTGCTGCCTGAGAAGGCACCAAGGAAAGCAA (SEQ ID NO: 8) | MKTLPAMLGTGKLFWVFFLIPYLDIWNIHGKESCDVQLYIKRQSEHSILAGDPFELECPVKYCANRPHVTWCKLNGTTCVKLEDRQTSWKEEKNISFFILHFEPVLPNDNGSYRCSANFQSNLIESHSTTLYVTDVKSASERPSKDEMASRPWLLYRLLPLGGLPLLITTCFCLFCCLRRHQGKQ (SEQ ID NO: 44) |
| BTLA | CD28 | ATGAAGACATTGCCTGCCATGCTTGGAACTGGGAAATTATTTTGGGTCTTCTTCTTAATCCCATATCTGGACATCTGGAACATCCATGGGAAAGAATCATGTGATGTACAGCTTTATATAAAGAGACAATCTGAACACTCCATCTTAGCAGGAGATCCCTTTGAACTAGAATGCCCTGTGAAATACTGTGCTAACAGGC | MKTLPAMLGTGKLFWVFFLIPYLDIWNIHGKESCDVQLYIKRQSEHSILAGDPFELECPVKYCANRPHVTWCKLNGTTCVKLEDRQTSWKEEKNISFFILHFEPVLPNDNGSYRCSANFQSNLIESHSTTLYVTDVKSASERPSKDEMCPSPLFPGPSKPFWVLVVVGGV |

TABLE 3-continued

| doMAIN | Domain | nucleic acid sequence encoding polypeptide | amino acid sequence of polypeptide |
|---|---|---|---|
| | | CTCATGTGACTTGGTGCAAGCTCAATGGAACAACATGTGT<br>AAAACTTGAAGATAGACAAACAAGTTGGAAGGAAGAGA<br>AGAACATTTCATTTTTCATTCTACATTTTGAACCAGTGCTT<br>CCTAATGACAATGGGTCATACCGCTGTTCTGCAAATTTTC<br>AGTCTAATCTCATTGAAAGCCACTCAACAACTCTTTATGT<br>GACAGATGTAAAAAGTGCCTCAGAACGACCCTCCAAGGA<br>CGAAATGTGTCCAAGTCCCCTATTTCCCGGACCTTCTAAG<br>CCCTTTTGGGTGCTGGTGGTGGTTGGTGGAGTCCTGGCTT<br>GCTATAGCTTGCTAGTAACAGTGGCCTTTATTATTTTCTG<br>GGTGAGGAGTAAGAGGAGCAGGCTCCTGCACAGTGACTA<br>CATGAACATGACTCCCCGCCGCCCCGGGCCCACCCGCAA<br>GCATTACCAGCCCTATGCCCCACCACGCGACTTCGCAGCC<br>TATCGCTCC (SEQ ID NO: 9) | LACYSLLVTVAFIIFWVRSKRSRLLHSDYMNMTP<br>RRPGPTRKHYQPYAPPRDFAAYRS (SEQ ID NO:<br>45) |
| TIM3 | truncated | ATGTTTTCACATCTTCCCTTTGACTGTGTCCTGCTGCTGCT<br>GCTGCTACTACTTACAAGGTCCTCAGAAGTGGAATACAG<br>AGCGGAGGTCGGTCAGAATGCCTATCTGCCCTGCTTCTAC<br>ACCCCAGCCGCCCCAGGGAACCTCGTGCCCGTCTGCTGG<br>GGCAAAGGAGCCTGTCCTGTGTTTGAATGTGGCAACGTG<br>GTGCTCAGGACTGATGAAAGGGATGTGAATTATTGGACA<br>TCCAGATACTGGCTAAATGGGGATTTCCGCAAAGGAGAT<br>GTGTCCCTGACCATAGAGAATGTGACTCTAGCAGACAGT<br>GGGATCTACTGCTGCCGGATCCAAATCCCAGGCATAATG<br>AATGATGAAAAATTTAACCTGAAGTTGGTCATCAAACCA<br>GCCAAGGTCACCCCTGCACCGACTCGGCAGAGAGACTTC<br>ACTGCAGCCTTTCCAAGGATGCTTACCACCAGGGGACAT<br>GGCCCAGCAGAGACACAGACACTGGGGAGCCTCCCTGAT<br>ATAAATCTAACACAAATATCCACATTGGCCAATGAGTTA<br>CGGGACTCTAGATTGGCCAATGACTTACGGGACTCTGGA<br>GCAACCATCAGAATAGGCATCTACATCGGAGCAGGGATC<br>TGTGCTGGGCTGGCTCTGGCTCTTATCTTCGGCGCTTTAA<br>TTTTCAAATGGTATTCTCATAGC (SEQ ID NO: 10) | MFSHLPFDCVLLLLLLLLTRSSEVEYRAEVGQNA<br>YLPCFYTPAAPGNLVPVCWGKGACPVFECGNVV<br>LRTDERDVNYWTSRYWLNGDFRKGDVSLTIENV<br>TLADSGIYCCRIQIPGIMNDEKFNLKLVIKPAKVT<br>PAPTRQRDFTAAFPRMLTTRGHGPAETQTLGSLP<br>DINLTQISTLANELRDSRLANDLRDSGATIRIGIYI<br>GAGICAGLALALIFGALIFKWYSHS (SEQ ID NO:<br>46) |
| TIM3 | CD28 | ATGTTTTCACATCTTCCCTTTGACTGTGTCCTGCTGCTGCT<br>GCTGCTACTACTTACAAGGTCCTCAGAAGTGGAATACAG<br>AGCGGAGGTCGGTCAGAATGCCTATCTGCCCTGCTTCTAC<br>ACCCCAGCCGCCCCAGGGAACCTCGTGCCCGTCTGCTGG<br>GGCAAAGGAGCCTGTCCTGTGTTTGAATGTGGCAACGTG<br>GTGCTCAGGACTGATGAAAGGGATGTGAATTATTGGACA<br>TCCAGATACTGGCTAAATGGGGATTTCCGCAAAGGAGAT<br>GTGTCCCTGACCATAGAGAATGTGACTCTAGCAGACAGT<br>GGGATCTACTGCTGCCGGATCCAAATCCCAGGCATAATG<br>AATGATGAAAAATTTAACCTGAAGTTGGTCATCAAACCA<br>GCCAAGGTCACCCCTGCACCGACTCGGCAGAGAGACTTC<br>ACTGCAGCCTTTCCAAGGATGCTTACCACCAGGGGACAT<br>GGCCCAGCAGAGACACAGACACTGGGGAGCCTCCCTGAT<br>ATAAATCTAACACAAATATCCACATTGGCCAATGAGTTA<br>CGGGACTCTAGATTGGCCAATGACTTACGGTGTCCAAGTC<br>CCCTATTTCCCGGACCTTCTAAGCCCTTTTGGGTGCTGGT<br>GGTGGTTGGTGGAGTCCTGGCTTGCTATAGCTTGCTAGTA<br>ACAGTGGCCTTTATTATTTTCTGGGTGAGGAGTAAGAGGA<br>GCAGGCTCCTGCACAGTGACTACATGAACATGACTCCTC<br>GCCGCCCTGGGCCCACCCGCAAGCATTACCAGCCCTATG<br>CCCCACCACGCGACTTCGCAGCCTATCGCTCC (SEQ ID NO:<br>11) | MFSHLPFDCVLLLLLLLLTRSSEVEYRAEVGQNA<br>YLPCFYTPAAPGNLVPVCWGKGACPVFECGNVV<br>LRTDERDVNYWTSRYWLNGDFRKGDVSLTIENV<br>TLADSGIYCCRIQIPGIMNDEKFNLKLVIKPAKVT<br>PAPTRQRDFTAAFPRMLTTRGHGPAETQTLGSLP<br>DINLTQISTLANELRDSRLANDLRCPSPLFPGPSK<br>PFWVLVVVGGVLACYSLLVTVAFIIFWVRSKRSR<br>LLHSDYMNMTPRRPGPTRKHYQPYAPPRDFAAY<br>RS (SEQ ID NO: 47) |
| TIGIT | truncated | ATGCGCTGGTGTCTCCTCCTGATCTGGGCCCAGGGGCTGA<br>GGCAGGCTCCCCTCGCCTCAGGAATGATGACAGGCACAA<br>TAGAAACAACGGGGAACATTTCTGCAGAGAAAGGTGGCT<br>CTATCATCTTACAATGTCACCTCTCCTCCACCACGGCACA<br>AGTGACCCAGGTCAACTGGGAGCAGCAGGACCAGCTTCT<br>GGCCATTTGTAATGCTGACTTGGGGTGGCACATCTCCCCA<br>TCCTTCAAGGATCGAGTGGCCCCAGGTCCCGGCCTGGGC<br>CTCACCCTCCAGTCGCTGACCGTGAACGATACAGGGGAG<br>TACTTCTGCATCTATCACACCTACCCTGATGGGACGTACA<br>CTGGGAGAATCTTCCTGGAGGTCCTAGAAAGCTCAGTGG<br>CTGAGCACGGTGCCAGGTTCCAGATTCCATTGCTTGGAGC<br>CATGGCCGCGACGCTGGTGGTCATCTGCACAGCAGTCAT<br>CGTGGTGGTCGCGTTGACTAGAAAGAAGAAAGCC (SEQ ID<br>NO: 12) | MRWCLLLIWAQGLRQAPLASGMMTGTIETTGNI<br>SAEKGGSIILQCHLSSTTAQVTQVNWEQQDQLLA<br>ICNADLGWHISPSFKDRVAPGPGLGLTLQSLTVN<br>DTGEYFCIYHTYPDGTYTGRIFLEVLESSVAEHG<br>ARFQIPLLGAMAATLVVICTAVIVVVALTRKKKA<br>(SEQ ID NO: 48) |
| TIGIT | CD28 | ATGCGCTGGTGTCTCCTCCTGATCTGGGCCCAGGGGCTGA<br>GGCAGGCTCCCCTCGCCTCAGGAATGATGACAGGCACAA<br>TAGAAACAACGGGGAACATTTCTGCAGAGAAAGGTGGCT<br>CTATCATCTTACAATGTCACCTCTCCTCCACCACGGCACA<br>AGTGACCCAGGTCAACTGGGAGCAGCAGGACCAGCTTCT<br>GGCCATTTGTAATGCTGACTTGGGGTGGCACATCTCCCCA<br>TCCTTCAAGGATCGAGTGGCCCCAGGTCCCGGCCTGGGC | MRWCLLLIWAQGLRQAPLASGMMTGTIETTGNI<br>SAEKGGSIILQCHLSSTTAQVTQVNWEQQDQLLA<br>ICNADLGWHISPSFKDRVAPGPGLGLTLQSLTVN<br>DTGEYFCIYHTYPDGTYTGRIFLEVLESSVACPSP<br>LFPGPSKPFWVLVVVGGVLACYSLLVTVAFIIFW<br>VRSKRSRLLHSDYMNMTPRRPGPTRKHYQPYAP |

TABLE 3-continued

| doMAIN | Domain | nucleic acid sequence encoding polypeptide | amino acid sequence of polypeptide |
|---|---|---|---|
| | | CTCACCCTCCAGTCGCTGACCGTGAACGATACAGGGGAG<br>TACTTCTGCATCTATCACACCTACCCTGATGGGACGTACA<br>CTGGGAGAATCTTCCTGGAGGTCCTAGAAAGCTCAGTGG<br>CTTGTCCAAGTCCCCTATTTCCCGGACCTTCTAAGCCCTTT<br>TGGGTGCTGGTGGTGGTTGGTGGAGTCCTGGCTTGCTATA<br>GCTTGCTAGTAACAGTGGCCTTTATTATTTTCTGGGTGAG<br>GAGTAAGAGGAGCAGGCTCCTGCACAGTGACTACATGAA<br>CATGACTCCCCGCCGCCCCGGGCCCACCCGCAAGCATTA<br>CCAGCCCTATGCCCCACCACGCGACTTCGCAGCCTATCGC<br>TCC (SEQ ID NO: 13) | PRDFAAYRS (SEQ ID NO: 49) |
| TGFbR2 | truncated | Atgggtcgggggctgctcaggggcctgtgg<br>ccgctgcacatcgtcctgtggacgcgtatc<br>gccagcacgatcccaccgcacgttcagaag<br>tcggttaataacgacatgatagtcactgac<br>aacaacggtgcagtcaagtttccacaactg<br>tgtaaattttgtgatgtgagattttccacc<br>tgtgacaaccagaaatcctgcatgagcaac<br>tgcagcatcacctccatctgtgagaagcca<br>caggaagtctgtgtggctgtatggagaaag<br>aatgacgagaacataacactagagacagtt<br>tgccatgaccccaagctcccctaccatgac<br>tttattctggaagatgctgcttctccaaag<br>tgcattatgaaggaaaaaaaaaagcctggt<br>gagactttcttcatgtgttcctgtagctct<br>gatgagtgcaatgacaacatcatcttctca<br>gaagaatataacaccagcaatcctgacttg<br>ttgctagtcatatttcaagtgacaggcatc<br>agcctcctgccaccactgggagttgccata<br>tctgtcatcatcatcttctactgctaccgc<br>gttaaccggcagcag<br>aagctgagttcatccgga (SEQ ID NO: 14) | MGRGLLRGLWPLHIVLWTRIASTIPPHVQKSVNN<br>DMIVTDNNGAVKFPQLCKFCDVRFSTCDNQKSC<br>MSNCSITSICEKPQEVCVAVWRKNDENITLETVC<br>HDPKLPYHDFILEDAASPKCIMKEKKKPGETFFM<br>CSCSSDECNDNIIFSEEYNTSNPDLLLVIFQVTGIS<br>LLPPLGVAISVIIIFYCYRVNRQQKLSSSG (SEQ ID<br>NO: 50) |
| TGFbR2 | 41BB | ATGGGTCGGGGGCTGCTCAGGGGCCTGTGGCCGCTGCAC<br>ATCGTCCTGTGGACGCGTATCGCCAGCACGATCCCACCGC<br>ACGTTCAGAAGTCGGTTAATAACGACATGATAGTCACTG<br>ACAACAACGGTGCAGTCAAGTTTCCACAACTGTGTAAAT<br>TTTGTGATGTGAGATTTTCCACCTGTGACAACCAGAAATC<br>CTGCATGAGCAACTGCAGCATCACCTCCATCTGTGAGAA<br>GCCACAGGAAGTCTGTGTGGCTGTATGGAGAAAGAATGA<br>CGAGAACATAACACTAGAGACAGTTTGCCATGACCCCAA<br>GCTCCCCTACCATGACTTTATTCTGGAAGATGCTGCTTCTC<br>CAAAGTGCATTATGAAGGaaaaaaaaaaGCCTGGTGAGACTT<br>TCTTCATGTGTTCCTGTAGCTCTGATGAGTGCAATGACAA<br>CATCATCTTCTCAGAAGAATATAACACCAGCAATCCTGAC<br>TTGTTGCTAGTCATATTTCAAGTGACAGGCATCAGCCTCC<br>TGCCACCACTGGGAGTTGCCATATCTGTCATCATCATCTT<br>CTACTGCTACCGCGTTAACCGGCAGAAACGGGGCAGAAA<br>GAAACTCCTGTATATATTCAAACAACCATTTATGAGACCA<br>GTACAAACTACTCAAGAGGAAGATGGCTGTAGCTGCCGA<br>TTTCCAGAAGAAGAAGAAGGAGGATGTGAACTG (SEQ ID<br>NO: 15) | MGRGLLRGLWPLHIVLWTRIASTIPPHVQKSVNN<br>DMIVTDNNGAVKFPQLCKFCDVRFSTCDNQKSC<br>MSNCSITSICEKPQEVCVAVWRKNDENITLETVC<br>HDPKLPYHDFILEDAASPKCIMKEKKKPGETFFM<br>CSCSSDECNDNIIFSEEYNTSNPDLLLVIFQVTGIS<br>LLPPLGVAISVIIIFYCYRVNRQKRGRKKLLYIFK<br>QPFMRPVQTTQEEDGCSCRFPEEEEGGCEL (SEQ<br>ID NO: 51) |
| TGFbR2 | Myd88 | ATGGGTCGGGGGCTGCTCAGGGGCCTGTGGCCGCTGCAC<br>ATCGTCCTGTGGACGCGTATCGCCAGCACGATCCCACCGC<br>ACGTTCAGAAGTCGGTTAATAACGACATGATAGTCACTG<br>ACAACAACGGTGCAGTCAAGTTTCCACAACTGTGTAAAT<br>TTTGTGATGTGAGATTTTCCACCTGTGACAACCAGAAATC<br>CTGCATGAGCAACTGCAGCATCACCTCCATCTGTGAGAA<br>GCCACAGGAAGTCTGTGTGGCTGTATGGAGAAAGAATGA<br>CGAGAACATAACACTAGAGACAGTTTGCCATGACCCCAA<br>GCTCCCCTACCATGACTTTATTCTGGAAGATGCTGCTTCTC<br>CAAAGTGCATTATGAAGGaaaaaaaaaaGCCTGGTGAGACTT<br>TCTTCATGTGTTCCTGTAGCTCTGATGAGTGCAATGACAA<br>CATCATCTTCTCAGAAGAATATAACACCAGCAATCCTGAC<br>TTGTTGCTAGTCATATTTCAAGTGACAGGCATCAGCCTCC<br>TGCCACCACTGGGAGTTGCCATATCTGTCATCATCATCTT<br>CTACTGCTACCGCGTTAACCGGCAGACACAGGTGGCGGC<br>CGACTGGACCGCGCTGGCGGAGGAGATGGACTTTGAGTA<br>CTTGGAGATCCGGCAACTGGAGACACAAGCGGACCCCAC<br>TGGCAGGCTGCTGGACGCCTGGCAGGGACGCCCTGGCGC<br>CTCTGTAGGCCGACTGCTCGAGCTGCTTACCAAGCTGGGC<br>CGCGACGACGTGCTGCTGGAGCTGGGACCCAGCATTGAG<br>GAGGATTGCCAAAAGTATATCTTGAAGCAGCAGCAGGAG<br>GAGGCTGAGAAGCCTTTACAGGTGGCCGCTGTAGACAGC<br>AGTGTCCCACGGACAGCA (SEQ ID NO: 16) | MGRGLLRGLWPLHIVLWTRIASTIPPHVQKSVNN<br>DMIVTDNNGAVKFPQLCKFCDVRFSTCDNQKSC<br>MSNCSITSICEKPQEVCVAVWRKNDENITLETVC<br>HDPKLPYHDFILEDAASPKCIMKEKKKPGETFFM<br>CSCSSDECNDNIIFSEEYNTSNPDLLLVIFQVTGIS<br>LLPPLGVAISVIIIFYCYRVNRQTQVAADWTALA<br>EEMDFEYLEIRQLETQADPTGRLLDAWQGRPGA<br>SVGRLLELLTKLGRDDVLLELGPSIEEDCQKYILK<br>QQQEEAEKPLQVAAVDSSVPRTA (SEQ ID NO:<br>52) |

TABLE 3-continued

| doMAIN | Domain | nucleic acid sequence encoding polypeptide | amino acid sequence of polypeptide |
|---|---|---|---|
| IL-10RA | truncated | ATGCTGCCGTGCCTCGTAGTGCTGCTGGCGGCGCTCCTCA GCCTCCGTCTTGGCTCAGACGCTCATGGGACAGAGCTGCC CAGCCCTCCGTCTGTGTGGTTTGAAGCAGAATTTTTCCAC CACATCCTCCACTGGACACCCATCCCAAATCAGTCTGAAA GTACCTGCTATGAAGTGGCGCTCCTGAGGTATGGAATAG AGTCCTGGAACTCCATCTCCAACTGTAGCCAGACCCTGTC CTATGACCTTACCGCAGTGACCTTGGACCTGTACCACAGC AATGGCTACCGGGCCAGAGTGCGGGCTGTGGACGGCAGC CGGCACTCCAACTGGACCGTCACCAACACCCGCTTCTCTG TGGATGAAGTGACTCTGACAGTTGGCAGTGTGAACCTAG AGATCCACAATGGCTTCATCCTCGGGAAGATTCAGCTACC CAGGCCCAAGATGGCCCCCGCAAATGACACATATGAAAG CATCTTCAGTCACTTCCGAGAGTATGAGATTGCCATTCGC AAGGTGCCGGGAAACTTCACGTTCACACACAAGAAAGTA AAACATGAAAACTTCAGCCTCCTAACCTCTGGAGAAGTG GGAGAGTTCTGTGTCCAGGTGAAACCATCTGTCGCTTCCC GAAGTAACAAGGGGATGTGGTCTAAAGAGGAGTGCATCT CCCTCACCAGGCAGTATTTCACCGTGACCAACGTCATCAT CTTCTTTGCCTTTGTCCTGCTGCTCTCCGGAGCCCTCGCCT ACTGCCTGGCCCTCCAGCTGTATGTGCGGCGCCGA (SEQ ID NO: 17) | MLPCLVVLLAALLSLRLGSDAHGTELPSPPSVWF EAEFFHHILHWTPIPNQSESTCYEVALLRYGIESW NSISNCSQTLSYDLTAVTLDLYHSNGYRARVRA VDGSRHSNWTVTNTRFSVDEVTLTVGSVNLEIH NGFILGKIQLPRPKMAPANDTYESIFSHFREYEIAI RKVPGNFTFTHKKVKHENFSLLTSGEVGEFCVQ VKPSVASRSNKGMWSKEECISLTRQYFTVTNVII FFAFVLLLSGALAYCLALQLYVRRR (SEQ ID NO: 53) |
| IL-10RA | IL-7RA | ATGCTGCCGTGCCTCGTAGTGCTGCTGGCGGCGCTCCTCA GCCTCCGTCTTGGCTCAGACGCTCATGGGACAGAGCTGCC CAGCCCTCCGTCTGTGTGGTTTGAAGCAGAATTTTTCCAC CACATCCTCCACTGGACACCCATCCCAAATCAGTCTGAAA GTACCTGCTATGAAGTGGCGCTCCTGAGGTATGGAATAG AGTCCTGGAACTCCATCTCCAACTGTAGCCAGACCCTGTC CTATGACCTTACCGCAGTGACCTTGGACCTGTACCACAGC AATGGCTACCGGGCCAGAGTGCGGGCTGTGGACGGCAGC CGGCACTCCAACTGGACCGTCACCAACACCCGCTTCTCTG TGGATGAAGTGACTCTGACAGTTGGCAGTGTGAACCTAG AGATCCACAATGGCTTCATCCTCGGGAAGATTCAGCTACC CAGGCCCAAGATGGCCCCCGCAAATGACACATATGAAAG CATCTTCAGTCACTTCCGAGAGTATGAGATTGCCATTCGC AAGGTGCCGGGAAACTTCACGTTCACACACAAGAAAGTA AAACATGAAAACTTCAGCCTCCTAACCTCTGGAGAAGTG GGAGAGTTCTGTGTCCAGGTGAAACCATCTGTCGCTTCCC GAAGTAACAAGGGGATGTGGTCTAAAGAGGAGTGCATCT CCCTCACCAGGCAGTATTTCACCGTGACCAACGTCCCTAT CTTACTAACCATCAGCATTTTGAGTTTTTTCTCTGTCGCTC TGTTGGTCATCTTGGCCTGTGTGTTATGGAAAAAAAGGAT TAAGCCTATCGTATGGCCCAGTCTCCCCGATCATAAGAAG ACTCTGGAACATCTTTGTAAGAAACCAAGAAAAAATTTA AATGTGAGTTTCAATCCTGAAAGTTTCCTGGACTGCCAGA TTCATAGGGTGGATGACATTCAAGCTAGAGATGAAGTGG AAGGTTTTCTGCAAGATACGTTTCCTCAGCAACTAGAAGA ATCTGAGAAGCAGAGGCTTGGAGGGGATGTGCAGAGCCC CAACTGCCCATCTGAGGATGTAGTCATCACTCCAGAAAG CTTTGGAAGAGATTCATCCCTCACATGCCTGGCTGGGAAT GTCAGTGCATGTGACGCCCCTATTCTCTCCTCTTCCAGGT CCCTAGACTGCAGGGAGAGTGGCAAGAATGGGCCTCATG TGTACCAGGACCTCCTGCTTAGCCTTGGGACTACAAACAG CACGCTGCCCCCTCCATTTTCTCTCCAATCTGGAATCCTG ACATTGAACCCAGTTGCTCAGGGTCAGCCCATTCTTACTT CCCTGGGATCAAATCAAGAAGAAGCATATGTCACCATGT CCAGCTTCTACCAAAACCAG (SEQ ID NO: 18) | MLPCLVVLLAALLSLRLGSDAHGTELPSPPSVWF EAEFFHHILHWTPIPNQSESTCYEVALLRYGIESW NSISNCSQTLSYDLTAVTLDLYHSNGYRARVRA VDGSRHSNWTVTNTRFSVDEVTLTVGSVNLEIH NGFILGKIQLPRPKMAPANDTYESIFSHFREYEIAI RKVPGNFTFTHKKVKHENFSLLTSGEVGEFCVQ VKPSVASRSNKGMWSKEECISLTRQYFTVTNVPI LLTISILSFFSVALLVILACVLWKKRIKPIVWPSLP DHKKTLEHLCKKPRKNLNVSFNPESFLDCQIHRV DDIQARDEVEGFLQDTFPQQLEESEKQRLGGDV QSPNCPSEDVVITPESFGRDSSLTCLAGNVSACD APILSSSRSLDCRESGKNGPHVYQDLLLSLGTTNS TLPPPFSLQSGILTLNPVAQGQPILTSLGSNQEEA YVTMSSFYQNQ (SEQ ID NO: 54) |
| IL-4RA | IL-7RA | ATGGGGTGGCTTTGCTCTGGGCTCCTGTTCCCTGTGAGCT GCCTGGTCCTGCTGCAGGTGGCAAGCTCTGGGAACATGA AGGTCTTGCAGGAGCCCACCTGCGTCTCCGACTACATGA GCATCTCTACTTGCGAGTGGAAGATGAATGGTCCCACCA ATTGCAGCACCGAGCTCCGCCTGTTGTACCAGCTGGTTTT TCTGCTCTCCGAAGCCCACACGTGTATCCCTGAGAACAAC GGAGGCGCGGGGTGCGTGTGCCACCTGCTCATGGATGAC GTGGTCAGTGCGGATAACTATACACTGGACCTGTGGGCT GGGCAGCAGCTGCTGTGGAAGGGCTCCTTCAAGCCCAGC GAGCATGTGAAACCCAGGGCCCCAGGAAACCTGACAGTT CACACCAATGTCTCCGACACTCTGCTGCTGACCTGGAGCA ACCCGTATCCCCCTGACAATTACCTGTATAATCATCTCAC CTATGCAGTCAACATTTGGAGTGAAAACGACCCGGCAGA TTTCAGAATCTATAACGTGACCTACCTAGAACCCTCCCTC CGCATCGCAGCCAGCACCCTGAAGTCTGGGATTTCCTACA GGGCACGGGTGAGGGCCTGGGCTCAGTGCTATAACACCA CCTGGAGTGAGTGGAGCCCCAGCACCAAGTGGCACAACT CCTACAGGGAGCCCTTCGAGCAGCACCTCCCTATCTTACT AACCATCAGCATTTTGAGTTTTTTCTCTGTCGCTCTGTTGG | MGWLCSGLLFPVSCLVLLQVASSGNMKVLQEPT CVSDYMSISTCEWKMNGPTNCSTELRLLYQLVF LLSEAHTCIPENNGGAGCVCHLLMDDVVSADNY TLDLWAGQQLLWKGSFKPSEHVKPRAPGNLTV HTNVSDTLLLTWSNPYPPDNYLYNHLTYAVNIW SENDPADFRIYNVTYLEPSLRIAASTLKSGISYR ARVRAWAQCYNTTWSEWSPSTKWHNSYREPFEQH LPILLTISILSFFSVALLVILACVLWKKRIKPIVW PSLPDHKKTLEHLCKKPRKNLNVSFNPESFLDCQ IHRVDDIQARDEVEGFLQDTFPQQLEESEKQRLG GDVQSPNCPSEDVVITPESFGRDSSLTCLAGNVS ACDAPILSSSRSLDCRESGKNGPHVYQDLLLSLG TTNSTLPPPFSLQSGILTLNPVAQGQPILTSLGS NQEEAYVTMSSFYQNQ (SEQ ID NO: 55) |

TABLE 3-continued

| doMAIN | Domain | nucleic acid sequence encoding polypeptide | amino acid sequence of polypeptide |
|---|---|---|---|
| | | TCATCTTGGCCTGTGTGTTATGGAAAAAAAGGATTAAGCC TATCGTATGGCCCAGTCTCCCCGATCATAAGAAGACTCTG GAACATCTTTGTAAGAAACCAAGAAAAAATTTAAATGTG AGTTTCAATCCTGAAAGTTTCCTGGACTGCCAGATTCATA GGGTGGATGACATTCAAGCTAGAGATGAAGTGGAAGGTT TTCTGCAAGATACGTTTCCTCAGCAACTAGAAGAATCTGA GAAGCAGAGGCTTGGAGGGGATGTGCAGAGCCCCAACTG CCCATCTGAGGATGTAGTCATCACTCCAGAAAGCTTTGGA AGAGATTCATCCCTCACATGCCTGGCTGGGAATGTCAGTG CATGTGACGCCCCTATTCTCTCCTCTTCCAGGTCCCTAGA CTGCAGGGAGAGTGGCAAGAATGGGCCTCATGTGTACCA GGACCTCCTGCTTAGCCTTGGGACTACAAACAGCACGCT GCCCCCTCCATTTCTCTCCAATCTGGAATCCTGACATTG AACCCAGTTGCTCAGGGTCAGCCCATTCTTACTTCCCTGG GATCAAATCAAGAAGAAGCATATGTCACCATGTCCAGCT TCTACCAAAACCAG (SEQ ID NO: 19) | |
| | IL-2RA | ATGGATTCATACCTGCTGATGTGGGGACTGCTCACGTTCA TCATGGTGCCTGGCTGCCAGGCAGAGCTCTGTGACGATG ACCCGCCAGAGATCCCACACGCCACATTCAAAGCCATGG CCTACAAGGAAGGAACCATGTTGAACTGTGAATGCAAGA GAGGTTTCCGCAGAATAAAAAGCGGGTCACTCTATATGC TCTGTACAGGAAACTCTAGCCACTCGTCCTGGGACAACC AATGTCAATGCACAAGCTCTGCCACTCGGAACACAACGA AACAAGTGACACCTCAACCTGAAGAACAGAAAGAAAGG AAAACCACAGAAATGCAAAGTCCAATGCAGCCAGTGGAC CAAGCGAGCCTTCCAGGTCACTGCAGGGAACCTCCACCA TGGGAAAATGAAGCCACAGAGAGAATTTATCATTTCGTG GTGGGGCAGATGGTTTATTATCAGTGCGTCCAGGGATAC AGGGCTCTACACAGAGGTCCTGCTGAGAGCGTCTGCAAA ATGACCCACGGGAAGACAAGGTGGACCCAGCCCCAGCTC ATATGCACAGGTGAAATGGAGACCAGTCAGTTTCCAGGT GAAGAGAAGCCTCAGGCAAGCCCCGAAGGCCGTCCTGAG AGTGAGACTTCCTGCCTCGTCACAACAACAGATTTTCAAA TACAGACAGAAATGGCTGCAACCATGGAGACGTCCATAT TTACAACAGAGTACCAGGTAGCAGTGGCCGGCTGTGTTTT CCTGCTGATCAGCGTCCTCCTCCTGAGTGGGCTCACCTGG CAGCGGAGACAGAGGAAGAGTAGAAGAACAATC (SEQ ID NO: 20) | MDSYLLMWGLLTFIMVPGCQAELCDDDPPEIPH ATFKAMAYKEGTMLNCECKRGFRRIKSGSLYML CTGNSSHSSWDNQCQCTSSATRNTTKQVTPQPE EQKERKTTEMQSPMQPVDQASLPGHCREPPPWE NEATERIYHFVVGQMVYYQCVQGYRALHRGPA ESVCKMTHGKTRWTQPQLICTGEMETSQFPGEE KPQASPEGRPESETSCLVTTTDFQIQTEMAATME TSIFTTEYQVAVAGCVFLLISVLLLSGLTWQRRQ RKSRRTI (SEQ ID NO: 56) |
| | IL-7RA | ATGACAATTCTAGGTACAACTTTTGGCATGGTTTTTTCTTT ACTTCAAGTCGTTTCTGGAGAAAGTGGCTATGCTCAAAAT GGAGACTTGGAAGATGCAGAACTGGATGACTACTCATTC TCATGCTATAGCCAGTTGGAAGTGAATGGATCGCAGCAC TCACTGACCTGTGCTTTTGAGGACCCAGATGTCAACATCA CCAATCTGGAATTTGAAATATGTGGGGCCCTCGTGGAGG TAAAGTGCCTGAATTTCAGGAAACTACAAGAGATATATT TCATCGAGACAAAGAAATTCTTACTGATTGGAAAGAGCA ATATATGTGTGAAGGTTGGAGAAAAGAGTCTAACCTGCA AAAAAATAGACCTAACCACTATAGTTAAACCTGAGGCTC CTTTTGACCTGAGTGTCGTCTATCGGGAAGGAGCCAATGA CTTTGTGGTGACATTTAATACATCACACTTGCAAAAGAAG TATGTAAAAGTTTTAATGCACGATGTAGCTTACCGCCAGG AAAAGGATGAAAACAAATGGACGCATGTGAATTTATCCA GCACAAAGCTGACACTCCTGCAGAGAAAGCTCCAACCGG CAGCAATGTATGAGATTAAAGTTCGATCCATCCCTGATCA CTATTTTAAAGGCTTCTGGAGTGAATGGAGTCCAAGTTAT TACTTCAGAACTCCAGAGATCAATAATAGCTCAGGGGAG ATGGATCCTATCTTACTAACCATCAGCATTTTGAGTTTTTT CTCTGTCGCTCTGTTGGTCATCTTGGCCTGTGTGTTATGGA AAAAAAGGATTAAGCCTATCGTATGGCCCAGTCTCCCCG ATCATAAGAAGACTCTGGAACATCTTTGTAAGAAACCAA GAAAAAATTTAAATGTGAGTTTCAATCCTGAAAGTTTCCT GGACTGCCAGATTCATAGGGTGGATGACATTCAAGCTAG AGATGAAGTGGAAGGTTTTCTGCAAGATACGTTTCCTCAG CAACTAGAAGAATCTGAGAAGCAGAGGCTTGGAGGGGAT GTGCAGAGCCCCAACTGCCCATCTGAGGATGTAGTCATC ACTCCAGAAAGCTTTGGAAGAGATTCATCCCTCACATGCC TGGCTGGGAATGTCAGTGCATGTGACGCCCCTATTCTCTC CTCTTCCAGGTCCCTAGACTGCAGGGAGAGTGGCAAGAA TGGGCCTCATGTGTACCAGGACCTCCTGCTTAGCCTTGGG ACTACAAACAGCACGCTGCCCCCTCCATTTCTCTCCAAT CTGGAATCCTGACATTGAACCCAGTTGCTCAGGGTCAGCC CATTCTTACTTCCCTGGGATCAAATCAAGAAGAAGCATAT GTCACCATGTCCAGCTTCTACCAAAACCAG (SEQ ID NO: 21) | MTILGTTFGMVFSLLQVVSGESGYAQNGDLEDA ELDDYSFSCYSQLEVNGSQHSLTCAFEDPDVNIT NLEFEICGALVEVKCLNFRKLQEIYFIETKKFLLIG KSNICVKVGEKSLTCKKIDLTTIVKPEAPFDLSVV YREGANDFVVTFNTSHLQKKYVKVLMHDVAYR QEKDENKWTHVNLSSTKLTLLQRKLQPAAMYEI KVRSIPDHYFKGFWSEWSPSYYFRTPEINNSSGE MDPILLTISILSFFSVALLVILACVLWKKRIKPIVW PSLPDHKKTLEHLCKKPRKNLNVSFNPESFLDCQ IHRVDDIQARDEVEGFLQDTFPQQLEESEKQRLG GDVQSPNCPSEDVVITPESFGRDSSLTCLAGNVS ACDAPILSSSRSLDCRESGKNGPHVYQDLLLSLG TTNSTLPPPFSLQSGILTLNPVAQGQPILTSLGSNQ EEAYVTMSSFYQNQ (SEQ ID NO: 57) |

TABLE 3-continued

| doMAIN | Domain | nucleic acid sequence encoding polypeptide | amino acid sequence of polypeptide |
|---|---|---|---|
| | 41BB | ATGGGAAACAGCTGTTACAACATAGTAGCCACTCTGTTG CTGGTCCTCAACTTTGAGAGGACAAGATCATTGCAGGAT CCTTGTAGTAACTGCCCAGCTGGTACATTCTGTGATAATA ACAGGAATCAGATTTGCAGTCCCTGTCCTCCAAATAGTTT CTCCAGCGCAGGTGGACAAAGGACCTGTGACATATGCAG GCAGTGTAAAGGTGTTTTCAGGACCAGGAAGGAGTGTTC CTCCACCAGCAATGCAGAGTGTGACTGCACTCCAGGGTTT CACTGCCTGGGGGCAGGATGCAGCATGTGTGAACAGGAT TGTAAACAAGGTCAAGAACTGACAAAAAAAGGTTGTAAA GACTGTTGCTTTGGGACATTTAACGATCAGAAACGTGGC ATCTGTCGACCCTGGACAAACTGTTCTTTGGATGGAAAGT CTGTGCTTGTGAATGGGACGAAGGAGAGGGACGTGGTCT GTGGACCATCTCCAGCCGACCTCTCTCCGGGAGCATCCTC TGTGACCCCGCCTGCCCCTGCGAGAGAGCCAGGACACTC TCCGCAGATCATCTCCTTCTTTCTTGCGCTGACGTCGACT GCGTTGCTCTTCCTGCTGTTCTTCCTCACGCTCCGTTTCTC TGTTGTTAAACGGGGCAGAAAGAAACTCCTGTATATATTC AAACAACCATTTATGAGACCAGTACAAACTACTCAAGAG GAAGATGGCTGTAGCTGCCGATTTCCAGAAGAAGAAGAA GGAGGATGTGAACTG (SEQ ID NO: 22) | MGNSCYNIVATLLLVLNFERTRSLQDPCSNCPAG TFCDNNRNQICSPCPPNSFSSAGGQRTCDICRQCK GVFRTRKECSSTSNAECDCTPGFHCLGAGCSMC EQDCKQGQELTKKGCKDCCFGTFNDQKRGICRP WTNCSLDGKSVLVNGTKERDVVCGPSPADLSPGAS SVTPPAPAREPGHSPQIISFFLALTSTALLFLLFF LTLRFSVVKRGRKKLLYIFKQPFMRPVQTTQEED GCSCRFPEEEEGGCEL (SEQ ID NO: 58) |
| Fas | truncated | ATGCTGGGCATCTGGACCCTCCTACCTCTGGTTCTTACGT CTGTTGCTAGATTATCGTCCAAAAGTGTTAATGCCCAAGT GACTGACATCAACTCCAAGGGATTGGAATTGAGGAAGAC TGTTACTACAGTTGAGACTCAGAACTTGGAAGGCCTGCAT CATGATGGCCAATTCTGCCATAAGCCCTGTCCTCCAGGTG AAAGGAAAGCTAGGGACTGCACAGTCAATGGGGATGAA CCAGACTGCGTGCCCTGCCAAGAAGGGAAGGAGTACACA GACAAAGCCCATTTTTCTTCCAAATGCAGAAGATGTAGAT TGTGTGATGAAGGACATGGCTTAGAAGTGGAAATAAACT GCACCCGGACCCAGAATACCAAGTGCAGATGTAAACCAA ACTTTTTTTGTAACTCTACTGTATGTGAACACTGTGACCCT TGCACCAAATGTGAACATGGAATCATCAAGGAATGCACA CTCACCAGCAACACCAAGTGCAAAGAGGAAGGATCCAGA TCTAACTTGGGGTGGCTTTGTCTTCTTCTTTTGCCAATTCC ACTAATTGTTTGGGTGAAGAGAAAGGAAGTACAGAAA (SEQ ID NO: 23) | MLGIWTLLPLVLTSVARLSSKSVNAQVTDINSKG LELRKTVTTVETQNLEGLHHDGQFCHKPCPPGE RKARDCTVNGDEPDCVPCQEGKEYTDKAHFSSK CRRCRLCDEGHGLEVEINCTRTQNTKCRCKPNFF CNSTVCEHCDPCTKCEHGIIKECTLTSNTKCKEE GSRSNLGWLCLLLLPIPLIVWVKRKEVQK (SEQ ID NO: 59) |
| Fas | CD28 | ATGCTGGGCATCTGGACCCTCCTACCTCTGGTTCTTACGT CTGTTGCTAGATTATCGTCCAAAAGTGTTAATGCCCAAGT GACTGACATCAACTCCAAGGGATTGGAATTGAGGAAGAC TGTTACTACAGTTGAGACTCAGAACTTGGAAGGCCTGCAT CATGATGGCCAATTCTGCCATAAGCCCTGTCCTCCAGGTG AAAGGAAAGCTAGGGACTGCACAGTCAATGGGGATGAA CCAGACTGCGTGCCCTGCCAAGAAGGGAAGGAGTACACA GACAAAGCCCATTTTTCTTCCAAATGCAGAAGATGTAGAT TGTGTGATGAAGGACATGGCTTAGAAGTGGAAATAAACT GCACCCGGACCCAGAATACCAAGTGCAGATGTAAACCAA ACTTTTTTTGTAACTCTACTGTATGTGAACACTGTGACCCT TGCACCAAATGTGAACATGGAATCATCAAGGAATGCACA CTCACCAGCAACACCAAGTGCAAAGAGGAAGGATCCAGA TCTAACTTGGGGTGGCTTTGTCTTCTTCTTTTGCCAATTCC ACTAATTGTTTGGGTGAAGAGAAAGGAAGTACAGAAAAG GAGTAAGAGGAGCAGGCTCCTGCACAGTGACTACATGAA CATGACTCCTCGCCGCCCTGGGCCTACCCGCAAGCATTAC CAGCCCTATGCCCCACCACGCGACTTCGCAGCCTATCGCT CC (SEQ ID NO: 24) | MLGIWTLLPLVLTSVARLSSKSVNAQVTDINSKG LELRKTVTTVETQNLEGLHHDGQFCHKPCPPGE RKARDCTVNGDEPDCVPCQEGKEYTDKAHFSSK CRRCRLCDEGHGLEVEINCTRTQNTKCRCKPNFF CNSTVCEHCDPCTKCEHGIIKECTLTSNTKCKEE GSRSNLGWLCLLLLPIPLIVWVKRKEVQKRSKRS RLLHSDYMNMTPRRPGPTRKHYQPYAPPRDFAA YRS (SEQ ID NO: 60) |
| Fas | 41BB | ATGCTGGGCATCTGGACCCTCCTACCTCTGGTTCTTACGT CTGTTGCTAGATTATCGTCCAAAAGTGTTAATGCCCAAGT GACTGACATCAACTCCAAGGGATTGGAATTGAGGAAGAC TGTTACTACAGTTGAGACTCAGAACTTGGAAGGCCTGCAT CATGATGGCCAATTCTGCCATAAGCCCTGTCCTCCAGGTG AAAGGAAAGCTAGGGACTGCACAGTCAATGGGGATGAA CCAGACTGCGTGCCCTGCCAAGAAGGGAAGGAGTACACA GACAAAGCCCATTTTTCTTCCAAATGCAGAAGATGTAGAT TGTGTGATGAAGGACATGGCTTAGAAGTGGAAATAAACT GCACCCGGACCCAGAATACCAAGTGCAGATGTAAACCAA ACTTTTTTTGTAACTCTACTGTATGTGAACACTGTGACCCT TGCACCAAATGTGAACATGGAATCATCAAGGAATGCACA CTCACCAGCAACACCAAGTGCAAAGAGGAAGGATCCAGA TCTAACTTGGGGTGGCTTTGTCTTCTTCTTTTGCCAATTCC ACTAATTGTTTGGGTGAAGAGAAAGGAAGTACAGAAAAA ACGGGGCAGAAAGAAACTCCTGTATATATTCAAACAACC ATTTATGAGACCAGTACAAACTACTCAAGAGGAAGATGG CTGTAGCTGCCGATTTCCAGAAGAAGAAGAAGGAGGATG TGAACTG (SEQ ID NO: 25) | MLGIWTLLPLVLTSVARLSSKSVNAQVTDINSKG LELRKTVTTVETQNLEGLHHDGQFCHKPCPPGE RKARDCTVNGDEPDCVPCQEGKEYTDKAHFSSK CRRCRLCDEGHGLEVEINCTRTQNTKCRCKPNFF CNSTVCEHCDPCTKCEHGIIKECTLTSNTKCKEE GSRSNLGWLCLLLLPIPLIVWVKRKEVQKKRGR KKLLYIFKQPFMRPVQTTQEEDGCSCRFPEEEEG GCEL (SEQ ID NO: 61) |

TABLE 3-continued

| doMAIN | Domain | nucleic acid sequence encoding polypeptide | amino acid sequence of polypeptide |
|---|---|---|---|
| Fas | Myd88 | ATGCTGGGCATCTGGACCCTCCTACCTCTGGTTCTTACGT CTGTTGCTAGATTATCGTCCAAAAGTGTTAATGCCCAAGT GACTGACATCAACTCCAAGGGATTGGAATTGAGGAAGAC TGTTACTACAGTTGAGACTCAGAACTTGGAAGGCCTGCAT CATGATGGCCAATTCTGCCATAAGCCCTGTCCTCCAGGTG AAAGGAAAGCTAGGGACTGCACAGTCAATGGGGATGAA CCAGACTGCGTGCCCTGCCAAGAAGGGAAGGAGTACACA GACAAAGCCCATTTTTCTTCCAAATGCAGAAGATGTAGAT TGTGTGATGAAGGACATGGCTTAGAAGTGGAAATAAACT GCACCCGGACCCAGAATACCAAGTGCAGATGTAAACCAA ACTTTTTTTGTAACTCTACTGTATGTGAACACTGTGACCCT TGCACCAAATGTGAACATGGAATCATCAAGGAATGCACA CTCACCAGCAACACCAAGTGCAAAGAGGAAGGATCCAGA TCTAACTTGGGGTGGCTTTGTCTTCTTCTTTTGCCAATTCC ACTAATTGTTTGGGTGAAGAGAAAGGAAGTACAGAAAAC ACAGGTGGCGGCCGACTGGACCGCGCTGGCGGAGGAGAT GGACTTTGAGTACTTGGAGATCCGGCAACTGGAGACACA AGCGGACCCCACTGGCAGGCTGCTGGACGCCTGGCAGGG ACGCCCTGGCGCCTCTGTAGGCCGACTGCTCGAGCTGCTT ACCAAGCTGGGCCGCGACGACGTGCTGCTGGAGCTGGGA CCCAGCATTGAGGAGGATTGCCAAAAGTATATCTTGAAG CAGCAGCAGGAGGAGGCTGAGAAGCCTTTACAGGTGGCC GCTGTAGACAGCAGTGTCCCACGGACAGCA (SEQ ID NO: 26) | MLGIWTLLPLVLTSVARLSSKSVNAQVTDINSKG LELRKTVTTVETQNLEGLHHDGQFCHKPCPPGE RKARDCTVNGDEPDCVPCQEGKEYTDKAHFSSK CRRCRLCDEGHGLEVEINCTRTQNTKCRCKPNFF CNSTVCEHCDPCTKCEHGIIKECTLTSNTKCKEE GSRSNLGWLCLLLLPIPLIVWVKRKEVQKTQVA ADWTALAEEMDFEYLEIRQLETQADPTGRLLDA WQGRPGASVGRLLELLTKLGRDDVLLELGPSIEE DCQKYILKQQQEEAEKPLQVAAVDSSVPRTA (SEQ ID NO: 62) |
| Fas | ICOS | ATGCTGGGCATCTGGACCCTCCTACCTCTGGTTCTTACGT CTGTTGCTAGATTATCGTCCAAAAGTGTTAATGCCCAAGT GACTGACATCAACTCCAAGGGATTGGAATTGAGGAAGAC TGTTACTACAGTTGAGACTCAGAACTTGGAAGGCCTGCAT CATGATGGCCAATTCTGCCATAAGCCCTGTCCTCCAGGTG AAAGGAAAGCTAGGGACTGCACAGTCAATGGGGATGAA CCAGACTGCGTGCCCTGCCAAGAAGGGAAGGAGTACACA GACAAAGCCCATTTTTCTTCCAAATGCAGAAGATGTAGAT TGTGTGATGAAGGACATGGCTTAGAAGTGGAAATAAACT GCACCCGGACCCAGAATACCAAGTGCAGATGTAAACCAA ACTTTTTTTGTAACTCTACTGTATGTGAACACTGTGACCCT TGCACCAAATGTGAACATGGAATCATCAAGGAATGCACA CTCACCAGCAACACCAAGTGCAAAGAGGAAGGATCCAGA TCTAACTTGGGGTGGCTTTGTCTTCTTCTTTTGCCAATTCC ACTAATTGTTTGGGTGAAGAGAAAGGAAGTACAGAAATG TTGGCTTACAAAAAAGAAGTATTCATCCAGTGTGCACGA CCCTAACGGTGAATACATGTTCATGAGAGCAGTGAACAC AGCCAAAAAATCTAGACTCACAGATGTGACCCTA (SEQ ID NO: 27) | MLGIWTLLPLVLTS VARLS SKS VNAQVTDINSKG LELRKTVTTVETQNLEGLHHDGQFCHKPCPPGE RKARDCTVNGDEPDCVPCQEGKEYTDKAHFSSK CRRCRLCDEGHGLEVEINCTRTQNTKCRCKPNFF CNSTVCEHCDPCTKCEHGIIKECTLTSNTKCKEE GSRSNLGWLCLLLLPIPLIVWVKRKEVQKCWLT KKKYSSSVHDPNGEYMFMRAVNTAKKSRLTDV TL (SEQ ID NO: 63) |
| TRAILR2 | truncated | ATGGAACAACGGGGACAGAATGCCCCGGCCGCTTCGGGG GCCCGGAAAAGACACGGCCCAGGACCTAGAGAGGCGCG GGGAGCCAGGCCTGGGCCCCGGGTCCCCAAGACCCTTGT GCTCGTTGTCGCCGCGGTCCTGCTGTTGGTCTCAGCTGAG TCTGCTCTGATCACCCAACAAGACCTAGCTCCCCAGCAGA GAGCGGCCCCACAACAAAAGAGGTCCAGCCCCTCAGAGG GATTGTGTCCACCTGGACACCATATCTCAGAAGACGGTA GAGATTGCATCTCCTGCAAATATGGACAGGACTATAGCA CTCACTGGAATGACCTCCTTTTCTGCTTGCGCTGCACCAG GTGTGATTCAGGTGAAGTGGAGCTAAGTCCCTGCACCAC GACCAGAAACACAGTGTGTCAGTGCGAAGAAGGCACCTT CCGGGAAGAAGATTCTCCTGAGATGTGCCGGAAGTGCCG CACAGGGTGTCCCAGAGGGATGGTCAAGGTCGGTGATTG TACACCCTGGAGTGACATCGAATGTGTCCACAAAGAATC AGGTACAAAGCACAGTGGGGAAGTCCCAGCTGTGGAGGA GACGGTGACCTCCAGCCCAGGGACTCCTGCCTCTCCCTGT TCTCTCTCAGGCATCATCATAGGAGTCACAGTTGCAGCCG TAGTCTTGATTGTGGCTGTGTTTGTTTGCAAGTCTTTACTG TGGAAG (SEQ ID NO: 28) | MEQRGQNAPAASGARKRHGPGPREARGARPGP RVPKTLVLVVAAVLLLVSAESALITQQDLAPQQR AAPQQKRSSPSEGLCPPGHHISEDGRDCISCKYG QDYSTHWNDLLFCLRCTRCDSGEVELSPCTTTR NTVCQCEEGTFREEDSPEMCRKCRTGCPRGMVK VGDCTPWSDIECVHKESGTKHSGEVPAVEETVTS SPGTPASPCSLSGIIIGVTVAAVVLIVAVFVCKSLL WK (SEQ ID NO: 64) |
| TRAILR2 | CD28 | ATGGAACAACGGGGACAGAATGCCCCGGCCGCTTCGGGG GCCCGGAAAAGACACGGCCCAGGACCTAGAGAGGCGCG GGGAGCCAGGCCTGGGCCCCGGGTCCCCAAGACCCTTGT GCTCGTTGTCGCCGCGGTCCTGCTGTTGGTCTCAGCTGAG TCTGCTCTGATCACCCAACAAGACCTAGCTCCCCAGCAGA GAGCGGCCCCACAACAAAAGAGGTCCAGCCCCTCAGAGG GATTGTGTCCACCTGGACACCATATCTCAGAAGACGGTA GAGATTGCATCTCCTGCAAATATGGACAGGACTATAGCA CTCACTGGAATGACCTCCTTTTCTGCTTGCGCTGCACCAG GTGTGATTCAGGTGAAGTGGAGCTAAGTCCCTGCACCAC GACCAGAAACACAGTGTGTCAGTGCGAAGAAGGCACCTT CCGGGAAGAAGATTCTCCTGAGATGTGCCGGAAGTGCCG CACAGGGTGTCCCAGAGGGATGGTCAAGGTCGGTGATTG | MEQRGQNAPAASGARKRHGPGPREARGARPGP RVPKTLVLVVAAVLLLVSAESALITQQDLAPQQR AAPQQKRSSPSEGLCPPGHHISEDGRDCISCKYG QDYSTHWNDLLFCLRCTRCDSGEVELSPCTTTR NTVCQCEEGTFREEDSPEMCRKCRTGCPRGMVK VGDCTPWSDIECVHKESGTKHSGEVPAVEETVTS SPGTPASPCSLSGIIIGVTVAAVVLIVAVFVCKSLL WKRSKRSRLLHSDYMNMTPRRPGPTRKHYQPY APPRDFAAYRS (SEQ ID NO: 65) |

TABLE 3-continued

| doMAIN | Domain | nucleic acid sequence encoding polypeptide | amino acid sequence of polypeptide |
|---|---|---|---|
| | | TACACCCTGGAGTGACATCGAATGTGTCCACAAAGAATC<br>AGGTACAAAGCACAGTGGGGAAGTCCCAGCTGTGGAGGA<br>GACGGTGACCTCCAGCCCAGGGACTCCTGCCTCTCCCTGT<br>TCTCTCTCAGGCATCATCATAGGAGTCACAGTTGCAGCCG<br>TAGTCTTGATTGTGGCTGTGTTTGTTTGCAAGTCTTTACTG<br>TGGAAGAGGAGTAAGAGGAGCAGGCTCCTGCACAGTGAC<br>TACATGAACATGACTCCTCGCCGCCCTGGGCCCACCCGCA<br>AGCATTACCAGCCCTATGCCCCACCACGCGACTTCGCAGC<br>CTATCGCTCC (SEQ ID NO: 29) | |
| | CCR10 | ATGGGGACCAAGCCCACAGAGCAGGTCTCCTGGGGACTT<br>TACTCCGGGTACGATGAGGAGGCCTATTCGGTTGGGCCG<br>CTGCCAG<br>AGCTCTGTTACAAGGCTGATGTCCAGGCTTTCAGTCGGGC<br>CTTCCAACCCAGTGTCTCCCTGATGGTGGCTGTACTGGGT<br>CTGGCTGGCAATGGCCTAGTCTTGGCCACCCATCTGGCTG<br>CTAGGCGAACTACCCGATCTCCCACCTCCGTTCACCTGCT<br>CCAGTTGGCCCTGGCTGACCTTTTATTGGCCCTGACTTTG<br>CCTTTTGCTGCAGCAGGGGCTCTTCAGGGCTGGAATCTAG<br>GAAGTACCACCTGCCGTGCCATCTCAGGCCTCTACTCGGC<br>CTCTTTCCACGCTGGCTTCCTCTTCCTAGCCTGTATCAGCG<br>CCGACCGCTATGTGGCCATCGCACGAGCTCTCCCAGCCG<br>GGCAGCGGCCCTCAACGCCTAGCCGAGCGCACTTGGTTT<br>CAGTCTTCGTGTGGCTGTTGTCGCTGTTTCTGGCTCTACCT<br>GCGCTCCTTTTCAGCCGGGACGGGCCACGTGAAGGCCAA<br>CGACGCTGTCGGCTCATTTTTCCCGAAAGCCTCACGCAGA<br>CTGTGAAAGGAGCAAGCGCAGTGGCGCAGGTGGTCCTCG<br>GCTTCGCGCTCCCTCTGGGCGTCATGGCAGCCTGTTATGC<br>GCTTCTGGGCCGAACGCTTCTGGCTGCCAGAGGGCCAGA<br>GCGGCGGCGTGCACTGCGCGtcgtggtggctttggtggt<br>ggccttcgtggtg<br>CTGCAGTTGCCCTACAGCCTTGCCCTGCTGCTGGATACAG<br>CCGATCTACTGGCAGCCCGCGAGCGGAGCTGCTCCTCCA<br>GCAAGCGCAAGGATCTAGCTTTGCTGGTCACCGGCGGCT<br>TGACCCTGGTCCGTTGCAGCCTCAATCCGGTGCTTTATGC<br>CTTTTTGGGCCTGCGTTTCCGACGGGATCTGCGGAGACTG<br>CTCCAGGGCGGAGGATGCAGCCCGAAGCCTAACCCTCGT<br>GGCCGCTGCCCTCGTCGACTCCGCCTTTCTTCCTGTTCTGC<br>TCCTACTGAGACCCACAGTCTCTCTTGGGACAAC (SEQ ID<br>NO: 30) | MGTKPTEQVSWGLYSGYDEEAYSVGPLPELCYK<br>ADVQAFSRAF<br>QPSVSLMVAVLGLAGNGLVLATHLAARRTTRSP<br>TSVHLLQLALADLLLALTLPFAAAGALQGWNLG<br>STTCRAISGLYSASFHAGFLFLACISADRYVAIAR<br>ALPAGQRPSTPSRAHLVSVFVWLLSLFLALPALL<br>FSRDGPREGQRRCRLIFPESLTQTVKGASAVAQV<br>VLGFALPLGVMAACYALLGRTLLAARGPERRRA<br>LRVVVALVVAFVVLQLPYSLALLLDTADLLAAR<br>ERSCSSSKRKDLALLVTGGLTLVRCSLNPVLYAF<br>LGLRFRRDLRRLLQGGGCSPKPNPRGRCPRRLRL<br>SSCSAPTETHSLSWDN (SEQ ID NO: 66) |
| | MCT4 | ATGGGAGGAGCCGTGGTGGATGAGGGACCTACAGGAGTC<br>AAGGCCCCTGATGGAGGATGGGGATGGGCTGTGCTCTTC<br>GGCTGTTTCGTCATCACTGGCTTCTCCTACGCCTTCCCCA<br>AGGCCGTCAGTGTCTTCTTCAAGGAGCTCATACAGGAGTT<br>TGGGATCGGCTACAGCGACACAGCCTGGATCTCCTCCATC<br>CTGCTGGCCATGCTCTACGGGACAGGTCCGCTCTGCAGTG<br>TGTGCGTGAACCGCTTTGGCTGCCGGCCCGTCATGCTTGT<br>GGGAGGTCTCTTTGCGTCGCTGGGCATGGTGGCTGCGTCC<br>TTTTGCCGGAGCATCATCCAGGTCTACCTCACCACTGGGG<br>TCATCACGGGGTTGGGTTTGGCACTCAACTTCCAGCCCTC<br>GCTCATCATGCTGAACCGCTACTTCAGCAAGCGGCGCCCT<br>ATGGCCAACGGACTGGCGGCAGCAGGTAGTCCTGTCTTC<br>CTGTGTGCCCTGAGTCCGCTGGGACAGCTGCTGCAGGATC<br>GCTACGGCTGGCGGGGCGGCTTCCTCATCCTGGGCGGCCT<br>GCTGCTTAACTGTTGTGTGTGTGCCGCACTCATGAGGCCT<br>CTGGTGGTCACGGCCCAGCCGGGCTCGGGACCGCCGCGA<br>CCTTCCCGACGACTGCTAGATCTGAGTGTCTTCCGAGATC<br>GCGGCTTTGTGCTTTACGCCGTGGCCGCCTCGGTCATGGT<br>GCTGGGACTCTTCGTCCCGCCCGTGTTCGTGGTGAGCTAC<br>GCCAAGGACCTGGGCGTGCCCGACACCAAGGCCGCCTTC<br>CTGCTCACCATCCTGGGCTTCATTGACATCTTCGCGCGAC<br>CGGCCGCAGGCTTCGTGGCGGGACTTGGAAAGGTGCGGC<br>CTTACTCCGTCTACCTCTTCAGCTTCTCCATGTTCTTCAAC<br>GGCCTCGCGGACCTGGCGGGTTCTACGGCGGGCGACTAC<br>GGCGGCCTCGTGGTCTTCTGCATCTTCTTTGGCATCTCCTA<br>CGGCATGGTGGGAGCCCTGCAGTTCGAGGTGCTCATGGC<br>CATCGTGGGCACCCACAAGTTCTCCAGTGCCATTGGCCTG<br>GTGCTGCTGATGGAGGCGGTGGCCGTGCTCGTCGGGCCT<br>CCTTCGGGAGGCAAACTCCTGGATGCGACCCACGTCTAC<br>ATGTACGTGTTCATCCTGGCGGGAGCCGAGGTGCTCACCT<br>CCTCCCTGATTTTGCTGCTGGGCAACTTCTTCTGCATTAG<br>GAAGAAGCCCAAAGAGCCACAGCCTGAGGTGGCGGCCG<br>CGGAGGAGGAGAAGCTCCACAAGCCTCCTGCAGACTCGG<br>GGGTGGACTTGCGGGAGGTGGAGCATTTCCTGAAGGCTG<br>AGCCTGAGAAAAACGGGGAGGTGGTTCACACCCCGGAAA<br>CAAGTGTC (SEQ ID NO: 31) | MGGAVVDEGPTGVKAPDGGWGWAVLFGCFVIT<br>GFSYAFPKAVSVFFKELIQEFGIGYSDTAWISSILL<br>AMLYGTGPLCSVCVNRFGCRPVMLVGGLFASLG<br>MVAASFCRSIIQVYLTTGVITGLGLALNFQPSLIM<br>LNRYFSKRRPMANGLAAAGSPVFLCALSPLGQL<br>LQDRYGWRGGFLILGGLLLNCCVCAALMRPLVV<br>TAQPGSGPPRPSRRLLDLSVFRDRGFVLYAVAAS<br>VMVLGLFVPPVFVVSYAKDLGVPDTKAAFLLTIL<br>GFIDIFARPAAGFVAGLGKVRPYSVYLFSFSMFF<br>NGLADLAGSTAGDYGGLVVFCIFFGISYGMVGA<br>LQFEVLMAIVGTHKFSSAIGLVLLMEAVAVLVGP<br>PSGGKLLDATHVYMYVFILAGAEVLTSSLILLLG<br>NFFCIRKKPKEPQPEVAAAEEEKLHKPP AD SGVD<br>LREVEHFLKAEPEKNGEVVHTPETSV (SEQ ID<br>NO: 67) |

TABLE 3-continued

| doMAIN | Domain | nucleic acid sequence encoding polypeptide | amino acid sequence of polypeptide |
|---|---|---|---|
| | SOD1 | ATGGCGACGAAGGCCGTGTGCGTGCTGAAGGGCGACGGC<br>CCAGTGCAGGGCATCATCAATTTCGAGCAGAAGGAAAGT<br>AATGGACCAGTGAAGGTGTGGGGAAGCATTAAAGGACTG<br>ACTGAAGGCCTGCATGGATTCCATGTTCATGAGTTTGGAG<br>ATAATACAGCAGGCTGTACCAGTGCAGGTCCTCACTTTAA<br>TCCTCTATCCAGAAAACACGGTGGGCCAAAGGATGAAGA<br>GAGGCATGTTGGAGACTTGGGCAATGTGACTGCTGACAA<br>AGATGGTGTGGCCGATGTGTCTATTGAAGATTCTGTGATC<br>TCACTCTCAGGAGACCATTGCATCATTGGCCGCACACTGG<br>TGGTCCATGAAAAAGCAGATGACTTGGGCAAAGGTGGAA<br>ATGAAGAAAGTACAAAGACAGGAAACGCTGGAAGTCGTT<br>TGGCTTGTGGTGTAATTGGGATCGCCCAA<br>(SEQ ID NO: 32) | MATKAVCVLKGDGPVQGIINFEQKESNGPVKVW<br>GSIKGLTEGLHGFHVHEFGDNTAGCTSAGPHFNP<br>LSRKHGGPKDEERHVGDLGNVTADKDGVADVSI<br>EDSVISLSGDHCIIGRTLVVHEKADDLGKGGNEE<br>STKTGNAGSRLACGVIGIAQ (SEQ ID NO: 68) |
| | TCF7 | ATGCCGCAGCTGGATTCTggcGGAGGAGGAgcgggcGGA<br>GGAGATGATctcggcgcgccgGATGAGCTGCTGGCCTTCC<br>AGGATGAAGGCGAGGAGCAGGATGACAAGAGCCGAGATAG<br>CGCCGCCGGTCCTGAGCGCGACCTGGCCGAGCTCAAGTCG<br>TCGCTTGTGAACGAATCCGAGGGAGCAGCCGGAGGAGCAG<br>GAATCCCGGGAGTTCCGGGAGCCGGCGCCGGAGCCCGAG<br>GCGAGGCCGAAGCTCTTGGACGAGAACACGCTGCGCAGA<br>GACTCTTCCCGGACAAACTTCCAGAGCCCCTGGAGGACG<br>GCCTGAAGGCCCCGGAGTGCACCAGCGGCATGTACAAAG<br>AGACCGTCTACTCCGCCTTCAATCTGCTCATGCATTACCC<br>ACCTCCTTCGGGAGCAGGACAGCACCCTCAGCCGCAGCC<br>TCCGCTGCACAAGGCCAATCAGCCTCCTCACGGTGTCCCT<br>CAACTCTCTCTCTACGAACATTTCAACAGCCCACATCCCA<br>CCCCTGCACCTGCGGACATCAGCCAGAAGCAAGTTCACA<br>GGCCTCTGCAGACCCCTGACCTCTCTGGCTTCTACTCCCT<br>GACCTCAGGCAGCATGGGGCAGCTCCCCCACACTGTGAG<br>CTGGTTCACCCACCCATCCTTGATGCTAGGTTCTGGTGTA<br>CCTGGTCACCCAGCAGCCATCCCTCACCCGGCCATTGTGC<br>CTCCTTCAGGGAAGCAGGAGCTGCAGCCTTTCGACCGCA<br>ACCTGAAGACACAAGCAGAGTCCAAGGCAGAGAAGGAG<br>GCCAAGAAGCCAACCATCAAGAAGCCCCTCAATGCCTTC<br>ATGCTGTACATGAAGGAGATGAGAGCCAAGGTCATTGCA<br>GAGTGCACACTTAAGGAGAGCGCTGCCATCAACCAGATC<br>CTGGGCCGCAGGTGGCACGCGCTGTCGCGAGAAGAGCAG<br>GCCAAGTACTATGAGCTGGCCCGCAAGGAGAGGCAGCTG<br>CACATGCAGCTATACCCAGGCTGGTCAGCGCGGGACAAC<br>TACGGGAAGAAGAAGAGGCGGTCGAGGGAAAAGCACCA<br>AGAATCCACCACAGGAGGAAAAAGAAATGCATTCGGTAC<br>TTACCCGGAGAAGGCCGCTGCCCCAGCCCCGTTCCTTCCG<br>ATGACAGTGCTC (SEQ ID NO: 33) | MPQLDSGGGGAGGGDDLGAPDELLAFQDEGEE<br>QDDKSRDSAAGPERDLAELKSSLVNESEGAAGG<br>AGIPGVPGAGAGARGEAEALGREHAAQRLFPDK<br>LPEPLEDGLKAPECTSGMYKETVYSAFNLLMHY<br>PPPSGAGQHPQPQPPLHKANQPPHGVPQLSLYEH<br>FNSPHPTPAPADISQKQVHRPLQTPDLSGFYSLTS<br>GSMGQLPHTVSWFTHPSLMLGSGVPGHPAAIPH<br>PAIVPPSGKQELQPFDRNLKTQAESKAEKEAKKP<br>TIKKPLNAFMLYMKEMRAKVIAECTLKESAAIN<br>QILGRRWHALSREEQAKYYELARKERQLHMQL<br>YPGWSARDNYGKKKRRSREKHQESTTGGKRNA<br>FGTYPEKAAAPAPFLPMTVL (SEQ ID NO: 69) |
| | INGFR | ATGGGGGCAGGTGCCACTGGCCGCGCCATGGACGGGCCG<br>CGCCTGCTGCTGTTGCTGCTTCTGGGGGTGTCCCTTGGAG<br>GTGCCAAGGAGGCATGCCCCACAGGCCTGTACACACACA<br>GCGGTGAGTGCTGCAAAGCCTGCAACCTGGGCGAGGGTG<br>TGGCCCAGCCTTGTGGAGCCAACCAGACCGTGTGTGAGC<br>CCTGCCTGGACAGCGTGACGTTCTCCGACGTGGTGAGCG<br>CGACCGAGCCGTGCAAGCCGTGCACCGAGTGCGTGGGGC<br>TCCAGAGCATGTCGGCGCCATGCGTGGAGGCCGACGACG<br>CCGTGTGCCGCTGCGCCTACGGCTACTACCAGGATGAGA<br>CGACTGGGCGCTGCGAGGCGTGCCGCGTGTGCGAGGCGG<br>GCTCGGGCCTCGTGTTCTCCTGCCAGGACAAGCAGAACA<br>CCGTGTGCGAGGAGTGCCCCGACGGCACGTATTCCGACG<br>AGGCCAACCACGTGGACCCGTGCCTGCCCTGCACCGTGT<br>GCGAGGACACCGAGCGCCAGCTCCGCGAGTGCACACGCT<br>GGGCCGACGCCGAGTGCGAGGAGATCCCTGGCCGTTGGA<br>TTACACGGTCCACACCCCCAGAGGGCTCGGACAGCACAG<br>CCCCCAGCACCCAGGAGCCTGAGGCACCTCCAGAACAAG<br>ACCTCATAGCCAGCACGGTGGCAGGTGTGGTGACCACAG<br>TGATGGGCAGCTCCCAGCCCGTGGTGACCCGAGGCACCA<br>CCGACAACCTCATCCCTGTCTATTGCTCCATCCTGGCTGC<br>TGTGGTTGTGGGTCTTGTGGCCTACATAGCCTTCAAGAGG<br>TGGAACAGC (SEQ ID NO: 34) | MGAGATGRAMDGPRLLLLLLLGVSLGGAKEAC<br>PTGLYTHSGECCKACNLGEGVAQPCGANQTVCE<br>PCLDSVTFSDVVSATEPCKPCTECVGLQSMSAPC<br>VEADDAVCRCAYGYYQDETTGRCEACRVCEAG<br>SGLVFSCQDKQNTVCEECPDGTYSDEANHVDPC<br>LPCTVCEDTERQLRECTRWADAECEEIPGRWITR<br>STPPEGSDSTAPSTQEPEAPPEQDLIASTVAGVVT<br>TVMGSSQPVVTRGTTDNLIPVYCSILAAVVVGLV<br>AYIAFKRWNS (SEQ ID NO: 70) |
| | GFP | GGATCGGGTGGGACTAGTGGCAGCAAGGGCGAGGAGCT<br>GTTCACCGGGGTGGTGCCCATCCTGGTCGAGCTGGACGG<br>CGACGTAAACGGCCACAAGTTCAGCGTGCGCGGCGAGGG<br>CGAGGGCGATGCCACCAACGGCAAGCTGACCCTGAAGTT<br>CATCTGCACCACCGGCAAGCTGCCCGTGCCCTGGCCCACC<br>CTCGTGACCACCCTGACCTACGGCGTGCAGTGCTTCAGCC<br>GCTACCCCGACCACATGAAGCGCCACGACTTCTTCAAGTC<br>CGCCATGCCCGAAGGCTACGTCCAGGAGCGCACCATCAG<br>CTTCAAGGACGACGGCACCTACAAGACCCGCGCCGAGGT<br>GAAGTTCGAGGGCGACACCCTGGTGAACCGCATCGAGCT | GSGGTSGSKGEELFTGVVPILVELDGDVNGHKFS<br>VRGEGEGDATNGKLTLKFICTTGKLPVPWPTLVT<br>TLTYGVQCFSRYPDHMKRHDFFKSAMPEGYVQE<br>RTISFKDDGTYKTRAEVKFEGDTLVNRIELKGIDF<br>KEDGNILGHKLEYNFNSHNVYITADKQKNGIKA<br>NFKIRHNVEDGSVQLADHYQQNTPIGDGPVLLP<br>DNHYLSTQSVLSKDPNEKRDHMVLLEFVTAAGI<br>TGTGAGSG (SEQ ID NO: 71) |

TABLE 3-continued

| doMAIN | Domain | nucleic acid sequence encoding polypeptide | amino acid sequence of polypeptide |
| --- | --- | --- | --- |
| | | GAAGGGCATCGACTTCAAGGAGGACGGCAACATCCTGGG<br>GCACAAGCTGGAGTACAACTTCAACAGCCACAACGTCTA<br>TATCACCGCCGACAAGCAGAAGAACGGCATCAAGGCCAA<br>CTTCAAGATCCGCCACAACGTGGAGGACGGCAGCGTGCA<br>GCTCGCCGACCACTACCAGCAGAACACCCCCATCGGCGA<br>CGGCCCCGTGCTGCTGCCCGACAACCACTACCTGAGCAC<br>CCAGTCCGTGCTGAGCAAAGACCCCAACGAGAAGCGCGA<br>TCACATGGTCCTgCTGGAgTTCGTGACCGCCGCCGGGATC<br>ACTggaaccggtGCTggaagtggt (SEQ ID NO: 35) | |
| | mCherry | GGATCGGGTGGGACTAGTGGCgtgagcaag<br>ggcgaggaggataacatggccatcatcaag<br>gagttcatgcgcttcaaggtgcacatggag<br>ggctccgtgaacggccacgagttcgagatc<br>gagggcgagggcgagggccgcccctacgag<br>ggcacccagaccgccaagctgaaggtgacc<br>aagggtggccccctgcccttcgcctgggac<br>atcctgtcccctcagttcatgtacggctcc<br>aaggcctacgtgaagcaccccgccgacatc<br>cccgactacttgaagctgtccttccccgag<br>ggcttcaagtgggagcgcgtgatgaacttc<br>gaggacggcggcgtggtgaccgtgacccag<br>gactcctccctgcaggacggcgagttcatc<br>tacaaggtgaagctgcgcggcaccaacttc<br>ccctccgacggccccgtaatgcagaagaag<br>accatgggctgggaggcctcctccgagcgg<br>atgtaccccgaggacggcgccctgaagggc<br>gagatcaagcagaggctgaagctgaaggac<br>ggcggccactacgacgctgaggtcaagacc<br>acctacaaggccaagaagcccgtgcagctg<br>cccggcgcctacaacgtcaacatcaagttg<br>gacatcacctcccacaacgaggactacacc<br>atcgtggaacagtacgaacgcgccgagggc<br>cgccactccaccggcggcatggacgagctg<br>tacaagg<br>gaaccggtGCTggaagtggt (SEQ ID NO: 36) | GSGGTSGVSKGEEDNMAIIKEFMRFKVHMEGSV<br>NGHEFEIEGEGEGRPYEGTQTAKLKVTKGGPLPF<br>AWDILSPQFMYGSKAYVKHPADIPDYLKLSFPEG<br>FKWERVMNFEDGGVVTVTQDSSLQDGEFIYKVK<br>LRGTNFPSDGPVMQKKTMGWEASSERMYPEDG<br>ALKGEIKQRLKLKDGGHYDAEVKTTYKAKKPV<br>QLPGAYNVNIKLDITSHNEDYTIVEQYERAEGRH<br>STGGMDELYKGTGAGSG (SEQ ID NO: 72) |

SEQ ID Nos: 73-116

PD-1 Extracellular domain

SEQ ID NO: 73

PGWFLDSPDRPWNPPTFSPALLVVTEGDNATFTCS

FSNTSESFVLNWYRMSPSNQTDKLAAFPEDRSQPG

QDCRFRVTQLPNGRDFHMSVVRARRNDSGTYLCGA

ISLAPKAQIKESLRAELRVTERRAEVPTAHPSPSP

RPAGQFQTLV

PD-1 Transmembrane domain

SEQ ID NO: 74

VGVVGGLLGSLVLLVWVLAVI

PD-1 Intracellular domain

SEQ ID NO: 75

CSRAARGTIGARRTGQPLKEDPSAVPVFSVDYGEL

DFQWREKTPEPPVPCVPEQTEYATIVFPSGMGT

SSPARRGSADGPRSAQPLRPEDGHCSWPL 4-1BB Extracellular domain

SEQ ID NO: 76

LQDPCSNCPAGTFCDNNRNQICSPCPPNSFSSAGG

QRTCDICRQCKGVFRTRKECSSTSNAECDCTPGFH

CLGAGCSMCEQDCKQGQELTKKGCKDCCFGTFNDQ

KRGICRPWTNCSLDGKSVLVNGTKERDVVCGPSPA

DLSPGASSVTPPAPAREPGHSPQ

-continued 4-1BB Transmembrane domain

SEQ ID NO: 77

IISFFLALTSTALLFLLFFLTLRFSVV 4-1BB Intracellular domain

SEQ ID NO: 78

KRGRKKLLYIFKQPFMRPVQTTQEEDGCSCRFPEE

EEGGCEL

ICOS Extracellular domain

SEQ ID NO: 79

EINGSANYEMFIFHNGGVQILCKYPDIVQQFKMQL

LKGGQILCDLTKTKGSGNTVSIKSLKFCHSQLSNN

SVSFFLYNLDHSHANYYFCNLSIFDPPPFKVTLTG

GYLHIYESQLCCQLK

ICOS TM

SEQ ID NO: 80

FWLPIGCAAFVVVCILGCILI

ICOS Intracellular domain

SEQ ID NO: 81

CWLTKKKYSSSVHDPNGEYMFMRAVNTAKKSRLTDVTL

CTLA4 Extracellular domain

SEQ ID NO: 82

KAMHVAQPAVVLASSRGIASFVCEYASPGKATEVR

VTVLRQADSQVTEVCAATYMMGNELTFLDDSICTG

TSSGNQVNLTIQGLRAMDTGLYICKVELMYPPPYY

LGIGNGTQIYVIDPEPCPDSD

-continued

CTLA4 Transmembrane domain
SEQ ID NO: 83
FLLWILAAVSSGLFFYSFLLT

CTLA4 Intracellular domain
SEQ ID NO: 84
AVSLSKMLKKRSPLTTGVYVKMPPTEPECEKQFQPYF
IPIN CD28 Extracellular domain
SEQ ID NO: 85
NKILVKQSPMLVAYDNAVNLSCKYSYNLFSREFRA
SLHKGLDSAVEVCVVYGNYSQQLQVYSKTGFNCDG
KLGNESVTFYLQNLYVNQTDIYFCKIEVMYPPPYL
DNEKSNGTIIHVKGKHLCPSPLFPGPSKP CD28 Transmembrane domain
SEQ ID NO: 86
FWVLVVVGGVLACYSLLVTVAFIIFWV CD28 Intracellular domain
SEQ ID NO: 87
RSKRSRLLHSDYMNMTPRRPGPTRKHYQPYAPPRD
FAAYRS CD200R Extracellular domain
SEQ ID NO: 88
QPNNSLMLQTSKENHALASSSLCMDEKQITQNYSK
VLAEVNTSWPVKMATNAVLCCPPIALRNLIIITWE
IILRGQPSCTKAYKKETNETKETNCTDERITWVSR
PDQNSDLQIRTVAITHDGYYRCIMVTPDGNFHRGY
HLQVLVTPEVTLFQNRNRTAVCKAVAGKPAAHISW
IPEGDCATKQEYWSNGTVTVKSTCHWEVHNVSTVT
CHVSH CD200R Transmembrane domain
SEQ ID NO: 89
LTGNKSLYIELLPVPGAKKSA CD200R Intracellular domain
SEQ ID NO: 90
KVNGCRKYKLNKTESTPVVEEDEMQPYASYTEKNN
PLYDTTNKVKASEALQSEVDTDLHTL BTLA Extracellular domain
SEQ ID NO: 91
KESCDVQLYIKRQSEHSILAGDPFELECPVKYCAN
RPHVTWCKLNGTTCVKLEDRQTSWKEEKNISFFIL
HFEPVLPNDNGSYRCSANFQSNLIESHSTTLYVTD
VKSASERPSKDEMASRPWLLYR BTLA Transmembrane domain
SEQ ID NO: 92
LLPLGGLPLLITTCFCLFCCL BTLA Intracellular domain
SEQ ID NO: 93
RRHQGKQNELSDTAGREINLVDAHLKSEQTEASTR
QNSQVLLSETGIYDNDPDLCFRMQEGSEVYSNPCL
EENKPGIVYASLNHSVIGPNSRLARNVKEAPTEYA
SICVRS -continued TIM-3 Extracellular domain
SEQ ID NO: 94
SEVEYRAEVGQNAYLPCFYTPAAPGNLVPVCWGKG
ACPVFECGNVVLRTDERDVNYWTSRYWLNGDFRKG
DVSLTIENVTLADSGIYCCRIQIPGIMNDEKFNLK
LVIKPAKVTPAPTRQRDFTAAFPRMLTTRGHGPAE
TQTLGSLPDINLTQISTLANELRDSRLANDLRDSG
ATIRIG TIM-3 Transmembrane domain
SEQ ID NO: 95
IYIGAGICAGLALALIFGALI TIM-3 Intracellular domain
SEQ ID NO: 96
FKWYSHSKEKIQNLSLISLANLPPSGLANAVAEGI
RSEENIYTIEENVYEVEEPNEYYCYVSSRQQPSQP
LGCRFAMP TIGIT Extracellular domain
SEQ ID NO: 97
MMTGTIETTGNISAEKGGSIILQCHLSSTTAQVTQ
VNWEQQDQLLAICNADLGWHISPSFKDRVAPGPGL
GLTLQSLTVNDTGEYFCIYHTYPDGTYTGRIFLEV
LESSVAEHGARFQIP TIGIT Transmembrane domain
SEQ ID NO: 98
LLGAMAATLVVICTAVIVVVA TIGIT Intracellular domain
SEQ ID NO: 99
LTRKKKALRIHSVEGDLRRKSAGQEEWSPSAPSPP
GSCVQAEAAPAGLCGEQRGEDCAELHDYFNVLSYR
SLGNCSFFTETG TGFβR2 Extracellular domain
SEQ ID NO: 100
TIPPHVQKSVNNDMIVTDNNGAVKFPQLCKFCDVR
FSTCDNQKSCMSNCS
ITSICEKPQEVCVAVWRKNDENITLETVCHDPKLP
YHDFILEDAASPKCIMKEKKKPGETFFMCSCSSDE
CNDNIIFSEEYNTSNPDLLLVIFQ TGFPR2 Transmembrane domain
SEQ ID NO: 101
VTGISLLPPLGVAISVIIIFY TGFβR2 Intracellular domain
SEQ ID NO: 102
CYRVNRQQKLSSTWETGKTRKLMEFSEHCAIILED
DRSDISSTCANNINHNTELLPIELDTLVGKGRFAE
VYKAKLKQNTSEQFETVAVKIFPYEEYASWKTEKD
IFSDINLKHENILQFLTAEERKTELGKQYWLITAF
HAKGNLQEYLTRHVISWEDLRKLGSSLARGIAHLH
SDHTPCGRPKMPIVHRDLKSSNILVKNDLTCCLCD
FGLSLRLDPTLSVDDLANSGQVGTARYMAPEVLES
RMNLENVESFKQTDVYSMALVLWEMTSRCNAVGEV -continued

KDYEPPFGSKVREHPCVESMKDNVLRDRGRPEIPS

FWLNHQGIQMVCETLTECWDHDPEARLTAQCVAER

FSELEHLDRLSGRSCSEEKIPEDGSLNTTK

IL-10RA Extracellular domain

SEQ ID NO: 103

HGTELPSPPSVWFEAEFFHHILHWTPIPNQSESTC

YEVALLRYGIESWNSISNCSQTLSYDLTAVTLDLY

HSNGYRARVRAVDGSRHSNWTVTNTRFSVDEVTLT

VGSVNLEIHNGFILGKIQLPRPKMAPANDTYESIF

SHFREYEIAIRKVPGNFTFTHKKVKHENFSLLTSG

EVGEFCVQVKPSVASRSNKGMWSKEECISLTRQYF

TVTN

IL-10RA Transmembrane domain

SEQ ID NO: 104

VIIFFAFVLLLSGALAYCLAL

IL-1 ORA Intracellular domain

SEQ ID NO: 105

QLYVRRRKKLPSVLLFKKPSPFIFISQRPSPETQD

TIHPLDEEAFLKVSPELKNLDLHGSTDSGFGSTKP

SLQTEEPQFLLPDPHPQADRTLGNREPPVLGDSCS

SGSSNSTDSGICLQEPSLSPSTGPTWEQQVGSNSR

GQDDSGIDLVQNSEGRAGDTQGGSALGHHSPPEPE

VPGEEDPAAVAFQGYLRQTRCAEEKATKTGCLEEE

SPLTDGLGPKFGRCLVDEAGLHPPALAKGYLKQDP

LEMTLASSGAPTGQWNQPTEEWSLLALSSCSDLGI

SDWSFAHDLAPLGCVAAPGGLLGSFNSDLVTLPLI

SSLQSSE

IL-4RA Extracellular domain

SEQ ID NO: 106

MKVLQEPTCVSDYMSISTCEWKMNGPTNCSTELRL

LYQLVFLLSEAHTCIPENNGGAGCVCHLLMDDVVS

ADNYTLDLWAGQQLLWKGSFKPSEHVKPRAPGNLT

VHTNVSDTLLLTWSNPYPPDNYLYNHLTYAVNIWS

ENDPADFRIYNVTYLEPSLRIAASTLKSGISYRAR

VRAWAQCYNTTWSEWSPSTKWHNSYREPFEQH

IL-4RA Transmembrane domain

SEQ ID NO: 107

LLLGVSVSCIVILAVCLLCYVSIT

IL-4RA Intracellular domain

SEQ ID NO: 108

KIKKEWWDQIPNPARSRLVAIIIQDAQGSQWEKRS

RGQEPAKCPHWKNCLTKLLPCFLEHNMKRDEDPHK

AAKEMPFQGSGKSAWCPVEISKTVLWPESISVVRC

VELFEAPVECEEEEEVEEEKGSFCASPESSRDDFQ

EGREGIVARLTESLFLDLLGEENGGFCQQDMGESC

LLPPSGSTSAHMPWDEFPSAGPKEAPPWGKEQPLH

-continued

LEPSPPASPTQSPDNLTCTETPLVIAGNPAYRSFS

NSLSQSPCPRELGPDPLLARHLEEVEPEMPCVPQL

SEPTTVPQPEPETWEQILRRNVLQHGAAAAPVSAP

TSGYQEFVHAVEQGGTQASAVVGLGPPGEAGYKAF

SSLLASSAVSPEKCGFGASSGEEGYKPFQDLIPGC

PGDPAPVPVPLFTFGLDREPPRSPQSSHLPSSSPE

HLGLEPGEKVEDMPKPPLPQEQATDPLVDSLGSGI

VYSALTCHLCGHLKQCHGQEDGGQTPVMASPCCGC

CCGDRSSPPTTPLRAPDPSPGGVPLEASLCPASLA

PSGISEKSKSSSSFHPAPGNAQSSSQTPKIVNFVS

VGPTYMRVS

IL-7RA Transmembrane domain

SEQ ID NO: 109

PILLTISILSFFSVALLVILACVLW

IL-7RA Intracellular domain

SEQ ID NO: 110

KKRIKPIVWPSLPDHKKTLEHLCKKPRKNLNVSFN

PESFLDCQIHRVDDIQARDEVEGFLQDTFPQQLEE

SEKQRLGGDVQSPNCPSEDVVITPESFGRDSSLTC

LAGNVSACDAPILSSSRSLDCRESGKNGPHVYQDL

LLSLGTTNSTLPPPFSLQSGILTLNPVAQGQPILT

SLGSNQEEAYVTMSSFYQNQ

Fas Extracellular domain

SEQ ID NO: 111

QVTDINSKGLELRKTVTTVETQNLEGLHHDGQFCH

KPCPPGERKARDCTVNGDEPDCVPCQEGKEYTDKA

HFSSKCRRCRLCDEGHGLEVEINCTRTQNTKCRCK

PNFFCNSTVCEHCDPCTKCEHGIIKECTLTSNTKC

KEEGSRSN

Fas Transmembrane domain

SEQ ID NO: 112

LGWLCLLLLPIPLIVWV

Fas Intracellular domain

SEQ ID NO: 113

KRKEVQKTCRKHRKENQGSHESPTLNPETVAINLS

DVDLSKYIITTIAGVMTLSQVKGFVRKNGVNEAKID

EIKNDNVQDTAEQKVQLLRNWHQLHGKKEAYDTLI

KDLKKANLCTLAEKIQTIILKDITSDSENSNFRNE

IQSLV

TRAILR2 Extracellular domain

SEQ ID NO: 114

ITQQDLAPQQRAAPQQKRSSPSEGLCPPGHHISED

GRDCISCKYGQDYSTHWNDLLFCLRCTRCDSGEVE

LSPCTTTRNTVCQCEEGTFREEDSPEMCRKCRTGC

PRGMVKVGDCTPWSDIECVHKESGTKHSGEVPAVE

ETVTSSPGTPASPCS

TRAILR2 Transmembrane domain

-continued

SEQ ID NO: 115

LSGIIIGVTVAAVVLIVAVFV

TRAILR2 Intracellular domain

SEQ ID NO: 116

CKSLLWKKVLPYLKGICSGGGGDPERVDRSSQRPG

AEDNVLNEIVSILQPTQVPEQEMEVQEPAEPTGVN

-continued

MLSPGESEHLLEPAEAERSQRRRLLVPANEGDPTE

TLRQCFDDFADLVPFDSWEPLMRKLGLMDNEIKVA

KAEAAGHRDTLYTMLIKWVNKTGRDASVHTLLDAL

ETLGERLAKQKIEDHLLSSGKFMYLEGNADSAMS

What is claimed is:

1. A method for identifying a targeted insertion in the genome of a cell comprising:

(a) introducing into a population of cells (i) a targeted nuclease that cleaves a target region in the genome of the cell to create a target insertion site; and (ii) a plurality of DNA templates that are different by sequence from each other, wherein each DNA template comprises:

i. a heterologous coding or noncoding nucleic acid sequence;

ii. a unique barcode nucleotide sequence that indicates the identity of the heterologous coding or noncoding nucleic acid sequence; and iii. a common primer binding sequence, wherein the 5' and 3' ends of each DNA template comprise nucleotide sequences that are homologous to genomic sequences flanking the target insertion site, and wherein one or both homologous nucleotide sequences comprise a mismatched nucleotide sequence compared to a homologous sequence in the genomic sequence, wherein the mismatched nucleotide sequence is not inserted into the target insertion site during recombination;

(b) allowing recombination to occur, thereby creating a population of modified cells;

(c) amplifying DNA from the cells with a pair of primers to generate amplified DNA, wherein a first primer is complementary to the common primer binding sequence, and wherein a second primer binds to the homologous sequence in the genomic sequence flanking the insertion site and does not bind to the mismatched nucleotide sequence in the DNA template; or wherein a first primer binds to a first homologous sequence in a 5' genomic region flanking the insertion site and does not bind to a mismatched nucleotide sequence in the DNA template at the same location as the first homologous sequence and a second primer binds to a second homologous sequence in a 3' genomic region flanking the insertion site and does not bind to a mismatched nucleotide sequence in the DNA template at the same location as the second homologous sequence; and (d) sequencing the amplified DNA to identify a DNA template inserted via homology directed repair into the target insertion site for a cell.

2. The method of claim 1, wherein the mismatched nucleotide sequence is about 3 to 40 nucleotides in length.

3. The method of claim 1, wherein the barcode sequence in the amplified DNA or the barcode sequence is sequenced.

4. The method of claim 1, further comprising determining the relative number of cells in the population having different DNA templates inserted in the target insertion site.

5. The method of claim 1, further comprising applying a selective pressure to the population of modified cells.

6. The method of claim 5, further comprising comparing the relative number of cells in the population having different DNA templates inserted in the target insertion site before and after applying the selective pressure to the cells.

7. The method of claim 1, wherein the DNA template is inserted by introducing a viral vector comprising the DNA template into the cell.

8. The method of claim 1, wherein the population of cells is a population of mammalian cells.

9. The method of claim 8, wherein the mammalian cells are human cells.

10. The method of claim 9, wherein the human cells are T cells.

11. The method of claim 10, wherein the T cells are regulatory T cells, effector T cells, or naïve T cells.

12. The method of claim 11, wherein the effector T cells are CD8+ T cells, CD4+ T cells, or CD8+ CD4+ T cells.

13. The method of claim 1, wherein the population of cells are primary cells.

14. The method of claim 1, wherein the DNA template comprises a nucleic acid encoding a heterologous polypeptide.

15. The method of claim 1, wherein the target insertion site is in exon 1 of a TCR-alpha subunit constant gene (TRAC) or exon 1 of a TCR-beta subunit constant gene (TRBC).

16. The method of claim 15, wherein the genomic sequences are human T-cell TCR locus sequences.

17. The method of claim 1, wherein the targeted nuclease is selected from the group consisting of an RNA-guided nuclease domain, a transcription activator-like effector nuclease (TALEN), a zinc finger nuclease (ZFN) and a megaTAL.

18. The method of claim 17, wherein the targeted nuclease, a guide RNA and the DNA template are introduced into the cell as a ribonucleoprotein complex (RNP)-DNA template complex, wherein the RNP-DNA template complex comprises:

(i) the RNP, wherein the RNP comprises the targeted nuclease and the guide RNA; and (ii) the DNA template.

* * * * *